(12) United States Patent
Sano et al.

(10) Patent No.: US 11,638,603 B2
(45) Date of Patent: *May 2, 2023

(54) SELECTIVE MODULATION OF INTRACELLULAR EFFECTS OF CELLS USING PULSED ELECTRIC FIELDS

(71) Applicant: Virginia Tech Intellectual Properties, Inc., Blacksburg, VA (US)

(72) Inventors: Michael B. Sano, Durham, NC (US); Christopher B. Arena, Burlington, NC (US); Scott S. Verbridge, Blacksburg, VA (US); Rafael V. Davalos, Blacksburg, VA (US)

(73) Assignee: Virginia Tech Intellectual Properties, Inc., Blacksburg, VA (US)

( * ) Notice: Subject to any disclaimer, the term of this patent is extended or adjusted under 35 U.S.C. 154(b) by 806 days.

This patent is subject to a terminal disclaimer.

(21) Appl. No.: 16/443,351

(22) Filed: Jun. 17, 2019

(65) Prior Publication Data

US 2019/0328445 A1    Oct. 31, 2019

Related U.S. Application Data

(63) Continuation of application No. 13/332,133, filed on Dec. 20, 2011, now Pat. No. 10,448,989, which is a
(Continued)

(51) Int. Cl.
*A61B 18/12* (2006.01)
*A61B 18/14* (2006.01)
(Continued)

(52) U.S. Cl.
CPC .............. *A61B 18/14* (2013.01); *A61N 1/327* (2013.01); *A61B 2018/0016* (2013.01);
(Continued)

(58) Field of Classification Search
CPC .......... A61B 2018/00613; A61B 18/14; A61B 18/1477; A61B 2018/00577;
(Continued)

(56) References Cited

U.S. PATENT DOCUMENTS 1,653,819 A    12/1927  Northcott
3,730,238 A    5/1973   Butler
(Continued)

FOREIGN PATENT DOCUMENTS

AU    7656800 A      4/2001
AU    2002315095 A1  12/2002
(Continued)

OTHER PUBLICATIONS

Griffiths, et al., A Dual-Frequency Electrical Impedance Tomography System, Phys. Med. Biol., 1989, vol. 34, No. 10, pp. 1465-1476.
(Continued)

*Primary Examiner* — Michael F Peffley
*Assistant Examiner* — Amanda L Zink
(74) *Attorney, Agent, or Firm* — New River Valley IP Law, P.C.; Michele L. Mayberry

(57) ABSTRACT

The present invention relates to the field of biomedical engineering and medical treatment of diseases and disorders. Methods, devices, and systems for in vivo treatment of cell proliferative disorders are provided. In embodiments, the methods comprise the delivery of high-frequency bursts of bipolar pulses to achieve the desired modality of cell death. More specifically, embodiments of the invention relate to a device and method for destroying aberrant cells, including tumor tissues, using high-frequency, bipolar electrical pulses having a burst width on the order of microseconds and duration of single polarity on the microsecond to nanosecond scale. In embodiments, the methods rely on conventional electroporation with adjuvant drugs or irreversible
(Continued)

electroporation to cause cell death in treated tumors. The invention can be used to treat solid tumors, such as brain tumors.

30 Claims, 35 Drawing Sheets

Related U.S. Application Data continuation-in-part of application No. 12/757,901, filed on Apr. 9, 2010, now Pat. No. 8,926,606.

(60) Provisional application No. 61/424,872, filed on Dec. 20, 2010, provisional application No. 61/285,618, filed on Dec. 11, 2009, provisional application No. 61/167,997, filed on Apr. 9, 2009.

(51) Int. Cl.
*A61N 1/32* (2006.01)
*A61B 18/00* (2006.01)

(52) U.S. Cl.
CPC .............. *A61B 2018/00577* (2013.01); *A61B 2018/00613* (2013.01); *A61B 2018/00761* (2013.01); *A61B 2018/00767* (2013.01)

(58) Field of Classification Search
CPC .... A61B 2018/00875; A61B 2034/104; A61B 18/1206; A61B 2018/0016; A61B 2018/00446; A61B 2018/00767; A61B 34/10; A61B 2018/1425; A61B 2018/143; A61B 18/00; A61B 18/12; A61B 18/1492; A61B 18/18; A61B 2018/0022; A61B 2018/00666; A61B 2018/00672; A61B 2018/00678; A61B 2018/00726; A61B 2018/00761; A61B 2018/00779; A61B 2018/00827; A61B 2018/00886; A61B 2018/00892; A61B 2018/126; A61B 2018/1286; A61B 2018/1467; A61B 2034/105; A61B 2034/256; A61B 2090/3925; A61B 2090/3966; A61B 34/25; A61B 5/01; A61B 5/0538; A61B 90/03

See application file for complete search history.

(56) References Cited

U.S. PATENT DOCUMENTS

| | | |
|---|---|---|
| 3,746,004 A | 7/1973 | Jankelson |
| 3,871,359 A | 3/1975 | Pacela |
| 4,016,886 A | 4/1977 | Doss et al. |
| 4,037,341 A | 7/1977 | Odle et al. |
| 4,216,860 A | 8/1980 | Heimann |
| 4,226,246 A | 10/1980 | Fragnet |
| 4,262,672 A | 4/1981 | Kief |
| 4,267,047 A | 5/1981 | Henne et al. |
| 4,278,092 A | 7/1981 | Borsanyi et al. |
| 4,299,217 A | 11/1981 | Sagae et al. |
| 4,311,148 A | 1/1982 | Courtney et al. |
| 4,336,881 A | 6/1982 | Babb et al. |
| 4,344,436 A | 8/1982 | Kubota |
| 4,392,855 A | 7/1983 | Oreopoulos et al. |
| 4,406,827 A | 9/1983 | Carim |
| 4,407,943 A | 10/1983 | Cole et al. |
| 4,416,276 A | 11/1983 | Newton et al. |
| 4,447,235 A | 5/1984 | Clarke |
| 4,469,098 A | 9/1984 | Davi |
| 4,489,535 A | 12/1984 | Veltman |
| 4,512,765 A | 4/1985 | Muto |
| 4,580,572 A | 4/1986 | Granek et al. |
| 4,636,199 A | 1/1987 | Victor |
| 4,672,969 A | 6/1987 | Dew |
| 4,676,258 A | 6/1987 | Inokuchi et al. |
| 4,676,782 A | 6/1987 | Yamamoto et al. |
| 4,687,471 A | 8/1987 | Twardowski et al. |
| 4,716,896 A | 1/1988 | Ackerman |
| 4,723,549 A | 2/1988 | Wholey et al. |
| D294,519 S | 3/1988 | Hardy |
| 4,756,838 A | 7/1988 | Veltman |
| 4,772,269 A | 9/1988 | Twardowski et al. |
| 4,798,585 A | 1/1989 | Inoue et al. |
| 4,810,963 A | 3/1989 | Blake-Coleman et al. |
| 4,813,929 A | 3/1989 | Semrad |
| 4,819,637 A | 4/1989 | Dormandy et al. |
| 4,822,470 A | 4/1989 | Chang |
| 4,836,204 A | 6/1989 | Landymore et al. |
| 4,840,172 A | 6/1989 | Augustine et al. |
| 4,863,426 A | 9/1989 | Ferragamo et al. |
| 4,885,003 A | 12/1989 | Hillstead |
| 4,886,496 A | 12/1989 | Conoscenti et al. |
| 4,886,502 A | 12/1989 | Poirier et al. |
| 4,889,634 A | 12/1989 | El-Rashidy |
| 4,903,707 A | 2/1990 | Knute et al. |
| 4,907,601 A | 3/1990 | Frick |
| 4,919,148 A | 4/1990 | Muccio |
| 4,920,978 A | 5/1990 | Colvin |
| 4,921,484 A | 5/1990 | Hillstead |
| 4,946,793 A | 8/1990 | Marshall, III |
| 4,976,709 A | 12/1990 | Sand |
| 4,981,477 A | 1/1991 | Schon et al. |
| 4,986,810 A | 1/1991 | Semrad |
| 4,987,895 A | 1/1991 | Heimlich |
| 5,019,034 A | 5/1991 | Weaver et al. |
| 5,031,775 A | 7/1991 | Kane |
| 5,052,391 A | 10/1991 | Silberstone et al. |
| 5,053,013 A | 10/1991 | Ensminger et al. |
| 5,058,605 A | 10/1991 | Slovak |
| 5,071,558 A | 12/1991 | Itoh |
| 5,098,843 A | 3/1992 | Calvin |
| 5,122,137 A | 6/1992 | Lennox |
| 5,134,070 A | 7/1992 | Casnig |
| 5,137,517 A | 8/1992 | Loney et al. |
| 5,141,499 A | 8/1992 | Zappacosta |
| D329,496 S | 9/1992 | Wotton |
| 5,156,597 A | 10/1992 | Verreet et al. |
| 5,173,158 A | 12/1992 | Schmukler |
| 5,186,715 A | 2/1993 | Phillips et al. |
| 5,186,800 A | 2/1993 | Dower |
| 5,188,592 A | 2/1993 | Hakki |
| 5,190,541 A | 3/1993 | Abele et al. |
| 5,192,312 A | 3/1993 | Orton |
| 5,193,537 A | 3/1993 | Freeman |
| 5,209,723 A | 5/1993 | Twardowski et al. |
| 5,215,530 A | 6/1993 | Hogan |
| 5,224,933 A | 7/1993 | Bromander |
| 5,227,730 A | 7/1993 | King et al. |
| 5,242,415 A | 9/1993 | Kantrowitz et al. |
| 5,273,525 A | 12/1993 | Hofmann |
| D343,687 S | 1/1994 | Houghton et al. |
| 5,277,201 A | 1/1994 | Stern |
| 5,279,564 A | 1/1994 | Taylor |
| 5,281,213 A | 1/1994 | Milder |
| 5,283,194 A | 2/1994 | Schmukler |
| 5,290,263 A | 3/1994 | Wigness et al. |
| 5,308,325 A | 5/1994 | Quinn et al. |
| 5,308,338 A | 5/1994 | Helfrich |
| 5,318,543 A | 6/1994 | Ross et al. |
| 5,318,563 A | 6/1994 | Malis et al. |
| 5,328,451 A | 7/1994 | Davis et al. |
| 5,334,167 A | 8/1994 | Cocanower |
| 5,348,554 A | 9/1994 | Imran et al. |
| D351,661 S | 10/1994 | Fischer |
| 5,383,917 A | 1/1995 | Desai et al. |
| 5,389,069 A | 2/1995 | Weaver |
| 5,391,158 A | 2/1995 | Peters |
| 5,403,311 A | 4/1995 | Abele et al. |
| 5,405,320 A | 4/1995 | Twardowski et al. |
| 5,425,752 A | 6/1995 | Nguyen |
| 5,439,440 A | 8/1995 | Hofmann |
| 5,458,625 A | 10/1995 | Kendall |

(56) References Cited

U.S. PATENT DOCUMENTS

| | | |
|---|---|---|
| 5,484,400 A | 1/1996 | Edwards et al. |
| 5,484,401 A | 1/1996 | Rodriguez et al. |
| 5,533,999 A | 7/1996 | Hood et al. |
| 5,536,240 A | 7/1996 | Edwards et al. |
| 5,536,267 A | 7/1996 | Edwards et al. |
| 5,540,737 A | 7/1996 | Fenn |
| 5,546,940 A | 8/1996 | Panescu et al. |
| 5,562,720 A | 10/1996 | Stern et al. |
| 5,575,811 A | 11/1996 | Reid et al. |
| D376,652 S | 12/1996 | Hunt et al. |
| 5,582,588 A | 12/1996 | Sakurai et al. |
| 5,586,982 A | 12/1996 | Abela |
| 5,588,424 A | 12/1996 | Insler et al. |
| 5,588,960 A | 12/1996 | Edwards et al. |
| 5,599,294 A | 2/1997 | Edwards et al. |
| 5,599,311 A | 2/1997 | Raulerson |
| 5,616,126 A | 4/1997 | Malekmehr et al. |
| 5,620,479 A | 4/1997 | Diederich |
| 5,626,146 A | 5/1997 | Barber et al. |
| D380,272 S | 6/1997 | Partika et al. |
| 5,634,899 A | 6/1997 | Shapland et al. |
| 5,643,197 A | 7/1997 | Brucker et al. |
| 5,645,855 A | 7/1997 | Lorenz |
| 5,672,173 A | 9/1997 | Gough et al. |
| 5,674,267 A | 10/1997 | Mir et al. |
| 5,683,384 A | 11/1997 | Gough et al. |
| 5,687,723 A | 11/1997 | Avitall |
| 5,690,620 A | 11/1997 | Knott |
| 5,697,905 A | 12/1997 | d'Ambrosio |
| 5,700,252 A | 12/1997 | Klingenstein |
| 5,702,359 A | 12/1997 | Hofmann et al. |
| 5,718,246 A | 2/1998 | Vona |
| 5,720,921 A | 2/1998 | Meserol |
| 5,735,847 A | 4/1998 | Gough et al. |
| 5,752,939 A | 5/1998 | Makoto |
| 5,778,894 A | 7/1998 | Dorogi et al. |
| 5,782,882 A | 7/1998 | Lerman et al. |
| 5,800,378 A | 9/1998 | Edwards et al. |
| 5,800,484 A | 9/1998 | Gough et al. |
| 5,807,272 A | 9/1998 | Kun et al. |
| 5,807,306 A | 9/1998 | Shapland et al. |
| 5,807,395 A | 9/1998 | Mulier et al. |
| 5,810,742 A | 9/1998 | Peariman |
| 5,810,762 A | 9/1998 | Hofmann |
| 5,830,184 A | 11/1998 | Basta |
| 5,836,897 A | 11/1998 | Sakurai et al. |
| 5,836,905 A | 11/1998 | Lemelson et al. |
| 5,843,026 A | 12/1998 | Edwards et al. |
| 5,843,182 A | 12/1998 | Goldstein |
| 5,865,787 A | 2/1999 | Shapland et al. |
| 5,868,708 A | 2/1999 | Hart et al. |
| 5,873,849 A | 2/1999 | Bernard |
| 5,904,648 A | 5/1999 | Arndt et al. |
| 5,919,142 A | 7/1999 | Boone et al. |
| 5,919,191 A | 7/1999 | Lennox et al. |
| 5,921,982 A | 7/1999 | Lesh et al. |
| 5,944,710 A | 8/1999 | Dev et al. |
| 5,947,284 A | 9/1999 | Foster |
| 5,947,889 A | 9/1999 | Hehrlein |
| 5,951,546 A | 9/1999 | Lorentzen |
| 5,954,745 A | 9/1999 | Gertler et al. |
| 5,957,919 A | 9/1999 | Laufer |
| 5,957,963 A | 9/1999 | Dobak |
| 5,968,006 A | 10/1999 | Hofmann |
| 5,983,131 A | 11/1999 | Weaver et al. |
| 5,984,896 A | 11/1999 | Boyd |
| 5,991,697 A | 11/1999 | Nelson et al. |
| 5,999,847 A | 12/1999 | Elstrom |
| 6,004,339 A | 12/1999 | Wijay |
| 6,009,347 A | 12/1999 | Hofmann |
| 6,009,877 A | 1/2000 | Edwards |
| 6,010,613 A | 1/2000 | Walters et al. |
| 6,016,452 A | 1/2000 | Kasevich |
| 6,029,090 A | 2/2000 | Herbst |
| 6,041,252 A | 3/2000 | Walker et al. |
| 6,043,066 A | 3/2000 | Mangano et al. |
| 6,050,994 A | 4/2000 | Sherman |
| 6,055,453 A | 4/2000 | Hofmann et al. |
| 6,059,780 A | 5/2000 | Gough et al. |
| 6,066,134 A | 5/2000 | Eggers et al. |
| 6,068,121 A | 5/2000 | McGlinch |
| 6,068,650 A | 5/2000 | Hofmann et al. |
| 6,071,281 A | 6/2000 | Burnside et al. |
| 6,074,374 A | 6/2000 | Fulton |
| 6,074,389 A | 6/2000 | Levine et al. |
| 6,085,115 A | 7/2000 | Weaver et al. |
| 6,090,016 A | 7/2000 | Kuo |
| 6,090,105 A | 7/2000 | Zepeda et al. |
| 6,090,106 A | 7/2000 | Goble et al. |
| D430,015 S | 8/2000 | Himbert et al. |
| 6,096,035 A | 8/2000 | Sodhi et al. |
| 6,102,885 A | 8/2000 | Bass |
| 6,106,521 A | 8/2000 | Blewett et al. |
| 6,109,270 A | 8/2000 | Mah et al. |
| 6,110,192 A | 8/2000 | Ravenscroft et al. |
| 6,113,593 A | 9/2000 | Tu et al. |
| 6,116,330 A | 9/2000 | Salyer |
| 6,120,493 A | 9/2000 | Hofmann |
| 6,122,599 A | 9/2000 | Mehta |
| 6,123,701 A | 9/2000 | Nezhat |
| 6,132,397 A | 10/2000 | Davis et al. |
| 6,132,419 A | 10/2000 | Hofmann |
| 6,134,460 A | 10/2000 | Chance |
| 6,139,545 A | 10/2000 | Utley et al. |
| 6,150,148 A | 11/2000 | Nanda et al. |
| 6,159,163 A | 12/2000 | Strauss et al. |
| 6,178,354 B1 | 1/2001 | Gibson |
| 1,437,941 A1 | 2/2001 | Frattini |
| 6,193,715 B1 | 2/2001 | Wrublewski et al. |
| 6,198,970 B1 | 3/2001 | Freed et al. |
| 6,200,314 B1 | 3/2001 | Sherman |
| 6,208,893 B1 | 3/2001 | Hofmann |
| 6,210,402 B1 | 4/2001 | Olsen et al. |
| 6,212,433 B1 | 4/2001 | Behl |
| 6,216,034 B1 | 4/2001 | Hofmann et al. |
| 6,219,577 B1 | 4/2001 | Brown, III et al. |
| 1,442,697 A1 | 5/2001 | Hajianpour |
| 6,233,490 B1 | 5/2001 | Kasevich |
| 6,235,023 B1 | 5/2001 | Lee et al. |
| 1,443,360 A1 | 6/2001 | Haberland |
| 6,241,702 B1 | 6/2001 | Lundquist et al. |
| 6,241,725 B1 | 6/2001 | Cosman |
| 1,445,198 A1 | 7/2001 | Frattini |
| 6,258,100 B1 | 7/2001 | Alferness et al. |
| 6,261,831 B1 | 7/2001 | Agee |
| 6,277,114 B1 | 8/2001 | Bullivant et al. |
| 6,278,895 B1 | 8/2001 | Bernard |
| 6,280,441 B1 | 8/2001 | Ryan |
| 6,283,988 B1 | 9/2001 | Laufer et al. |
| 6,283,989 B1 | 9/2001 | Laufer et al. |
| 6,284,140 B1 | 9/2001 | Sommermeyer et al. |
| 6,287,293 B1 | 9/2001 | Jones et al. |
| 6,287,304 B1 | 9/2001 | Eggers et al. |
| 6,296,636 B1 | 10/2001 | Cheng et al. |
| 6,298,726 B1 | 10/2001 | Adachi et al. |
| 6,299,633 B1 | 10/2001 | Laufer |
| 6,300,108 B1 | 10/2001 | Rubinsky et al. |
| 1,450,391 A1 | 11/2001 | Hunt et al. |
| 6,312,428 B1 | 11/2001 | Eggers et al. |
| 6,326,177 B1 | 12/2001 | Schoenbach et al. |
| 6,327,505 B1 | 12/2001 | Medhkour et al. |
| 6,328,689 B1 | 12/2001 | Gonzalez et al. |
| 6,347,247 B1 | 2/2002 | Dev et al. |
| 6,349,233 B1 | 2/2002 | Adams |
| 6,351,674 B2 | 2/2002 | Silverstone |
| 6,375,634 B1 | 4/2002 | Carroll |
| 6,387,671 B1 | 5/2002 | Rubinsky et al. |
| 6,398,779 B1 | 6/2002 | Buysse et al. |
| 6,403,348 B1 | 6/2002 | Rubinsky et al. |
| 6,405,732 B1 | 6/2002 | Edwards et al. |
| 6,411,852 B1 | 6/2002 | Danek et al. |
| 6,419,674 B1 | 7/2002 | Bowser et al. |
| 6,428,802 B1 | 8/2002 | Atala |
| 6,443,952 B1 | 9/2002 | Mulier et al. |

(56) References Cited

U.S. PATENT DOCUMENTS

| | | |
|---|---|---|
| 6,463,331 B1 | 10/2002 | Edwards |
| 6,470,211 B1 | 10/2002 | Ideker et al. |
| 6,482,221 B1 | 11/2002 | Hebert et al. |
| 6,482,619 B1 | 11/2002 | Rubinsky et al. |
| 6,485,487 B1 | 11/2002 | Sherman |
| 6,488,673 B1 | 12/2002 | Laufer et al. |
| 6,488,678 B2 | 12/2002 | Sherman |
| 6,488,680 B1 | 12/2002 | Francischelli et al. |
| 6,491,706 B1 | 12/2002 | Alferness et al. |
| 6,493,589 B1 | 12/2002 | Medhkour et al. |
| 6,493,592 B1 | 12/2002 | Leonard et al. |
| 6,500,173 B2 | 12/2002 | Underwood et al. |
| 6,503,248 B1 | 1/2003 | Levine |
| 6,506,189 B1 | 1/2003 | Rittman et al. |
| 6,514,248 B1 | 2/2003 | Eggers et al. |
| 6,520,183 B2 | 2/2003 | Amar |
| 6,526,320 B2 | 2/2003 | Mitchell |
| D471,640 S | 3/2003 | McMichael et al. |
| D471,641 S | 3/2003 | McMichael et al. |
| 6,530,922 B2 | 3/2003 | Cosman et al. |
| 6,533,784 B2 | 3/2003 | Truckai et al. |
| 6,537,976 B1 | 3/2003 | Gupta |
| 6,540,695 B1 | 4/2003 | Burbank et al. |
| 6,558,378 B2 | 5/2003 | Sherman et al. |
| 6,562,604 B2 | 5/2003 | Rubinsky et al. |
| 6,569,162 B2 | 5/2003 | He |
| 6,575,969 B1 | 6/2003 | Rittman et al. |
| 6,589,161 B2 | 7/2003 | Corcoran |
| 6,592,594 B2 | 7/2003 | Rimbaugh et al. |
| 6,607,529 B1 | 8/2003 | Jones et al. |
| 6,610,054 B1 | 8/2003 | Edwards et al. |
| 6,611,706 B2 | 8/2003 | Avrahami et al. |
| 6,613,211 B1 | 9/2003 | Mccormick et al. |
| 6,616,657 B2 | 9/2003 | Simpson et al. |
| 6,627,421 B1 | 9/2003 | Unger et al. |
| D480,816 S | 10/2003 | McMichael et al. |
| 6,634,363 B1 | 10/2003 | Danek et al. |
| 6,638,253 B2 | 10/2003 | Breznock |
| 6,653,091 B1 | 11/2003 | Dunn et al. |
| 6,666,858 B2 | 12/2003 | Lafontaine |
| 6,669,691 B1 | 12/2003 | Taimisto |
| 6,673,070 B2 | 1/2004 | Edwards et al. |
| 6,678,558 B1 | 1/2004 | Dimmer et al. |
| 6,689,096 B1 | 2/2004 | Loubens et al. |
| 6,692,493 B2 | 2/2004 | Mcgovern et al. |
| 6,694,979 B2 | 2/2004 | Deem et al. |
| 6,694,984 B2 | 2/2004 | Habib |
| 6,695,861 B1 | 2/2004 | Rosenberg et al. |
| 6,697,669 B2 | 2/2004 | Dev et al. |
| 6,697,670 B2 | 2/2004 | Chomenky et al. |
| 6,702,808 B1 | 3/2004 | Kreindel |
| 6,712,811 B2 | 3/2004 | Underwood et al. |
| D489,973 S | 5/2004 | Root et al. |
| 6,733,516 B2 | 5/2004 | Simons et al. |
| 6,753,171 B2 | 6/2004 | Karube et al. |
| 6,761,716 B2 | 7/2004 | Kadhiresan et al. |
| D495,807 S | 9/2004 | Agbodoe et al. |
| 6,795,728 B2 | 9/2004 | Chornenky et al. |
| 6,801,804 B2 | 10/2004 | Miller et al. |
| 6,812,204 B1 | 11/2004 | McHale et al. |
| 6,837,886 B2 | 1/2005 | Collins et al. |
| 6,847,848 B2 | 1/2005 | Sterzer et al. |
| 6,860,847 B2 | 3/2005 | Mferness et al. |
| 6,865,416 B2 | 3/2005 | Dev et al. |
| 6,881,213 B2 | 4/2005 | Ryan et al. |
| 6,892,099 B2 | 5/2005 | Jaafar et al. |
| 6,895,267 B2 | 5/2005 | Panescu et al. |
| 6,905,480 B2 | 6/2005 | McGuckin et al. |
| 6,912,417 B1 | 6/2005 | Bernard et al. |
| 6,927,049 B2 | 8/2005 | Rubinsky et al. |
| 6,941,950 B2 | 9/2005 | Wilson et al. |
| 6,942,681 B2 | 9/2005 | Johnson |
| 6,958,062 B1 | 10/2005 | Gough et al. |
| 6,960,189 B2 | 11/2005 | Bates et al. |
| 6,962,587 B2 | 11/2005 | Johnson et al. |
| 6,972,013 B1 | 12/2005 | Zhang et al. |
| 6,972,014 B2 | 12/2005 | Eum et al. |
| 6,989,010 B2 | 1/2006 | Francischelli et al. |
| 6,994,689 B1 | 2/2006 | Zadno-Azizi et al. |
| 6,994,706 B2 | 2/2006 | Chornenky et al. |
| 7,011,094 B2 | 3/2006 | Rapacki et al. |
| 7,012,061 B1 | 3/2006 | Reiss et al. |
| 7,027,869 B2 | 4/2006 | Danek et al. |
| 7,036,510 B2 | 5/2006 | Zgoda et al. |
| 7,053,063 B2 | 5/2006 | Rubinsky et al. |
| 7,054,685 B2 | 5/2006 | Dimmer et al. |
| 7,063,698 B2 | 6/2006 | Whayne et al. |
| 7,087,040 B2 | 8/2006 | McGuckin et al. |
| 7,097,612 B2 | 8/2006 | Bertolero et al. |
| 7,100,616 B2 | 9/2006 | Springmeyer |
| 7,113,821 B1 | 9/2006 | Sun et al. |
| 7,130,697 B2 | 10/2006 | Chornenky et al. |
| 7,211,083 B2 | 5/2007 | Chornenky et al. |
| 7,232,437 B2 | 6/2007 | Berman et al. |
| 7,250,048 B2 | 7/2007 | Francischelli et al. |
| D549,332 S | 8/2007 | Matsumoto et al. |
| 7,257,450 B2 | 8/2007 | Auth et al. |
| 7,264,002 B2 | 9/2007 | Danek et al. |
| 7,267,676 B2 | 9/2007 | Chornenky et al. |
| 7,273,055 B2 | 9/2007 | Danek et al. |
| 7,291,146 B2 | 11/2007 | Steinke et al. |
| 7,331,940 B2 | 2/2008 | Sommerich |
| 7,331,949 B2 | 2/2008 | Marisi |
| 7,341,558 B2 | 3/2008 | Torre et al. |
| 7,344,533 B2 | 3/2008 | Pearson et al. |
| D565,743 S | 4/2008 | Phillips et al. |
| D571,478 S | 6/2008 | Horacek |
| 7,387,626 B2 | 6/2008 | Edwards et al. |
| 7,399,747 B1 | 7/2008 | Clair et al. |
| D575,399 S | 8/2008 | Matsumoto et al. |
| D575,402 S | 8/2008 | Sandor |
| 7,419,487 B2 | 9/2008 | Johnson et al. |
| 7,434,578 B2 | 10/2008 | Dillard et al. |
| 7,449,019 B2 | 11/2008 | Uchida et al. |
| 7,451,765 B2 | 11/2008 | Adler |
| 7,455,675 B2 | 11/2008 | Schur et al. |
| 7,476,203 B2 | 1/2009 | DeVore et al. |
| 7,520,877 B2 | 4/2009 | Lee et al. |
| 7,533,671 B2 | 5/2009 | Gonzalez et al. |
| D595,422 S | 6/2009 | Mustapha |
| 7,544,301 B2 | 6/2009 | Shah et al. |
| 7,549,984 B2 | 6/2009 | Mathis |
| 7,565,208 B2 | 7/2009 | Harris et al. |
| 7,571,729 B2 | 8/2009 | Saadat et al. |
| 7,632,291 B2 | 12/2009 | Stephens et al. |
| 7,655,004 B2 | 2/2010 | Long |
| 7,674,249 B2 | 3/2010 | Ivorra et al. |
| 7,680,543 B2 | 3/2010 | Azure |
| D613,418 S | 4/2010 | Ryan et al. |
| 7,718,409 B2 | 5/2010 | Rubinsky et al. |
| 7,722,606 B2 | 5/2010 | Azure |
| 7,742,795 B2 | 6/2010 | Stone et al. |
| 7,765,010 B2 | 7/2010 | Chornenky et al. |
| 7,771,401 B2 | 8/2010 | Hekmat et al. |
| RE42,016 E | 12/2010 | Chornenky et al. |
| D630,321 S | 1/2011 | Hamilton |
| D631,154 S | 1/2011 | Hamilton |
| RE42,277 E | 4/2011 | Jaafar et al. |
| 7,918,852 B2 | 4/2011 | Tullis et al. |
| 7,937,143 B2 | 5/2011 | Demarais et al. |
| 7,938,824 B2 | 5/2011 | Chornenky et al. |
| 7,951,582 B2 | 5/2011 | Gazit et al. |
| 7,955,827 B2 | 6/2011 | Rubinsky et al. |
| RE42,835 E | 10/2011 | Chornenky et al. |
| D647,628 S | 10/2011 | Helfteren |
| 8,048,067 B2 | 11/2011 | Davalos et al. |
| RE43,009 E | 12/2011 | Chornenky et al. |
| 8,109,926 B2 | 2/2012 | Azure |
| 8,114,070 B2 | 2/2012 | Rubinsky et al. |
| 8,162,918 B2 | 4/2012 | Ivorra et al. |
| 8,187,269 B2 | 5/2012 | Shadduck et al. |
| 8,221,411 B2 | 7/2012 | Francischelli et al. |
| 8,231,603 B2 | 7/2012 | Hobbs et al. |
| 8,240,468 B2 | 8/2012 | Wilkinson et al. |

(56) References Cited

U.S. PATENT DOCUMENTS

| | | |
|---|---|---|
| 8,251,986 B2 | 8/2012 | Chornenky et al. |
| 8,267,927 B2 | 9/2012 | Dalal et al. |
| 8,267,936 B2 | 9/2012 | Hushka et al. |
| 8,282,631 B2 | 10/2012 | Davalos et al. |
| 8,298,222 B2 | 10/2012 | Rubinsky et al. |
| 8,348,921 B2 | 1/2013 | Ivorra et al. |
| 8,361,066 B2 | 1/2013 | Long et al. |
| D677,798 S | 3/2013 | Hart et al. |
| 8,425,455 B2 | 4/2013 | Nentwick |
| 8,425,505 B2 | 4/2013 | Long |
| 8,454,594 B2 | 6/2013 | Demarais et al. |
| 8,465,464 B2 | 6/2013 | Travis et al. |
| 8,465,484 B2 | 6/2013 | Davalos et al. |
| 8,506,564 B2 | 8/2013 | Long et al. |
| 8,511,317 B2 | 8/2013 | Thapliyal et al. |
| 8,518,031 B2 | 8/2013 | Boyden et al. |
| 8,562,588 B2 | 10/2013 | Hobbs et al. |
| 8,603,087 B2 | 12/2013 | Rubinsky et al. |
| 8,632,534 B2 | 1/2014 | Pearson et al. |
| 8,634,929 B2 | 1/2014 | Chornenky et al. |
| 8,647,338 B2 | 2/2014 | Chornenky et al. |
| 8,715,276 B2 | 5/2014 | Thompson et al. |
| 8,753,335 B2 | 6/2014 | Moshe et al. |
| 8,814,860 B2 | 8/2014 | Davalos et al. |
| 8,835,166 B2 | 9/2014 | Phillips et al. |
| 8,845,635 B2 | 9/2014 | Daniel et al. |
| 8,880,195 B2 | 11/2014 | Azure |
| 8,903,488 B2 | 12/2014 | Callas et al. |
| 8,906,006 B2 | 12/2014 | Chornenky et al. |
| 8,926,606 B2 | 1/2015 | Davalos et al. |
| 8,958,888 B2 | 2/2015 | Chornenky et al. |
| 8,968,542 B2 | 3/2015 | Davalos et al. |
| 8,992,517 B2 | 3/2015 | Davalos et al. |
| 9,005,189 B2 | 4/2015 | Davalos et al. |
| 9,078,665 B2 | 7/2015 | Moss et al. |
| 9,149,331 B2 | 10/2015 | Deem et al. |
| 9,173,704 B2 | 11/2015 | Hobbs et al. |
| 9,198,733 B2 | 12/2015 | Neal, II et al. |
| 9,283,051 B2 | 3/2016 | Garcia et al. |
| 9,414,881 B2 * | 8/2016 | Callas ............... A61B 18/14 |
| 9,598,691 B2 | 3/2017 | Davalos |
| 9,764,145 B2 | 9/2017 | Callas et al. |
| 9,867,652 B2 | 1/2018 | Sano et al. |
| 9,943,599 B2 | 4/2018 | Gehl et al. |
| 10,117,701 B2 | 11/2018 | Davalos et al. |
| 10,117,707 B2 | 11/2018 | Garcia et al. |
| 10,154,874 B2 | 12/2018 | Davalos et al. |
| 10,238,447 B2 | 3/2019 | Neal et al. |
| 10,245,098 B2 | 4/2019 | Davalos et al. |
| 10,245,105 B2 | 4/2019 | Davalos et al. |
| 10,272,178 B2 | 4/2019 | Davalos et al. |
| 10,286,108 B2 | 5/2019 | Davalos et al. |
| 10,292,755 B2 | 5/2019 | Davalos et al. |
| 10,448,989 B2 | 10/2019 | Arena et al. |
| 10,470,822 B2 | 11/2019 | Garcia et al. |
| 10,471,254 B2 | 11/2019 | Sano et al. |
| 10,537,379 B2 | 1/2020 | Sano et al. |
| 10,694,972 B2 | 6/2020 | Davalos et al. |
| 10,702,326 B2 | 7/2020 | Neal et al. |
| 10,828,085 B2 | 11/2020 | Davalos et al. |
| 10,828,086 B2 | 11/2020 | Davalos et al. |
| 10,959,772 B2 | 3/2021 | Davalos et al. |
| 11,254,926 B2 | 2/2022 | Garcia et al. |
| 11,272,979 B2 | 3/2022 | Garcia et al. |
| 11,311,329 B2 | 4/2022 | Davalos et al. |
| 11,382,681 B2 | 7/2022 | Arena et al. |
| 11,406,820 B2 | 8/2022 | Sano et al. |
| 2001/0039393 A1 | 11/2001 | Mori et al. |
| 2001/0044596 A1 | 11/2001 | Jaafar |
| 2001/0046706 A1 | 11/2001 | Rubinsky et al. |
| 2001/0047167 A1 | 11/2001 | Heggeness |
| 2001/0051366 A1 | 12/2001 | Rubinsky et al. |
| 2002/0002393 A1 | 1/2002 | Mitchell |
| 2002/0010491 A1 | 1/2002 | Schoenbach et al. |
| 2002/0022864 A1 | 2/2002 | Mahvi et al. |
| 2002/0040204 A1 | 4/2002 | Dev et al. |
| 2002/0049370 A1 | 4/2002 | Laufer et al. |
| 2002/0052601 A1 | 5/2002 | Goldberg et al. |
| 2002/0055731 A1 | 5/2002 | Atala et al. |
| 2002/0065541 A1 | 5/2002 | Fredricks et al. |
| 2002/0072742 A1 | 6/2002 | Schaefer et al. |
| 2002/0077314 A1 | 6/2002 | Falk et al. |
| 2002/0077676 A1 | 6/2002 | Schroeppel et al. |
| 2002/0082543 A1 | 6/2002 | Park et al. |
| 2002/0099323 A1 | 7/2002 | Dev et al. |
| 2002/0104318 A1 | 8/2002 | Jaafar et al. |
| 2002/0111615 A1 | 8/2002 | Cosman et al. |
| 2002/0112729 A1 | 8/2002 | DeVore et al. |
| 2002/0115208 A1 | 8/2002 | Mitchell et al. |
| 2002/0119437 A1 | 8/2002 | Grooms et al. |
| 2002/0133324 A1 | 9/2002 | Weaver et al. |
| 2002/0137121 A1 | 9/2002 | Rubinsky et al. |
| 2002/0138075 A1 | 9/2002 | Edwards et al. |
| 2002/0138117 A1 | 9/2002 | Son |
| 2002/0143365 A1 | 10/2002 | Herbst |
| 2002/0147462 A1 | 10/2002 | Mair et al. |
| 2002/0156472 A1 | 10/2002 | Lee et al. |
| 2002/0161361 A1 | 10/2002 | Sherman et al. |
| 2002/0183684 A1 | 12/2002 | Dev et al. |
| 2002/0183735 A1 | 12/2002 | Edwards et al. |
| 2002/0183740 A1 | 12/2002 | Edwards et al. |
| 2002/0188242 A1 | 12/2002 | Wu |
| 2002/0193784 A1 | 12/2002 | McHale et al. |
| 2002/0193831 A1 | 12/2002 | Edward |
| 2003/0009110 A1 | 1/2003 | Tu et al. |
| 2003/0016168 A1 | 1/2003 | Jandrell |
| 2003/0055220 A1 | 3/2003 | Legrain |
| 2003/0055420 A1 | 3/2003 | Kadhiresan et al. |
| 2003/0059945 A1 | 3/2003 | Dzekunov et al. |
| 2003/0060856 A1 | 3/2003 | Chornenky et al. |
| 2003/0078490 A1 | 4/2003 | Damasco et al. |
| 2003/0088189 A1 | 5/2003 | Tu et al. |
| 2003/0088199 A1 | 5/2003 | Kawaji |
| 2003/0096407 A1 | 5/2003 | Atala et al. |
| 2003/0105454 A1 | 6/2003 | Cucin |
| 2003/0109871 A1 | 6/2003 | Johnson et al. |
| 2003/0127090 A1 | 7/2003 | Gifford et al. |
| 2003/0130711 A1 | 7/2003 | Pearson et al. |
| 2003/0135242 A1 | 7/2003 | Mongeon et al. |
| 2003/0149451 A1 | 8/2003 | Chomenky et al. |
| 2003/0153960 A1 | 8/2003 | Chornenky et al. |
| 2003/0154988 A1 | 8/2003 | DeVore et al. |
| 2003/0159700 A1 | 8/2003 | Laufer et al. |
| 2003/0166181 A1 | 9/2003 | Rubinsky et al. |
| 2003/0170898 A1 | 9/2003 | Gundersen et al. |
| 2003/0194808 A1 | 10/2003 | Rubinsky et al. |
| 2003/0195385 A1 | 10/2003 | DeVore |
| 2003/0195406 A1 | 10/2003 | Jenkins et al. |
| 2003/0199050 A1 | 10/2003 | Mangano et al. |
| 2003/0208200 A1 | 11/2003 | Palanker et al. |
| 2003/0208236 A1 | 11/2003 | Heil et al. |
| 2003/0212394 A1 | 11/2003 | Pearson et al. |
| 2003/0212412 A1 | 11/2003 | Dillard et al. |
| 2003/0225360 A1 | 12/2003 | Eppstein et al. |
| 2003/0228344 A1 | 12/2003 | Fields et al. |
| 2004/0009459 A1 | 1/2004 | Anderson et al. |
| 2004/0019371 A1 | 1/2004 | Jaafar et al. |
| 2004/0055606 A1 | 3/2004 | Hendricksen et al. |
| 2004/0059328 A1 | 3/2004 | Daniel et al. |
| 2004/0059389 A1 | 3/2004 | Chornenky et al. |
| 2004/0068228 A1 | 4/2004 | Cunningham |
| 2004/0116965 A1 | 6/2004 | Falkenberg |
| 2004/0133194 A1 | 7/2004 | Eum et al. |
| 2004/0138715 A1 | 7/2004 | Groeningen et al. |
| 2004/0146877 A1 | 7/2004 | Diss et al. |
| 2004/0153057 A1 | 8/2004 | Davison |
| 2004/0176855 A1 | 9/2004 | Badylak |
| 2004/0193042 A1 | 9/2004 | Scampini et al. |
| 2004/0193097 A1 | 9/2004 | Hofmann et al. |
| 2004/0199159 A1 | 10/2004 | Lee et al. |
| 2004/0200484 A1 | 10/2004 | Springmeyer |
| 2004/0206349 A1 | 10/2004 | Alferness et al. |
| 2004/0210248 A1 | 10/2004 | Gordon et al. |
| 2004/0230187 A1 | 11/2004 | Lee et al. |

(56) References Cited

U.S. PATENT DOCUMENTS

| | | |
|---|---|---|
| 2004/0236376 A1 | 11/2004 | Miklavcic et al. |
| 2004/0243107 A1 | 12/2004 | Macoviak et al. |
| 2004/0267189 A1 | 12/2004 | Mavor et al. |
| 2004/0267340 A1 | 12/2004 | Cioanta et al. |
| 2005/0004507 A1 | 1/2005 | Schroeppel et al. |
| 2005/0010209 A1 | 1/2005 | Lee et al. |
| 2005/0010259 A1 | 1/2005 | Gerber |
| 2005/0013870 A1 | 1/2005 | Freyman et al. |
| 2005/0020965 A1 | 1/2005 | Rioux et al. |
| 2005/0043726 A1 | 2/2005 | McHale et al. |
| 2005/0048651 A1* | 3/2005 | Ryttsen ............ C12M 35/02 435/459 |
| 2005/0049541 A1 | 3/2005 | Behar et al. |
| 2005/0061322 A1 | 3/2005 | Freitag |
| 2005/0066974 A1 | 3/2005 | Fields et al. |
| 2005/0112141 A1 | 5/2005 | Terman |
| 2005/0143817 A1 | 6/2005 | Hunter et al. |
| 2005/0165393 A1 | 7/2005 | Eppstein |
| 2005/0171522 A1 | 8/2005 | Christopherson |
| 2005/0171523 A1 | 8/2005 | Rubinsky et al. |
| 2005/0171574 A1 | 8/2005 | Rubinsky et al. |
| 2005/0182462 A1 | 8/2005 | Chornenky et al. |
| 2005/0197619 A1 | 9/2005 | Rule et al. |
| 2005/0261672 A1 | 11/2005 | Deem et al. |
| 2005/0267407 A1 | 12/2005 | Goldman |
| 2005/0282284 A1 | 12/2005 | Rubinsky et al. |
| 2005/0283149 A1 | 12/2005 | Thorne et al. |
| 2005/0288684 A1 | 12/2005 | Aronson et al. |
| 2005/0288702 A1 | 12/2005 | McGurk et al. |
| 2005/0288730 A1 | 12/2005 | Deem et al. |
| 2006/0004356 A1 | 1/2006 | Bilski et al. |
| 2006/0004400 A1 | 1/2006 | McGurk et al. |
| 2006/0009748 A1 | 1/2006 | Mathis |
| 2006/0015147 A1 | 1/2006 | Persson et al. |
| 2006/0020347 A1 | 1/2006 | Barrett |
| 2006/0024359 A1 | 2/2006 | Walker et al. |
| 2006/0025760 A1 | 2/2006 | Podhajsky |
| 2006/0074413 A1 | 4/2006 | Behzadian |
| 2006/0079838 A1 | 4/2006 | Walker et al. |
| 2006/0079845 A1 | 4/2006 | Howard et al. |
| 2006/0079883 A1 | 4/2006 | Elmouelhi et al. |
| 2006/0085054 A1 | 4/2006 | Zikorus et al. |
| 2006/0089635 A1 | 4/2006 | Young et al. |
| 2006/0121610 A1 | 6/2006 | Rubinsky et al. |
| 2006/0142801 A1 | 6/2006 | Demarais et al. |
| 2006/0149123 A1 | 7/2006 | Vidlund et al. |
| 2006/0173490 A1 | 8/2006 | Lafontaine et al. |
| 2006/0182684 A1 | 8/2006 | Beliveau |
| 2006/0195146 A1 | 8/2006 | Tracey et al. |
| 2006/0212032 A1 | 9/2006 | Daniel et al. |
| 2006/0212078 A1 | 9/2006 | Demarais et al. |
| 2006/0217703 A1 | 9/2006 | Chornenky et al. |
| 2006/0224188 A1 | 10/2006 | Libbus et al. |
| 2006/0235474 A1 | 10/2006 | Demarais |
| 2006/0247619 A1 | 11/2006 | Kaplan et al. |
| 2006/0264752 A1* | 11/2006 | Rubinsky ............ A61N 1/0412 606/41 |
| 2006/0264807 A1 | 11/2006 | Westersten et al. |
| 2006/0269531 A1 | 11/2006 | Beebe et al. |
| 2006/0276710 A1 | 12/2006 | Krishnan |
| 2006/0278241 A1 | 12/2006 | Ruano |
| 2006/0283462 A1 | 12/2006 | Fields et al. |
| 2006/0293713 A1 | 12/2006 | Rubinsky et al. |
| 2006/0293725 A1 | 12/2006 | Rubinsky et al. |
| 2006/0293730 A1 | 12/2006 | Rubinsky et al. |
| 2006/0293731 A1 | 12/2006 | Rubinsky et al. |
| 2006/0293734 A1 | 12/2006 | Scott et al. |
| 2007/0010805 A1 | 1/2007 | Fedewa et al. |
| 2007/0016183 A1 | 1/2007 | Lee et al. |
| 2007/0016185 A1 | 1/2007 | Tullis et al. |
| 2007/0021803 A1 | 1/2007 | Deem et al. |
| 2007/0025919 A1 | 2/2007 | Deem et al. |
| 2007/0043345 A1 | 2/2007 | Davalos et al. |
| 2007/0060989 A1 | 3/2007 | Deem et al. |
| 2007/0078391 A1 | 4/2007 | Wortley et al. |
| 2007/0088347 A1 | 4/2007 | Young et al. |
| 2007/0093789 A1 | 4/2007 | Smith |
| 2007/0096048 A1 | 5/2007 | Clerc |
| 2007/0118069 A1 | 5/2007 | Persson et al. |
| 2007/0129711 A1 | 6/2007 | Altshuler et al. |
| 2007/0129760 A1 | 6/2007 | Demarais et al. |
| 2007/0151848 A1 | 7/2007 | Novak et al. |
| 2007/0156135 A1 | 7/2007 | Rubinsky et al. |
| 2007/0191889 A1 | 8/2007 | Lang |
| 2007/0203486 A1 | 8/2007 | Young |
| 2007/0230757 A1 | 10/2007 | Trachtenberg et al. |
| 2007/0239099 A1 | 10/2007 | Goldfarb et al. |
| 2007/0244521 A1 | 10/2007 | Bornzin et al. |
| 2007/0287950 A1 | 12/2007 | Kjeken et al. |
| 2007/0295336 A1 | 12/2007 | Nelson et al. |
| 2007/0295337 A1 | 12/2007 | Nelson et al. |
| 2008/0015571 A1 | 1/2008 | Rubinsky et al. |
| 2008/0021371 A1 | 1/2008 | Rubinsky et al. |
| 2008/0027314 A1 | 1/2008 | Miyazaki et al. |
| 2008/0027343 A1 | 1/2008 | Fields et al. |
| 2008/0033340 A1 | 2/2008 | Heller et al. |
| 2008/0033417 A1 | 2/2008 | Nields et al. |
| 2008/0045880 A1 | 2/2008 | Kjeken et al. |
| 2008/0052786 A1 | 2/2008 | Lin et al. |
| 2008/0065062 A1 | 3/2008 | Leung et al. |
| 2008/0071262 A1 | 3/2008 | Azure |
| 2008/0097139 A1 | 4/2008 | Clerc et al. |
| 2008/0097422 A1 | 4/2008 | Edwards et al. |
| 2008/0103529 A1 | 5/2008 | Schoenbach et al. |
| 2008/0121375 A1 | 5/2008 | Richason et al. |
| 2008/0125772 A1 | 5/2008 | Stone et al. |
| 2008/0132826 A1 | 6/2008 | Shadduck et al. |
| 2008/0132884 A1* | 6/2008 | Rubinsky ............ A61B 18/1477 606/50 |
| 2008/0132885 A1 | 6/2008 | Rubinsky et al. |
| 2008/0140064 A1 | 6/2008 | Vegesna |
| 2008/0146934 A1 | 6/2008 | Czygan et al. |
| 2008/0154259 A1 | 6/2008 | Gough et al. |
| 2008/0167649 A1 | 7/2008 | Edwards et al. |
| 2008/0171985 A1 | 7/2008 | Karakoca |
| 2008/0190434 A1 | 8/2008 | Wai |
| 2008/0200911 A1 | 8/2008 | Long |
| 2008/0200912 A1 | 8/2008 | Long |
| 2008/0208052 A1 | 8/2008 | LePivert et al. |
| 2008/0210243 A1 | 9/2008 | Clayton et al. |
| 2008/0214986 A1 | 9/2008 | Ivorra et al. |
| 2008/0236593 A1 | 10/2008 | Nelson et al. |
| 2008/0249503 A1 | 10/2008 | Fields et al. |
| 2008/0262489 A1 | 10/2008 | Steinke |
| 2008/0269586 A1 | 10/2008 | Rubinsky et al. |
| 2008/0269838 A1 | 10/2008 | Brighton et al. |
| 2008/0275465 A1 | 11/2008 | Paul et al. |
| 2008/0281319 A1 | 11/2008 | Paul et al. |
| 2008/0283065 A1 | 11/2008 | Chang et al. |
| 2008/0288038 A1 | 11/2008 | Paul et al. |
| 2008/0300589 A1 | 12/2008 | Paul et al. |
| 2008/0306427 A1 | 12/2008 | Bailey |
| 2008/0312599 A1 | 12/2008 | Rosenberg |
| 2009/0018206 A1 | 1/2009 | Barkan et al. |
| 2009/0024075 A1 | 1/2009 | Schroeppel et al. |
| 2009/0029407 A1 | 1/2009 | Gazit et al. |
| 2009/0038752 A1 | 2/2009 | Weng et al. |
| 2009/0062788 A1 | 3/2009 | Long et al. |
| 2009/0062792 A1 | 3/2009 | Vakharia et al. |
| 2009/0062795 A1 | 3/2009 | Vakharia et al. |
| 2009/0081272 A1 | 3/2009 | Clarke et al. |
| 2009/0105703 A1 | 4/2009 | Shadduck |
| 2009/0114226 A1 | 5/2009 | Deem et al. |
| 2009/0125009 A1 | 5/2009 | Zikorus et al. |
| 2009/0138014 A1 | 5/2009 | Bonutti |
| 2009/0143705 A1 | 6/2009 | Danek et al. |
| 2009/0157166 A1 | 6/2009 | Singhal et al. |
| 2009/0163904 A1 | 6/2009 | Miller et al. |
| 2009/0171280 A1 | 7/2009 | Samuel et al. |
| 2009/0177111 A1 | 7/2009 | Miller et al. |
| 2009/0186850 A1 | 7/2009 | Kiribayashi et al. |
| 2009/0192508 A1 | 7/2009 | Laufer et al. |
| 2009/0198231 A1 | 8/2009 | Esser et al. |
| 2009/0228001 A1 | 9/2009 | Pacey |

(56) References Cited

U.S. PATENT DOCUMENTS

| | | |
|---|---|---|
| 2009/0247933 A1 | 10/2009 | Maor et al. |
| 2009/0248012 A1 | 10/2009 | Maor et al. |
| 2009/0269317 A1 | 10/2009 | Davalos |
| 2009/0275827 A1 | 11/2009 | Aiken et al. |
| 2009/0281477 A1 | 11/2009 | Mikus et al. |
| 2009/0292342 A1 | 11/2009 | Rubinsky et al. |
| 2009/0301480 A1 | 12/2009 | Elsakka et al. |
| 2009/0306544 A1 | 12/2009 | Ng et al. |
| 2009/0306545 A1 | 12/2009 | Elsakka et al. |
| 2009/0318905 A1 | 12/2009 | Bhargav et al. |
| 2009/0326366 A1 | 12/2009 | Krieg |
| 2009/0326436 A1 | 12/2009 | Rubinsky et al. |
| 2009/0326570 A1 | 12/2009 | Brown |
| 2010/0004623 A1 | 1/2010 | Hamilton, Jr. et al. |
| 2010/0006441 A1 | 1/2010 | Renaud et al. |
| 2010/0023004 A1 | 1/2010 | Francischelli et al. |
| 2010/0030211 A1* | 2/2010 | Davalos .................. C12N 13/00 606/41 |
| 2010/0049190 A1 | 2/2010 | Long et al. |
| 2010/0057074 A1 | 3/2010 | Roman et al. |
| 2010/0069921 A1 | 3/2010 | Miller et al. |
| 2010/0087813 A1 | 4/2010 | Long |
| 2010/0130975 A1 | 5/2010 | Long |
| 2010/0147701 A1 | 6/2010 | Field |
| 2010/0152725 A1 | 6/2010 | Pearson et al. |
| 2010/0160850 A1 | 6/2010 | Ivorra et al. |
| 2010/0168735 A1 | 7/2010 | Deno et al. |
| 2010/0174282 A1 | 7/2010 | Demarais et al. |
| 2010/0179530 A1 | 7/2010 | Long |
| 2010/0196984 A1 | 8/2010 | Rubinsky et al. |
| 2010/0204560 A1 | 8/2010 | Salahieh et al. |
| 2010/0204638 A1 | 8/2010 | Hobbs et al. |
| 2010/0222677 A1 | 9/2010 | Placek et al. |
| 2010/0228234 A1 | 9/2010 | Hyde et al. |
| 2010/0228247 A1 | 9/2010 | Paul et al. |
| 2010/0241117 A1 | 9/2010 | Paul et al. |
| 2010/0249771 A1 | 9/2010 | Pearson et al. |
| 2010/0250209 A1 | 9/2010 | Pearson et al. |
| 2010/0255795 A1 | 10/2010 | Rubinsky et al. |
| 2010/0256628 A1 | 10/2010 | Pearson et al. |
| 2010/0256630 A1 | 10/2010 | Hamilton, Jr. et al. |
| 2010/0261994 A1* | 10/2010 | Davalos .............. A61B 18/1477 600/407 |
| 2010/0286690 A1 | 11/2010 | Paul et al. |
| 2010/0298823 A1 | 11/2010 | Cao et al. |
| 2010/0331758 A1 | 12/2010 | Davalos et al. |
| 2011/0017207 A1 | 1/2011 | Hendricksen et al. |
| 2011/0034209 A1 | 2/2011 | Rubinsky et al. |
| 2011/0064671 A1 | 3/2011 | Bynoe |
| 2011/0092973 A1 | 4/2011 | Nuccitelli et al. |
| 2011/0106221 A1 | 5/2011 | Robert et al. |
| 2011/0112531 A1 | 5/2011 | Landis et al. |
| 2011/0118727 A1 | 5/2011 | Fish et al. |
| 2011/0118732 A1 | 5/2011 | Rubinsky et al. |
| 2011/0130834 A1 | 6/2011 | Wilson et al. |
| 2011/0144524 A1 | 6/2011 | Fish et al. |
| 2011/0144635 A1 | 6/2011 | Harper et al. |
| 2011/0144657 A1 | 6/2011 | Fish et al. |
| 2011/0152678 A1 | 6/2011 | Mjuri et al. |
| 2011/0166499 A1 | 7/2011 | Demarais et al. |
| 2011/0176037 A1 | 7/2011 | Benkley |
| 2011/0202053 A1 | 8/2011 | Moss et al. |
| 2011/0217730 A1 | 9/2011 | Gazit et al. |
| 2011/0251607 A1 | 10/2011 | Kruecker et al. |
| 2011/0301587 A1 | 12/2011 | Deem et al. |
| 2012/0034131 A1 | 2/2012 | Rubinsky et al. |
| 2012/0059255 A1 | 3/2012 | Paul et al. |
| 2012/0071870 A1 | 3/2012 | Salahieh et al. |
| 2012/0071872 A1 | 3/2012 | Rubinsky et al. |
| 2012/0071874 A1 | 3/2012 | Davalos et al. |
| 2012/0085649 A1 | 4/2012 | Sano et al. |
| 2012/0089009 A1 | 4/2012 | Omary et al. |
| 2012/0090646 A1 | 4/2012 | Tanaka et al. |
| 2012/0095459 A1 | 4/2012 | Callas et al. |
| 2012/0109122 A1 | 5/2012 | Arena et al. |
| 2012/0130289 A1 | 5/2012 | Demarais et al. |
| 2012/0150172 A1 | 6/2012 | Ortiz et al. |
| 2012/0165813 A1 | 6/2012 | Lee et al. |
| 2012/0179091 A1 | 7/2012 | Ivorra et al. |
| 2012/0226218 A1 | 9/2012 | Phillips et al. |
| 2012/0226271 A1 | 9/2012 | Callas et al. |
| 2012/0265186 A1 | 10/2012 | Burger et al. |
| 2012/0277741 A1 | 11/2012 | Davalos et al. |
| 2012/0303020 A1 | 11/2012 | Chornenky et al. |
| 2012/0310236 A1 | 12/2012 | Placek et al. |
| 2013/0030239 A1 | 1/2013 | Weyh et al. |
| 2013/0090646 A1* | 4/2013 | Moss .................. A61B 18/1815 606/41 |
| 2013/0108667 A1 | 5/2013 | Soikum et al. |
| 2013/0110106 A1 | 5/2013 | Richardson |
| 2013/0184702 A1 | 7/2013 | Neal, II et al. |
| 2013/0196441 A1 | 8/2013 | Rubinsky et al. |
| 2013/0197425 A1 | 8/2013 | Golberg et al. |
| 2013/0202766 A1 | 8/2013 | Rubinsky et al. |
| 2013/0218157 A1* | 8/2013 | Callas .................... A61B 18/14 606/41 |
| 2013/0253415 A1 | 9/2013 | Sano et al. |
| 2013/0281968 A1 | 10/2013 | Davalos et al. |
| 2013/0345697 A1 | 12/2013 | Garcia et al. |
| 2013/0345779 A1 | 12/2013 | Maor et al. |
| 2014/0017218 A1 | 1/2014 | Scott et al. |
| 2014/0039489 A1 | 2/2014 | Davalos et al. |
| 2014/0046322 A1 | 2/2014 | Callas et al. |
| 2014/0066913 A1 | 3/2014 | Sherman |
| 2014/0081255 A1 | 3/2014 | Johnson et al. |
| 2014/0088578 A1 | 3/2014 | Rubinsky et al. |
| 2014/0121663 A1 | 5/2014 | Pearson et al. |
| 2014/0121728 A1 | 5/2014 | Dhillon et al. |
| 2014/0163551 A1 | 6/2014 | Maor et al. |
| 2014/0207133 A1 | 7/2014 | Model et al. |
| 2014/0296844 A1 | 10/2014 | Kevin et al. |
| 2014/0309579 A1 | 10/2014 | Rubinsky et al. |
| 2014/0378964 A1 | 12/2014 | Pearson |
| 2015/0088120 A1 | 3/2015 | Garcia et al. |
| 2015/0088220 A1 | 3/2015 | Callas et al. |
| 2015/0112333 A1 | 4/2015 | Chorenky et al. |
| 2015/0126922 A1 | 5/2015 | Willis |
| 2015/0152504 A1 | 6/2015 | Lin |
| 2015/0164584 A1 | 6/2015 | Davalos et al. |
| 2015/0173824 A1 | 6/2015 | Davalos et al. |
| 2015/0201996 A1 | 7/2015 | Rubinsky et al. |
| 2015/0265349 A1 | 9/2015 | Moss et al. |
| 2015/0289923 A1 | 10/2015 | Davalos et al. |
| 2015/0320478 A1 | 11/2015 | Cosman, Jr. et al. |
| 2015/0320488 A1 | 11/2015 | Moshe et al. |
| 2015/0320999 A1 | 11/2015 | Nuccitelli et al. |
| 2015/0327944 A1 | 11/2015 | Robert et al. |
| 2016/0022957 A1 | 1/2016 | Hobbs et al. |
| 2016/0066977 A1 | 3/2016 | Neal et al. |
| 2016/0074114 A1 | 3/2016 | Pearson et al. |
| 2016/0113708 A1 | 4/2016 | Moss et al. |
| 2016/0143698 A1 | 5/2016 | Garcia et al. |
| 2016/0235470 A1 | 8/2016 | Callas et al. |
| 2016/0287313 A1 | 10/2016 | Rubinsky et al. |
| 2016/0287314 A1 | 10/2016 | Arena et al. |
| 2016/0338758 A9 | 11/2016 | Davalos et al. |
| 2016/0338761 A1 | 11/2016 | Chornenky et al. |
| 2016/0354142 A1 | 12/2016 | Pearson et al. |
| 2016/0367310 A1 | 12/2016 | Onik et al. |
| 2017/0035501 A1 | 2/2017 | Chornenky et al. |
| 2017/0189579 A1 | 7/2017 | Davalos |
| 2017/0209620 A1 | 7/2017 | Davalos et al. |
| 2017/0266438 A1 | 9/2017 | Sano |
| 2017/0319851 A1 | 11/2017 | Athos et al. |
| 2017/0348525 A1 | 12/2017 | Sano et al. |
| 2017/0360326 A1 | 12/2017 | Davalos |
| 2018/0071014 A1 | 3/2018 | Neal et al. |
| 2018/0125565 A1 | 5/2018 | Sano et al. |
| 2018/0161086 A1 | 6/2018 | Davalos et al. |
| 2018/0198218 A1 | 7/2018 | Regan et al. |
| 2019/0029749 A1 | 1/2019 | Garcia |
| 2019/0046255 A1 | 2/2019 | Davalos et al. |
| 2019/0069945 A1 | 3/2019 | Davalos et al. |
| 2019/0076528 A1 | 3/2019 | Soden et al. |

(56) References Cited

U.S. PATENT DOCUMENTS

| | | | |
|---|---|---|---|
| 2019/0083169 A1 | 3/2019 | Single et al. |
| 2019/0133671 A1 | 5/2019 | Davalos et al. |
| 2019/0175248 A1 | 6/2019 | Neal, II |
| 2019/0175260 A1 | 6/2019 | Davalos |
| 2019/0223938 A1 | 7/2019 | Arena et al. |
| 2019/0232048 A1 | 8/2019 | Latouche et al. |
| 2019/0233809 A1 | 8/2019 | Neal et al. |
| 2019/0256839 A1 | 8/2019 | Neal et al. |
| 2019/0282294 A1 | 9/2019 | Davalos et al. |
| 2019/0328445 A1 | 10/2019 | Sano et al. |
| 2019/0351224 A1 | 11/2019 | Sano et al. |
| 2019/0376055 A1 | 12/2019 | Davalos et al. |
| 2020/0046432 A1 | 2/2020 | Garcia et al. |
| 2020/0046967 A1 | 2/2020 | Ivey et al. |
| 2020/0093541 A9 | 3/2020 | Neal et al. |
| 2020/0197073 A1 | 6/2020 | Sano et al. |
| 2020/0260987 A1 | 8/2020 | Davalos et al. |
| 2020/0323576 A1 | 10/2020 | Neal et al. |
| 2020/0405373 A1 | 12/2020 | O'Brien et al. |
| 2021/0022795 A1 | 1/2021 | Davalos et al. |
| 2021/0023362 A1 | 1/2021 | Lorenzo et al. |
| 2021/0052882 A1 | 2/2021 | Wasson et al. |
| 2021/0113265 A1 | 4/2021 | D'Agostino et al. |
| 2021/0137410 A1 | 5/2021 | O'Brien et al. |
| 2021/0186600 A1 | 6/2021 | Davalos et al. |
| 2021/0361341 A1 | 11/2021 | Neal et al. |
| 2021/0393312 A1 | 12/2021 | Davalos et al. |
| 2022/0151688 A1 | 5/2022 | Garcia et al. |
| 2022/0161027 A1 | 5/2022 | Aycock et al. |

FOREIGN PATENT DOCUMENTS

| | | | |
|---|---|---|---|
| AU | 2003227960 A1 | 12/2003 |
| AU | 2005271471 A2 | 2/2006 |
| AU | 2006321570 A1 | 6/2007 |
| AU | 2006321574 A1 | 6/2007 |
| AU | 2006321918 A1 | 6/2007 |
| AU | 2009243079 A2 | 1/2011 |
| AU | 2015259303 A1 | 11/2016 |
| CA | 2297846 A1 | 2/1999 |
| CA | 2378110 A1 | 2/2001 |
| CA | 2445392 A1 | 11/2002 |
| CA | 2458676 A1 | 3/2003 |
| CA | 2487284 A1 | 12/2003 |
| CA | 2575792 A1 | 2/2006 |
| CA | 2631940 A1 | 6/2007 |
| CA | 2631946 A1 | 6/2007 |
| CA | 2632604 A1 | 6/2007 |
| CA | 2722296 A1 | 11/2009 |
| CA | 2751462 A1 | 11/2010 |
| CN | 1525839 A | 9/2004 |
| CN | 101534736 A | 9/2009 |
| CN | 102238921 A | 11/2011 |
| CN | 102421386 A | 4/2012 |
| CN | 106715682 A | 5/2017 |
| CN | 112807074 A | 5/2021 |
| DE | 863111 | 1/1953 |
| DE | 4000893 | 7/1991 |
| DE | 60038026 | 2/2009 |
| EP | 0218275 A1 | 4/1987 |
| EP | 0339501 A2 | 11/1989 |
| EP | 0378132 A | 7/1990 |
| EP | 0533511 A1 | 3/1993 |
| EP | 0998235 A1 | 5/2000 |
| EP | 0528891 B1 | 7/2000 |
| EP | 1196550 A2 | 4/2002 |
| EP | 1439792 A1 | 7/2004 |
| EP | 1442765 A1 | 8/2004 |
| EP | 1462065 A2 | 9/2004 |
| EP | 1061983 B1 | 11/2004 |
| EP | 1493397 A1 | 1/2005 |
| EP | 1506039 A1 | 2/2005 |
| EP | 0935482 B1 | 5/2005 |
| EP | 1011495 B1 | 11/2005 |
| EP | 1796568 A1 | 6/2007 |
| EP | 1207797 B1 | 2/2008 |
| EP | 1406685 B1 | 6/2008 |
| EP | 1424970 B1 | 12/2008 |
| EP | 2280741 A1 | 2/2011 |
| EP | 2381829 A1 | 11/2011 |
| EP | 2413833 A1 | 2/2012 |
| EP | 2488251 A2 | 8/2012 |
| EP | 2642937 A2 | 10/2013 |
| EP | 1791485 B1 | 12/2014 |
| EP | 2373241 B1 | 1/2015 |
| EP | 1962710 B1 | 8/2015 |
| EP | 1962708 B1 | 9/2015 |
| EP | 1962945 B1 | 4/2016 |
| EP | 3143124 A1 | 3/2017 |
| EP | 3852868 A1 | 7/2021 |
| ES | 2300272 | 6/2008 |
| ES | 2315493 | 4/2009 |
| JP | 2001510702 A | 8/2001 |
| JP | 2003505072 A | 2/2003 |
| JP | 2003506064 A | 2/2003 |
| JP | 2004203224 A | 7/2004 |
| JP | 2004525726 A | 8/2004 |
| JP | 2004303590 A | 10/2004 |
| JP | 2005501596 A | 1/2005 |
| JP | 2005526579 A | 9/2005 |
| JP | 2008508946 A | 3/2008 |
| JP | 4252316 B2 | 4/2009 |
| JP | 2009518130 A | 5/2009 |
| JP | 2009518150 A | 5/2009 |
| JP | 2009518151 A | 5/2009 |
| JP | 2009532077 A | 9/2009 |
| JP | 2010503496 A | 2/2010 |
| JP | 2011137025 | 7/2011 |
| JP | 2011137025 A | 7/2011 |
| JP | 2012510332 A | 5/2012 |
| JP | 2012515018 A | 7/2012 |
| JP | 2012521863 A | 9/2012 |
| JP | 2014501574 A | 1/2014 |
| JP | 2017518805 A | 7/2017 |
| JP | 6594901 B2 | 10/2019 |
| JP | 2019193668 A | 11/2019 |
| JP | 7051188 B2 | 4/2022 |
| KR | 101034682 A | 5/2011 |
| WO | 9104014 | 4/1991 |
| WO | 9634571 | 11/1996 |
| WO | 9639531 A | 12/1996 |
| WO | 9810745 | 3/1998 |
| WO | 9814238 A | 4/1998 |
| WO | 9901076 | 1/1999 |
| WO | 9904710 | 2/1999 |
| WO | 0020554 A | 4/2000 |
| WO | 0107583 A | 2/2001 |
| WO | 0107584 A | 2/2001 |
| WO | 0107585 A | 2/2001 |
| WO | 0110319 A | 2/2001 |
| WO | 0148153 A | 7/2001 |
| WO | 2001048153 A1 | 7/2001 |
| WO | 0170114 A1 | 9/2001 |
| WO | 0181533 A | 11/2001 |
| WO | 02078527 A | 10/2002 |
| WO | 02089686 A | 11/2002 |
| WO | 02100459 A | 12/2002 |
| WO | 2003020144 A1 | 3/2003 |
| WO | 2003047684 A2 | 6/2003 |
| WO | 03099382 A | 12/2003 |
| WO | 2004037341 A2 | 5/2004 |
| WO | 2004080347 A2 | 9/2004 |
| WO | 2005065284 A | 7/2005 |
| WO | 2006017666 A2 | 2/2006 |
| WO | 2006031541 A1 | 3/2006 |
| WO | 2006130194 A2 | 12/2006 |
| WO | 2007067628 A1 | 6/2007 |
| WO | 2007067937 A2 | 6/2007 |
| WO | 2007067938 A2 | 6/2007 |
| WO | 2007067939 A2 | 6/2007 |
| WO | 2007067940 A2 | 6/2007 |
| WO | 2007067941 A2 | 6/2007 |
| WO | 2007067943 A2 | 6/2007 |
| WO | 2007070361 A2 | 6/2007 |

(56) References Cited

FOREIGN PATENT DOCUMENTS

| | | | |
|---|---|---|---|
| WO | 2007100727 A2 | 9/2007 |
| WO | 2007123690 A2 | 11/2007 |
| WO | 2008063195 A1 | 5/2008 |
| WO | 2008034103 A3 | 11/2008 |
| WO | 2009046176 A1 | 4/2009 |
| WO | 2007137303 | 7/2009 |
| WO | 2009134876 A | 11/2009 |
| WO | 2009135070 A1 | 11/2009 |
| WO | 2009137800 A2 | 11/2009 |
| WO | 2010064154 A1 | 6/2010 |
| WO | 2010080974 A1 | 7/2010 |
| WO | 2010117806 A1 | 10/2010 |
| WO | 2010118387 A | 10/2010 |
| WO | 2010132472 A1 | 11/2010 |
| WO | 2010151277 A | 12/2010 |
| WO | 2011047387 A | 4/2011 |
| WO | 2011062653 A1 | 5/2011 |
| WO | 2011072221 A1 | 6/2011 |
| WO | 2012051433 A2 | 4/2012 |
| WO | 2012071526 A | 5/2012 |
| WO | 2012071526 A2 | 5/2012 |
| WO | 2012088149 A | 6/2012 |
| WO | 2015175570 A1 | 11/2015 |
| WO | 2016100325 A1 | 6/2016 |
| WO | 2016164930 A1 | 10/2016 |
| WO | 2017117418 A1 | 7/2017 |
| WO | 2020061192 A1 | 3/2020 |
| WO | 2022066768 A1 | 3/2022 |

OTHER PUBLICATIONS

Griffiths, The Importance of Phase Measurement in Electrical Impedance Tomography, Phys. Med. Biol., 1987, vol. 32, No. 11, pp. 1435-1444.

Griffiths, Tissue Spectroscopy with Electrical Impedance Tomography: Computer Simulations, IEEE Transactions on Biomedical Engineering, vol. 42, No. 9, Sep. 1995.

Gumerov, et al., The Dipole Approximation Method and Its Coupling with the Regular Boundary Element Method for Efficient Electrical Impedance Tomography, Boundary Element Technology XIII, 1999.

Hapala, Breaking the Barrier: Methods for Reversible Permeabilization of Cellular Membranes, Critical Reviews in Biotechnology, 17(2): 105-122, 1997.

Helczynska et al., "Hypoxia promotes a dedifferentiated phenotype in ductal breast carcinoma in situ." Cancer Research, vol. 63, pp. 1441-1444 (2003).

Heller, et al., Clinical Applications of Electrochemotherapy, Advanced Drug Delivery Reviews, vol. 35, pp. 119-129, 1999.

Hjouj, M., et al., "Electroporation-Induced BBB Disruption and Tissue Damage Depicted by MRI", Neuro-Oncology 13: Issue suppl 3, abstract ET-32 (2011).

Hjouj, M., et al., "MRI Study on Reversible and Irreversible Electroporation Induced Blood Brain Barrier Disruption", Plos One, Aug. 2012, 7:8, e42817.

Hjouj, Mohammad et al., "Electroporation-Induced BBB Disruption and Tissue Damage Depicted by MRI," Abstracts from 16th Annual Scientific Meeting of the Society for Neuro-Oncology in Conjunction with the AANS/CNS Section on Tumors, Nov. 17-20, 2011, Orange County California, Neuro-Oncology Supplement, vol. 13, Supplement 3, p. ii114.

Ho, et al., Electroporation of Cell Membranes: A Review, Critical Reviews in Biotechnology, 16(4): 349-362, 1996.

Holder, et al., Assessment and Calibration of a Low-Frequency System for Electrical Impedance Tomography (EIT), Optimized for Use in Imaging Brain Function in Ambulant Human Subjects, Annals of the New York Academy of Science, vol. 873, Issue 1, Electrical Bl, pp. 512-519, 1999.

Hu, Q., et al., "Simulations of transient membrane behavior in cells subjected to a high-intensity ultrashort electric pulse". Physical Review E, 71(3) (2005).

Huang, et al., Micro-Electroporation: Improving the Efficiency and Understanding of Electrical Permeabilization of Cells, Biomedical Microdevices, vol. 2, pp. 145-150, 1999.

Hughes, et al., An Analysis of Studies Comparing Electrical Impedance Tomography with X-Ray Videofluoroscopy in the Assessment of Swallowing, Physiol. Meas. 15, 1994, pp. A199-A209.

Ibey et al., "Selective cytotoxicity of intense nanosecond-duration electric pulses in mammalian cells." Biochimica Et Biophysica Acta-General Subjects, vol. 1800, pp. 1210-1219 (2010).

Issa, et al., The TUNA Procedure for BPH: Review of the Technology: The TUNA Procedure for BPH: Basic Procedure and Clinical Results, Reprinted from Infections in Urology, Jul./Aug. 1998 and Sep./Oct. 1998.

Ivanuša, et al., MRI Macromolecular Contrast Agents as Indicators of Changed Tumor Blood Flow, Radiol. Oncol. 2001; 35(2): 139-47.

Ivorra et al., "In vivo electric impedance measurements during and after electroporation of rat live." Bioelectrochemistry, vol. 70, pp. 287-295 (2007).

Ivorra et al., "In vivo electrical conductivity measurements during and after tumor electroporation: conductivity changes reflect the treatment outcome." Physics in Medicine and Biology, vol. 54, pp. 5949-5963 (2009).

Ivorra,"Bioimpedance monitoring for physicians: an overview." Biomedical Applications Group, 35 pages (2002).

Ivorra, A., ed. "Tissue Electroporation as a Bioelectric Phenomenon: Basic Concepts. Irreversible Electroporation", ed. B. Rubinsky., Springer Berlin Heidelberg. 23-61 (2010).

J.F. Edd and R.V. Davalos, "Mathematical modeling of irreversible electroporation for treatment planning," Technology in Cancer Research and Treatment, 6, pp. 275-286, 2007.

Jarm et al., "Antivascular effects of electrochemotherapy: implications in treatment of bleeding metastases." Expert Rev Anticancer Ther. vol. 10, pp. 729-746 (2010).

Jaroszeski, et al., In Vivo Gene Delivery by Electroporation, Advanced Drug Delivery Review, vol. 35, pp. 131-137, 1999.

Jensen et al., "Tumor volume in subcutaneous mouse xenografts measured by microCT is more accurate and reproducible than determined by 18FFDG-microPET or external caliper." BMC medical Imaging vol. 8:16, 9 Pages (2008).

Jordan, D.W., et al., "Effect of pulsed, high-power radiofrequency radiation on electroporation of mammalian cells". Ieee Transactions on Plasma Science, 32(4): p. 1573-1578 (2004).

Jossinet et al., Electrical Impedance Endo-Tomography: Imaging Tissue From Inside, IEEE Transactions on Medical Imaging, vol. 21, No. 6, Jun. 2002, pp. 560-565.

Katsuki, S., et al., "Biological effects of narrow band pulsed electric fields", Ieee Transactions on Dielectrics and Electrical Insulation,. 14(3): p. 663-668 (2007).

Kingham et al., "Ablation of perivascular hepatic malignant tumors with irreversible electroporation." Journal of the American College of Surgeons, 2012. 215(3), p. 379-387.

Kinosita and Tsong, "Formation and resealing of pores of controlled sizes in human erythrocyte membrane." Nature, vol. 268 (1977) pp. 438-441.

Kinosita and Tsong, "Voltage-induced pore formation and hemolysis of human erythrocytes." Biochimica et Biophysica Acta (BBA)-Biomembranes, 471 (1977) pp. 227-242.

Kinosita et al., "Electroporation of cell membrane visualized under a pulsed-laser fluorescence microscope." Biophysical Journal, vol. 53, pp. 1015-1019 (1988).

Kinosita, et al., Hemolysis of Human Erythrocytes by a Transient Electric Field, Proc. Natl. Acad. Sci. USA, vol. 74, No. 5, pp. 1923-1927, 1977.

Kirson et al., "Alternating electric fields arrest cell proliferation in animal tumor models and human brain tumors." Proceedings of the National Academy of Sciences vol. 104, pp. 10152-10157 (2007).

Kolb, J.F., et al., "Nanosecond pulsed electric field generators for the study of subcellular effects", Bioelectromagnetics, 27(3): p. 172-187 (2006).

Kotnik and Miklavcic, "Theoretical evaluation of voltage inducement on internal membranes of biological cells exposed to electric fields." Biophysical Journal, vol. 90(2), pp. 480-491 (2006).

(56) References Cited

OTHER PUBLICATIONS

Kotnik et al., "Sensitivity of transmembrane voltage induced by applied electric fields—A theoretical analysis", Bioelectrochemistry and Bioenergetics, vol. 43, Issue 2, 1997, pp. 285-291.

Kotnik, T. and D. Miklavcic, "Theoretical evaluation of the distributed power dissipation in biological cells exposed to electric fields", Bioelectromagnetics, 21(5): p. 385-394 (2000).

Kotnik, T., et al., "Cell membrane electropemneabilization by symmetrical bipolar rectangular pulses. Part II. Reduced electrolytic contamination", Bioelectrochemistry, 54(1): p. 91-5 (2001).

Kotnik, T., et al., "Cell membrane electropemneabilization by symmetrical bipolar rectangular pulses". Part I. Increased efficiency of permeabilization. Bioelectrochemistry, 54(1): p. 83-90 (2001).

Kotnik, T., et al., "Role of pulse shape in cell membrane electropermeabilization", Biochimica Et Biophysica Acta-Biomembranes, 1614(2): p. 193-200 (2003).

Labeed et al., "Differences in the biophysical properties of membrane and cytoplasm of apoptotic cells revealed using dielectrophoresis." Biochimica et Biophysica Acta (BBA)-General Subjects, vol. 1760, pp. 922-929 (2006).

Lackovic, I., et al., "Three-dimensional Finite-element Analysis of Joule Heating in Electrochemotherapy and in vivo Gene Electrotransfer", Ieee Transactions on Dielectricsand Electrical Insulation, 16(5): p. 1338-1347 (2009).

Laufer et al., "Electrical impedance characterization of normal and cancerous human hepatic tissue." Physiological Measurement, vol. 31, pp. 995-1009 (2010).

Lebar et al., "Inter-pulse interval between rectangular voltage pulses affects electroporation threshold of artificial lipid bilayers." IEEE Transactions on NanoBioscience, vol. 1 (2002) pp. 116-120.

Lee, E. W. et al. Advanced Hepatic Ablation Technique for Creating Complete Cell Death : Irreversible Electroporation. Radiology 255, 426-433, doi: 10.1148/radiol.10090337 (2010).

Lee, E.W., et al., "Imaging guided percutaneous irreversible electroporation: ultrasound and immunohistological correlation", Technol Cancer Res Treat 6: 287-294 (2007).

Li, W., et al., "The Effects of Irreversible Electroporation (IRE) on Nerves" PloS One, Apr. 2011, 6(4), e18831.

Liu, et al., Measurement of Pharyngeal Transit Time by Electrical Impedance Tomography, Clin. Phys. Physiol. Meas., 1992, vol. 13, Suppl. A, pp. 197-200.

Co-Pending U.S. Appl. No. 16/520,901, Second Preliminary Amendment filed Feb. 4, 2020.

Co-Pending U.S. Appl. No. 16/535,451 Preliminary Amendment filed Aug. 8, 2019, 3 pages.

Co-Pending U.S. Appl. No. 16/535,451 Second Preliminary Amendment filed Oct. 9, 2019, 15 pages.

Co-Pending U.S. Appl. No. 16/535,451 Third Preliminary Amendment filed Nov. 5, 2019, 4 pages.

Co-Pending Application No. EP 15793361.5, Claim amendment filed Jul. 18, 2018.

Co-Pending Application No. EP 15793361.5, European Search Report dated Dec. 4, 2017.

Co-Pending Application No. JP 2016-567747 Amendment filed Jul. 18, 2019, 7 pgs.

Co-Pending Application No. JP 2016-567747 English translation of amended claims filed Jul. 18, 2019, 6 pgs.

Co-Pending Application No. JP 2016-567747 , First Office Action (Translation) dated Feb. 21, 2019, 5 pages.

Co-Pending Application No. JP 2016-567747, First Office Action dated Feb. 21, 2019, 4 pages.

Co-Pending Application No. JP 2019-133057, amended claims (English language version) filed Aug. 2019.

Co-Pending Application No. PCT/US15/30429, International Search Report and Written Opinion dated Oct. 16, 2015, 19 pages.

Co-Pending U.S. Appl. No. 13/332,133, Amendment with RCE after Board Decision, dated Mar. 29, 2019, 16 pages.

Co-Pending U.S. Appl. No. 13/332,133, Board Decision dated Jan. 29, 2019, 13 pages.

Co-Pending U.S. Appl. No. 13/332,133, File History through Aug. 1, 2017, 160 pages.

Co-Pending U.S. Appl. No. 13/332,133, Notice of Allowance, dated May 31, 2019, 5 pages.

Co-Pending U.S. Appl. No. 13/332,133, Office Actions and Responses through Mar. 2018, 221 pages.

Co-Pending U.S. Appl. No. 14/017,210, Acceptance of 312 Amendment dated Sep. 12, 2018, 1 page.

Co-Pending U.S. Appl. No. 14/017,210, AFCP dated Aug. 13, 2018, 9 pages.

Co-Pending U.S. Appl. No. 14/017,210, Final Office Action dated Apr. 11, 2018, 10 pages.

Co-Pending U.S. Appl. No. 14/017,210, Final Office Action dated Aug. 30, 2016, 11 pages.

Co-Pending U.S. Appl. No. 14/017,210, Final Office Action dated May 1, 2017, 11 pages.

Co-Pending U.S. Appl. No. 14/017,210, Non-Final Office Action dated Dec. 15, 2016, 8 pages.

Co-Pending U.S. Appl. No. 14/017,210, Non-Final Office Action dated Oct. 25, 2017, 9 pages.

Co-Pending U.S. Appl. No. 14/017,210, Non-Final Office Action, dated Sep. 8, 2015, 8 pages.

Co-Pending U.S. Appl. No. 14/017,210, Notice of Allowance (after Dec. 12, 2018 RCE) dated Jan. 9, 2019, 5 pages.

Co-Pending U.S. Appl. No. 14/017,210, Notice of Allowance dated Sep. 12, 2018, 7 pages.

Co-Pending U.S. Appl. No. 14/017,210, Petition dated Dec. 11, 2015, 5 pages.

Co-Pending U.S. Appl. No. 14/017,210, Petition Decision dated Aug. 12, 2016, 9 pages.

Co-Pending U.S. Appl. No. 14/017,210, Petition Decision dated Aug. 2, 2016, 5 pages.

Co-Pending U.S. Appl. No. 14/017,210, Priority Petition Dec. 11, 2015, 5 pages.

Co-Pending U.S. Appl. No. 14/017,210, RCE dated Aug. 1, 2017, 13 pages.

Co-Pending U.S. Appl. No. 14/017,210, RCE dated Nov. 30, 2016, 13 pages.

Co-Pending U.S. Appl. No. 14/017,210, RCE filed Aug. 1, 2017, 13 pages.

Co-Pending U.S. Appl. No. 14/017,210, Response to Aug. 30, 2016 Final Office Action, dated Nov. 30, 2016, 10 pages.

Co-Pending U.S. Appl. No. 14/017,210, Response to Dec. 15, 2016 Non-Final Office Action dated Mar. 20, 2017, 9 pages.

Co-Pending Application No. U.S. Appl. No. 14/017,210, Response to May 1, 2017 Final Office Action dated Aug. 1, 2017, 10 pages.

Co-Pending U.S. Appl. No. 14/017,210, Response to Non-Final Office Action dated Mar. 8, 2016, 16 pages.

Co-Pending U.S. Appl. No. 14/017,210, Response to Oct. 25, 2017 Non-Final Office Action dated Jan. 25, 2018, 11 pages.

Co-Pending U.S. Appl. No. 14/017,210, Response to Sep. 8, 2015 Non-Final Office Action, dated Mar. 8, 2016, 57 pages.

Co-Pending Chinese Application No. 201580025135.6 English translation of Sep. 25, 2019 Office action.

Co-Pending Chinese Application No. 201580025135.6 Preliminary Amendment filed with application Nov. 14, 2016.

Corovic et al., "Analytical and numerical quantification and comparison of the local electric field in the tissue for different electrode configurations," Biomed Eng Online, 6, 14 pages, 2007.

Cowley, Good News for Boomers, Newsweek, Dec. 30, 1996/Jan. 6, 1997.

Cox, et al., Surgical Treatment of Atrial Fibrillation: A Review, Europace (2004) 5, S20-S-29.

Crowley, Electrical Breakdown of Biomolecular Lipid Membranes as an Electromechanical Instability, Biophysical Journal, vol. 13, pp. 711-724, 1973.

Dahl et al., "Nuclear shape, mechanics, and mechanotransduction." Circulation Research vol. 102, pp. 1307-1318 (2008).

Daskalov, I., et al., "Exploring new instrumentation parameters for electrochemotherapy—Attacking tumors with bursts of biphasic pulses instead of single pulses", IEEE Eng Med Biol Mag, 18(1): p. 62-66 (1999).

(56) References Cited

OTHER PUBLICATIONS

Daud, A.I., et al., "Phase I Trial of Interleukin-12 Plasmid Electroporation in Patients With Metastatic Melanoma," Journal of Clinical Oncology, 26, 5896-5903, Dec. 20, 2008.
Davalos et al., "Electrical impedance tomography for imaging tissue electroporation," IEEE Transactions on Biomedical Engineering, 51, pp. 761-767, 2004.
Talele, S. and p. Gaynor, "Non-linear time domain model of electropermeabilization: Response of a single cell to an arbitrary applied electric field", Journal of Electrostatics, 65(12): p. 775-784 (2007).
Talele, S., et al., "Modelling single cell electroporation with bipolar pulse parameters and dynamic pore radii". Journal of Electrostatics, 68(3): p. 261-274 (2010).
Teissie, J. and T.Y. Tsong, "Electric-Field Induced Transient Pores in Phospholipid-Bilayer Vesicles". Biochemistry, 20(6): p. 1548-1554 (1981).
Tekle, Ephrem, R. Dean Astumian, and P. Boon Chock, Electroporation by using bipolar oscillating electric field: An improved method for DNA transfection of NIH 3T3 cells, Proc. Natl. Acad. Sci., vol. 88, pp. 4230-4234, May 1991, Biochemistry.
Thompson, et al., To determine whether the temperature of 2% lignocaine gel affects the initial discomfort which may be associated with its instillation into the male urethra, BJU International (1999), 84, 1035-1037.
Thomson et al., "Investigation of the safety of irreversible electroporation in humans," J Vasc Interv Radiol, 22, pp. 611-621, 2011.
Tibbitt et al., "Hydrogels as Extracellular Matrix Mimics for 3D Cell Culture", Jul. 2009, Biotechnol Bioeng, 103 (4),655-663.
TUNA—Suggested Local Anesthesia Guidelines, no date available.
Verbridge et al., "Oxygen-Controlled Three-Dimensional Cultures to Analyze Tumor Angiogenesis." Tissue Engineering, Part A vol. 16, pp. 2133-2141 (2010).
Vernier, P.T., et al., "Nanoelectropulse-driven membrane perturbation and small molecule permeabilization", Bmc Cell Biology, 7 (2006).
Vidamed, Inc., Transurethral Needle Ablation (TUNA): Highlights from Worldwide Clinical Studies, Vidamed's Office TUNA System, 2001.
Wasson, Elisa M. et al. The Feasibility of Enhancing Susceptibility of Glioblastoma Cells to IRE Using a Calcium Adjuvant. Annals of Biomedical Engineering, vol. 45, No. 11, Nov. 2017 pp. 2535-2547.
Weaver et al., "A brief overview of electroporation pulse strength-duration space: A region where additional intracellular effects are expected." Bioelectrochemistry vol. 87, pp. 236-243 (2012).
Weaver, Electroporation: A General Phenomenon for Manipulating Cells and Tissues, Journal of Cellular Biochemistry, 51: 426-435, 1993.
Weaver, et al., Theory of Electroporation: A Review, Bioelectrochemistry and Bioenergetics, vol. 41, pp. 136-160, 1996.
Weaver, J. C., Electroporation of biological membranes from multicellular to nano scales, IEEE Trns. Dielectr. Electr. Insul. 10, 754-768 (2003).
Weaver, J.C., "Electroporation of cells and tissues", IEEE Transactions on Plasma Science, 28(1): p. 24-33 (2000).
Weisstein: Cassini Ovals. From MathWorld—A. Wolfram Web Resource; Apr. 30, 2010; http://mathworid.wolfram.com/ (updated May 18, 2011).
Wimmer, Thomas, et al., "Planning Irreversible Electroporation (IRE) in the Porcine Kidney: Are Numerical Simulations Reliable for Predicting Empiric Ablation Outcomes?", Cardiovasc Intervent Radiol. Feb. 2015 ; 38(1): 182-190. doi:1 0.1007/S00270-014-0905-2.
Yang et al., "Dielectric properties of human leukocyte subpopulations determined by electrorotation as a cell separation criterion." Biophysical Journal, vol. 76, pp. 3307-3314 (1999).
Yao et al., "Study of transmembrane potentials of inner and outer membranes induced by pulsed-electric-field model and simulation." IEEE Trans Plasma Sci, 2007. 35(5): p. 1541-1549.

Zhang, Y., et al., MR imaging to assess immediate response to irreversible electroporation for targeted ablation of liver tissues: preclinical feasibility studies in a rodent model. Radiology, 2010. 256(2): p. 424-32.
Zimmermann, et al., Dielectric Breakdown of Cell Membranes, Biophysical Journal, vol. 14, No. 11, pp. 881-899, 1974.
Zlotta, et al., Long-Term Evaluation of Transurethral Needle Ablation of the Prostate (TUNA) for Treatment of Benign Prostatic Hyperplasia (BPH): Clinical Outcome After 5 Years. (Abstract) Presented at 2001 AUA National Meeting, Anaheim, CA—Jun. 5, 2001.
Zlotta, et al., Possible Mechanisms of Action of Transurethral Needle Ablation of the Prostate on Benign Prostatic Hyperplasia Symptoms: a Neurohistochemical Study, Reprinted from Journal of Urology, vol. 157, No. 3, Mar. 1997, pp. 894-899.
Alberts et al., "Molecular Biology of the Cell," 3rd edition, Garland Science, New York, 1994, 1 page.
Al-Sakere et al., "Tumor ablation with irreversible electroporation." PLoS ONE, Issue 11, e1135, 8 pages, 2007.
Amasha, et al., Quantitative Assessment of Impedance Tomography for Temperature Measurements in Microwave Hyperthermia, Clin. Phys. Physiol. Meas., 1998, Suppl. A, 49-53.
Andreason, Electroporation as a Technique for the Transfer of Macromolecules into Mammalian Cell Lines, J. Tiss Cult. Meth., 15:56-62, 1993.
Appelbaum et al., "US Findings after Irreversible Electroporation Ablation: Radiologic-Pathologic Correlation," Radiology, 262, pp. 117-125, Jan. 1, 2012.
Arena et al. "High-Frequency Irreversible Electroporation (H-FIRE) for Non-thermal Ablation without Muscle Contraction." Biomed. Eng. Online, vol. 10, 20 pages (2011).
Arena, C.B., et al., "A three-dimensional in vitro tumor platform for modeling therapeutic irreversible electroporation." Biophysical Journal, 2012.103(9): p. 2033-2042.
Arena, Christopher B., et al., "Towards the development of latent heat storage electrodes for electroporation-based therapies", Applied Physics Letters, 101, 083902 (2012).
Arena, Christopher B., et al.,"Phase Change Electrodes for Reducing Joule Heating During Rreversible Electroporation". Proceedings of the ASME 2012 Summer Bioengineering Conference, SBC2012, Jun. 20-23, 2012, Fajardo, Puerto Rico.
Asami et al., "Dielectric properties of mouse lymphocytes and erythrocytes." Biochimica et Biophysica Acta (BBA)-Molecular Cell Research, 1010(1989) pp. 49-55.
Bagla, S. and Papadouris, D., "Percutaneous Irreversible Electroporation of Surgically Unresectable Pancreatic Dancer: A Case Report" J. Vascular Int. Radiol. 23(1), 142-145 (2012).
Baker, et al., Calcium-Dependent Exocytosis in Bovine Adrenal Medullary Cells with Leaky Plasma Membranes, Nature, vol. 276, pp. 620-622, 1978.
Ball, C., K.R. Thomson, and H. Kavnoudias, "Irreversible electroporation: a new challenge in "out of-operating theater" anesthesia." Anesth Analg, 2010. 110(5): p. 1305-9.
Bancroft, et al., Design of a Flow Perfusion Bioreactor System for Bone Tissue-Engineering Applications, Tissue Engineering, vol. 9, No. 3, 2003, p. 549-554.
Baptista et al., "The Use of Whole Organ Decellularization for the Generation of a Vascularized Liver Organoid," Heptatology, vol. 53, No. 2, pp. 604-617 (2011).
Barber, Electrical Impedance Tomography Applied Potential Tomography, Advances in Biomedical Engineering, Beneken and Thevenin, eds , IOS Press, pp. 165-173, 1993.
Beebe, S.J., et al., "Diverse effects of nanosecond pulsed electric fields on cells and tissues", DNA and Cell Biology, 22(12): 785-796 (2003).
Beebe, S.J., et al., Nanosecond pulsed electric field (nsPEF) effects on cells and tissues: apoptosis induction and tumor growth inhibition. PPPS-2001 Pulsed Power Plasma Science 2001, 28th IEEE International Conference on Plasma Science and 13th IEEE International Pulsed Power Conference, Digest of Technical Papers (Cat. No 01CH37251). IEEE, Part vol. 1, 2001, pp. 211-215, vol. I, Piscataway, NJ, USA.

(56) References Cited

OTHER PUBLICATIONS

Beebe, S.J., et al.,, "Nanosecond, high-intensity pulsed electric fields induce apoptosis in human cells", FASEB J, 17 (9): p. 1493-5 (2003).
Belehradek, J., et al., "Electropermeabilization of Cells in Tissues Assessed by the Qualitative and Quantitative Electroloading of Bleomycin", Biochimica Et Biophysica Acta-Biomembranes, 1190(1): p. 155-163 (1994).
Ben-David, et al., "Characterization of Irreversible Electroporation Ablation in Vivo Porcine Liver," Am J Roentgenol, vol. 198, pp. W62-W68, 2012.
Benz, R., et al. "Reversible electrical breakdown of lipid bilayer membranes: a charge-pulse relaxation study". J Membr Biol, 48(2): p. 181-204 (1979).
Blad, et al., Impedance Spectra of Tumour Tissue in Comparison with Normal Tissue; a Possible Clinical Application tor Electrical Impedance Tomography, Physiol. Meas. 17 (1996) A105-A115.
Bolland, F., et al., "Development and characterisation of a full-thickness acellular porcine bladder matrix for tissue engineering", Biomaterials, Elsevier Science Publishers, Barking, GB, vol. 28, No. 6, Nov. 28, 2006, pp. 1061-1070.
Boone, K., Barber, D. & Brown, B. Review—Imaging with electricity: report of the European Concerted Action on Impedance Tomography. J Med. Eng. Technol. 21, 201-232 (1997).
Bower et al., "Irreversible electroporation of the pancreas: definitive local therapy without systemic effects." Journal of surgical oncology, 2011. 104(1): p. 22-28.
BPH Management Strategies: Improving Patient Satisfaction, Urology Times, May 2001, vol. 29, Supplement 1.
Brown, et al., Blood Flow Imaging Using Electrical Impedance Tomography, Clin. Phys. Physiol. Meas., 1992, vol. 13, Suppl. A, 175-179.
Brown, S.G., Phototherapy of tumors. World J. Surgery, 1983. 7: p. 700-9.
Cannon et al., "Safety and early efficacy of irreversible electroporation for hepatic tumors in proximity to vital structures." Journal of Surgical Oncology, 6 pages (2012).
Carpenter A.E et al., "CellProfiler: image analysis software for identifying and quantifying cell phenotypes." Genome Biol. 2006; 7(10): R100. Published online Oct. 31, 2006, 11 pages.
Cemazar M, Parkins CS, Holder AL, Chaplin DJ, Tozer GM, et al., "Electroporation of human microvascular endothelial cells: evidence for an anti-vascular mechanism of electrochemotherapy", Br J Cancer 84: 565-570 (2001).
Chandrasekar, et al., Transurethral Needle Ablation of the Prostate (TUNA)—a Propsective Study, Six Year Follow Up, (Abstract), Presented at 2001 National Meeting, Anaheim, CA, Jun. 5, 2001.
Chang, D.C., "Cell Poration and Cell-Fusion Using an Oscillating Electric-Field". Biophysical Journal, 56(4): p. 641-652 (1989).
Charpentier, K.P., et al., "Irreversible electroporation of the pancreas in swine: a pilot study." HPB: the official journal of the International Hepato Pancreato Biliary Association, 2010. 12(5): p. 348-351.
Chen et al., "Classification of cell types using a microfluidic device for mechanical and electrical measurement on single cells." Lab on a Chip, vol. 11, pp. 3174-3181 (2011).
Chen, M.T., et al., "Two-dimensional nanosecond electric field mapping based on cell electropermeabilization", PMC Biophys, 2(1):9 (2009).
Clark et al., "The electrical properties of resting and secreting pancreas." The Journal of Physiology, vol. 189, pp. 247-260 (1967).
Coates, C.W.,et al, "The Electrical Discharge of the Electric Eel, Electrophorous Electricus," Zoologica, 1937, 22(1), pp. 1-32.
Co-Pending U.S. Appl. No. 12/757,901, File History 2018.
Cook, et al., ACT3: A High-Speed, High-Precision Electrical Impedance Tomograph, IEEE Transactions on Biomedical Engineering, vol. 41, No. 8, Aug. 1994.
Co-Pending U.S. Appl. No. 12/906,923, Office Actions and Responses Jul. 2017, 55 pages.
Co-Pending U.S. Appl. No. 14/558,631, Final Office Action dated Sep. 1, 2017, 9 pages.
Co-Pending U.S. Appl. No. 14/558,631, Non-Final Office Action dated Jan. 8, 2018, 5 pages.
Co-Pending U.S. Appl. No. 14/558,631, Non-Final Office Action dated Mar. 13, 2017, 10 pages.
Co-Pending U.S. Appl. No. 14/558,631, Notice of Allowance dated Jul. 17, 2018, 2 pages.
Co-Pending U.S. Appl. No. 14/558,631, Notice of Allowance dated Jun. 21, 2018, 7 pages.
Co-Pending U.S. Appl. No. 14/558,631, Response to Jan. 8, 2018 Non-Final Office Action dated Apr. 9, 2018, 8 pages.
Co-Pending U.S. Appl. No. 14/558,631, Response to Mar. 13, 2017 Non-Final Office Action dated Jul. 13, 2017, 10 pages.
Co-Pending U.S. Appl. No. 14/558,631, Response to Sep. 1, 2017 Final Office Action dated Dec. 1, 2017, 7 pages.
(Arena, Christopher B. et al.) Co-pending U.S. Appl. No. 15/186,653, filed Jun. 20, 2016, and published as U.S. Publication No. 2016/0287314 on Oct. 6, 2016.
(Arena, Christopher B. et al.) Co-pending U.S. Appl. No. 16/372,520, filed Apr. 2, 2019, which published as 20190223938 on Jul. 25, 2019.
(Arena, Christopher B. et al.) Co-Pending Application No. PCT/US11/66239, filed Dec. 20, 2011.
(Arena, Christopher B. et al.) Co-Pending U.S. Appl. No. 13/332,133, filed Dec. 20, 2011 and published as U.S. Publication No. 2012/0109122 on May 3, 2012.
(Davalos, Rafael et al.) Co-pending U.S. Appl. No. 10/571,162, filed Oct. 18, 2006 (published as 2007/0043345 on Feb. 22, 2007).
(Davalos, Rafael et al.) Co-Pending U.S. Appl. No. 12/757,901, filed Apr. 9, 2010.
(Davalos, Rafael V. et al.) Co-Pending U.S. Appl. No. 12/491,151, filed Jun. 24, 2009, and published as U.S. Publication No. 2010/0030211 on Feb. 4, 2010.
(Davalos, Rafael V. et al.) Co-Pending U.S. Appl. No. 12/609,779, filed Oct. 30, 2009, and published as U.S. Publication No. 2010/0331758 on Dec. 30, 2010.
(Davalos, Rafael V. et al.) Co-Pending U.S. Appl. No. 13/919,640, filed Jun. 17, 2013, and published as U.S Publication No. 2013/0281968 on Oct. 24, 2013.
(Davalos, Rafael V. et al.) Co-Pending U.S. Appl. No. 14/686,380, filed Apr. 14, 2015 and Published as US 2015/0289923 on Oct. 15, 2015.
(Davalos, Rafael V. et al.) Co-pending U.S. Appl. No. 15/424,335, filed Feb. 3, 2017, and published as U.S Publication No. 2017/0189579 on Jul. 6, 2017.
(Davalos, Rafael V. et al.) Co-pending U.S. Appl. No. 15/536,333, filed Jun. 15, 2017, and published as U.S. Publication No. 2017/0360326 on Dec. 21, 2017.
(Davalos, Rafael V. et al.) Co-pending U.S. Appl. No. 15/881,414, filed Jan. 26, 2018, and published as U.S. Publication No. 2018/0161086 on Jun. 14, 2018.
(Davalos, Rafael V. et al.) Co-pending U.S. Appl. No. 16/177,745, filed Nov. 1, 2018, and published as U.S. Publication No. 2019/0069945 on Mar. 7, 2019.
(Davalos, Rafael V. et al.) Co-pending U.S. Appl. No. 16/232,962 filed Dec. 26, 2018, and published as U.S Publication No. 2019/0133671 on May 9, 2019.
(Davalos, Rafael V. et al.) Co-pending U.S. Appl. No. 16/275,429, filed Feb. 14, 2019, which published as 2019/0175260 on Jun. 13, 2019.
(Davalos, Rafael V. et al.) Co-pending U.S. Appl. No. 16/535,451 filed Aug. 8, 2019, and Published as U.S. Publication No. 2019/0376055 on Dec. 12, 2019.
(Davalos, Rafael V. et al.) Co-Pending Application No. PCT/US10/30629, filed Apr. 9, 2010.
(Davalos, Rafael V. et al.) Co-Pending U.S. Appl. No. 14/017,210, filed Sep. 3, 2013, and published as U.S. Publication No. 2014/0039489 on Feb. 6, 2014.
(Davalos, Rafael V. et al.) Co-Pending U.S. Appl. No. 14/627,046, filed Feb. 20, 2015, and published as U.S. Publication No. 2015/0164584 on Jun. 18, 2015.

(56) References Cited

OTHER PUBLICATIONS (Davalos, Rafael V. et al.) Co-Pending U.S. Appl. No. 14/686,380, filed Apr. 14, 2015, and published on U.S. Publication No. 2015/0289923 on Oct. 15, 2015.
(Davalos, Rafael V.) Co-Pending U.S. Appl. No. 12/432,295 9, filed Apr. 29, 2009, and published as U.S. Publication No. 2009/0269317-A1 on Oct. 29, 2009.
(Davalos, Rafael V.) Co-pending U.S. Appl. No. 15/423,986, filed Feb. 3, 2017, and published as U.S. Publication No. 2017/0209620 on Jul. 27, 2017.
(Garcia, Paulo A. et al.) Co-Pending U.S. Appl. No. 14/012,832, filed Aug. 28, 2013, and published as U.S. Publication No. 2013/0345697 on Dec. 26, 2013.
(Garcia, Paulo A. et al.) Co-Pending U.S. Appl. No. 14/558,631, filed Dec. 2, 2014, and published as U.S. Publication No. 2015/0088120 on Mar. 26, 2015.
(Garcia, Paulo A. et al.) Co-Pending U.S. Appl. No. 15/011,752 filed on Feb. 1, 2016, and published as U.S Publication No. 2016/0143698 on May 26, 2016.
(Garcia, Paulo A. et al.) Co-Pending U.S. Appl. No. 16/655,845, filed Oct. 17, 2019.
(Mahajan, Roop L. et al.) Co-Pending U.S. Appl. No. 13/958,152, filed Aug. 2, 2013.
(Neal, Robert E. et al.) Co-Pending U.S. Appl. No. 12/906,923, filed Oct. 18, 2010.
(Neal, Robert E. et al.) Co-Pending U.S. Appl. No. 14/808,679, filed Jul. 24, 2015 and Published as U.S. Publication No. 2015/0327944 on Nov. 19, 2015.
(Neal, Robert E. et al.) Co-pending U.S. Appl. No. 16/375,878, filed Apr. 5, 2019, which published on Aug. 1, 2019 as US 2019-0233809 A1.
(Neal, Robert E. et al.) Co-Pending U.S. Appl. No. 16/404,392, filed May 6, 2019, and published as U S. Publication No. 2019/0256839 on Aug. 22, 2019.
(Neal, Robert E. et al.) Co-Pending U.S. Appl. No. 13/550,307, filed Jul. 16, 2012, and published as U.S. Publication No. 2013/0184702 on Jul. 18, 2013.
(Neal, Robert et al.) Co-pending U.S. Appl. No. 16/280,511, filed Feb. 20, 2019, and published as U.S. Publication No. 2019/0175248 on Jun. 13, 2019.
(Pearson, Robert M. et al.) Co-pending U.S. Appl. No. 12/751,826, filed Mar. 31, 2010 (published as 2010/0250209 on Sep. 30, 2010).
(Pearson, Robert M. et al.) Co-pending U.S. Appl. No. 12/751,854, filed Mar. 31, 2010 (published as 2010/0249771 on Sep. 30, 2010).
(Sano, Michael B. et al.) Co-Pending U.S. Appl. No. 13/989,175, filed May 23, 2013, and published as U.S. Publication No. 2013/0253415 on Sep. 26, 2013.
(Sano, Michael B. et al.) Co-Pending U.S. Appl. No. 15/310,114, filed Nov. 10, 2016, and published as U.S. Publication No. 2017/0266438 on Sep. 21, 2017.
(Sano, Michael B. et al.) Co-Pending U.S. Appl. No. 15/843,888, filed Dec. 15, 2017, and published as U.S Publication No. 2018/0125565 on May 10, 2018.
(Sano, Michael B. et al.) Co-Pending U.S. Appl. No. 16/443,351, filed Jun. 17, 2019 (published as 20190328445 on Oct. 31, 2019).
(Sano, Michael B. et al.) Co-Pending U.S. Appl. No. 16/520,901, filed Jul. 24, 2019, and published as U.S. Publication No. 2019/0351224 on Nov. 21, 2019.
(Sano, Michael B. et al.) Co-Pending Application No. AU 2015259303, filed Oct. 24, 2016.
(Sano, Michael B. et al.) Co-Pending Application No. CN 201580025135.6, filed Nov. 14, 2016 (Chinese language and english language versions).
(Sano, Michael B. et al.) Co-Pending Application No. EP 15793361.5, filed Dec. 12, 2016.
(Sano, Michael B. et al.) Co-pending application No. HK 17112121.8, filed Nov. 20, 2017 and published as U.S Publication No. HK1238288 on Apr. 27, 2018.
(Sano, Michael B. et al.) Co-Pending Application No. JP 2016-567747, filed Nov. 10, 2016.
(Sano, Michael B. et al.) Co-pending Application No. JP 2019-133057, filed Jul. 18, 2019.
A.I. Daud et al., "Phase I Trial of Interleukin-12 Plasmid Electroporation in Patients With Metastatic Melanoma," Journal of Clinical Oncology, 26, pp. 5896-5903, 2008.
Abidor, I.G., et al., "Electric Breakdown of Bilayer Lipid-Membranes .1. Main Experimental Facts and Their Qualitative Discussion", Bioelectrochemistry and Bioenergetics, 6(1): p. 37-52 (1979).
Agerholm-Larsen, B., et al., "Preclinical Validation of Electrochemotherapy as an Effective Treatment for Brain Fumors", Cancer Research 71: 3753-3762 (2011).
Long, G., et al., "Targeted Tissue Ablation With Nanosecond Pulses", Ieee Transactions on Biomedical Engineering, 58(8) (2011).
Lundqvist, et al., Altering the Biochemical State of Individual Cultured Cells and Organelles with Ultramicroelectrodes, Proc Natl. Acad. Sci. USA, vol. 95, p. 10356-10360, Sep. 1998.
Lurquin, Gene Transfer by Electroporation, Molecular Biotechnology, vol. 7, 1997.
Lynn, et al., A New Method for the Generation and Use of Focused Ultrasound in Experimental Biology, The Journal of General Physiology, vol. 26, 179-193, 1942.
M. Marty et al., "Electrochemotherapy—An easy, highly effective and safe treatment of cutaneous and subcutaneous metastases: Results of ESOPE (European Standard Operating Procedures of Electrochemotherapy) study," European Journal of Cancer Supplements, 4, pp. 3-13, 2006.
Maček Lebar and Miklavčič, "Cell electropermeabilization to small molecules in vitro: control by pulse parameters." Radiology and Oncology, vol. 35(3), pp. 193-202 (2001).
Mahmood, F., et al., "Diffusion-Weighted MRI for Verification of Electroporation-Based Treatments", Journal of Membrane Biology 240: 131-138 (2011).
Mahnic-Kalamiza, et al., "Educational application for visualization and analysis of electric field strength in multiple electrode electroporation," BMC Med Educ, vol. 12:102, 13 pages, 2012.
Malpica et al., "Grading ovarian serous carcinoma using a two-tier system." The American Journal of Surgical Pathology, vol. 28, pp. 496-504 (2004).
Maor et al., The Effect of Irreversible Electroporation on Blood Vessels, Tech. in Cancer Res. and Treatment, vol. 6, No. 4, Aug. 2007, pp. 307-312.
Maor, E., A. Ivorra, and B. Rubinsky, Non Thermal Irreversible Electroporation: Novel Technology for Vascular Smooth Muscle Cells Ablation, PLoS ONE, 2009, 4(3): p. e4757.
Maor, E., A. Ivorra, J. Leor, and B. Rubinsky, Irreversible electroporation attenuates neointimal formation after angioplasty, IEEE Trans Biomed Eng, Sep. 2008, 55(9): p. 2268-74.
Marszalek et al., "Schwan equation and transmembrane potential induced by alternating electric field." Biophysical Journal, vol. 58, pp. 1053-1058 (1990).
Martin, n.R.C.G., et al., "Irreversible electroporation therapy in the management of locally advanced pancreatic adenocarcinoma." Journal of the American College of Surgeons, 2012. 215(3): p. 361-369.
Miklavcic et al., "A validated model of in vivo electric field distribution in tissues for electrochemotherapy and for DNA alectrotransfer for gene therapy," Biochimica et Biophysica Acta, 1523, pp. 73-83, 2000.
Miklavčič, et al., The Importance of Electric Field Distribution for Effective in Vivo Electroporation of Tissues, Biophysical Journal, vol. 74, May 1998, pp. 2152-2158.
Miller, L., et al., Cancer cells ablation with irreversible electroporation, Technology in Cancer Research and Treatment 4 (2005) 699-706.
Mir et al., "Mechanisms of Electrochemotherapy" Advanced Drug Delivery Reviews 35:107-118 (1999).
Mir, et al., Effective Treatment of Cutaneous and Subcutaneous Malignant Tumours by Electrochemotherapy, British Journal of Cancer, vol. 77, No. 12, pp. 2336-2342, 1998.
Mir, et al., Electrochemotherapy Potentiation of Antitumour Effect of Bleomycin by Local Electric Pulses, European Journal of Cancer, vol. 27, No. 1, pp. 68-72, 1991.

(56) References Cited

OTHER PUBLICATIONS

Mir, et al., Electrochemotherapy, a Novel Antitumor Treatment: First Clinical Trial, C.R. Acad. Sci. Paris, Ser. III, vol. 313, pp. 613-618, 1991.

Mir, L.M. and Orlowski, S., The basis of electrochemotherapy, in Electrochemotherapy, electrogenetherapy, and transdermal drug delivery: electrically mediated delivery of molecules to cells, M.J. Jaroszeski, R. Heller, R. Gilbert, Editors, 2000, Humana Press, p. 99-118.

Mir, L.M., et al., Electric Pulse-Mediated Gene Delivery to Various Animal Tissues, in Advances in Genetics, Academic Press, 2005, p. 83-114.

Mir, Therapeutic Perspectives of In Vivo Cell Electropermeabilization, Bioelectrochemistry, vol. 53, pp. 1-10, 2000.

Mulhall et al., "Cancer, pre-cancer and normal oral cells distinguished by dielectrophoresis." Analytical and Bioanalytical Chemistry, vol. 401, pp. 2455-2463 (2011).

Narayan, et al., Establishment and Characterization of a Human Primary Prostatic Adenocarcinoma Cell Line (ND-1), The Journal of Urology, vol. 148, 1600-1604, Nov. 1992.

Naslund, Cost-Effectiveness of Minimally Invasive Treatments and Transurethral Resection (TURP) in Benign Prostatic Hyperplasia (BPH), (Abstract), Presented at 2001 AUA National Meeting,, Anaheim, CA, Jun. 5, 2001.

Naslund, Michael J., Transurethral Needle Ablation of the Prostate, Urology, vol. 50, No. 2, Aug. 1997.

Neal II et al., "A Case Report on the Successful Treatment of a Large Soft-Tissue Sarcoma with Irreversible Electroporation," Journal of Clinical Oncology, 29, pp. 1-6, 2011.

Neal II et al., "Experimental Characterization and Numerical Modeling of Tissue Electrical Conductivity during Pulsed Electric Fields for Irreversible Electroporation Treatment Planning," Biomedical Engineering, IEEE Transactions on Biomedical Engineering, vol. 59, pp. 1076-1085, 2012.

Neal II, R. E., et al., "Successful Treatment of a Large Soft Tissue Sarcoma with Irreversible Electroporation", Journal of Clinical Oncology, 29:13, e372-e377 (2011).

Neal II, R. E., et al., "Treatment of breast cancer through the application of irreversible electroporation using a novel minimally invasive single needle electrode." Breast Cancer Research and Treatment, 2010. 123(1): p. 295-301.

Neal II, Robert E. and R.V. Davalos, The Feasibility of Irreversible Electroporation for the Treatment of Breast Cancer and Other Heterogeneous Systems, Ann Biomed Eng, 2009, 37(12): p. 2615-2625.

Neal Re II, et al. (2013) Improved Local and Systemic Anti-Tumor Efficacy for Irreversible Electroporation in Immunocompetent versus Immunodeficient Mice. PLoS ONE 8(5): e64559. https://doi.org/10.1371/journal.pone.0064559.

Nesin et al., "Manipulation of cell volume and membrane pore comparison following single cell permeabilization with 60- and 600-ns electric pulses." Biochimica et Biophysica Acta (BBA)—Biomembranes, vol. 1808, pp. 792-801 (2011).

Neumann, et al., Gene Transfer into Mouse Lyoma Cells by Electroporation in High Electric Fields, J. Embo., vol. 1, No. 7, pp. 841-845, 1982.

Neumann, et al., Permeability Changes Induced by Electric Impulses in Vesicular Membranes, J. Membrane Biol., vol. 10, pp. 279-290, 1972.

Nikolova, B., et al., "Treatment of Melanoma by Electroporation of Bacillus Calmette-Guerin". Biotechnology & Biotechnological Equipment, 25(3): p. 2522-2524 (2011).

Nuccitelli, R., et al., "A new pulsed electric field therapy for melanoma disrupts the tumor's blood supply and causes complete remission without recurrence", Int J Cancer, 125(2): p. 438-45 (2009).

O'Brien et al., "Investigation of the Alamar Blue (resazurin) fluorescent dye for the assessment of mammalian cell cytotoxicity." European Journal of Biochemistry, vol. 267, pp. 5421-5426 (2000).

Okino, et al., Effects of High-Voltage Electrical Impulse and an Anticancer Drug on In Vivo Growing Tumors, Japanese Journal of Cancer Research, vol. 78, pp. 1319-1321, 1987.

Onik, et al., Sonographic Monitoring of Hepatic Cryosurgery in an Experimental Animal Model, AJR American J. of Roentgenology, vol. 144, pp. 1043-1047, May 1985.

Onik, et al., Ultrasonic Characteristics of Frozen Liver, Cryobiology, vol. 21, pp. 321-328, 1984.

Onik, G. and B. Rubinsky, eds. "Irreversible Electroporation: First Patient Experience Focal Therapy of Prostate Cancer. Irreversible Electroporation", ed B. Rubinsky 2010, Springer Berlin Heidelberg, pp. 235-247.

Onik, G., P. Mikus, and B. Rubinsky, "Irreversible electroporation: implications for prostate ablation." Technol Cancer Res Treat, 2007. 6(4): p. 295-300.

Organ, L.W., Electrophysiological principles of radiofrequency lesion making, Apply. Neurophysiol., 1976. 39: p. 69-76.

Ott, H. C., et al., "Perfusion-decellularized matrix: using nature's platform to engineer a bioartificial heart", Nature Medicine, Nature Publishing Group, New York, NY, US, vol. 14, No. 2, Feb. 1, 2008, pp. 213-221.

Paszek et al., "Tensional homeostasis and the malignant phenotype." Cancer Cell, vol. 8, pp. 241-254 (2005).

Pavselj, et al., "The course of tissue permeabilization studied on a mathematical model of a subcutaneous tumor in small animals," IEEE Trans Biomed Eng, vol. 52, pp. 1373-1381, 2005.

Pending Application No. AU 2009243079, First Examination Report, Jan. 24, 2014, 4 pages.

Pending Application No. AU 2009243079, Voluntary Amendment filed Dec. 6, 2010, 35 pages.

Pending Application No. AU 2015259303, First Examination Report dated Oct. 26, 2020, 6 pages.

Pending Application No. CA 2,722,296 Examination Report dated Apr. 2, 2015, 6 pages.

Pending Application No. CN 201580025135.6 English translation of Apr. 29, 2020 Office action, 7 pages.

Pending Application No. CN 201580025135.6 Response to Sep. 25, 2019 Office action, filed Feb. 10, 2020, English language version and original document.

Pending Application No. CN 201580025135.6, First Office Action, dated Sep. 25, 2019 (Chinese and English Versions, each 6 pages).

Pending Application No. CN 201580025135.6, Response to First Office Action, Feb. 7, 2020, (Chinese Vrsion, 13 pages, and English Version, 10 pages).

Pending Application No. CN 201580025135.6, Second Office Action, dated Apr. 29, 2020 (Chinese Version, 4 pages, and English Version, 7 pages).

Pending Application No. EP 09739678.2 Extended European Search Report dated May 11, 2012, 7 pages.

Pending Application No. EP 09739678.2, Communication pursuant to Rule 94.3, Apr. 16, 2014, 3 pages.

Pending Application No. EP 09739678.2, Office Action dated Apr. 16, 2014, 3 pages.

Pending Application No. EP 09739678.2, Response to Extended European Search Report and Communication pursuant to Rules 70(2) and 70a(2) EPC, dated Dec. 10, 2012.

Pending Application No. EP 10824248.8, Extended Search Report (Jan. 20, 2014), 6 pages.

Pending Application No. EP 10824248.8, Invitation Pursuant to rule 62a(1) EPC (Sep. 25, 2013), 2 pages.

Pending Application No. EP 10824248.8, Communication Pursuant to Rule 70(2) dated Feb. 6, 2014, 1 page.

Pending Application No. EP 10824248.8, Response to Invitation Pursuant to rule 62a(1) EPC (Sep. 25, 2013), Response filed Nov. 18, 2013.

Pending Application No. EP 11842994.3, Communication Pursuant to Rules 70(2) and 70a(2) EPC dated Apr. 28, 2014, 1 page.

Pending Application No. EP 11842994.3, Extended European Search Report dated Apr. 9, 2014, 34 pages.

Pending Application No. JP 2013-541050, Voluntary Amendment filed Oct. 29, 2013, 4 pages (with English Version of the Claims, 2 pages).

(56) References Cited

OTHER PUBLICATIONS

Pending Application No. JP 2016-567747, Decision to Grant with English Version of allowed claims, 9 pages.
Pending Application No. JP 2019-133057, Office Action dated Sep. 14, 2020, 5 pages (and English translation, 6 pages).
Qiao et al. Electrical properties of breast cancer cells from impedance measurement of cell suspensions, 2010, Journal of Physics, 224, 1-4 (2010).
Ringel-Scaia, V. M. et al., High-frequency irreversible electroporation is an effective tumor ablation strategy that induces immunologic cell death and promotes systemic anti-tumor immunity. EBioMedicine, 2019, 44, 112-125.
Rossmeisl, John H. et al. Safety and feasibility of the NanoKnife system for irreversible electroporation ablative treatment of canine spontaneous intracranial gliomas. J. Neurosurgery 123.4 (2015): 1008-1025.
SAI Infusion Technologies, "Rabbit Ear Vein Catheters", https://www.sai-infusion.com/products/rabbit-ear-catheters, Aug. 10, 2017 webpage printout, 5 pages.
Sanchez, B., G. Vandersteen, R. Bragos, and J. Schoukens, "Basics of broadband impedance spectroscopy measurements using periodic excitations," Measurement Science and Technology, vol. 23, No. 10, p. 105501, 2012.
Sanchez, B., G. Vandersteen, R. Bragos, and J. Schoukens, "Optimal multisine excitation design for broadband electrical impedance spec-troscopy," Measurement Science and Technology, vol. 22, No. 11, p. 115601, 2011.
Shao, Qi et al. Engineering T cell response to cancer antigens by choice of focal therapeutic conditions, International Journal of Hyperthermia, 2019, DOI: 10.1080/02656736.2018.1539253.
U.S. Appl. No. 12/491,151 (U.S. Pat. No. 8,992,517), file history through Feb. 2015, 113 pages.
U.S. Appl. No. 12/609,779 (U.S. Pat. No. 8,465,484), file history through May 2013, 100 pages.
U.S. Appl. No. 12/757,901 (U.S. Pat. No. 8,926,606), file history through Jan. 2015, 165 pages.
U.S. Appl. No. 12/906,923 (U.S. Pat. No. 9,198,733), file history through Nov. 2015, 55 pages.
U.S. Appl. No. 13/332,133 (U.S. Pat. No. 10,448,989), file history through Sep. 2019, 226 pages.
U.S. Appl. No. 13/550,307 (U.S. Pat. No. 10,702,326), file history through May 2020, 224 pages.
U.S. Appl. No. 13/919,640 (U.S. Pat. No. 8,814,860), file history through Jul. 2014, 41 pages.
U.S. Appl. No. 13/958,152, file history through Dec. 2019, 391 pages.
U.S. Appl. No. 13/989,175 (U.S. Pat. No. 9,867,652), file history through Dec. 2017, 200 pages.
U.S. Appl. No. 14/012,832 (U.S. Pat. No. 9,283,051), file history through Nov. 2015, 17 pages.
U.S. Appl. No. 14/017,210 (U.S. Pat. No. 10,245,098), file history through Jan. 2019, 294 pages.
U.S. Appl. No. 14/558,631 (U.S. Pat. No. 10,117,707), file history through Jul. 2018, 58 pages.
U.S. Appl. No. 14/627,046 (U.S. Pat. No. 10,245,105), file history through Feb. 2019, 77 pages.
U.S. Appl. No. 14/940,863 (U.S. Pat. No. 10,238,447), file history through Oct. 2019, 23 pages.
U.S. Appl. No. 15/011,752 (U.S. Pat. No. 10,470,822), file history through Jul. 2019, 54 pages.
U.S. Appl. No. 15/186,653 (U.S. Pat. No. 10,292,755), file history through Mar. 2019, 21 pages.
U.S. Appl. No. 15/310,114 (U.S. Pat. No. 10,471,254), file history through Aug. 2019, 44 pages.
U.S. Appl. No. 15/423,986 (U.S. Pat. No. 10,286,108), file history through Jan. 2019, 124 pages.
U.S. Appl. No. 15/424,335 (U.S. Pat. No. 10,272,178), file history through Feb. 2019, 57 pages.
U.S. Appl. No. 15/536,333 (U.S. Pat. No. 10,694,972), file history through Apr. 2020, 78 pages.
Co-Pending U.S. Appl. No. 14/808,679, Interview Summary, dated Apr. 26, 2019, 3 pages.
Co-Pending U.S. Appl. No. 14/808,679, Preliminary Amendment dated Jul. 24, 2015, 6 pages.
Co-Pending U.S. Appl. No. 14/808,679, Restriction Requirement dated Mar. 19, 2018, 7 pages.
Co-Pending U.S. Appl. No. 14/808,679, 3rd Renewed Petition, Dec. 9, 2019 and Petition Decision dated Dec. 18, 2019, 11 pages.
Co-Pending U.S. Appl. No. 14/808,679, Final Office Action dated Jan. 11, 2019, 12 pages.
Co-Pending U.S. Appl. No. 14/808,679, Non-Final Office Action dated Sep. 10, 2018, 12 pages.
Co-Pending U.S. Appl. No. 14/808,679, Petition Decision, dated Oct. 1, 2019, 5 pages.
Co-Pending U.S. Appl. No. 14/808,679, Petition Decision, dated Oct. 23, 2019, 6 pages.
Co-Pending U.S. Appl. No. 14/808,679, Petition Decision, dated Dec. 3, 2019, 5 pages.
Co-Pending U.S. Appl. No. 14/808,679, Petition for Priority and Supplemental Response, filed May 8, 2019, 25 pages.
Co-Pending U.S. Appl. No. 14/808,679, Petition Supplement, dated Sep. 25, 2019, 10 pages.
Co-Pending U.S. Appl. No. 14/808,679, Petition, dated May 8, 2019, 2 pages.
Co-Pending U.S. Appl. No. 14/808,679, Preliminary Amendment, filed Jul. 27, 2015, 9 pages.
Co-Pending U.S. Appl. No. 14/808,679, RCE filed Apr. 11, 2019, 8 pages.
Co-Pending U.S. Appl. No. 14/808,679, Renewed Petition, filed Oct. 9, 2019, 1 pages.
Co-Pending U.S. Appl. No. 14/808,679, Response to Mar. 19, 2018 Restriction Requirement dated May 21, 2018, 2 pages.
Co-Pending U.S. Appl. No. 14/808,679, Response to Sep. 10, 2018 Non-Final Office Action dated Dec. 10, 2018, 9 pages.
Co-Pending U.S. Appl. No. 14/808,679, Second Renewed Petition, filed Oct. 31, 2019, 3 pages.
Co-Pending U.S. Appl. No. 14/808,679, Supplemental Response, dated May 8, 2019, 16 pages.
Co-Pending U.S. Appl. No. 15/186,653, Notice of Allowance dated Aug. 1, 2018, 7 pages.
Co-Pending U.S. Appl. No. 15/186,653, Notice of Allowance dated Mar. 20, 2019, 14 pages.
Co-Pending U.S. Appl. No. 15/186,653, Preliminary Amendment, dated Jun. 21, 2016, 5 pages.
Co-Pending U.S. Appl. No. 15/310,114, Corrected notice of allowance dated Aug. 6, 2019, 9 pages.
Co-Pending U.S. Appl. No. 15/310,114, Non-Final Office Action dated Mar. 6, 2019 Non-Final Office Action filed Jun. 4, 2019, 153 pages.
Co-Pending U.S. Appl. No. 15/310,114, Notice of Allowance, dated Aug. 19, 2019, 3 pages.
Co-Pending U.S. Appl. No. 15/310,114, Notice of Allowance, dated Jun. 21, 2019, 6 pages.
Co-Pending U.S. Appl. No. 15/310,114, Preliminary Amendment, dated Nov. 10, 2016, 9 pages.
Co-Pending U.S. Appl. No. 15/310,114, Response to Mar. 6, 2019 Non-Final Office Action filed Jun. 4, 2019, 8 pages.
Co-pending U.S. Appl. No. 15/881,414 Amendment and Petition for Priority Claim dated Jul. 26, 2018, 26 pages.
Co-pending U.S. Appl. No. 15/881,414, filed Apr. 26, 2018 Non-Final Office Action, 8 pages.
Co-pending U.S. Appl. No. 15/881,414 Notice of Allowance dated Oct. 24, 2018, 7 pages.
Co-pending U.S. Appl. No. 15/881,414 Petition Decision dated Oct. 9, 2018, 9 pages.
Co-pending U.S. Appl. No. 16/177,745, Applicant-initiated interview summary dated Dec. 16, 2019, 3 pages.
Co-pending U.S. Appl. No. 16/177,745, Final office action dated Jan. 9, 2020, 8 pages.
Co-pending U.S. Appl. No. 16/177,745, Non-final office action dated Aug. 20, 2019, 10 pages.
Co-pending U.S. Appl. No. 16/177,745, Preliminary Amendment dated Dec. 19, 2018, 7 pages.

(56) References Cited

OTHER PUBLICATIONS

Co-pending U.S. Appl. No. 16/177,745, Response to Aug. 20, 2019 Non-final office action dated Nov. 20, 2019, 10 pages.
Co-pending U.S. Appl. No. 16/232,962 Applicant-initiated interview Summary dated Dec. 16, 2019, 3 pages.
Co-pending U.S. Appl. No. 16/232,962 Final office action dated Jan. 9, 2020, 7 pages.
Co-pending U.S. Appl. No. 16/232,962 Non-Final office action dated Aug. 20, 2019, 9 pages.
Co-Pending U.S. Appl. No. 16/232,962 Response to Aug. 20, 2019 Non-final office action dated Nov. 20, 2019, 10 pages.
Co-pending U.S. Appl. No. 16/372,520 Preliminary Amendment filed Apr. 9, 2019, 7 pages.
Co-Pending U.S. Appl. No. 16/375,878, Preliminary Amendment, filed Apr. 9, 2019, 9 pages.
Co-pending U.S. Appl. No. 16/404,392, Non-Final Office Action dated Sep. 6, 2019, 8pgs.
Co-pending U.S. Appl. No. 16/404,392, Petition for Priority, filed Jun. 4, 2019, 2 pages.
Co-pending U.S. Appl. No. 16/404,392, Preliminary Amendment, filed Jun. 4, 2019, 9 pages.
Co-pending U.S. Appl. No. 16/404,392, Preliminary Amendment, filed Jun. 6, 2019, 5 pages.
Co-pending U.S. Appl. No. 16/404,392, Response to Non-Final Office action dated Sep. 6, 2019, filed Dec. 6, 2019, 8 pages.
Co-pending U.S. Appl. No. 16/520,901, Preliminary Amendment filed Aug. 14, 2019.
Min, M., U. Pliquett, T. Nacke, A. Barthel, P. Annus, and R. Land, "Broadband excitation for short-time impedance spectroscopy," Physiological measurement, vol. 29, No. 6, p. S185, 2008.
Neal II, R. E et al. In Vitro and Numerical Support for Combinatorial Irreversible Electroporation and Electrochemotherapy Glioma Treatment. Annals of Biomedical Engineering, Oct. 29, 2013, 13 pages.
O'Brien, T. J. et al., "Effects of internal electrode cooling on irreversible electroporation using a perfused organ model," Int. J Hyperth., vol. 35, No. 1, pp. 44-55, 2018.
Pakhomova, O. N., Gregory, B., Semenov I., and Pakhomov, A. G., BBA—Biomembr., 2014, 1838, 2547-2554.
PCT Application No. PCT/US15/65792, International Search Report (dated Feb. 9, 2016), Written Opinion (Feb. 9, 2016), and International Preliminary Report on Patentability (Jun. 20, 2017), 15 pages.
PCT Application No. PCT/US19/51731, International Search Report and Written Opinion dated Feb. 20, 2020, 19 pgs.
PCT Application No. PCT/US19/51731, Invitation to Pay Additional Search Fees dated Oct. 28, 2019, 2 pgs.
Pending U.S. Appl. No. 14/686,380, Final Office Action dated May 9, 2018,14 pages.
Pending U.S. Appl. No. 14/686,380, Final Office Action dated Oct. 6, 2020, 14 pages.
Pending U.S. Appl. No. 14/686,380, Final Office Action dated Sep. 3, 2019, 28 pages.
Pending U.S. Appl. No. 14/686,380, Non-Final Office Action dated Feb. 13, 2020, 11 pages.
Pending U.S. Appl. No. 14/686,380, Non-Final Office Action dated May 1, 2019, 18 pages.
Pending U.S. Appl. No. 14/686,380, Non-Final Office Action dated Nov. 22, 2017, 11 pages.
Pending U.S. Appl. No. 14/686,380, Response to Feb. 13, 2020 Non-Final Office Action, filed Jul. 1, 2020, 8 pages.
Pending U.S. Appl. No. 14/686,380, Response to Jul. 19, 2017 Restriction Requirement, dated Sep. 15, 2017, 2 pages.
Pending U.S. Appl. No. 14/686,380, Response to May 9, 2018 Final Office Action with RCE, dated Aug. 30, 2018, 14 pages.
Pending U.S. Appl. No. 14/686,380, Response to Non-Final Office Action Filed Aug. 1, 2019, 11 pages.
Pending U.S. Appl. No. 14/686,380, Response to Nov. 22, 2017 Non-Final Office Action dated Mar. 28, 2018, 11 pages.
Pending U.S. Appl. No. 14/686,380, Response to Oct. 6, 2020 Final Office Action with RCE, dated Jan. 6, 2020, 11 pages.
Pending U.S. Appl. No. 14/686,380, Response to Sep. 3, 2019 Final Office Action, filed Jan. 3, 2020, 10 pages.
Pending U.S. Appl. No. 14/686,380, Restriction Requirement Jul. 19, 2017, 7 pages.
Pending U.S. Appl. No. 14/808,679, Final Office Action dated Dec. 28, 2020, 11 pages.
Pending U.S. Appl. No. 14/808,679, Non-Final Office Action dated Jun. 12, 2020, 10 pages.
Pending U.S. Appl. No. 14/808,679, Response to Non-Final Office Action dated Jun. 12, 2020, filed Sep. 14, 2020, 9 pages.
Pending U.S. Appl. No. 16/152,743 Preliminary Amendment filed Oct. 5, 2018, 7 pages.
Pending U.S. Appl. No. 16/152,743, Non-Final Office Action dated Sep. 25, 2020, 10 pages.
Pending U.S. Appl. No. 16/152,743, Petition for Delayed Claim for Priority dated Dec. 28, 2020, 2 pages.
Pending U.S. Appl. No. 16/152,743, Response to Sep. 25, 2020 Non-Final Office Action dated Dec. 28, 2020, 9 pages.
Pending U.S. Appl. No. 16/152,743, Second Preliminary Amendment filed May 2, 2019, 6 pages.
Pending U.S. Appl. No. 16/210,771, Non-Final Office Action dated Sep. 3, 2020, 9 pages.
Pending U.S. Appl. No. 16/210,771, Preliminary Amendment filed Dec. 5, 2018, 8 pages.
Pending U.S. Appl. No. 16/210,771, Response to Restriction Requirement, filed Jul. 8, 2020, 7 pages.
Pending U.S. Appl. No. 16/210,771, Response to Sep. 3, 2020 Non-Final Office Action filed Jan. 4, 2021, 11 pages.
Pending U.S. Appl. No. 16/210,771, Restriction Requirement, dated Jun. 9, 2020, 7 pages.
Pending U.S. Appl. No. 16/210,771, Second Preliminary Amendment filed Oct. 14, 2019, 7 pages.
Pending U.S. Appl. No. 16/275,429 Notice of Allowance dated Nov. 10, 2020, 9 pages.
Pending U.S. Appl. No. 16/275,429 Preliminary Amendment filed Mar. 28, 2019, 6 pages.
Pending U.S. Appl. No. 16/280,511, Non-final Office Action dated Dec. 4, 2020, 10 pgs.
Pending U.S. Appl. No. 16/280,511, Preliminary Amendment filed Nov. 2, 2020, 6 pages.
Pending U.S. Appl. No. 16/375,878, Second Preliminary Amendment, filed Feb. 5, 2020, 3 pages.
Pending U.S. Appl. No. 16/404,392, Final Office Action dated Mar. 20, 2020, 8pgs.
Pending U.S. Appl. No. 16/404,392, Interview Summary dated Sep. 6, 2019, 8pgs.
Pending U.S. Appl. No. 16/404,392, Non-Final Office Action dated Nov. 13, 2020, 8pgs.
Pending U.S. Appl. No. 16/404,392, Response to Final Office action dated Mar. 20, 2020, filed Sep. 18, 2020, 7 pages.
Pending U.S. Appl. No. 16/655,845, Preliminary Amendment filed Oct. 16, 2020, 6 pages.
Pending U.S. Appl. No. 16/747,219, Preliminary Amendment filed Jan. 20, 2020, 5 pages.
Pending U.S. Appl. No. 16/747,219, Preliminary Amendment filed Jan. 4, 2021, 5 pages.
Pending U.S. Appl. No. 16/865,031, Preliminary Amendment filed May 1, 2020, 7 pages.
Pending U.S. Appl. No. 16/865,772, Preliminary Amendment filed May 4, 2020, 6 pages.
Pending U.S. Appl. No. 16/915,760, Preliminary Amendment filed Jul. 6, 2020, 5 pages.
U.S. Appl. No. 15/843,888 (U.S. Pat. No. 10,537,379), file history through Sep. 2019, 33 pages.
U.S. Appl. No. 15/881,414 (U.S. Pat. No. 10,154,874), file history through Nov. 2018, 13 pages.
U.S. Appl. No. 16/177,745 (U.S. Pat. No. 10,828,085), file history through Jun. 2020, 57 pages.
U.S. Appl. No. 16/232,962 (U.S. Pat. No. 10,828,086), file history through Jun. 2020, 44 pages.
Van Den Bos, W. et al., "MRI and contrast-enhanced ultrasound imaging for evaluation of focal irreversible electroporation treat-

(56) References Cited

OTHER PUBLICATIONS ment: results from a phase i-ii study in patients undergoing ire followed by radical prostatectomy," European radiology, vol. 26, No. 7, pp. 2252-2260, 2016.
Voyer, D., A. Silve, L. M. Mir, R. Scorretti, and C. Poignard, "Dynamical modeling of tissue electroporation," Bioelectrochemistry, vol. 119, pp. 98-110, 2018.
Zhao, Y., S. Bhonsle, S. Dong, Y. Lv, H. Liu, A. Safaai-Jazi, R. V. Davalos, and C. Yao, "Characterization of conductivity changes during high-frequency irreversible electroporation for treatment planning," IEEE Transactions on Biomedical Engineering, vol. 65, No. 8, pp. 1810-1819, 2017.
Pavselj, N., et al., "A numerical model of skin electroporation as a method to enhance gene transfection in skin. 11th Mediterranean Conference on Medical and Biological Engineering and Computing", vols. 1 and 2, 16(1-2): p. 597-601 (2007).
PCT International Preliminary Report on Patentability of Corresponding International Application No. PCT/2011/062067, dated May 28, 2013.
PCT International Preliminary Report on Patentability of Corresponding International Application No. PCT/20111066239, dated Jun. 25, 2013.
PCT International Search Report (dated Aug. 2, 2011), Written Opinion (dated Aug. 2, 2011), and International Preliminary Report on Patentability (dated Apr. 17, 2012) of PCT/US10/53077.
PCT International Search Report (dated Aug. 22, 2012), and Written Opinion (Aug. 22, 2012) of PCT/US11/66239.
PCT International Search Report (dated Aug. 26, 2005), Written Opinion (dated Aug. 26, 2005), and International Preliminary Report on Patentability (dated Jun. 26, 2006) of PCT/US2004/043477.
PCT International Search Report (dated Jan. 19, 2010), Written Opinion (dated Jan. 19, 2010), and International Preliminary Report on Patentability (dated Jan. 4, 2010) of PCT/US09/62806, 15 pgs.
PCT International Search Report (Jul. 15, 2010), Written Opinion (dated Jul. 15, 2010), and International Preliminary Report on Patentability (dated Oct. 11, 2011) from PCT/US2010/030629.
PCT International Search Report (dated Jul. 9, 2009), Written Opinion (dated Jul. 9, 2009), and International Preliminary Report on Patentability (dated Nov. 2, 2010) of PCT/US2009/042100.
PCT International Search Report and Written Opinion (dated Jul. 25, 2012) of PCT/US2011/062067.
PCT International Search Report, 4 pgs, (dated Jul. 30, 2010), Written Opinion, 7 pgs, (dated Jul. 30, 2010), and International Preliminary Report on Patentability, 8 pgs, (dated Oct. 4, 2011) from PCT/US2010/029243.
PCT IPRP for PCT/US15/30429 (WO2015175570), dated Nov. 15, 2016.
Phillips, M., Maor, E. & Rubinsky, B. Non-Thermal Irreversible Electroporation for Tissue Decellularization. J. Biomech. Eng, doi:10.1115/1.4001882 (2010).
Piñero, et al., Apoptotic and Necrotic Cell Death Are Both Induced by Electroporation in HL60 Human Promyeloid Leukaemia Cells, Apoptosis, vol. 2, No. 3, 330-336, Aug. 1997.
Polak et al., "On the Electroporation Thresholds of Lipid Bilayers: Molecular Dynamics Simulation Investigations." The Journal of Membrane Biology, vol. 246, pp. 843-850 (2013).
Precision Office Tuna System, When Patient Satisfaction is Your Goal, VidaMed 2001.
Pucihar et al., "Numerical determination of transmembrane voltage induced on irregularly shaped cells." Annals of Biomedical Engineering, vol. 34, pp. 642-652 (2006).
Rajagopal, V. and S.G. Rockson, Coronary restenosis: a review of mechanisms and management, The American Journal of Medicine, 2003, 115(7): p. 547-553.
Reberšek, M. and D. Miklavčič, "Advantages and Disadvantages of Different Concepts of Electroporation Pulse Generation," Automatika 52(2011) 1, 12-19.
Rols, M. P., et al., Highly Efficient Transfection of Mammalian Cells by Electric Field Pulses: Application to Large Volumes of Cell Culture by Using a Flow System, Eur. J. Biochem. 1992, 206, pp. 115-121.
Ron et al., "Cell-based screening for membranal and cytoplasmatic markers using dielectric spectroscopy." Biophysical chemistry, 135 (2008) pp. 59-68.
Rossmeisl et al., "Pathology of non-thermal irreversible electroporation (N-Tire)-induced ablation of the canine brain." Journal of Veterinary Science vol. 14, pp. 433-440 (2013).
Rossmeisl, "New Treatment Modalities for Brain Tumors in Dogs and Cats." Veterinary Clinics of North America: Small Animal Practice 44, pp. 1013-1038 (2014).
Rubinsky et al., "Optimal Parameters for the Destruction of Prostate Cancer Using Irreversible Electroporation." The Journal of Urology, 180 (2008) pp. 2668-2674.
Rubinsky, B., "Irreversible Electroporation in Medicine", Technology in Cancer Research and Treatment, vol. 6, No. 4, Aug. 1, 2007, pp. 255-259.
Rubinsky, B., ed, Cryosurgery. Annu Rev. Biomed. Eng. vol. 2 2000. 157-187.
Rubinsky, B., et al., "Irreversible Electroporation: a New Ablation Modality—Clinical Implications" Technol. Cancer Res. Treatment 6(1), 37-48 (2007).
Sabuncu et al., "Dielectrophoretic separation of mouse melanoma clones." Biomicrofluidics, vol. 4, 7 pages (2010).
Salford, L. G., et al. "A new brain tumour therapy combining bleomycin with in vivo electropermeabilization", Biochem. Biophys. Res. Commun., 194(2): 938-943 (1993).
Salmanzadeh et al., "Investigating dielectric properties of different stages of syngeneic murine ovarian cancer cells" Biomicrofluidics 7, 011809 (2013), 12 pages.
Salmanzadeh et al., "Dielectrophoretic differentiation of mouse ovarian surface epithelial cells, macrophages, and fibroblasts using contactless dielectrophoresis." Biomicrofluidics, vol. 6, 13 Pages (2012).
Salmanzadeh et al., "Sphingolipid Metabolites Modulate Dielectric Characteristics of Cells in a Mouse Ovarian Cancer Progression Model." Integr. Biol., 5(6), pp. 843-852 (2013).
Sano et al., "Contactless Dielectrophoretic Spectroscopy: Examination of the Dielectric Properties of Cells Found in Blood." Electrophoresis, 32, pp. 3164-3171, 2011.
Sano et al., "In-vitro bipolar nano- and microsecond electro-pulse bursts for irreversible electroporation therapies." Bioelectrochemistry vol. 100, pp. 69-79 (2014).
Sano et al., "Modeling and Development of a Low Frequency Contactless Dielectrophoresis (cDEP) Platform to Sort Cancer Cells from Dilute Whole Blood Samples." Biosensors & Bioelectronics, 8 pages (2011).
Sano, M. B., et al., "Towards the creation of decellularized organ constructs using irreversible electroporation and active mechanical perfusion", Biomedical Engineering Online, Biomed Central LTD, London, GB, vol. 9, No. 1, Dec. 10, 2010, p. 83.
Saur et al., "CXCR4 expression increases liver and lung metastasis in a mouse model of pancreatic cancer." Gastroenterology, vol. 129, pp. 1237-1250 (2005).
Schmukler, Impedance Spectroscopy of Biological Cells, Engineering in Medicine and Biology Society, Engineering Advances: New Opportunities for Biomedical Engineers, Proceedings of the 16th Annual Internal Conference of the IEEE, vol. 1, p. A74, downloaded from IEEE Xplore website, 1994.
Schoenbach et al., "Intracellular effect of ultrashort electrical pulses." Bioelectromagnetics, 22 (2001) pp. 440-448.
Seibert et al., "Clonal variation of MCF-7 breast cancer cells in vitro and in athymic nude mice." Cancer Research, vol. 43, pp. 2223-2239 (1983).
Seidler et al., "A Cre-loxP-based mouse model for conditional somatic gene expression and knockdown in vivo by using avian retroviral vectors." Proceedings of the National Academy of Sciences, vol. 105, pp. 10137-10142 (2008).

(56) References Cited

OTHER PUBLICATIONS

Sel, D., Lebar, A. M. & Miklavcic, D. Feasibility of employing model-based optimization of pulse amplitude and electrode distance for effective tumor electropermeabilization. IEEE Trans Biomed Eng 54, 773-781 (2007).
Sel, et al., "Sequential finite element model of tissue electropermeabilization," IEEE Trans Biomed Eng, vol. 52, pp. 816-827, 2005.
Sersa, et al., Reduced Blood Flow and Oxygenation in Sa-1 Tumours after Electrochemotherapy with Cisplatin, British Journal of Cancer, 87, 1047-1054, 2002.
Sersa, et al., Tumour Blood Flow Modifying Effects of Electrochemotherapy: a Potential Vascular Targeted Mechanism, Radiol. Oncol., 37(1): 43-8, 2003.
Sharma, A., et al., "Review on Thermal Energy Storage with Phase Change Materials and Applications", Renewable Sustainable Energy Rev. 13(2), 318-345 (2009).
Sharma, et al., Poloxamer 188 Decreases Susceptibility of Artificial Lipid Membranes to Electroporation, Biophysical Journal, vol. 71, No. 6, pp. 3229-3241, Dec. 1996.
Shiina, S., et al, Percutaneous ethanol injection therapy for hepatocellular carcinoma: results in 146 patients. AJR, 1993, 160: p. 1023-8.
Szot et al., "3D in vitro bioengineered tumors based on collagen I hydrogels." Biomaterials vol. 32, pp. 7905-7912 (2011).
Talele, S. and P. Gaynor, "Non-linear time domain model of electropermeabilization: Effect of extracellular conductivity and applied electric field parameters", Journal of Electrostatics,66(5-6): p. 328-334 (2008).
(Davalos, Rafael et al.) Co-Pending Application No. PCT/US04/43477, filed Dec. 21, 2004.
(Davalos, Rafael V. et al) Co-pending Application No. PCT/US10/53077, filed Oct. 18, 2010.
(Davalos, Rafael V. et al.) Co-pending U.S. Appl. No. 16/352,759, filed Mar. 13, 2019.
(Davalos, Rafael V. et al.) Co-pending U.S. Appl. No. 16/865,031, filed May 1, 2020.
(Davalos, Rafael V. et al.) Co-pending U.S. Appl. No. 17/069,359 filed Oct. 13, 2020.
(Davalos, Rafael V. et al.) Co-Pending Application No. AU 2009243079, filed Apr. 29, 2009 (see PCT/US2009/042100 for documents as filed).
(Davalos, Rafael V. et al.) Co-Pending Application No. PCT/US09/62806, filed Oct. 30, 2009.
(Davalos, Rafael V. et al.) Co-pending application No. PCT/US19/51731 filed Sep. 18, 2019.
(Davalos, Rafael V. et al.) Co-Pending International Application No. PCT/US15/65792, filed Dec. 15, 2015.
(Davalos, Rafael V.) Co-Pending Application No. CA 2,722,296, filed Apr. 29, 2009, Amended Claims (7 pages).
(Davalos, Rafael V.) Co-Pending Application No. EP 09739678.2 filed Apr. 29, 2009, Amended Claims (3 pages).
(Davalos, Rafael V.) Co-Pending U.S. Appl. No. PCT/US09/42100, filed Apr. 29, 2009.
(Garcia, Paulo A. et al.) Co-pending U.S. Appl. No. 16/152,743, filed Oct. 5, 2018.
(Latouche, Eduardo et al.) Co-pending U.S. Appl. No. 16/210,771, filed Dec. 5, 2018, and which published as US Patent Publication No. 2019/0232048 on Aug. 1, 2019.
(Lorenzo, Melvin F. et al.) Co-pending U.S. Appl. No. 16/938,778 filed Jul. 24, 2020.
(Neal, Robert E. et al.) Co-pending U.S. Appl. No. 16/865,772 filed May 4, 2020.
(Neal, Robert E. et al.) Co-pending U.S. Appl. No. 14/940,863, filed Nov. 13, 2015 and Published as US 2016/0066977 on Mar. 10, 2016.
(Neal, Robert et al.) Co-Pending Application No. EP 10824248.8, filed May 9, 2012, Amended Claims (3 pages).
(O'Brien, Timothy J. et al.) Co-Pending U.S. Appl. No. 16/915,760, filed June 29, 2020.
(O'Brien, Timothy J. et al.) Co-Pending U.S. Appl. No. 17/152,379, filed Jan. 19, 2021.
(Pearson, Robert M. et al) Co-pending Application No. PCT/US2010/029243, filed Mar. 30, 2010, published as WO 2010/117806 on Oct_ 14, 2010.
(Sand, Michael B. et al) Co-Pending Application No. PCT/US2015/030429, Filed May 12, 2015, Published on Nov. 19, 2015 as WO 2015/175570.
(Sano, Michael B. et al.) Co-Pending U.S. Appl. No. 16/747,219, filed Jan. 20, 2020.
(Sano, Michael B. et al.) Co-Pending Application No. CN 202011281572.3, filed Nov. 16, 2020, (Chinese version, 129 pages (see also WO 2015/175570), English Version of claims, 2 pages).
(Sano, Michael B. et al.) Co-Pending Application No. EP 11842994.3, filed Jun. 24, 2013, Amended Claims (18 pages).
(Sano, Michael B. et al.) Co-Pending Application No. JP 2013-541050, filed May 22, 2013.
(Sano, Michael et al.) Co-Pending Application No. PCT/US11/62067, filed Nov. 23, 2011.
(Wasson, Elisa M. et al.) Co-pending U.S. Appl. No. 17/000,049, filed Aug. 21, 2020.
Beitel-White, N., S. Bhonsle, R. Martin, and R. V. Davalos, "Electrical characterization of human biological tissue for irreversible electroporation treatments," in 2018 40th Annual International Conference of the IEEE Engineering in Medicine and Biology Society (EMBC). IEEE, 2018, pp. 4170-4173.
Ben-David, E. et al., "Irreversible Electroporation: Treatment Effect Is Susceptible to Local Environment and Tissue Properties," Radiology, vol. 269, No. 3, 2013, 738-747.
Bhonsle, S. et al., "Characterization of Irreversible Electroporation Ablation with a Validated Perfused Organ Model," J. Vasc. Interv. Radiol., vol. 27, No. 12, pp. 1913-1922.e2, 2016.
Bhonsle, S., M. F. Lorenzo, A. Safaai-Jazi, and R. V. Davalos, "Characterization of nonlinearity and dispersion in tissue impedance during high-frequency electroporation," IEEE Transactions on Biomedical Engineering, vol. 65, No. 10, pp. 2190-2201, 2018.
Bonakdar, M., E. L Latouche, R. L. Mahajan, and R. V. Davalos, "The feasibility of a smart surgical probe for verification of IRE treatments using electrical impedance spectroscopy," IEEE Trans. Biomed. Eng., vol. 62, No. 11, pp. 2674-2684, 2015.
Bondarenko, A. and G. Ragoisha, Eis spectrum analyser (the program is available online at http://www.abc.chemistry.bsu.by/vi/analyser/.
Boussetta, N., N. Grimi, N. I. Lebovka, and E. Vorobiev, "Cold" electroporation in potato tissue induced by pulsed electric field, Journal of food engineering, vol. 115, No. 2, pp. 232-236, 2013.
Bulvik, B. E. et al. "Irreversible Electroporation versus Radiofrequency Ablation☐: A Comparison of Local and Systemic Effects in a Small Animal Model," Radiology, vol. 280, No. 2, 2016, 413-424.
Castellvi, Q., B. Mercadal, and A. Ivorra, "Assessment of electroporation by electrical impedance methods," in Handbook of electroporation. Springer-Verlag, 2016, pp. 671-690.
Creason, S. C., J. W. Hayes, and D. E. Smith, "Fourier transform faradaic admittance measurements iii. comparison of measurement efficiency for various test signal waveforms," Journal of Electroanalytical chemistry and interfacial electrochemistry, vol. 47, No. 1, pp. 9-46, 1973.
De Senneville, B. D. et al., "MR thermometry for monitoring tumor ablation," European radiology, vol. 17, No. 9, pp. 2401-2410, 2007.
Frandsen, S. K., H. Gissel, P. Hojman, T. Tramm, J. Eriksen, and J. Gehl. Direct therapeutic applications of calcium electroporation to effectively induce tumor necrosis. Cancer Res. 72:1336-41, 2012.
Garcia-Sánchez, T., A. Azan, I. Leray, J. Rosell-Ferrer, R. Bragos, and L M. Mir, "Interpulse multifrequency electrical mpedance measurements during electroporation of adherent differentiated myotubes," Bioelectrochemistry, vol. 105, pp. 123-135, 2015.
Gawad, S., T. Sun, N. G. Green, and H. Morgan, "Impedance spectroscopy using maximum length sequences: Application to single cell analysis," Review of Scientific Instruments, vol. 78, No. 5, p. 054301, 2007.
Granot, Y., A. Ivorra, E. Maor, and B. Rubinsky, "In vivo imaging of irreversible electroporation by means of electrical impedance tomography," Physics in Medicine & Biology, vol. 54, No. 16, p. 4927, 2009.

(56) References Cited

OTHER PUBLICATIONS

Hoejholt, K. L. et al. Calcium electroporation and electrochemotherapy for cancer treatment: Importance of cell membrane composition investigated by lipidomics, calorimetry and in vitro efficacy. Scientific Reports (Mar. 18, 2019) 9:4758, p. 1-12.

Ivey, J. W., E. L. Latouche, M. B. Sano, J. H. Rossmeisl, R. V. Davalos, and S. S. Verbridge, "Targeted cellular ablation based on the morphology of malignant cells," Sci. Rep., vol. 5, pp. 1-17, 2015.

Kranjc, M., S. Kranjc, F. Bajd, G. Sersa, I. Sersa, and D. Miklavcic, "Predicting irreversible electroporation-induced tissue damage by means of magnetic resonance electrical impedance tomography," Scientific reports, vol. 7, No. 1, pp. 1-10, 2017.

Latouche, E. L., M. B. Sano, M. F. Lorenzo, R. V. Davalos, and R. C. G. Martin, "Irreversible electroporation for the ablation of pancreatic malignancies: A patient-specific methodology," J. Surg. Oncol., vol. 115, No. 6, pp. 711-717, 2017.

Lee, R. C., D. J. Canaday, and S. M. Hammer. Transient and stable ionic permeabilization of isolated skeletal muscle cells after electrical shock. J. Burn Care Rehabil. 14:528-540, 1993.

Martinsen, O. G. And Grimnes, S., Bioimpedance and bioelectricity basics. Academic press, 2011.

Min, M., A. Giannitsis, R. Land, B. Cahill, U. Pliquett, T. Nacke, D. Frense, G. Gastrock, and D. Beckmann, "Comparison of rectangular wave excitations in broad band impedance spectroscopy for microfluidic applications," in World Congress on Medical Physics and Biomedical Engineering, Sep. 7-12, 2009, Munich, Germany. Springer, 2009, pp. 85-88.

Davalos et al., "Theoretical analysis of the thermal effects during in vivo tissue electroporation." Bioelectrochemistry, vol. 61(1-2): pp. 99-107, 2003.

Davalos et al., "Tissue ablation with irreversible electroporation." Annals of Biomedical Engineering, vol. 33, No. 2, pp. 223-231 (Feb. 2005).

Davalos, et al., A Feasibility Study for Electrical Impedance Tomography as a Means to Monitor Tissue Electroporation for Molecular Medicine, IEEE Transactions on Biomedical Engineering, vol. 49, No. 4, Apr. 2002.

Davalos, R. V. & Rubinsky, B. Temperature considerations during irreversible electroporation. International Journal of Heat and Mass Transfer 51, 5617-5622, doi:10.1016/j.ijheatmasstransfer.2008.04.046 (2008).

Davalos, Real-Time Imaging for Molecular Medicine through Electrical Impedance Tomography of Electroporation, Dissertation for Ph.D. In Engineering-Mechanical Engineering, Graduate Division of University of California, Berkeley, 2002.

De Vuyst, E., et al., "In situ bipolar Electroporation for localized cell loading with reporter dyes and investigating gap unctional coupling", Biophysical Journal, 94(2): p. 469-479 (2008).

Dean, Nonviral Gene Transfer to Skeletal, Smooth, and Cardiac Muscle in Living Animals, Am J. Physiol Cell Physiol 289: 233-245, 2005.

Demirbas, M. F., "Thermal Energy Storage and Phase Change Materials: An Overview" Energy Sources Part B 1(1), 85-95 (2006).

Dev, et al., Medical Applications of Electroporation, IEEE Transactions of Plasma Science, vol. 28, No. 1, pp. 206-223, Feb. 2000.

Dev, et al., Sustained Local Delivery of Heparin to the Rabbit Arterial Wall with an Electroporation Catheter, Catheterization and Cardiovascular Diagnosis, Nov. 1998, vol. 45, No. 3, pp. 337-343.

Duraiswami, et al., Boundary Element Techniques for Efficient 2-D and 3-D Electrical Impedance Tomography, Chemical Engineering Science, vol. 52, No. 13, pp. 2185-2196, 1997.

Duraiswami, et al., Efficient 2D and 3D Electrical Impedance Tomography Using Dual Reciprocity Boundary Element Techniques, Engineering Analysis with Boundary Elements 22, (1998) 13-31.

Duraiswami, et al., Solution of Electrical Impedance Tomography Equations Using Boundary Element Methods, Boundary Element Technology XII, 1997, pp. 226-237.

Edd et al., "Mathematical modeling of irreversible electroporation for treatment planning." Technology in Cancer Research and Treatment, vol. 6, No. 4, pp. 275-286 (2007).

Edd, J., et al., In-Vivo Results of a New Focal Tissue Ablation Technique: Irreversible Electroporaton, IEEE Trans. Biomed. Eng. 53 (2006) p. 1409-1415.

Ellis TL, Garcia PA, Rossmeisl JH, Jr., Henao-Guerrero N, Robertson J, et al., "Nonthermal irreversible electroporation for intracranial surgical applications. Laboratory investigation", J Neurosurg 114: 681-688 (2011).

Eppich et al., "Pulsed electric fields for selection of hematopoietic cells and depletion of tumor cell contaminants." Nature Biotechnology 18, pp. 882-887 (2000).

Erez, et al, Controlled Destruction and Temperature Distributions in Biological Tissues Subjected to Monoactive Electrocoagulation, Transactions of the ASME: Journal of Mechanical Design, vol. 102, Feb. 1980.

Ermolina et al., "Study of normal and malignant white blood cells by time domain dielectric spectroscopy." IEEE Transactions on Dielectrics and Electrical Insulation, 8 (2001) pp. 253-261.

Esser, A.T., et al., "Towards solid tumor treatment by irreversible electroporation: intrinsic redistribution of fields and currents in tissue". Technol Cancer Res Treat, 6(4): p. 261-74 (2007).

Esser, A.T., et al., "Towards Solid Tumor Treatment by Nanosecond Pulsed Electric Fields", Technology in Cancer Research & Treatment, 8(4): p. 289-306 (2009).

Faroja, M., et al., "Irreversible Electroporation Ablation: Is the entire Damage Nonthermal?", Radiology, 266(2), 462-470 (2013).

Fischbach et al., "Engineering tumors with 3D scaffolds." Nat Meth 4, pp. 855-860 (2007).

Flanagan et al., "Unique dielectric properties distinguish stem cells and their differentiated progeny." Stem Cells, vol. 26, pp. 656-665 (2008).

Fong et al., "Modeling Ewing sarcoma tumors in vitro with 3D scaffolds." Proceedings of the National Academy of Sciences vol. 110, pp. 6500-6505 (2013).

Foster RS, "High-intensity focused ultrasound in the treatment of prostatic disease", European Urology, 1993, vol. 23 Suppl 1, pp. 29-33.

Foster, R.S., et al., Production of Prostatic Lesions in Canines Using Transrectally Administered High-Intensity Focused Ultrasound. Eur. Urol., 1993; 23: 330-336.

Fox, et al., Sampling Conductivity Images via MCMC, Mathematics Department, Auckland University, New Zealand, May 1997.

Freeman, S.A., et al., Theory of Electroporation of Planar Bilayer-Membranes—Predictions of the Aqueous Area, Change in Capacitance, and Pore-Pore Separation. Biophysical Journal, 67(1): p. 42-56 (1994).

Garcia et al., "Irreversible electroporation (IRE) to treat brain cancer." ASME Summer Bioengineering Conference, Marco Island, FL, Jun. 25-29, 2008, 2 pages.

Garcia et al., "Non-thermal irreversible electroporation (N-TIRE) and adjuvant fractionated radiotherapeutic multimodal therapy for intracranial malignant glioma in a canine patient," Technol Cancer Res Treat, 10, pp. 73-83, 2011.

Garcia et al., "Towards a Predictive Model of Electroporation-Based Therapies using Pre-Pulse Electrical Measurements" Abstract presented in the IEEE Engineering in Medicine and Biology Conference in Aug. 28, 2012 in San Diego, California, 4 pages.

Garcia P.A., et al., "7.0-T Magnetic Resonance Imaging Characterization of Acute Blood-Brain-Barrier Disruption Achieved with Intracranial Irreversible Electroporation", PLOS ONE, Nov. 2012, 7:11, e50482.

Garcia P.A., et al., "Pilot study of irreversible electroporation for intracranial surgery", Conf Proc IEEE Eng Med Biol Soc, 2009:6513-6516, 2009.

Garcia, et al. "A Parametric Study Delineating Irreversible Electroporation from Thermal Damage Based on a Minimally Invasive Intracranial Procedure," Biomed Eng Online, vol. 10:34, 22 pp. 2011.

Garcia, P. et al. Intracranial nonthermal irreversible electroporation: in vivo analysis. J Membr Biol 236, 127-136 (2010).

Garcia, Paulo A., Robert E. Neal II and Rafael V. Davalos, Chapter 3, Non-Thermal Irreversible Electroporation for Tissue Ablation, In:

(56) References Cited

OTHER PUBLICATIONS

Electroporation in Laboratory and Clinical Investigations ISBN 978-1-61668-327-6 Editors: Enrico P. Spugnini and Alfonso Baldi, 2010, 22 pages.
Gascoyne et al., "Membrane changes accompanying the induced differentiation of Friend murine erythroleukemia cells studied by dielectrophoresis." Biochimica et Biophysica Acta (BBA)-Biomembranes, vol. 1149, pp. 119-126 (1993).
Gauger, et al., A Study of Dielectric Membrane Breakdown in the Fucus Egg, J. Membrane Biol., vol. 48, No. 3, pp. 249-264, 1979.
Gehl, et al., In Vivo Electroporation of Skeletal Muscle: Threshold, Efficacy and Relation to Electric Field Distribution, Biochimica et Biphysica Acta 1428, 1999, pp. 233-240.
Gençer, et al., Electrical Impedance Tomography: Induced-Current Imaging Achieved with a Multiple Coil System, IEEE Transactions on Biomedical Engineering, vol. 43, No. 2, Feb. 1996.
Gilbert, et al., Novel Electrode Designs for Electrochemotherapy, Biochimica et Biophysica Acta 1334, 1997, pp. 9-14.
Gilbert, et al., The Use of Ultrasound Imaging for Monitoring Cryosurgery, Proceedings 6th Annual Conference, IEEE Engineering in Medicine and Biology, 107-111, 1984.
Gilbert, T. W., et al., "Decellularization of tissues and organs", Biomaterials, Elsevier Science Publishers, Barking, GB, vol. 27, No. 19, Jul. 1, 2006, pp. 3675-3683.
Gimsa et al., "Dielectric spectroscopy of single human erythrocytes at physiological ionic strength: dispersion of the cytoplasm." Biophysical Journal, vol. 71, pp. 495-506 (1996).
Glidewell, et al., the Use of Magnetic Resonance Imaging Data and the Inclusion of Anisotropic Regions in Electrical Impedance Tomography, Biomed, Sci. Instrum. 1993; 29: 251-7.
Golberg, A. and Rubinsky, B., "A statistical model for multidimensional irreversible electroporation cell death in tissue." Biomed Eng Online, 9, 13 pages, 2010.
Gothelf, et al., Electrochemotherapy: Results of Cancer Treatment Using Enhanced Delivery of Bleomycin by Electroporation, Cancer Treatment Reviews 2003: 29: 371-387.
Gowrishankar T.R., et al., "Microdosimetry for conventional and supra-electroporation in cells with organelles". Biochem Biophys Res Commun, 341(4): p. 1266-76 (2006).
(Aycock, Kenneth N. et al.) Co-pending U.S. Appl. No. 17/535,742, filed Nov. 26, 2021.
(Davalos, Rafael et al.) Co-Pending Application No. PCT/US21/51551, filed Sep. 22, 2021.
(Davalos, Rafael V. et al.) Co-pending U.S. Appl. No. 17/172,731, filed Feb. 10, 2021.
(Davalos, Rafael V. et al.) Co-pending U.S. Appl. No. 17/277,662, filed Mar. 18, 2021.
(Davalos, Rafael V. et al.) Co-pending Application No. 198614893 filed Apr. 16, 2021 (See PCT/US19/51731), (3 pages).
(Garcia, Paulo A. el al.) Co-pending U.S. Appl. No. 17/591,992, filed Feb. 3, 2022.
(Neal, Robert el al.) Co-pending U.S. Appl. No. 17/338,960, filed Jun. 4, 2021.
(Sano, Michael B. et al.) Co-pending U.S. Appl. No. 17/862,486, filed Jul. 12, 2022.
Alinezhadbalalami, N. et al., "Generation of Tumor-activated T cells Using Electroporation", Bioelectrochemistry 142 (2021) 107886, Jul. 13, 2021, 11 pages.
Arena, C. B. et al., "Theoretical Considerations of Tissue Electroporation With High-Frequency Bipolar Pulses," IEEE Trans. Biomed. Eng., vol. 58, No. 5, 1474-1482, 2011, 9 pages.
Bhonsle, S. P. et al., "Mitigation of impedance changes due to electroporation therapy using bursts of high-frequency bipolar pulses," Biomed. Eng. (NY)., vol. 14, No. Suppl 3, 14 pages, 2015.
Buist et al., "Efficacy of multi-electrode linear irreversible electroporation," Europace, vol. 23, No. 3, pp. 464-468, 2021, 5 pages.
Butikofer, R. et al., "Electrocutaneous Nerve Stimulation-I: Model and Experiment," IEEE Trans. Biomed. Eng., vol. BME-25, No. 6, 526-531, 1978, 6 pages.

Butikofer, R. et al., "Electrocutaneous Nerve Stimulation-II: Stimulus Waveform Selection," IEEE Trans. Biomed. Eng., vol. BME-26, No. 2, 69-75, 1979, abstract only, 2 pages.
Cosman, E. R. et al., "Electric and Thermal Field Effects in Tissue Around Radiofrequency Electrodes," Pain Med., vol. 6, no. 6, 405-424, 2005, 20 pages.
Groen, M. H. A. et al., "In Vivo Analysis of the Origin and Characteristics of Gaseous Microemboli during Catheter-Mediated Irreversible Electroporation," Europace, 2021, 23(1), 139-146.
Guenther, E. et al., "Electrical breakdown in tissue electroporation," Biochem. Biophys. Res. Commun., vol. 467, No. 4, 736-741, Nov. 2015, 15 pages.
Macherey, O. et al., "Asymmetric pulses in cochlear implants: Effects of pulse shape, polarity, and rate," JARO—J. Assoc. Res. Otolaryngol., vol. 7, No. 3, 253-266, 2006, 14 pages.
McIntyre, C. C. et al., "Modeling the excitability of mammalian nerve fibers: Influence of afterpotentials on the recovery cycle," J. Neurophysiol., vol. 87, No. 2, 995-1006, 2002, 12 pages.
McNeal, D. R., "Analysis of a Model for Excitation of Myelinated Nerve," IEEE Trans. Biomed. Eng., vol. BME-23, No. 4, 329-337, 1976, 9 pages.
Mercadal, B. et al., "Avoiding nerve stimulation in irreversible electroporation: A numerical modeling study," Phys. Med. Biol., vol. 62, No. 20, 8060-8079, 2017, 28 pages.
Miklavčič, D. et al., "The effect of high frequency electric pulses on muscle contractions and antitumor efficiency in vivo for a potential use in clinical electrochemotherapy," Bioelectrochemistry, vol. 65, 121-128, 2004, 8 pages.
Partridge, B. R. et al., "High-Frequency Irreversible Electroporation for treatment of Primary Liver Cancer: A Proof-of-Principle Study in Canine Hepatocellular Carcinoma," J. Vasc. Interv. Radiol., vol. 31, No. 3, 482-491.e4, Mar. 2020, 19 pages.
Patent No. JP 7051188, Opposition dated Jul. 4, 2022 (16 pages) with English translation (13 pages).
PCT Application No. PCT/US19/51731, International Preliminary Report on Patentability dated Mar. 23, 2021, 13 pages.
Pending U.S. Appl. No. PCT/US21/51551, International Search Report and Written Opinion dated Dec. 29, 2021, 14 pages.
Pending U.S. Appl. No. 14/686,380, Advisory Action dated Oct. 20, 2021, 3 pages.
Pending U.S. Appl. No. 14/686,380, Appeal Brief filed Nov. 5, 2021, 21 pages.
Pending U.S. Appl. No. 14/686,380, Applicant Initiated Interview Summary dated Feb. 9, 2021, 3 pages.
Pending U.S. Appl. No. 14/686,380, Applicant Initiated Interview Summary dated Mar. 8, 2021, 2 pages.
Pending U.S. Appl. No. 14/686,380, Examiners Answer to Appeal Brief, dated Feb. 18, 2022, 16 pages.
Pending U.S. Appl. No. 14/686,380, Reply Brief, dated Apr. 12, 2022, 4 pages.
Pending U.S. Appl. No. 14/686,380, Amendment after Notice of Appeal, dated Oct. 12, 2021, 6 pages.
Pending U.S. Appl. No. 14/686,380, Non-Final Office Action dated May 7, 2021, 17 pages.
Pending U.S. Appl. No. 14/808,679, Appeal Brief, filed Jun. 3, 2021, 25 pages.
Pending U.S. Appl. No. 14/808,679, Appeal Decision dated Jul. 19, 2022, 8 pages.
Pending U.S. Appl. No. 14/808,679, Examiner's Answer to Appeal Brief, dated Sep. 15, 2021, 6 pages.
Pending U.S. Appl. No. 14/808,679, Notice of Allowance dated Aug. 17, 2022, 8 pages.
Pending U.S. Appl. No. 14/808,679, Panel Decision from Pre-Appeal Brief Review, dated Apr. 26, 2021, 2 pages.
Pending U.S. Appl. No. 14/808,679, Pre-Appeal Brief Reasons for Request for Review, dated Mar. 29, 2021, 5 pages.
Pending U.S. Appl. No. 14/808,679, Reply Brief, dated Nov. 15, 2021, 5 pages.
Pending U.S. Appl. No. 16/210,771, Applicant-Initiated Interview Summary dated Aug. 13, 2021, 4 pages.
Pending U.S. Appl. No. 16/210,771, Final Office Action dated Apr. 13, 2022, 10 pages.

(56) References Cited

OTHER PUBLICATIONS

Pending U.S. Appl. No. 16/210,771, Final Office Action dated May 14, 2021, 13 pages.
Pending U.S. Appl. No. 16/210,771, Non-Final Office Action dated Oct. 7, 2021, 10 pages.
Pending U.S. Appl. No. 16/210,771, Response to Apr. 13, 2022 Final Office Action, dated Jul. 13, 2022, 7 pages.
Pending U.S. Appl. No. 16/210,771, Response to May 14, 2021 Final Office Action, filed Aug. 16, 2021, 6 pages.
Pending U.S. Appl. No. 16/210,771, Response to Oct. 7, 2021 Non-Final Office Action, dated Jan. 7, 2022, 7 pages.
Pending U.S. Appl. No. 16/210,771, Rule 1.132 Declaration dated Jan. 7, 2022, 3 pages.
Pending U.S. Appl. No. 16/375,878, Applicant-Initiated Interview Summary dated Aug. 23, 2022, 7 pages.
U.S. Appl. No. 16/280,511, file history through Aug. 2021, 31 pages.
U.S. Appl. No. 16/352,759 (U.S. Pat. No. 11,311,329), file history through Mar. 2022, 258 pages.
U.S. Appl. No. 16/372,520 (U.S. Pat. No. 11,382,681), file history through Jun. 2022, 107 pages.
U.S. Appl. No. 16/404,392 (U.S. Pat. No. 11,254,926), file history through Jan. 2022, 153 pages.
U.S. Appl. No. 16/520,901 (U.S. Pat. No. 11,406,820, file history through May 2022, 39 pages.
Valdez, C. M. et al., "The interphase interval within a bipolar nanosecond electric pulse modulates bipolar cancellation," Bioelectromagnetics, vol. 39, No. 6, 441-450, 2018, 28 pages.
Verma, A. et al., "Primer on Pulsed Electrical Field Ablation: Understanding the Benefits and Limitations," Circ. Arrhythmia Electrophysiol., No. September, pp. 1-16, 2021, 16 pages.
Vižintin, A. et al., "Effect of interphase and interpulse delay in high-frequency irreversible electroporation pulses on cell survival, membrane permeabilization and electrode material release," Bioelectrochemistry, vol. 134, Aug. 2020, 14 pages.
Wandel, A. et al. "Optimizing Irreversible Electroporation Ablation with a Bipolar Electrode," Journal of Vascular and Interventional Radiology, vol. 27, Issue 9, 1441-1450.e2, 2016.
Yarmush, M. L. et al., "Electroporation-Based Technologies for Medicine: Principles, Applications, and Challenges," Annu. Rev. Biomed. Eng., vol. 16, No. 1, 295-320, 2014, 29 pages.
Zhao, J. et al."Irreversible electroporation reverses resistance to immune checkpoint blockade in pancreatic cancer", Nature Communications (2019) 10:899, 14 pages.
Pending U.S. Appl. No. 16/375,878, Final Office Action dated Apr. 15, 2022, 8 pages.
Pending U.S. Appl. No. 16/375,878, Non-Final Office Action dated Jun. 24, 2021, 8 pages.
Pending U.S. Appl. No. 16/375,878, Response to Apr. 15, 2022 Final Office Action, dated Aug. 15, 2022, 8 pages.
Pending U.S. Appl. No. 16/375,878, Response to Jun. 24, 2021 Non-Final Office Action, dated Dec. 22, 2021, 8 pages.
Pending U.S. Appl. No. 16/443,351, Non-Final Office Action, dated Jun. 10, 2022, 15 pages.
Pending U.S. Appl. No. 16/535,451 Applicant-Initiated Interview Summary for interview held Apr. 7, 2022, 1 page.
Pending U.S. Appl. No. 16/535,451 Final Office Action, dated Feb. 4, 2022, 7 pages.
Pending U.S. Appl. No. 16/535,451 Non-Final Office Action, dated Apr. 19, 2022, 6 pages.
Pending U.S. Appl. No. 16/535,451 Non-Final Office Action, dated Jun. 24, 2021, 12 pages.
Pending U.S. Appl. No. 16/535,451 Notice of Allowance, dated May 16, 2022, 9 pages.
Pending U.S. Appl. No. 16/535,451 Response to Apr. 19, 2022 Non-Final Office Action, dated Apr. 27, 2022, 6 pages.
Pending U.S. Appl. No. 16/535,451 Response to Jun. 24, 2021 Non-Final Office Action, dated Oct. 26, 2021, 10 pages.
Pending U.S. Appl. No. 16/655,845, Final Office Action, dated Jul. 26, 2022, 7 pages.
Pending U.S. Appl. No. 16/655,845, Non-Final Office Action, dated Mar. 1, 2022, 8 pages.
Pending U.S. Appl. No. 16/655,845, Response to Mar. 1, 2022 Non-Final Office Action, dated Jun. 1, 2022, 10 pages.
Pending U.S. Appl. No. 16/655,845, Response to Oct. 21, 2021 Restriction Requirement, dated Dec. 21, 2021, 7 pages.
Pending U.S. Appl. No. 16/655,845, Restriction Requirement, dated Oct. 21, 2021, 6 pages.
Pending U.S. Appl. No. 16/747,219, Applicant-Initiated Interview Summary dated Aug. 3, 2022, 4 pages.
Pending U.S. Appl. No. 16/747,219, Non-Final Office Action dated Mar. 31, 2022, 12 pages.
Pending U.S. Appl. No. 16/747,219, Response to Mar. 31, 2022 Non-Final Office Action, dated Aug. 1, 2022, 8 pages.
Pending U.S. Appl. No. 16/865,031, Second Preliminary Amendment, filed Sep. 17, 2021, 10 pages.
Pending U.S. Appl. No. 16/865,772, Final Office Action dated Aug. 22, 2022, 18 pages.
Pending U.S. Appl. No. 16/865,772, Non-Final Office Action dated Apr. 11, 2022, 16 pages.
Pending U.S. Appl. No. 16/865,772, Response to Apr. 11, 2022 Non-Final Office Action, dated Jul. 11, 2022, 8 pages.
Pending U.S. Appl. No. 16/865,772, Second Preliminary Amendment filed Jun. 30, 2020, 4 pages.
Pending U.S. Appl. No. 16/865,772, Third Preliminary Amendment, filed Sep. 17, 2021, 6 pages.
Pending U.S. Appl. No. 17/069,359, Preliminary Amendment, filed Sep. 17, 2021, 6 pages.
Pending U.S. Appl. No. 17/172,731, Preliminary Amendment, filed Jun. 27, 2022, 9 pages.
Pending U.S. Appl. No. 17/172,731, Preliminary Amendment, filed Sep. 17, 2021, 7 pages.
Pending U.S. Appl. No. 17/277,662 Preliminary Amendment filed Mar. 18, 2021, 8 pages.
Pending U.S. Appl. No. 17/338,960, Response to Notice to File Missing Parts and Amendment, filed Aug. 16, 2021, 7 pages.
Pending Application No. 19861489.3 Extended European Search Report dated May 16, 2022 (8 pages).
Pending Application No. 19861489.3 Response to Communication pursuant to Rules 161(2) and 162 EPC, filed Nov. 16, 2021, 7 pages.
Pending Application No. AU 2015259303, Certificate of Grant dated Feb. 10, 2022, 1 page.
Pending Application No. AU 2015259303, Notice of Acceptance and Allowed Claims, dated Oct. 15, 2021, 7 pages.
Pending Application No. AU 2015259303, Response to First Examination Report dated Sep. 20, 2021, 126 pages.
Pending Application No. CN 202011281572.3, Amendment filed Sep. 8, 2021 (16 pages) with English Version of the Amended Claims (7 pages).
Pending Application No. EP 15793361.5, Communication Pursuant to Article 94(3) EPC, dated May 3, 2021, 4 pages.
Pending Application No. EP 15793361.5, Response to May 3, 2021 Communication Pursuant to Article 94(3) EPC, dated Nov. 12, 2021, 12 pages.
Pending Application No. JP 2019-133057, Office Action dated Sep. 1, 2021, 3 pages (and English translation, 4 pages).
Pending Application No. JP 2019-133057, Request for Amendment and Appeal filed Dec. 23, 2021 (8 pages) with English Translation of the Amended Claims (2 pages).
Pending Application No. JP 2019-133057, Response to Sep. 14, 2020 Office Action filed Mar. 18, 2021 (6 pages) with English Version of claims and response (5 pages).
Polajžer' T. et al., "Cancellation effect is present in high-frequency reversible and irreversible electroporation," Bioelectrochemistry, vol. 132, 2020, 11 pages.
Reilly, J. P. et al., "Sensory Effects of Transient Electrical Stimulation-Evaluation with a Neuroelectric Model," IEEE Trans. Biomed. Eng., vol. BME-32, No. 12, 1001-1011, 1985, 11 pages.
Rogers, W. R. et al., "Strength-duration curve an electrically excitable tissue extended down to near 1 nanosecond," IEEE Trans. Plasma Sci., vol. 32, No. 4 II, 1587-1599, 2004, 13 pages.

(56) References Cited

OTHER PUBLICATIONS

Rubinsky, L. et al., "Electrolytic Effects During Tissue Ablation by Electroporation," Technol. Cancer Res. Treat., vol. 15, No. 5, NP95-103, 2016, 9 pages.

Sano, M. B. et al., "Burst and continuous high frequency irreversible electroporation protocols evaluated in a 3D tumor model," Phys. Med. Biol., vol. 63, No. 13, 2018, 17 pages.

Sano, M. B. et al., "Reduction of Muscle Contractions During Irreversible Electroporation Therapy Using High-Frequency Bursts of Alternating Polarity Pulses: a Laboratory Investigation in an Ex Vivo Swine Model," J. Vasc. Interv. Radiol., vol. 29, No. 6, 893-898.e4, Jun. 2018, 18 pages.

U.S. Appl. No. 16/152,743 (U.S. Pat. No. 11,272,979), file history through Jan. 2022, 89 pages.

U.S. Appl. No. 16/275,429 (U.S. Pat. No. 10,959,772), file history through Feb. 2021, 18 pages.

(Garcia, Paulo A. et al.) Co-Pending U.S. Appl. No. 18/100,835, filed Jan. 24, 2023, Specification, Claims, Figures.

Pending U.S. Appl. No. 14/686,380, Appeal Decision dated Jan. 30, 2023,15 pages.

Pending U.S. Appl. No. 16/210,771, Amendment after Notice of Allowance dated Dec. 29, 2022, 6 pages.

Pending U.S. Appl. No. 16/375,878, Non-Final Office Action dated Jan. 23, 2023, 8 pages.

Pending U.S. Appl. No. 16/747,219, Response to Nov. 10, 2022 Final Office Action, dated Feb. 10, 2023, 6 pages.

Pending U.S. Appl. No. 16/865,031, Response to Nov. 28, 2022 Non-Final Office Action, dated Feb. 27, 2023, 10 pages.

Pending U.S. Appl. No. 16/865,772, Non-Final Office Action dated Jan. 20, 2023, 17 pages.

Pending U.S. Appl. No. 16/865,772, Response to Aug. 22, 2022 Final Office Action, dated Dec. 22, 2022, 8 pages.

Pending U.S. Appl. No. 16/915,760, Non-Final Office Action dated Jan. 19, 2023, 8 pages.

Pending U.S. Appl. No. 17/069,359, Response to Nov. 25, 2022 Non-Final Office Action, dated Feb. 27, 2023, 7 pages.

Pending U.S. Appl. No. 17/172,731, Non-Final Office Action dated Feb. 15, 2023, 7 pages.

Pending U.S. Appl. No. 18/100,835, Preliminary Amendment filed Jan. 26, 2023, 8 pages.

Pending U.S. Appl. No. 18/100,835, Second Preliminary Amendment filed Feb. 6, 2023, 6 pages.

Pending Application No. 19861489.3 Response to May 16, 2022 Extended European Search Report, dated Dec. 13, 2022, 136 pages.

Patent No. JP 7051188, Notice of Reasons for Revocation dated Jan. 30, 2023 (3 pages) with English translation (5 pages).

* cited by examiner

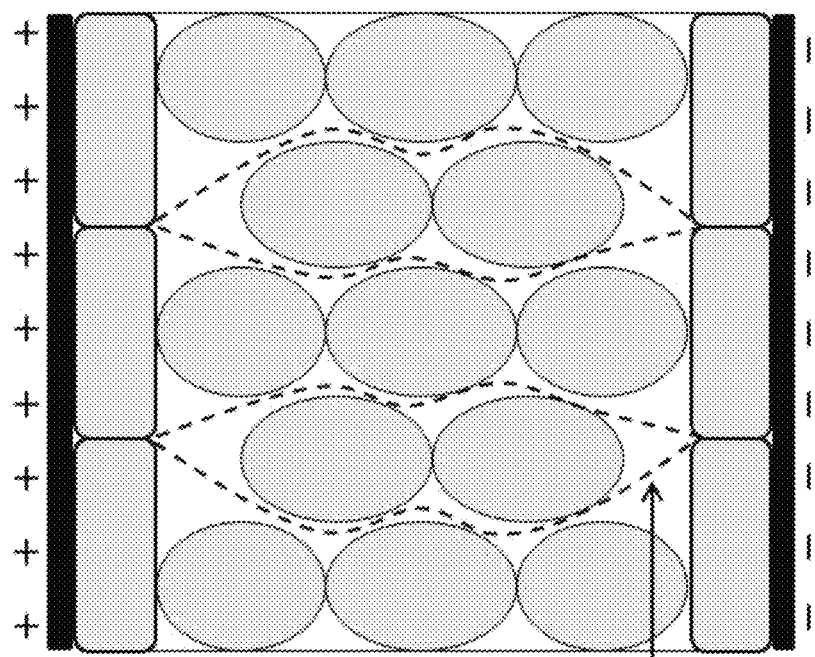
FIG. 1B
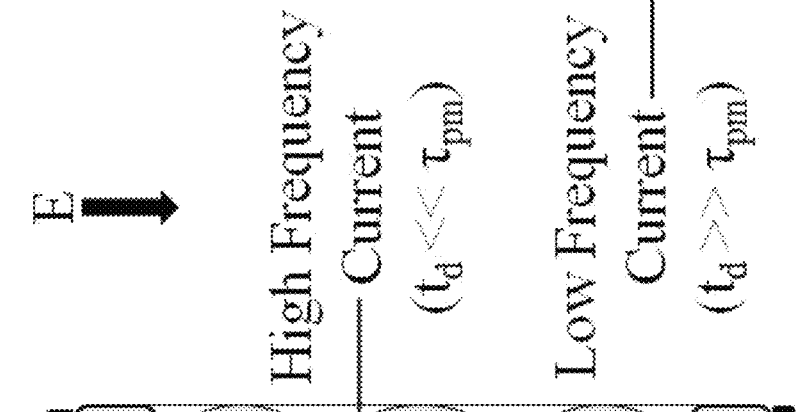
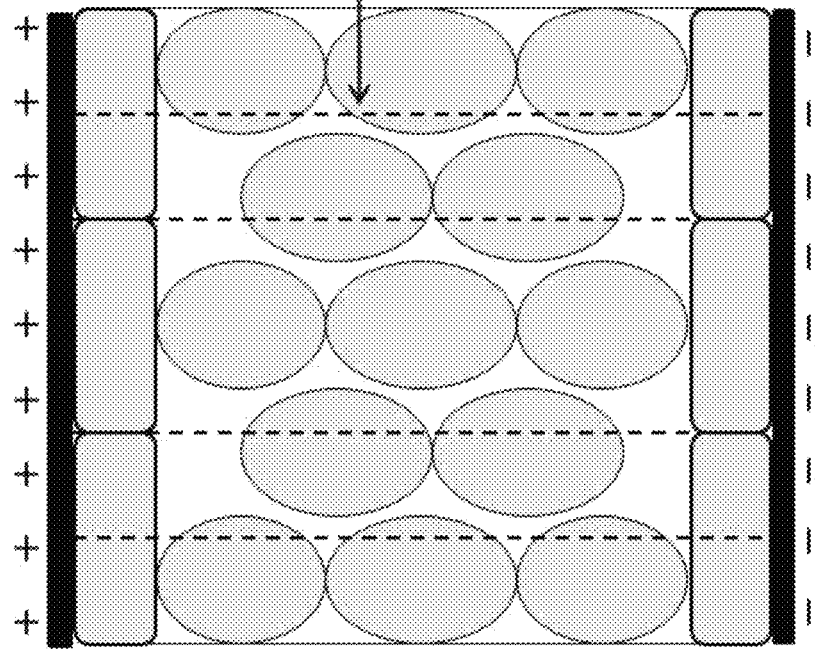
FIG. 1A

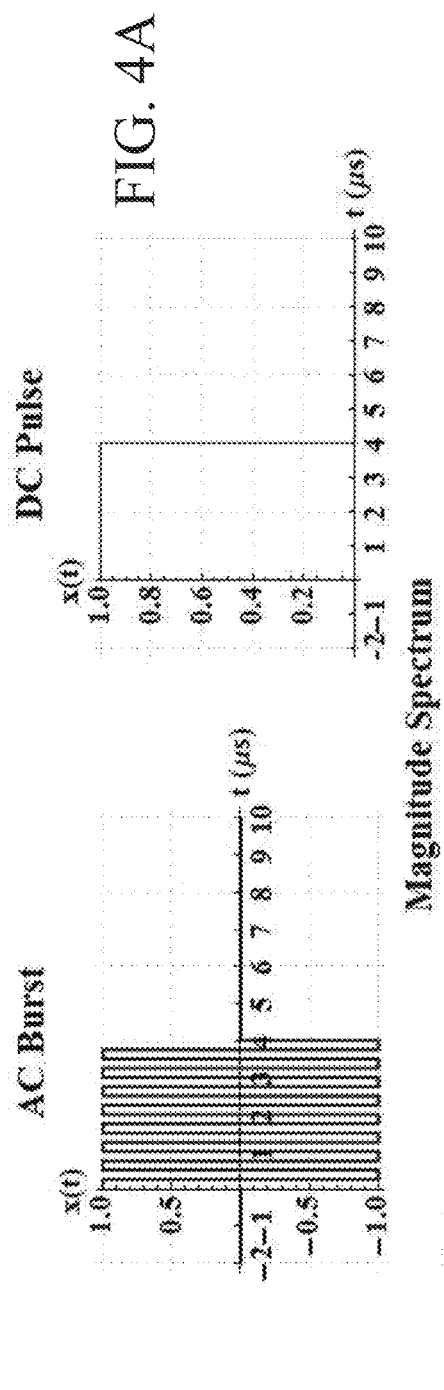
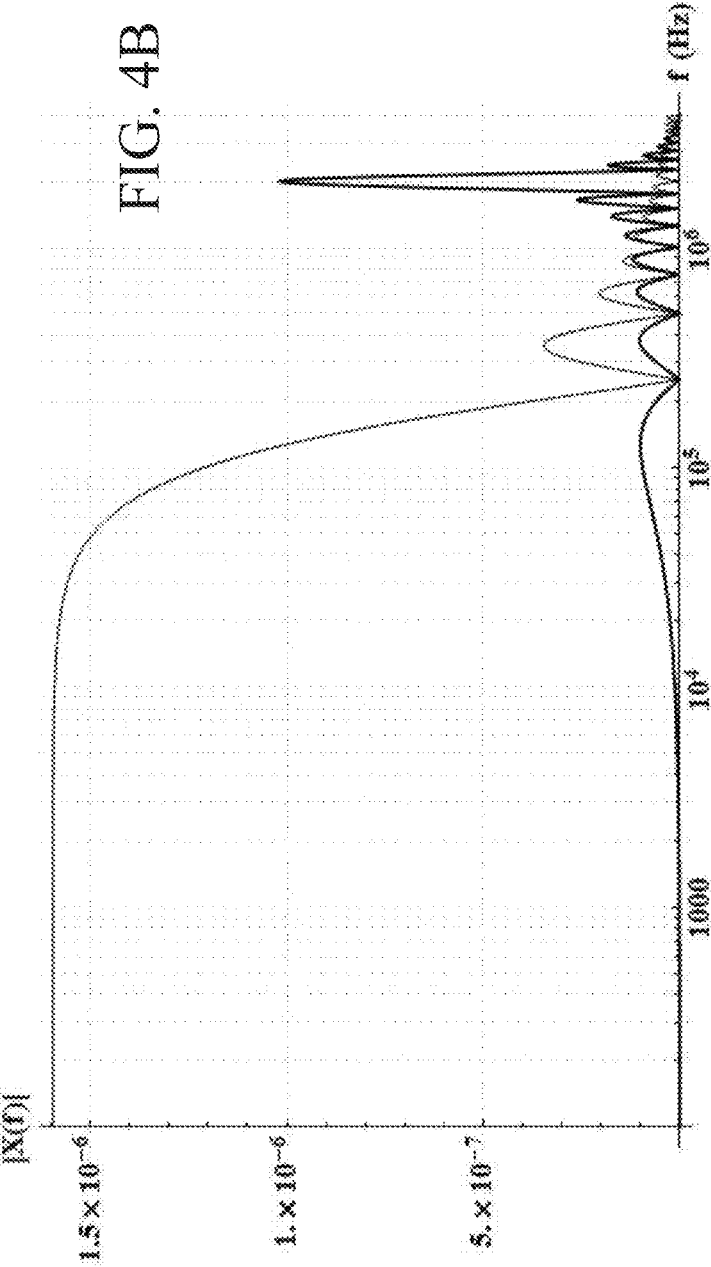
FIG. 4A
FIG. 4B

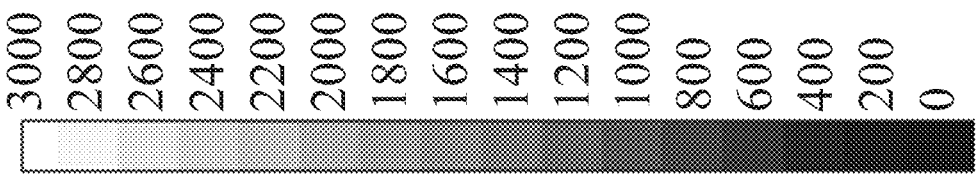
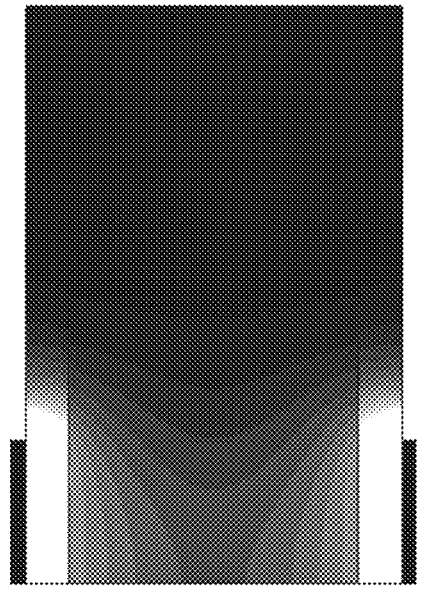
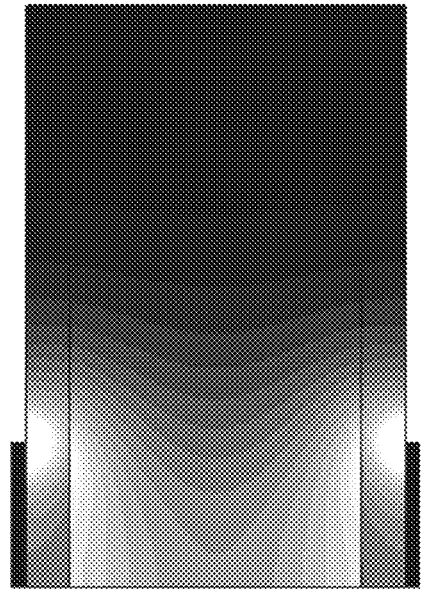
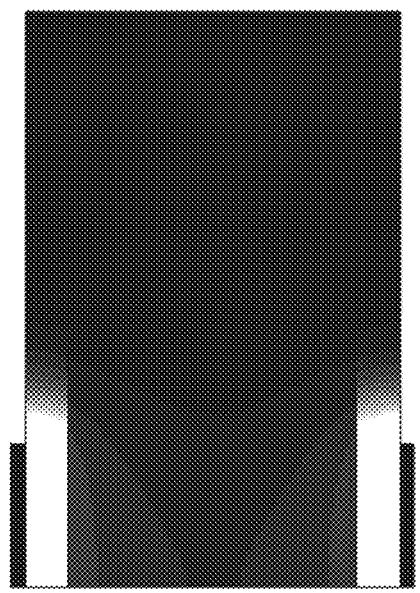
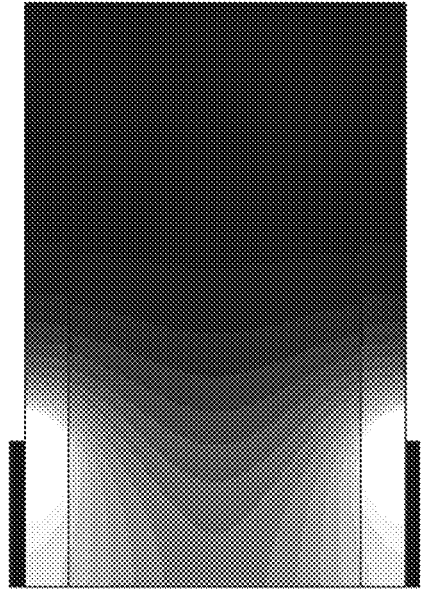
FIG. 9A  FIG. 9B  FIG. 9C  FIG. 9D

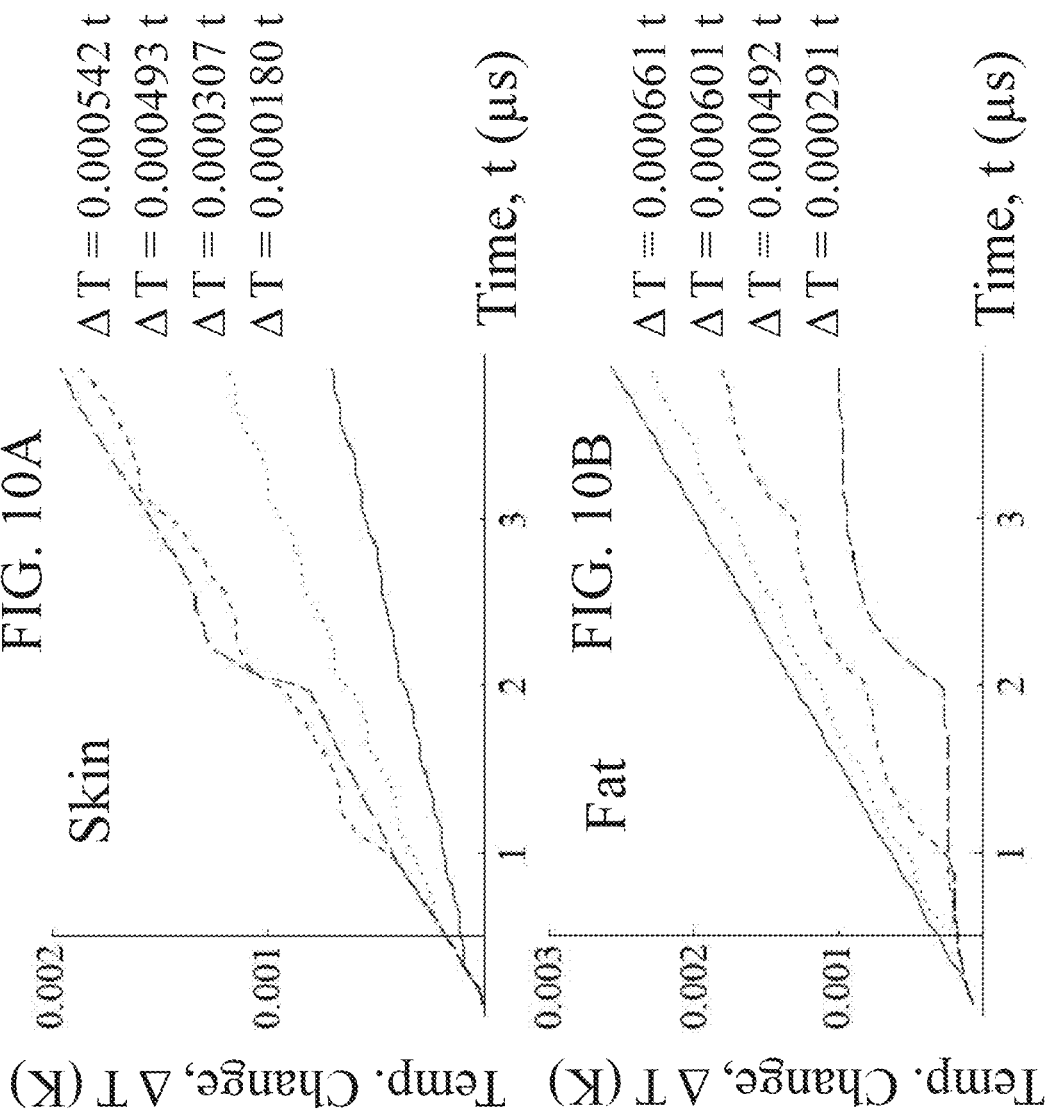

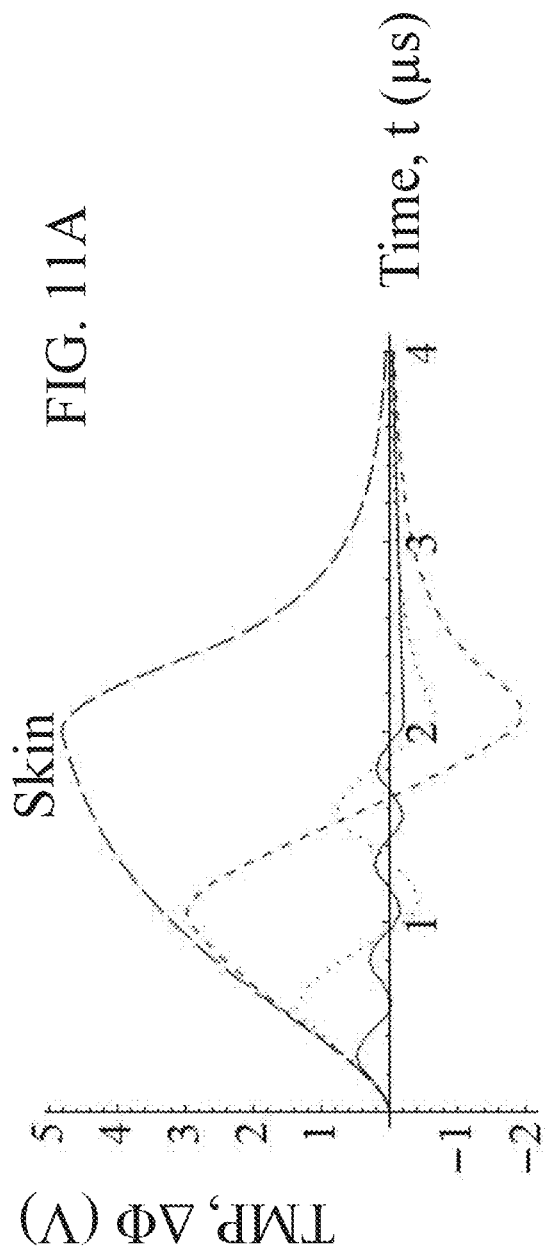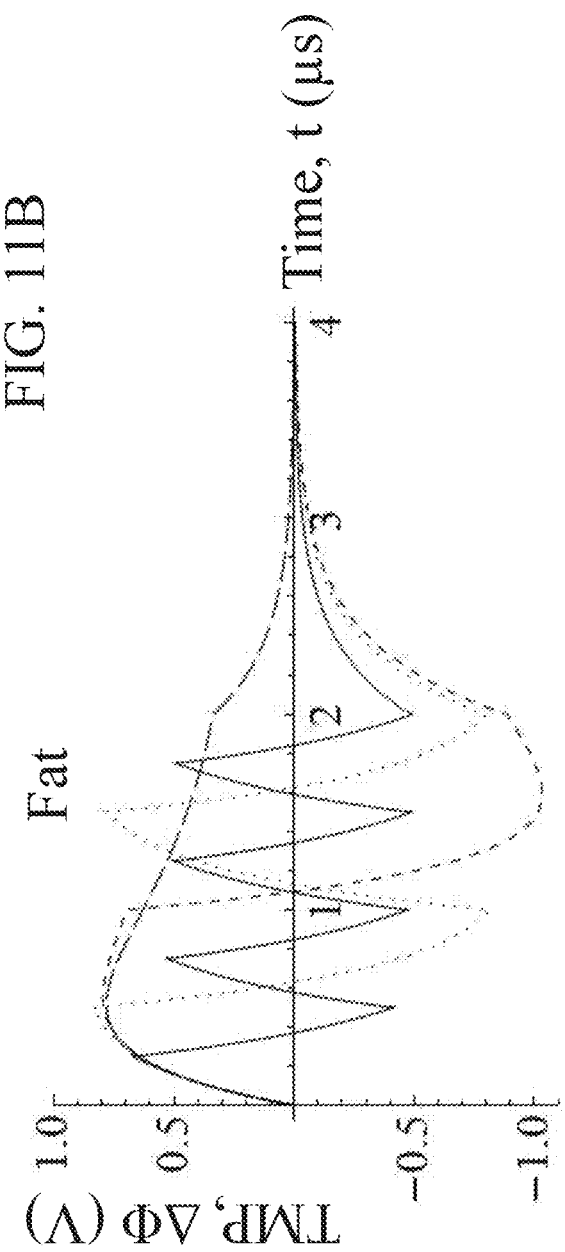

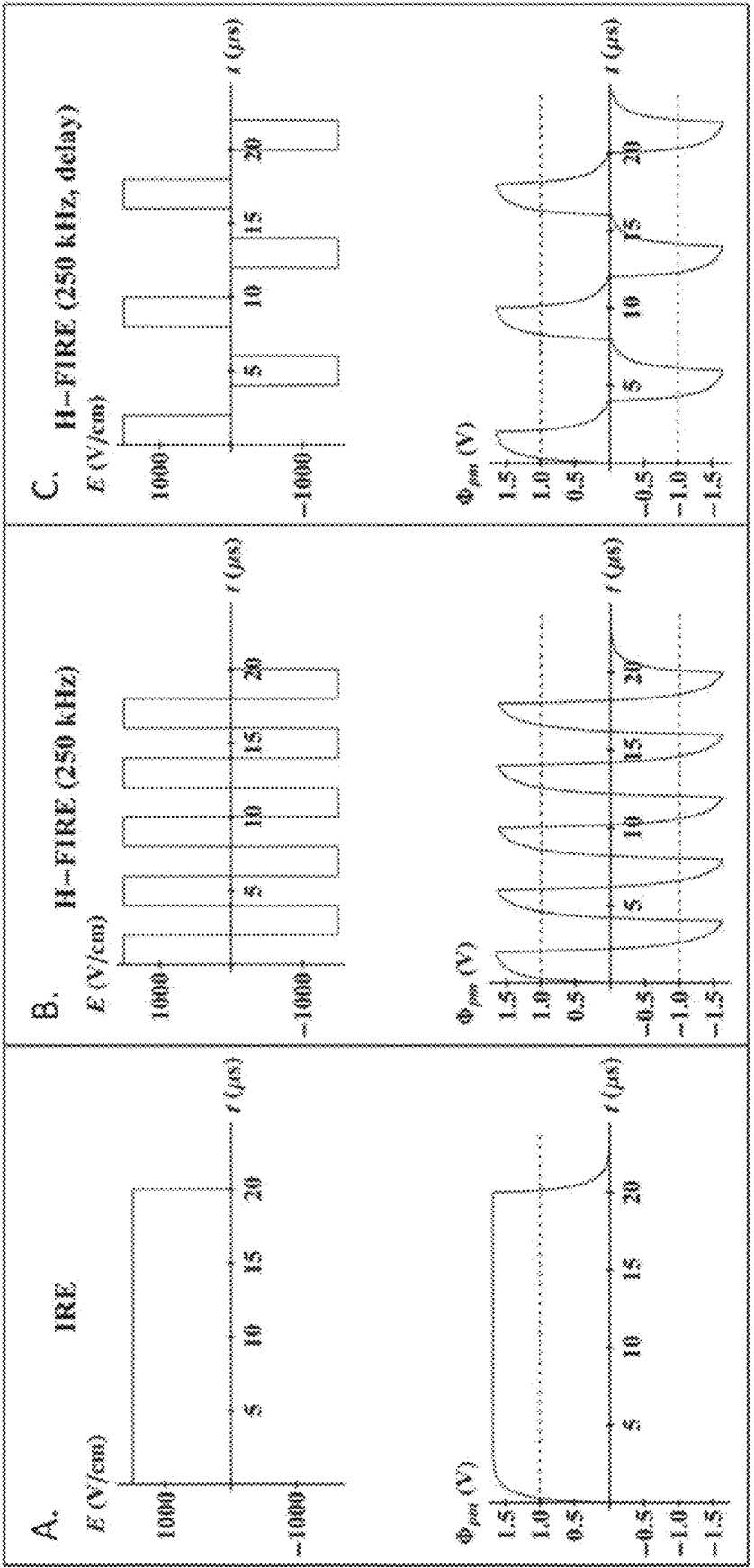

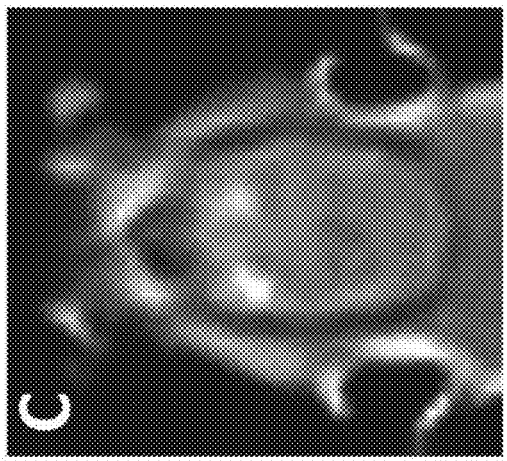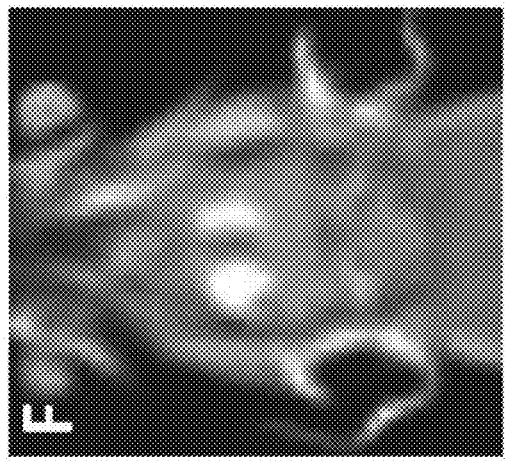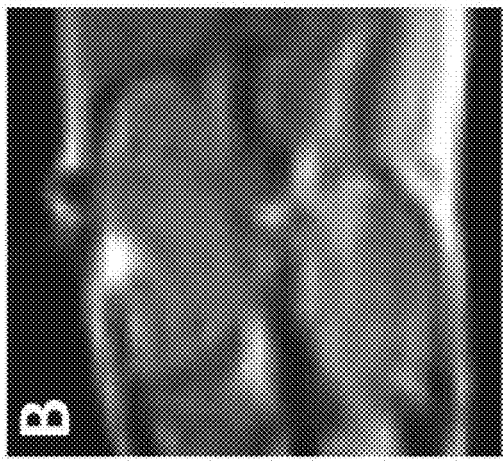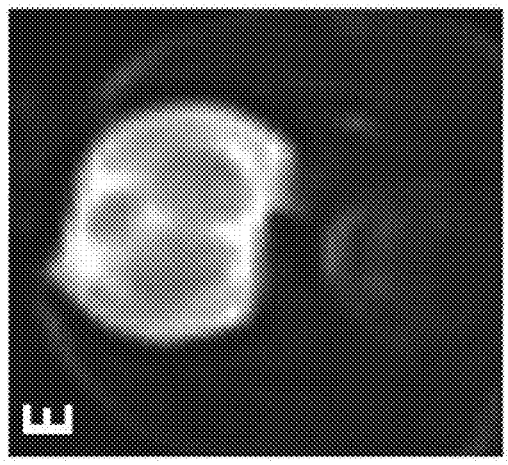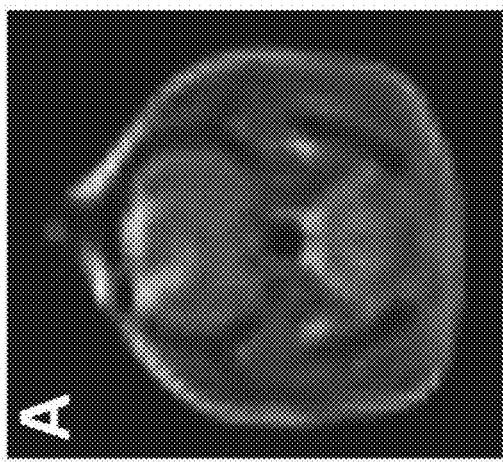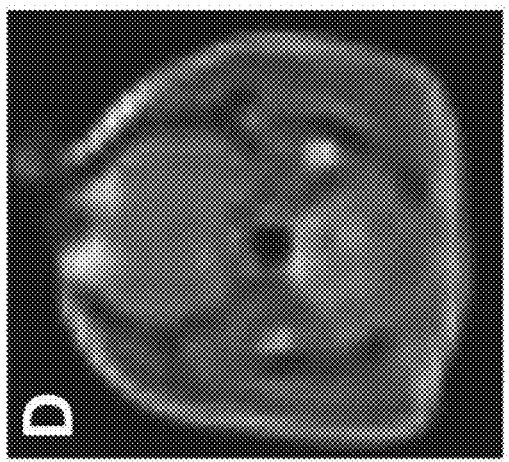

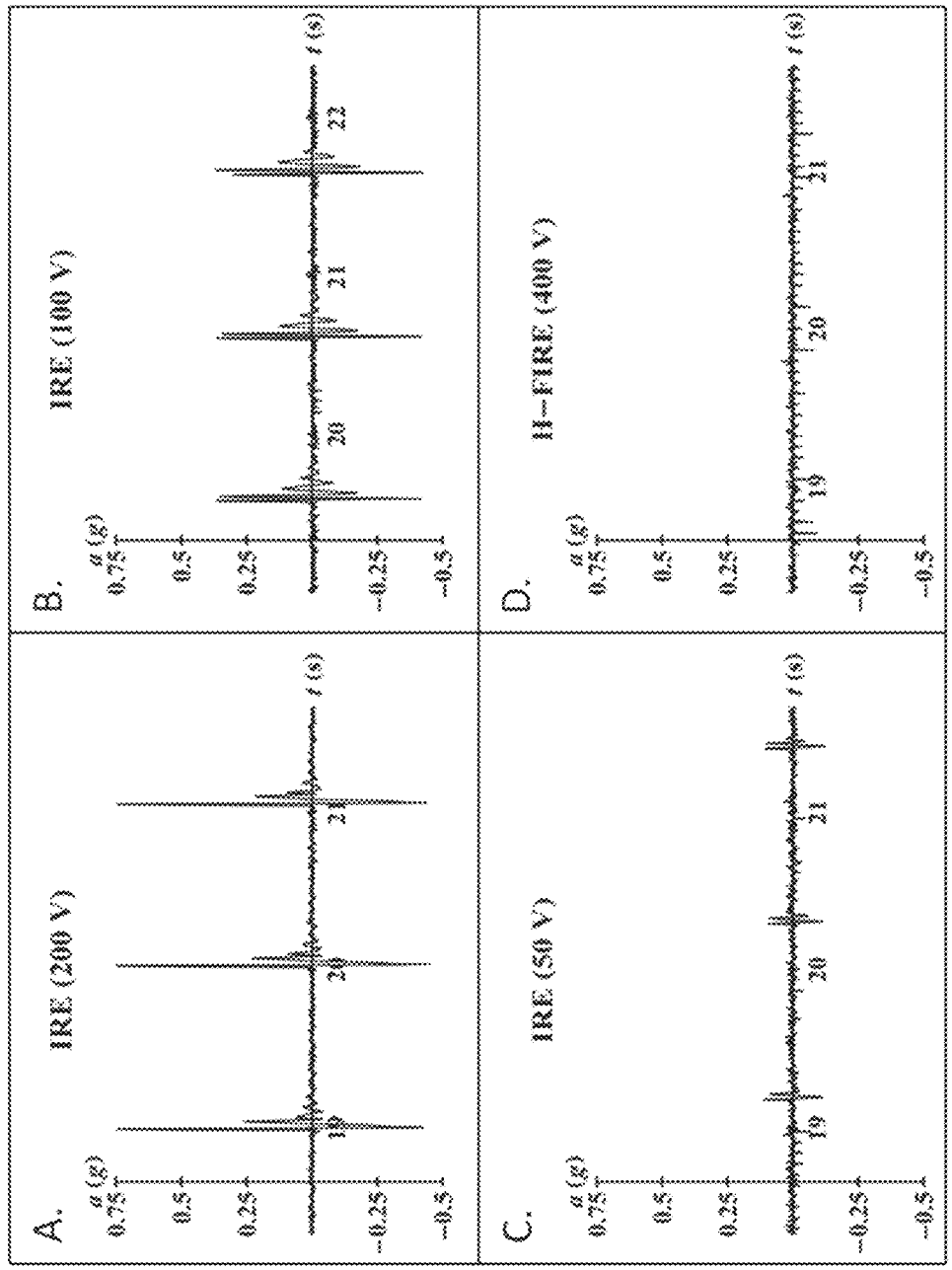

SELECTIVE MODULATION OF INTRACELLULAR EFFECTS OF CELLS USING PULSED ELECTRIC FIELDS

CROSS-REFERENCE TO RELATED APPLICATIONS

The present application is a Continuation of and claims priority to and the benefit of the filing date of U.S. patent application Ser. No. 13/332,133 filed Dec. 20, 2011, which published as U.S. Patent Application Publication No. 20120109122 on May 3, 2012, and which patented as U.S. Pat. No. 10,448,989 on Oct. 22, 2019. The '133 application relies on and claims priority to and the benefit of the filing date of U.S. Provisional Patent Application No. 61/424,872 filed Dec. 20, 2010. The '133 application is a Continuation-In-Part (CIP) application of U.S. patent application Ser. No. 12/757,901, filed Apr. 9, 2010 (patented as U.S. Pat. No. 8,926,606 on Jan. 6, 2015), which relies on and claims priority to and the benefit of the filing date of U.S. Provisional Patent Application Nos. 61/167,997, filed Apr. 9, 2009, and 61/285,618 filed Dec. 11, 2009. The '133 application is also related to International Patent Application No. PCT/US11/66239, filed Dec. 20, 2011, which published as WO 2012/088149 on Jun. 28, 2012 and which claims priority to and the benefit of the filing date of U.S. Provisional Patent Application No. 61/424,872 filed Dec. 20, 2010. The entire disclosures of all of these patent applications are hereby incorporated herein by reference.

STATEMENT OF GOVERNMENT INTEREST

This invention was made with government support under Contract No. CBET-0933335 awarded by National Science Foundation. The government has certain rights in the invention.

BACKGROUND OF THE INVENTION

Field of the Invention

The present invention relates to the field of biomedical engineering and medical treatment of diseases and disorders. More specifically, embodiments of the invention relate to a device and method for destroying aberrant cells, including tumor tissues, using high-frequency, bipolar electrical pulses having a burst width on the order of microseconds and duration of single polarity on the microsecond to nanosecond scale.

Description of Related Art

Electroporation based therapies typically involve delivering multiple, unipolar pulses with a short duration (~100 µs) through electrodes inserted directly into, or adjacent to, the target tissue. See Nuccitelli, R., X. Chen, A. G. Pakhomov, W. H. Baldwin, S. Sheikh, J. L. Pomicter, W. Ren, C. Osgood, R. J. Swanson, J. F. Kolb, S. J. Beebe, and K. H. Schoenbach, *A new pulsed electric field therapy for melanoma disrupts the tumor's blood supply and causes complete remission without recurrence*. Int J Cancer, 2009. 125(2): p. 438-45; Davalos, R. V., L. M. Mir, and B. Rubinsky, *Tissue ablation with irreversible electroporation*. Ann Biomed Eng, 2005. 33(2): p. 223-31 ("Davalos 2005"); Payselj, N., V. Preat, and D. Miklavcic, *A numerical model of skin electroporation as a method to enhance gene transfection in skin*. 11th Mediterranean Conference on Medical and Biological Engineering and Computing 2007, Vols 1 and 2, 2007. 16(1-2): p. 597-601 ("Payselj 2007"); and Payselj, N., Z. Bregar, D. Cukjati, D. Batiuskaite, L. M. Mir, and D. Miklavcic, *The course of tissue permeabilization studied on a mathematical model of a subcutaneous tumor in small animals*. Ieee Transactions on Biomedical Engineering, 2005. 52(8): p. 1373-1381.

The extent of electroporation is attributed to the induced buildup of charge across the plasma membrane, or transmembrane potential (TMP). See Abidor, I. G., V. B. Arakelyan, L. V. Chernomordik, Y. A. Chizmadzhev, V. F. Pastushenko, and M. R. Tarasevich, *Electric Breakdown of Bilayer Lipid-Membranes .1. Main Experimental Facts and Their Qualitative Discussion*. Bioelectrochemistry and Bioenergetics, 1979. 6(1): p. 37-52; Benz, R., F. Beckers, and U. Zimmermann, *Reversible electrical breakdown of lipid bilayer membranes: a charge-pulse relaxation study*. J Membr Biol, 1979. 48(2): p. 181-204; Neumann, E. and K. Rosenheck, *Permeability changes induced by electric impulses in vesicular membranes*. J Membr Biol, 1972. 10(3): p. 279-90; Teissie, J. and T. Y. Tsong, *Electric-Field Induced Transient Pores in Phospholipid-Bilayer Vesicles*. Biochemistry, 1981. 20(6): p. 1548-1554; Zimmermann, U., G. Pilwat, and F. Riemann, *Dielectric breakdown of cell membranes*. Biophys J, 1974. 14(11): p. 881-99; and Kinosita, K. and T. Y. Tsong, *Formation and Resealing of Pores of Controlled Sizes in Human Erythrocyte-Membrane*. Nature, 1977. 268(5619): p. 438-441.

Once the TMP reaches a critical voltage, it is thought that permeabilizing defects, or pores, form in the plasma membrane in attempt to limit further TMP rise. Pore formation can either be reversible to allow for the introduction of foreign particles into viable cells, or irreversible to promote cell death through a loss of homeostasis. Known devices and methods of performing electroporation clinically involve several drawbacks, including painful muscle contractions, unpredictable treatment outcomes, and a high potential for thermal damage in low passive conductivity tissues.

IRE performed with unipolar pulses causes intense muscle contractions. Therefore, clinical applications of IRE require the administration of general anesthesia and neuroparalytic agents in order to eliminate the discomfort caused by muscle contractions seen during each pulse. See Talele, S. and P. Gaynor, *Non-linear time domain model of electropermeabilization: Response of a single cell to an arbitrary applied electric field*. Journal of Electrostatics, 2007. 65(12): p. 775-784. Receiving paralytic agents is undesirable for patients, and may deter them from seeking an electroporation based therapy. Further, in some cases, even with an adequate neuromuscular blockade, muscle contractions are still visible (see Payselj 2007), and questions remain as to what constitutes an appropriate dosage. Muscle contractions may affect the location of implanted needle electrodes, which can invalidate treatment planning algorithms. Additionally, in treatments near vital structures, displacement of the implanted electrodes may cause unavoidable collateral damage.

The time course of the pulsed electric field and dielectric properties of the tissue control the TMP development and the extent to which the transient defects form and reseal within the membrane. Knowledge of these two components can be used to predict treatment outcomes. However, predictions are complicated in heterogeneous tissues, or organs with multiple types of parenchymal tissue. There is often an intricate and unknown geometrical arrangement between tissues of low and high electrical conductivity, and the conductivity can change in real-time due to the phenomenon of electroporation, the extent of which is highly unpredictable without prior knowledge.

Low conductivity tissues, such as epithelial layers, often contain a dense packing of cells with reduced extracellular current pathways. As such, the resistance of the extracellular space is increased. Additionally, when pulses much longer than the charging time of the plasma membrane (~1 µs) are applied (see T. R., A. T. Esser, Z. Vasilkoski, K. C. Smith, and J. C. Weaver, *Microdosimetry for conventional and supra-electroporation in cells with organelles*. Biochem Biophys Res Commun, 2006. 341(4): p. 1266-76, "Gowrishankar 2006"), the current is confined to the extracellular space prior to the onset of electroporation, as shown in FIGS. 1A-B. As shown, when the pulse duration ($t_d$) is much less than the plasma membrane time constant ($\tau_{pm}$), current flows through both intracellular and extracellular spaces (FIG. 1A). In the case that $t_d$ is much greater than $\tau_{pm}$, current flow is restricted to the narrower extracellular spaces (FIG. 1B). Consequently, there is a large voltage drop across tissues with low conductivity, which increases the potential for deleterious Joule heating effects, such as thermal damage.

SUMMARY OF THE INVENTION

The present invention provides an advancement over tissue ablation techniques previously devised by providing methods for precisely and rapidly killing diseased, damaged, disordered, or otherwise undesirable biological tissues in situ. More specifically, the present invention provides methods comprising electric pulse therapies for ablating target cells and tissues for the treatment of diseases and disorders. Surprisingly, it has been found that the use of ultra-short pulses that have the ability to cause cell death can be effective as a treatment process for aberrant cell growths. The inventors have developed electroporation techniques using nanosecond-scale pulses as a controlled, precise way to destroy aberrant cells of a tissue or organ, without the deleterious side effect of heating the healthy cells in the vicinity of the undesirable cells. In these methods, one or more electrodes are placed within, near, or around the targeted region to deliver a series of high energy electric pulses to promote cell death. The packing of cells within a tissue is largely heterogeneous, and most organs are covered with epithelial cells joined by tight junctions to form a continuous sheet that rests on a layer of fibrous connective tissue. Further, organs can contain multiple sites of epithelial cells within underlying layers of tissue, for example, the cells forming the lining of ducts. Tight junctions are the preferred sites for electroporation when microsecond-scale pulses longer than the charging time of the membrane are employed, because current is confined to the extracellular space once the surrounding cell membranes are fully charged. Therefore, the voltage drop and resulting electric field is larger across layers of tissue containing tight junctions where current pathways are reduced. This, in turn, reduces the amount of underlying tissue that can be treated. The epithelial layer acts as a shield, absorbing a majority of the voltage drop. This problem can be alleviated through the use of electric pulses with durations shorter than the charging time of plasma membranes, such as on the order of about 1-1,000 nanoseconds. Then it is possible for the field to reach the underlying layers of tissue, because current can flow through both the extracellular and intracellular spaces. All cells present in the organ, regardless of their packing, experience a homogenous electric field distribution. It is advantageous to tune the pattern of pulse delivery to the tissue of interest. Depending on electrode and tissue geometry, pulses can be "stacked" in a monopolar or bipolar train, and individual pulses within each train can be delivered from different electrodes, such that cell death only occurs in targeted regions where the integration of pulses both temporally and spatially yields electroporation. The present disclosure documents how electroporation can effectively be done with nanosecond pulses using a series of pulses (applied from differing electrode pairs or the same set). The present invention provides advancements over conventional tissue electroporation by utilizing high-frequency, bipolar pulses. Pulsing protocols according to embodiments of the invention involve bursts of bipolar pulses with a burst width on the order of microseconds and duration of single polarity on the microsecond to nanosecond scale, as shown in FIG. 2. The total burst width of the high-frequency pulses (~100-1000 ns duration of single polarity) is on the order of hundreds of microseconds, the time delay in between bursts is on the order of seconds, and the total number of bursts can be adjusted.

The advantages of electric pulse therapies over other ablation techniques lay within their ability to kill tissue through a non-thermal mechanism. The methods of the invention use electroporation to kill target cells while preserving the extracellular matrix, nerves, major blood vessels, and other sensitive structures of the treated tissues, enhancing treatment outcome. Furthermore, the ablation area can be predicted using numerical modeling for accurate treatment planning, and application of the procedure can be monitored in real-time using ultrasound and confirmed with both ultrasound and MRI, among other imaging techniques. The methods of the invention allow for killing of target cells and tissues, and exhibit rapid lesion creation and resolution, prompting the repopulation of the region with healthy cells. Though treatment success is not dependent upon the immune system, a tumor specific immune response capable of helping to destroy any residual micro-metastases occurs when the invention is practiced to kill tumor cells, decreasing the chances of recurrence. It is possible for the electric field to penetrate tissue heterogeneities when high-frequency electric fields are employed, because capacitive coupling is enhanced allowing current to flow through both extracellular and intracellular spaces. See Gowrishankar, T. R. and J. C. Weaver, *An approach to electrical modeling of single and multiple cells*. Proceedings of the National Academy of Sciences of the United States of America, 2003. 100(6): p. 3203-3208; and Ivorra, A., ed. *Tissue Electroporation as a Bioelectric Phenomenon: Basic Concepts*. Irreversible Electroporation, ed. B. Rubinsky. 2010, Springer Berlin Heidelberg. 23-61. In this case, all cells present in the organ, regardless of their packing and morphology, experience a macroscopically homogeneous electric field distribution. See Esser, A. T., K. C. Smith, T. R. Gowrishankar, and J. C. Weaver, *Towards Solid Tumor Treatment by Nanosecond Pulsed Electric Fields*. Technology in Cancer Research & Treatment, 2009. 8(4): p. 289-306. This results in more predictable and uniform treatment outcomes without the electric energy being preferentially deposited into regions of tissue with a lower passive conductivity. As a result, Joule heating is also more uniformly distributed throughout the tissue, which mitigates the potential for thermal damage in regions with a low passive conductivity.

Enhanced capacitive coupling also limits the change in tissue electrical conductivity due to electroporation. Therefore, prior knowledge of how the conductivity of a tissue is modulated in response to electroporation is not required to accurately predict the electric field distribution. As a result, simplified algorithms can be implemented for treatment planning.

High-frequency, bipolar waveforms are also included in embodiments of the invention for mitigating or completely eliminating muscle contractions during electroporation based therapies. It is well known in the field of functional electrical stimulation that the threshold for nerve stimulation increases as the center frequency of bipolar waveforms increases. Further, muscle twitch forces are reduced as frequency increases. The present invention demonstrates that a range of frequencies exist where non-thermal tissue ablation can be achieved without causing nerve excitation or muscle contraction. In the context of this specification, it is noted that the term ablation is used to indicate destruction of cells, but not necessarily destruction of the supportive stroma.

Clinically, this translates to performing IRE without the requirement of paralytic agents (or a reduction in the amount of paralytic agents administered) in all procedures, and without the further requirement of general anesthesia in minimally invasive procedures. Additionally, other complications caused by IRE with unipolar electric pulses are alleviated, including electrode displacement and pain associated with intense muscle contractions.

Examples of heterogeneous systems include, but are not limited to, tumors surrounded by or containing any type of epithelial layer, such as a skin fold geometry, or systems comprised of multiple tissue types including, brain, bone, breast, pancreatic, kidney, or lung. In this specification, an epithelial layer is defined as a dense packing of cells that restrict the flow of materials (e.g., electrical current) resulting in a low passive electrical conductivity.

The present invention applies to all electroporation based therapies. Recently, electroporation has been utilized in vivo as a means to destroy cancer cells within tissues in both reversible and irreversible modalities. Reversible electroporation is being studied to facilitate the delivery of anticancer drugs and DNA into cancer cells through the plasma membrane in the form of electrochemotherapy (ECT) and electrogenetherapy (EGT), respectively. Irreversible electroporation (IRE) promotes cell death resulting in the development of a tissue lesion. It is an independent means to ablate substantial volumes of targeted tissue without the use of harmful adjuvant chemicals if used prior to the onset of thermal injury. See Davalos 2005. By not relying on thermal processes, IRE has been shown to spare the extracellular matrix and architecture of nerves and blood vessels.

More specifically, the present invention provides new devices and methods for the treatment of diseases and disorders, such as hemic and solid neoplasias, which improves conventional clinical practice associated with electroporating target tissues.

Included in embodiments of the invention is a method of treating a subject suffering from a neoplasia comprising: implanting at least one device for emitting electric pulses into or adjacent a neoplastic site within the body of a subject; and delivering one or more electric pulse to the neoplastic site, such that amplitude and duration of the pulse are in the range of about 1500 V/cm to 2500 V/cm for 10 μs or less which is capable of inducing irreversible electroporation. Methods of the invention also include non-invasive methods of treating a subject comprising non-invasively placing at least one device for emitting electric pulses around a region of the body containing a neoplastic site within; and delivering one or more electric pulse, such that amplitude and duration of the pulse are in the range of about 1500 V/cm to 2500 V/cm for 10 μs or less which is capable of inducing irreversible electroporation.

According to embodiments of the invention, such methods can employ multiple pulses administered in a pulse burst having a duration of less than 10 ms. The step of providing an electric charge involves applying an appropriate series of electrical pulses to the cells to be treated, where the pulses are characterized by being of relatively high voltage and relatively short duration. According to the invention, the electrical pulses have a duration that is less than the charging time of plasma membranes and have a voltage that is sufficient for cell killing but not so high as to cause substantial killing of surrounding, non-target, healthy cells by thermal heating. Because the method of treating can be applied to numerous cells, tissues, and organs, the precise pulse duration and voltage will vary depending on the particular application. However, pulse lengths in general are on the nanosecond range and voltages are at least about 500 V. Further guidance on selecting parameters is provided below.

Such methods can employ one or more pulses or a plurality of pulses in a pulsing protocol, wherein the amplitude of the pulse is in the range of about 500 V/cm to 1500 V/cm. Amplitude in the context of this specification refers to the voltage-distance ratio of a pulse, such as for 1500 V/cm the voltage is 750V over a distance of 0.5 cm.

Such methods can have a pulse duration in the range of about 2 MHz (250 ns) to about 500 kHz (1 μs). For example, the pulse duration can be about 1 MHz (500 ns). In preferred embodiments, the duration of each pulse is in the range of about 100 to 10,000 ns. The method can include emitting multiple electric pulses such that the temporal and spatial summation of such pulses results in the generation of an electric field of about 500 V/cm to 2500 V/cm for 10,000 microseconds or less to induce IRE. Alternatively, the method can include emitting multiple electric pulses such that the temporal and spatial summation of such pulses results in the generation of an electric field of about 1 kV/cm to 50 kV/cm for 1,000 nanoseconds or less to induce supra-poration in addition to IRE. It is to be recognized that, in various embodiments, the individual electric pulses can be monophasic while in other embodiments, the individual electric pulses can be biphasic. In certain preferred embodiments, a train of monophasic pulses is delivered in one direction, followed by a subsequent pulse train of opposite polarity. Depending on the outcome desired, the waveforms or the electric pulses are triangular, square, sinusoidal, exponential, or trapezoidal. Other geometric shapes are contemplated as well. In some embodiments, an electrode is connected to a system for employing electrical impedance tomography (EIT), computed tomography (CT), Magnetic Resonance Imaging (MRI), or ultrasound to image the tissue prior to treatment by applying small alternating currents that themselves do not damage the tissue.

Any number of probes or electrodes can be used invasively, semi-invasively, or non-invasively according to embodiment of the invention. In preferred embodiments, two or more electrically conductive regions are used within a single device for emitting the electrical pulses. Similarly, in any of the methods according to the invention, two or more devices can be used to deliver multiple electric pulses at different positions within, on, or near a body.

Custom treatment area shapes can be created through varying electrode activation patterns in combination with any of the embodiments of the invention.

The methods can also employ delivery of a bipolar burst of pulses. In embodiments, a bipolar burst of pulses can be delivered with multiple pulses in a single phase before a polarity switch. Even further, total burst width of any pulse protocol according to the invention can be between 1 µs and 10,000 µs. In preferred embodiments, the methods can have a duration of single polarity within a bipolar burst of between about 100 ns and 100,000 ns. The concept of alternating polarity of pulses can be extended to the use of multiple electrodes. For example, a combination of three electrodes can be used to deliver three sequential sets of alternating polarity pulses to a target tissue. More specifically, Electrode A can be used to deliver a 500 ns pulse at 1000 V at a starting time (T=0) and a 500 ns pulse at −1000 V at T=1 µs. Electrode B can be used to deliver a 500 ns pulse at 1000 V at T=500 ns, and a 500 ns pulse at −1000 V at T=1.5 µs. Electrode C can be used to deliver a 500 ns pulse at 1000 V at T=1 µs, and a −1000V pulse at T=2.0 µs. Of course, this concept can be applied using any numbers of electrodes and pulse times to achieve highly directed cell killing.

The shape of the electric pulses delivered using methods of the invention can be square, ramp, sinusoidal, exponential, or trapezoidal.

In preferred embodiments, two or more electric pulse bursts can be administered with a delay between bursts. In preferred embodiments, a delay between bursts can be on the order of seconds. For example, in bipolar protocols a selected positive voltage (+V) can be applied for a selected period of time (e.g., 50 µs), then a zero voltage applied for a selected period of time (e.g., 75 µs), then a negative voltage (−V) can be applied (e.g., 50 µs). The voltage can be applied in any number of individual pulses, as a pulse or pulse burst.

Also included in embodiments of the invention is a method of delivering electric pulses such that amplitude and duration of single polarity are selected to be capable of administering electroporation to electrically excitable tissue without stimulation of the tissue.

Further included is a method of delivering electric pulses such that amplitude and duration of single polarity are selected to be capable of administering electroporation to electrically excitable tissue with reduced stimulation of the tissue as compared with higher amplitude and longer duration pulse protocols. Preferably tissue stimulation that is avoided or prevented refers to a muscle contraction.

In embodiments, the neoplastic site, region of the body, or electrically excitable tissue can be nerve tissue, muscle, or an organ containing nerves and/or muscle tissue.

Any embodiment of the invention can employ applying electric pulses having an amplitude and duration in the range of about 1500 V/cm to 2500 V/cm for 10 ms or less which is capable of inducing irreversible electroporation.

Method embodiments of the invention can be used to build up the transmembrane potential of a tissue to a critical value (~1V) by delivering trains of less than 1 µs bipolar pulses. For example, multiple monopolar pulses can be delivered at a pulse duration of about 5 MHz prior to a polarity switch, then delivered at a pulse duration of about 5 MHz after polarity switch.

Methods of the invention may or may not employ administering of a drug designed to induce a neural blockade. The methods can include administration of general, local, or no anesthesia for treatment of tissues with electroporation based therapies. In preferred embodiments, no neural blockade is required for treatment of tissues with electroporation based therapies, or lower dosages of a neural blockade can be used in embodiments of the invention to achieve the same results as using higher doses with lower frequency pulsing protocols.

The pulses of any method of the invention can be delivered on a short enough timescale to flow through epithelial cells but are long enough to induce electroporation in underlying cells. In specific embodiments, a frequency of 500 kHz or 1 MHz or 250 kHz is used to treat underlying fat cells in a layer of fat disposed under the epidermis.

Methods according to the invention can be modified to provide for administering non-thermal IRE, IRE, and/or reversible electroporation.

Treatment planning according to embodiments of the invention can result in more predictable outcomes in homogeneous and heterogeneous tissues than compared with lower frequency pulsing protocols.

Any one or more of the methods, devices, or systems, or parts thereof, can be combined with other methods, devices, systems, or parts thereof mentioned in this specification to obtain additional embodiments within the scope of this invention.

Devices and systems for implementing any one or more of the above mentioned methods are also within the scope of the invention.

BRIEF DESCRIPTION OF THE DRAWINGS

The accompanying drawings illustrate certain aspects of some of the embodiments of the present invention, and should not be used to limit the invention. Together with the written description the drawings serve to explain certain principles of the invention.

FIGS. 1A-B are schematic illustrations showing electrical current pathways through epithelial layers and bulk tissue prior to the onset of electroporation.

FIGS. 4A-B are graphs showing respectively 2 MHz AC burst with a width of 4 µs, and a DC pulse with a duration of 4 µs of equal amplitude (FIG. 4A); and magnitude spectrum of the AC burst (thick) and DC pulse (thin) (FIG. 4B).

FIGS. 9A-D are schematic diagrams showing the electric field, norm (V/cm) contours predicted by the FEM at the end of a 2 µs burst with an amplitude of 2600 V and a frequency of 250 kHz (FIG. 9A), 500 kHz (FIG. 9B), 1 MHz (FIG. 9C), and 2 MHz (FIG. 9D).

FIGS. 10A-B are graphs showing temperature changes predicted by the FEM at the center of the skin (FIG. 10A) and fat (FIG. 10B) for various frequencies of 250 kHz (- -), 500 kHz (- - -), 1 MHz (• • •), and 2 MHz (-).

FIGS. 11A-B are graphs of TMP predicted by the FEM at the center of the skin (FIG. 11A) and fat (FIG. 11B) for frequencies of 250 kHz (- -), 500 kHz (- - -), 1 MHz (• • •), and 2 MHz (-).

FIG. 15A-C are waveforms of IRE with unipolar pulses and high-frequency IRE with the corresponding TMP development across the plasma membrane ($\Phi_{pm}$) for a 1500 V/cm unipolar pulse (FIG. 15A) and a 1500 V/cm bipolar burst without a delay (FIG. 15B) and with a delay (FIG. 15C).

FIGS. 21A-F are MRIs of lesions in rat brain appearing as focal hyper-intense regions (white) compared to adjacent untreated cerebrocortical tissue (gray). FIGS. 21A-C were obtained from Rat #3, in which both the left and right cerebral hemispheres were treated with high-frequency waveforms at 300 V/250 kHz and 400 V/250 kHz, respectively. FIGS. D-F were obtained from Rat #4, which underwent high-frequency, bipolar pulses in the right cerebrum at 400 V/500 kHz, and conventional IRE with unipolar pulses at 50 V in the left cerebrum.

FIGS. 22A-D are data recordings of acceleration (a) versus time during treatments with unipolar IRE pulses and high-frequency IRE pulses.

In FIG. 24C, the homogeneous solution is shown for a constant pulse.

DETAILED DESCRIPTION OF VARIOUS EMBODIMENTS OF THE INVENTION

Figure 2:
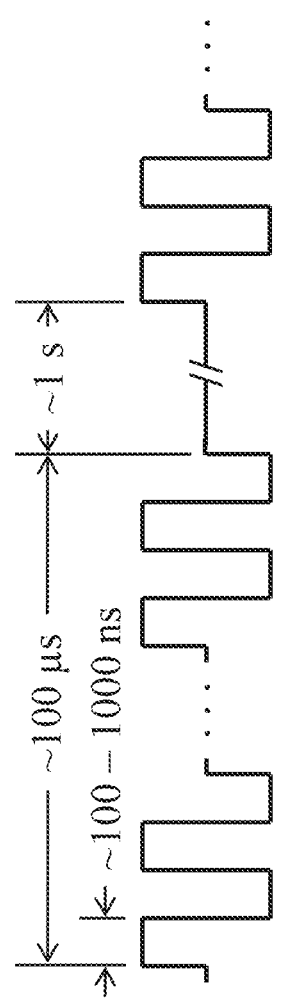
FIG. 2 is a schematic diagram of a representative pulsing protocol for electroporation based therapy according to embodiments of the present invention.
Figure 3A:
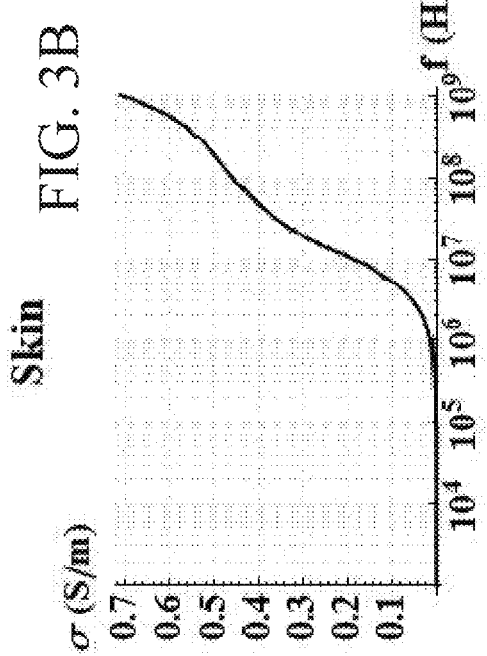
FIGS. 3A-D are graphs showing dielectric properties (σ and $\varepsilon_r$) as a function of frequency for skin and fat.
Figure 3B:
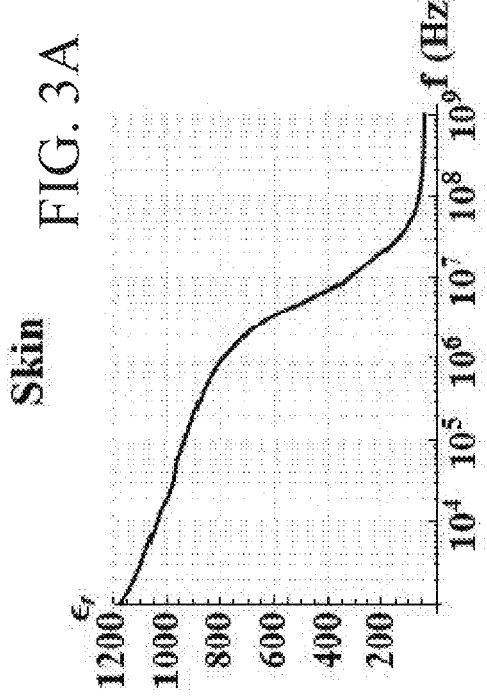
Figure 3C:
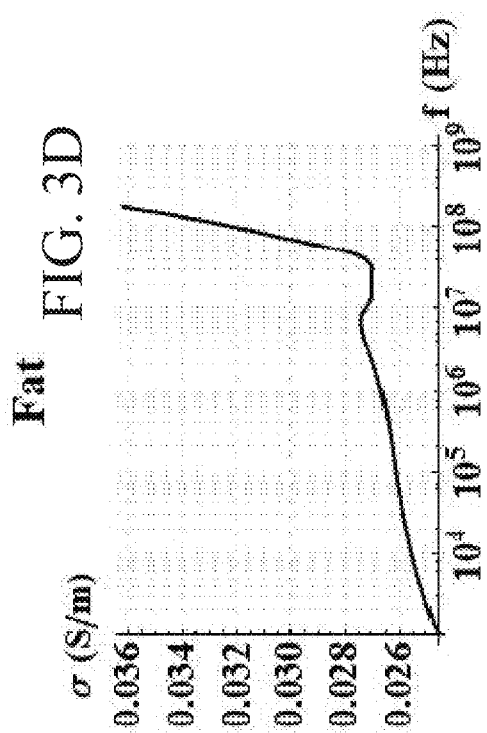
Figure 3D:
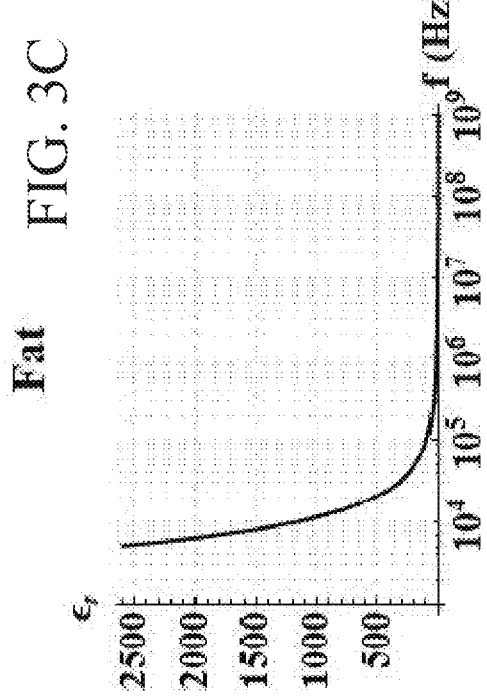

Reference will now be made in detail to various exemplary embodiments of the invention. It is to be understood that the following discussion of exemplary embodiments is not intended as a limitation on the invention. Rather, the following discussion is provided to give the reader a more detailed understanding of certain aspects and features of the invention. Electroporation is a non-thermal, non-linear biophysical mechanism in which the application of an external pulsed electric field leads to an increase in the permeability of cellular membranes. While direct evidence for the exact mechanism of electroporation has yet to be discovered, experiments indicate that the extent of electroporation is attributed to the induced buildup of charge, and consequently, potential difference across the membrane, commonly referred to as the transmembrane potential (TMP). Increasing the TMP has been described to produce various permeabilizing effects on cellular membranes, including those that add to thermal fluctuations within the membrane, wherein the formation of hydrophilic, aqueous pores becomes energetically favorable. The field strength and duration control the onset of permeabilization in the membrane and the extent to which transient permeabilizing defects are allowed to reseal. If the pulse parameters are tuned such that the membrane defects are only temporary, and the cell remains viable, the process is termed reversible electroporation. Reversible electroporation can be used to introduce molecules into cells that, under normal conditions, would not permeate cellular membranes. Reversible electroporation is being studied to facilitate the delivery of anticancer drugs (electrochemotherapy; ECT) and DNA (electrogenetherapy; EGT) into cancer cells through the plasma membrane. There is a narrow window of pulse parameters where ECT and EGT have proven to be effective without reducing cell viability by IRE. IRE results when membrane defects are permanent, leading to cell death presumably through a loss of homeostasis. It is recognized as independent means to destroy substantial volumes of targeted tissue without the use of harmful adjuvant drugs and prior to the onset of thermal injury. Due to its inherent non-thermal nature, IRE promotes preservation of sensitive structures, such as nerves and blood vessel extracellular matrix components. To maintain its non-thermal benefits, the pulse parameters for IRE procedures are restricted to those that minimize any associated Joule heating. The pulse duration employed in IRE is larger than the charging time of the plasma membrane, which is typically on the order of a microsecond. Supra-poration results when the applied pulse is shorter than the charging time of the plasma membrane, and the electric field is able to penetrate the cell. As a result, cell death in supra-poration is induced presumably through damage to intracellular organelles. Because organelles are smaller in diameter than cells, the amplitude required to raise the TMP on organelles up to around 1 V is greater than that in electroporation procedures, but, due to the ultra-short nature of the pulses, the accompanying Joule heating is still negligible. While immediate necrosis is suspected as the primary mechanism of cell death following IRE, apoptosis triggered by DNA fragmentation and the release of calcium from intracellular stores occurs in cells exposed to sufficiently high nsPEFs.

Electric pulse therapies are minimally invasive procedures that involve placing electrodes into or around a targeted tissue and delivering a series of short and intense electric pulses in an attempt to localize the treatments to the cancer cells and spare the surrounding healthy cells. When a tumor is located deep within an organ, a minimally invasive needle or catheter based device is needed for the electrodes to reach the tumor. In some instances, the organ puncture required by these designs can, in itself, damage the surrounding healthy cells. For example, even a slight puncture of the pancreas from the insertion of a single needle (0.3 mm diameter) results in widespread cellular injury that may manifest as pancreatitis, which is known to mediate additional postoperative complications. Therefore, treatment of pancreatic cancer and cancers arising in other organs that are sensitive to puncture is limited to the use of non-puncturing plate electrodes placed around the organ. Plate electrodes are best suited to treat tumors lying close to the skin, because of the high potential drop that occurs across epithelial layers, where the field is the largest, limiting the amount of deeper tissue that can be permeabilized without first permeabilizing the overlying layers. Plate electrodes will have a similar problem when placed around organs to treat deep seated tumors, because the energy must be directed through multiple layers of heterogeneous tissue. For example, most organs of the abdominal cavity, including portions of the anterior and inferior surfaces of the pancreas, are covered by the peritoneum. Epithelial cells of the peritoneum are joined by tight junctions to form a continuous sheet that rests on a layer of fibrous connective tissue.

Transport lattice models of multicellular systems have shown that epithelial layers containing tight junctions are preferred sites for electroporation when ECT, EGT, or IRE pulsing protocols are employed. As mentioned, this has to do with the fact that the electrical current associated with pulses longer than around 1000 ns is confined to extracellular spaces prior to the onset of electroporation. When high resistance tight junctions are present, the field is highly concentrated across the cells, because extracellular current pathways are reduced. Further, the extent of electroporation in underlying cells is reduced, because the epithelial layer absorbs a majority of the potential drop. It is possible for the field to reach the underlying cells when ultra-short are employed, because current can flow through both extracellular and intracellular spaces. In this case, all cells present in the organ, regardless of their packing and morphology, experience a homogeneous electric field distribution. Therefore, ultra-short pulses can be delivered to treat hard to reach tumors, or cancer cells that are encapsulated by one or more epithelial layers. When applied in a train, ultra-short pulses can raise the TMP across the plasma membrane above a critical permeabilizing threshold, if each pulse within the train starts before the cell has had time to discharge from the previous pulse.

The effects of integrating multiple, ultra-short pulses on tissue electroporation can be controlled by altering both the electrode type and electrode configuration. As mentioned, it is desirable in some instances to deliver all of the energy from non-puncturing plate electrodes surrounding the target tissue. In this case, the pulses can be delivered in either a monopolar pulse train, where the integration of the pulses serves to raise the TMP to the critical permeabilizing threshold, or a bipolar pulse train, where each pulse within the train can raise the TMP to the critical permeabilizing threshold, and the switch in polarity serves to prevent the charging of epithelial layers and subsequent shielding of underlying layer of tissue. Further, the number of non-puncturing electrodes can be expanded so that each pulse within the train is delivered from a different electrode in attempt to expose only cancer cells in targeted regions to a lethal dose of energy and spare the surrounding healthy cells. The invention also includes the application of ultra-short pulse trains through puncturing energized or grounded electrodes located directly adjacent to or within the targeted tissue. In this case, the electrode configuration can be controlled as before to effectively bypass epithelial layers and ensure homogeneous treatment of innately heterogeneous tissue.

Examples describing all designs covered in the claims of the present invention are given subsequently throughout the text.

Despite being a well-known technique, there is significant controversy about the mechanisms governing electroporation. Weaver, J. C., *Electroporation of cells and tissues*. IEEE Transactions on Plasma Science, 2000. 28(1): p. 24-33. Even though the biophysical phenomenon at the molecular level is not known, the hypothesis is that in the presence of an externally applied electric field, the lipid bilayer in cellular membranes rearranges to create water-filled structures. These structures (or pores) provide a pathway for ions and molecules through the membranes that normally are impermeable. The dynamics of membrane poration is considered a four-step process: pore induction, expansion, stabilization and resealing. Weaver, J. C. and Y. A. Chizmadzhev, *Theory of electroporation: a review*. Bioelectrochem. Bioenerg., 1996. 41: p. 135-60. Initial thermal fluctuations are responsible for the presence of hydrophobic pores. There exists a critical radius where it is more energetically favorable for a hydrophobic pore to transition to a hydrophilic pore. In addition, increasing the TMP reduces this critical radius and increases the stability of a hydrophilic pore. Kinosita, K., Jr., S. Kawato, and A. Ikegami, *A theory of fluorescence polarization decay in membranes*. Biophys J, 1977. 20(3): p. 289-305. When the pore reaches this metastable state, it becomes permeable to small molecules. The presence of the induced transmembrane potential lowers the energy required for the pore's existence. Freeman, S. A., M. A. Wang, and J. C. Weaver, *Theory of Electroporation of Planar Bilayer-Membranes—Predictions of the Aqueous Area, Change in Capacitance, and Pore-Pore Separation*. Biophysical Journal, 1994. 67(1): p. 42-56. When the electric field has been turned off, the membrane starts to return to its normal membrane potential and resealing of the pores takes place.

As mentioned, applied electric pulses alter the transmembrane potential (TMP) of cellular membranes. When membranes are treated as two, spherical, ideal dielectric shells containing and surrounded by a conductive medium, the analytical solution for induced TMP across the plasma membrane and nuclear envelope can be described as a function of time by solving the Laplace equation.

Analysis in the frequency domain yields:

$$TMP_{pm}(s) = F_{pm}(\Lambda_n, \Lambda_{ne}, \Lambda_c, \Lambda_{pm}, \Lambda_e) E(s) \cos \theta,$$

$$TMP_{nc}(S) = F_{ne}(\Lambda_n, \Lambda_{ne}, \Lambda_c, \Lambda_{pm}, \Lambda_e) E(s) \cos \theta,$$

where the subscripts n, ne, c, pm, and e describe cellular regions corresponding to the nucleoplasm, nuclear envelop, cytoplasm, plasma membrane, and extracellular space, respectively. The term F represents a transfer function of the TMP that reflects the geometric and dielectric properties of the cellular regions as a function of the complex admittance, which is given by the equation $\Lambda = \sigma + \epsilon s$, where s is the complex frequency. The exact formulation for F is lengthy and is given by Kotnik and Miklavcic (Biophysical Journal, 2006). The term E represents the Laplace transform of the pulsed electric field as a function of time. In some of the following examples, the pulse duration was using a Heaviside step function (ideal rise time) in order to investigate the timescale of complete plasma membrane and nuclear envelope charging and discharging, respectively. In the following examples, the equations were solved and converted back into the time domain by taking the inverse Laplace transform according to, $TMP(t) = L^{-1}[(TMP(s)]$. The properties of the different cellular regions were defined according to the following table:

TABLE 1

| Geometry | Conductivity (S/m) | Relative Permittivity | Dimensions (m) |
|---|---|---|---|
| Conductive Gel | 4 | 80.0 | — |
| Extracellular Space | 0.6 | 80.0 | — |
| Epithelial layer | $2.1 \times 10^{-5}$ | 7.0 | $28.0 \times 10^{-9}$ (thickness) |
| Plasma Membrane | $5.3 \times 10^{-6}$ | 7.0 | $7.0 \times 10^{-9}$ (thickness) |
| Cytoplasm | 0.13 | 60.0 | $10.0 \times 10^{-6}$ (diameter) |
| Nuclear Envelope | $4.3 \times 10^{-3}$ | 22.8 | $40.0 \times 10^{-9}$ (thickness) |
| Nucleoplasm | 0.18 | 120.0 | $5.0 \times 10^{-6}$ (diameter) |

When an electric field is applied across or between two electrodes placed within a homogeneous solution, the field distribution is predicted by the Laplace equation:

$$-\nabla \cdot (\sigma \nabla V) - \varepsilon_0 \varepsilon_r \nabla \cdot \left(\frac{\partial \nabla V}{\partial t}\right) = 0$$

where $\sigma$ and $\epsilon_r$ are the conductivity and relative permittivity, respectively, for a given region. This equation is readily solved by implementing finite-element techniques. The inclusion of a permittivity term accounts for the reactive component of tissue in time dependent pulsing, which is required for obtaining accurate potential distributions in heterogeneous models. Calculations of the TMP across the plasma membrane and nuclear envelope were performed in the following examples by taking the difference between potentials on both sides of the respective membranes.

Both electroporation of the plasma membrane and supraporation of intracellular membranes are ideal when pulses are applied as to not induce any deleterious thermal effects. However, the differences between the protocols in terms of pulse duration can have a significant influence on the mechanisms of electric field-tissue interaction. The dielectric permittivity and conductivity of a given tissue are typically functions of frequency. At varying frequencies, different mechanisms of charge transfer contribute differently to the permittivity and conductivity. Further, most tissues are heterogeneous and exhibit multiple mechanisms of charge transfer.

Figure 25A:
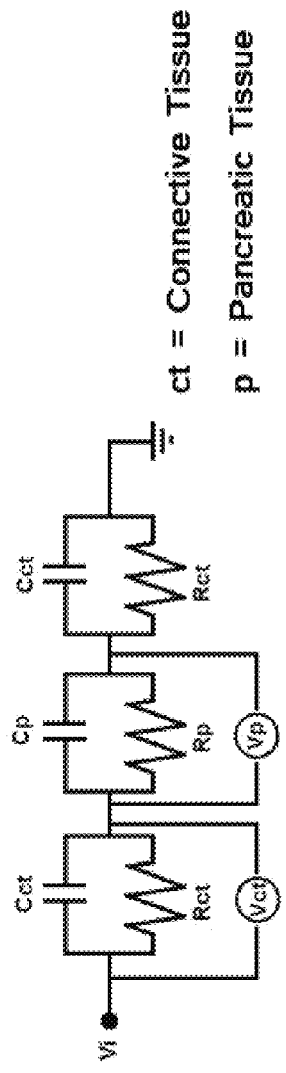
FIG. 25 depicts an illustration of the equivalent circuit model of the pancreas in 25A, and the output is shown in 25B for the voltage drop across the connective tissue membrane (ct) and pancreatic layer (p) following the application of 10 µs (left) and 10 ns (right) square-wave electric pulses.
Figure 25B:
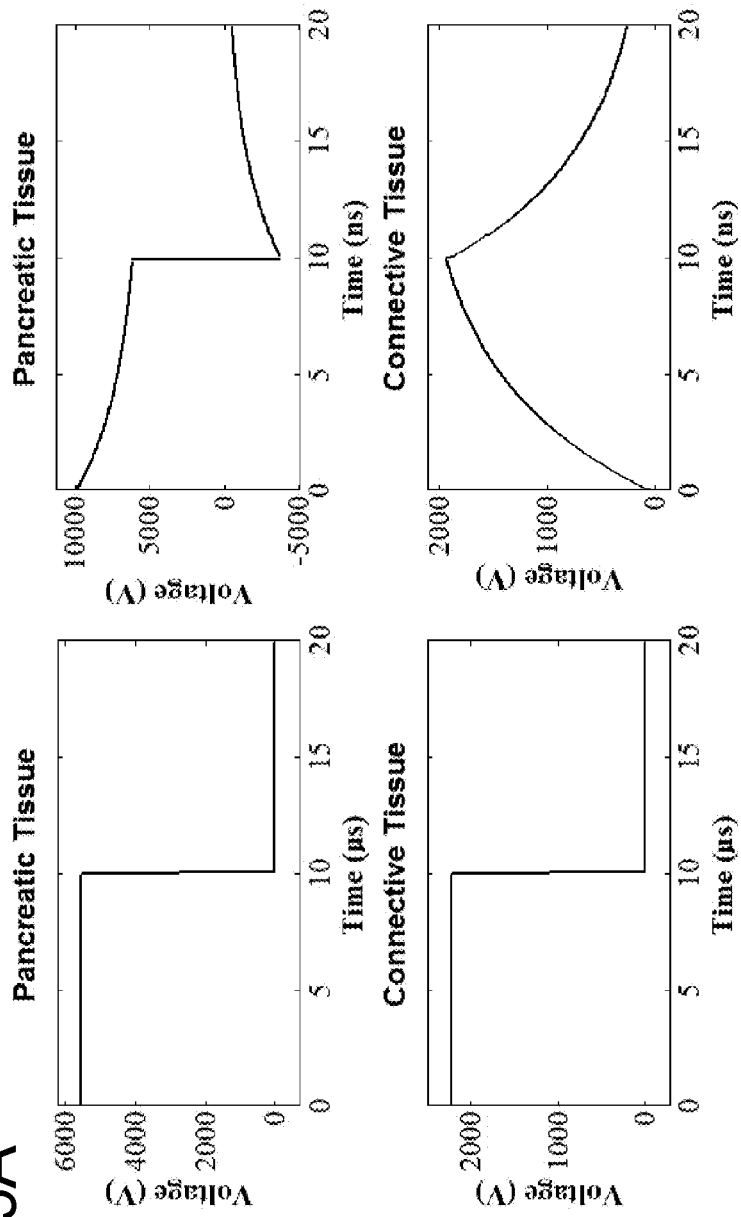
Figure 27A:
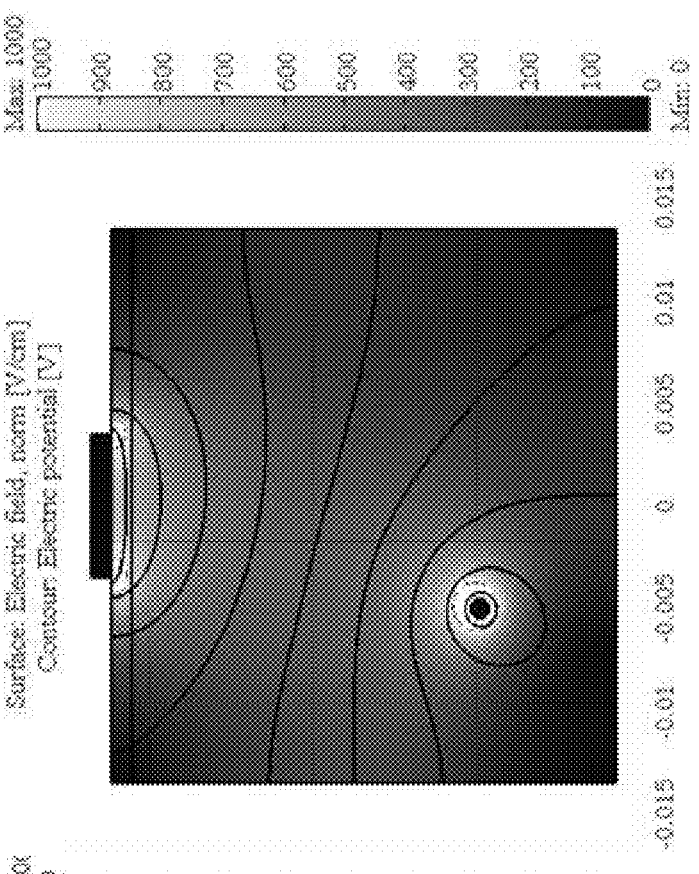
FIG. 27 depicts a model of the treatment area in a pancreas undergoing IRE around an internal ground electrode when the energized electrodes are placed externally around the connective tissue capsule covering the pancreas. 27A shows treatment with 1000 V and 10 µs square-wave pulses. 27B shows treatment with 1000 V and 10 ns square-wave pulses.
Figure 27B:
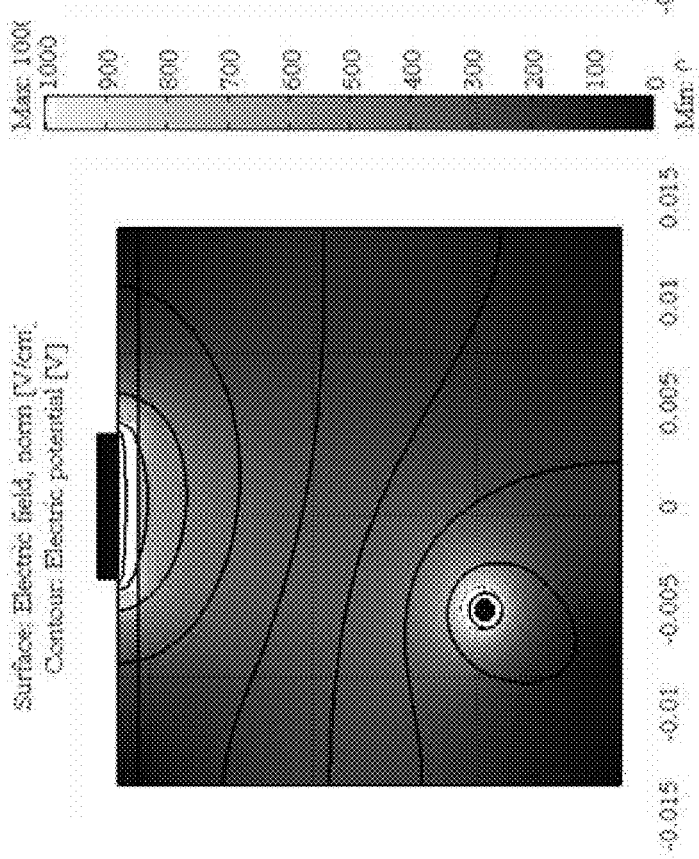

Biological tissues are classified as heterogeneous dielectrics, and Maxwell-Wagner effects describe electrical processes at the interface between different dielectrics. There may be free or bound surface charges at the interface, and it is the presence of free charges that is responsible for altering the electric field across the interface. Organs are often compartmentalized, with thin membranes comprising the compartment walls. For example, the lung, the heart, the brain, and the stomach all have multilayer membranes. These membranes have a large influence on current flow, and the ultra-short pulse durations employed in supraporation protocols can bypass (or electrically short) these membranes, such as the connective tissue capsule surrounding the pancreas, because the pulse duration is shorter than the charging time of the cell membrane, which is defined for a single shell model as:

$$\tau = aC_{pm}\left(\frac{1}{2\sigma_e} + \frac{1}{\sigma_c}\right)$$

where Cpm is the capacitance of the membrane, ($\sigma_e$ is the conductivity of the external medium, and ($\sigma_c$ is the conductivity of the internal medium. An equivalent circuit model with ideal components (resistors with frequency independent values) can be implemented to describe various interfaces between tissue layers. For the case of three slabs of tissue placed in series between capacitor plates, which mimics noninvasive treatment of pancreatic cancer, the individual tissue components are represented by a parallel combination of a resistor and a capacitor, and the individual components are connected in series to represent the whole organ. The sections in direct contact with the electrodes represent the connective tissue capsule surrounding the pancreas, and the center section is a homogeneous portion of pancreatic tissue. In order to calculate the capacitances and resistances in the circuit model of the pancreas, data on the specific conductivity and relative permittivity of connective tissue and pancreatic tissue is needed. Biological tissue is neither a perfect dielectric nor a perfect conductor, and the values for conductivity and permittivity are dependent upon the frequency of the applied electric field. In electroporation and supra-poration protocols, voltage is delivered to the electrodes in a square pulse waveform, where most of the energy resides at 0 Hz. Therefore, data for connective tissue (estimated to be similar to wet skin) and pancreatic tissue conductivity and permittivity at 0 Hz is used. After applying input voltage of 10 kV as a square pulse waveform for a specified duration, the voltage drop across the connective tissue can be decreased by reducing the pulse duration into the nanosecond time range (see FIG. 25). These results are confirmed by the finite-element solution, as described in FIG. 27. In a similar fashion, a tumor with a higher complex impedance as compared to the surrounding healthy tissue experiences a higher voltage drop when nanosecond pulses are employed, resulting in a targeted electric field therapy.

Figure 26:
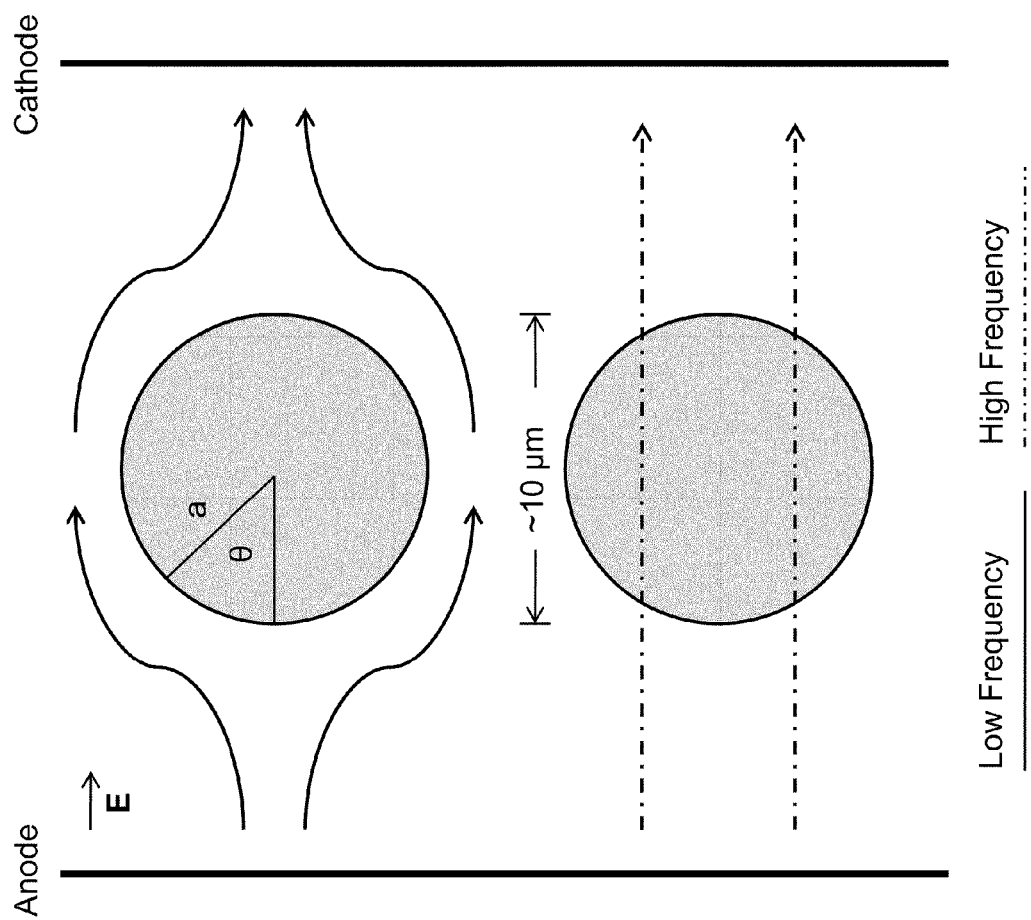
FIG. 26 illustrates the low frequency and high frequency current paths for a volume of cells surrounded by interstitial fluid placed in a uniform electric field.

Electric circuit theory can also be extended to model individual cells, because the wavelength of the pulses in electroporation and supra-poration protocols is evidently much larger than the dimensions of the object of interest. At high frequencies (pulse durations shorter than the chagrining time of the membrane), current is able to penetrate the cell membrane, which has a high capacitance and low conductivity, and at low frequencies (pulse durations longer than the chagrining time of the membrane) current tends to travel around the cells (see FIG. 26). As mentioned, in order to take advantage of the ability of ultra-short pulses to bypass tissue heterogeneities in IRE protocols, multiple ultra-short pulses can be combined to generate an electric field capable of inducing a transmembrane potential of 1 V on the plasma membrane of cells. Individual cell responses to electroporation protocols have been assessed with charge-relaxation studies in patch clamp experiments. Additionally, rapid freezing methods have allowed for the characterization of the time sequence of electropores. This information indicates that after approximately 100 ns after the offset of square pulse waveform, the cell membrane begins discharging. Therefore, if multiple ultra-short pulses can be delivered across a cell membrane with less than around 100 ns in between the pulses, then cell can remain polarized long enough for the transmembrane potential to reach 1 V. Specific data on the optimal duty cycle and pulse duration is given in FIG. 10. The analytical solution for the maximum TMP on the plasma membrane of leukemia cells was solved at the pole. As expected, results indicate that as duty cycle is decreased, maximum TMP drops, and the same is true as pulse duration is decreased. However, the induced TMP is less sensitive to changes in pulse duration as compared to changes in duty cycle. Therefore, the pulse generators in the present invention are best suited when operated above a 50% duty cycle at a variety of pulse lengths.

The present invention is distinguishable from conventional electric pulse therapies at least in part in embodiments by the pulse parameters and electrode configurations that are utilized. Trains of pulses are applied in a distinct fashion to induce plasma membrane electroporation. Individual pulses comprising the trains have durations on the order of the charging time of the plasma membrane (nanoseconds) and amplitudes that are characteristic of ECT, EGT, or IRE. This is as opposed to supra-poration, which requires greater amplitudes (kilovolts) to disrupt intracellular membranes. In embodiments, the temporal and spatial summation of the pulses is such that the TMP on the plasma membrane reaches the critical threshold required for electroporation. This constraint can be met in various ways for the treatment of certain tissues or whole organs. If individual pulses have durations much less than the charging time of the plasma membrane, then multiple pulses must be sequenced to reach the critical TMP. The treatment can then be targeted by delivering each pulse from a different electrode in a custom electrode array placed into or around the desired ablation zone. If individual pulses have durations similar to the charging time of the plasma membrane, then no sequencing is required to reach the critical TMP. However, to treat tissues surrounded by or containing epithelial layers with reduced current pathways, it is still advantageous to apply multiple pulses of alternating polarity to penetrate through these layers and treat the entire volume.

The invention thus encompasses using multiple short electrical pulses to cause killing of target cells by either electroporation or supra-poration. Accordingly, in one aspect, the present invention provides a method of treating targeted aberrant cell growth in a subject. In general, the method includes externally placing or reversibly implanting into a tissue or organ of a subject at least one electrode in proximity to target cells. The electrode(s) may be provided as bare electrically conducting elements, or may be provided as part of a device that includes, among other things, an electrically insulating cover or sheath covering at least a portion of the electrode(s). Once in position, a series of two or more electrical pulses are applied to the target cells in proximity to the electrode(s) to cause cell death as a result of IRE or supra-poration. The electrical pulses are provided as a series of pulses of from 1 picosecond (ps) to 1,000 nanoseconds (ns) or higher (e.g., 10,000 ns) at voltages above about 500 V. The pulses are continued until a desired level of cell killing of target cells is achieved. In embodiments, cell killing is monitored in real-time, although the desired level of cell killing can be accurately predicted beforehand using mathematical modeling on computers. Upon achieving a desired level of cell killing, pulsing is discontinued and the electrode(s) are removed from the treated tissue or organ. Where necessary or desirable, tissue damage due to insertion of the electrode(s) is repaired surgically.

The method of treating according to the invention is, in embodiments, a method of treating a subject suffering from aberrant cell growth in or on a tissue or organ. By aberrant, it is meant that the cells are characterized by the progressive or uncontrolled proliferation of cells that have an abnormality such that they are not regulated properly by normal methods. The method thus can be considered, in embodiments, as a method of treating a disease or disorder involving aberrant cell growth or aberrant failure of cells to die normally. Exemplary embodiments of diseases and disorders are those that affect tissues characterized by relatively high permittivity, such as the outer layer of the pancreas, bone, and the central nervous system, such as the brain and spinal cord. Unlike the present methods, other electroporation methods known in the art are not effective for use on tissues characterized by high permittivity.

The dielectric permittivity and conductivity of a given tissue are typically functions of frequency. A comparison of the dielectric properties between skin and fat is presented in Table 2. This data was obtained by interpolating the results from Gabriel et al. (FIGS. 3A-D). Gabriel, S., R. W. Lau, and C. Gabriel, *The dielectric properties of biological tissues .2. Measurements in the frequency range 10 Hz to 20 GHz*. Physics in Medicine and Biology, 1996. 41(11): p. 2251-2269. At varying frequencies, different mechanisms of charge transfer contribute differently to the permittivity and conductivity. Stoy, R. D., K. R. Foster, and H. P. Schwan, *Dielectric properties of mammalian tissues from 0.1 to 100 MHz: a summary of recent data*. Phys Med Biol, 1982. 27(4): p. 501-13.

TABLE 2

Conductivity of skin and fat as a function of frequency.

| Frequency | Waveform | Property | Tissue | |
|---|---|---|---|---|
| | | | Skin | Fat |
| 250 kHz | ⊓ ←2 μs→ | $\sigma$ [S/m] $\varepsilon_r$ | 0.00216 888 | 0.0263 47 |
| 500 kHz | ⊓⊔ | $\sigma$ [S/m] $\varepsilon_r$ | 0.00485 851 | 0.0265 33 |
| | ⊓⊓⊔⊔ | $\sigma$ [S/m] $\varepsilon_r$ | 0.0119 792 | 0.0267 25 |
| 2 MHz | ⊓⊓⊓⊓⊔⊔⊔⊔ | $\sigma$ [S/m] $\varepsilon_r$ | 0 0090 700 | 0.0270 20 |

In general, as the frequency increases, so does the conductivity of the skin and fat. According to Table 2, the difference in conductivity between skin (s) and fat (f) is reduced as the frequency increases from 250 kHz to 2 MHz ($\sigma_s/\sigma_{f-1}$).

Therefore, if electroporation is used to treat a tumor within a heterogeneous skin fold geometry, the electric field distribution in the surrounding skin and fat would be more homogenous if high-frequency waveforms are utilized. Oftentimes tissue impedance has patient-to-patient variability and the impedance distribution and any impedance changes may be difficult to determine for a particular patient. This point is emphasized further in EXAMPLE 1. Because rectangular waveforms are comprised of components with various frequencies and amplitudes, tissue properties at frequencies associated with the center frequency, defined as the inverse of twice the duration of single polarity, are chosen when studying AC bursts. This is illustrated in FIGS. 4A-B. By taking the absolute value of the Fourier Transform of an AC burst and a DC pulse, the magnitude spectrum can be obtained. While the DC pulse transmits a majority of its power at low frequencies (0 Hz), the AC burst has a characteristic peak at the center frequency (2 MHz in this case).

The benefits of bipolar pulses have been studied for electroporation applications at the single-cell level. Theoretically, Talele et al. have shown that asymmetrical electroporation due to the resting TMP (~0.1 V) (see Gowrishankar 2006) of cells seen when unipolar pulses are delivered (see Chang, D. C., *Cell Poration and Cell-Fusion Using an Oscillating Electric-Field*. Biophysical Journal, 1989. 56(4): p. 641-652, "Chang 1989"; and Tekle, E., R. D. Astumian, and P. B. Chock, *Electroporation by Using Bipolar Oscillating Electric-Field—an Improved Method for DNA Transfection of Nih 3t3 Cells*. Proceedings of the National Academy of Sciences of the United States of America, 1991. 88(10): p. 4230-4234, "Tekle 1991") can be alleviated by switching to bipolar pulses. Talele, S. and P. Gaynor, *Non-linear time domain model of electropermeabilization: Response of a single cell to an arbitrary applied electric field*. Journal of Electrostatics, 2007. 65(12): p. 775-784. Experimentally, this leads to increased efficiency of macromolecule uptake through the membrane. Chang 1989; and Tekle 1991. Depending on the extracellular conductivity, bipolar pulses with a frequency of 1 MHz (i.e. 500 ns duration of single polarity) can also lessen the dependence of electroporation on cell size, allowing more cells to be electroporated. Talele, S. and P. Gaynor, *Non-linear time domain model of electropermeabilization: Effect of extracellular conductivity and applied electric field parameters*. Journal of Electrostatics, 2008. 66(5-6): p. 328-334; and Talele, S., P. Gaynor, M. J. Cree, and J. van Ekeran, *Modelling single cell electroporation with bipolar pulse parameters and dynamic pore radii*. Journal of Electrostatics, 2010. 68(3): p. 261-274. In general, pore formation increases as long as the TMP is sustained above a critical threshold (~1 V). Gowrishankar 2006. Bipolar pulses require higher field strengths to induce a given TMP as compared to a unipolar pulse of equivalent duration. This is accentuated when the frequency of the bipolar pulses is increased, because the time interval above the critical TMP is reduced. Talele, S., P. Gaynor, M. J. Cree, and J. van Ekeran, *Modelling single cell electroporation with bipolar pulse parameters and dynamic pore radii*. Journal of Electrostatics, 2010. 68(3): p. 261-274. Kotnik et al. have explored the benefits of bipolar pulse trains at significantly lower frequencies, up to 1 kHz (i.e. 500 μs duration of single polarity). At lower frequencies, theoretical results show that the pore formation symmetry can also be normalized with bipolar pulses. Kotnik, T., L. M. Mir, K. Flisar, M. Puc, and D. Miklavcic, *Cell membrane electropermeabilization by symmetrical bipolar rectangular pulses. Part I. Increased efficiency of permeabilization*. Bioelectrochemistry, 2001. 54(1): p. 83-90, "Kotnik I 2001." Experimentally, bipolar pulses reduce electrolytic contamination (see Kotnik, T., D. Miklavcic, and L. M. Mir, *Cell membrane electropermeabilization by symmetrical bipolar rectangular pulses. Part II. Reduced electrolytic contamination*. Bioelectrochemistry, 2001. 54(1): p. 91-5) and the required field strength for reversible electroporation, while the field strength required for IRE remains unchanged. Kotnik I 2001. The authors attribute this to the fact that when the duration of single polarity is much longer than the plasma membrane charging time, permeabilized area differences on the membrane between unipolar and bipolar pulses decreases as pulse amplitude increases.

Bipolar pulse delivery has been studied in vivo for reversible applications of electroporation using center frequencies that are two orders of magnitude lower than that used in embodiments of the present invention. Daskalov et al. have demonstrtated that pulses delivered at 1 kHz are associated with less patient pain in during electrochemotherapy. Daskalov, I., N. Mudrov, and E. Peycheva, *Exploring new instrumentation parameters for electrochemotherapy—Attacking tumors with bursts of biphasic pulses instead of single pulses*. IEEE Eng Med Biol Mag, 1999. 18(1): p. 62-66. Similarly, Nikolova et al. has recently demonstrated the same findings during electrochemotherapy with a Bacillus Calmette-Guerin vaccine. Nikolova, B., I. Tsoneva, and E. Peycheva, *Treatment of Melanoma by Electroporation of Bacillus Calmette-Guerin*. Biotechnology & Biotechnological Equipment, 2011. 25(3): p. 2522-2524. Both authors attribute the reduction in patient pain due to the associated reduction in muscle contractions seen with bipolar pulses.

There is a balance between employing pulses that are delivered at a high enough frequency to reduce the conductivity mismatch between different tissues but have a duration of single polarity long enough to induce electroporation of cells comprising the tissues. As mentioned, electrical current associated with pulses longer than ~1 μs is confined to extracellular spaces prior to the onset of electroporation. Ivorra, A., ed. *Tissue Electroporation as a Bioelectric Phenomenon: Basic Concepts*. Irreversible Electroporation, ed. B. Rubinsky. 2010, Springer Berlin Heidelberg. 23-61; and Esser, A. T., K. C. Smith, T. R. Gowrishankar, and J. C. Weaver, *Towards solid tumor treatment by irreversible electroporation: intrinsic redistribution of fields and currents in tissue*. Technol Cancer Res Treat, 2007. 6(4): p. 261-74. This can be attributed to the migration of charges towards biological membranes following the application of an external electric field. The time required for a membrane to become charged to 63% of its steady state value is defined as the charging time constant of the membrane. Displacement currents across the plasma membrane allow organelles to be exposed to fields during the time that it takes the plasma membrane to reach steady state. Esser, A. T., K. C. Smith, T. R. Gowrishankar, and J. C. Weaver, *Towards Solid Tumor Treatment by Nanosecond Pulsed Electric Fields*. Technology in Cancer Research & Treatment, 2009. 8(4): p. 289-306. Once steady state is achieved, the counter-field developed along the plasma membrane due to the accumulation of charges is significant enough to shield the field from entering the cell, and current is directed through extracellular spaces. Only after permeabilization of the membrane does ionic conduction allow the field to re-enter the cell. Kolb, J. F., S. Kono, and K. H. Schoenbach, *Nanosecond pulsed electric field generators for the study of subcellular effects*. Bioelectromagnetics, 2006. 27(3): p. 172-187. If extracellular current pathways between cells are reduced, as in layers of epithelial cells connected by tight or gap junctions (see Jones, D. M., R. H. Smallwood, D. R. Hose, B. H. Brown, and D. C. Walker, *Modelling of epithelial tissue impedance measured using three different designs of probe*. Physiological Measurement, 2003. 24(2): p. 605-623), the field is highly concentrated across the layer, and the extent of electroporation in underlying cells is reduced. This problem is alleviated when the duration of single polarity approaches the membrane time constant.

By treating cells as a series of spherical, dielectric shells containing and surrounded by a conductive medium, the analytical solution for induced TMP across the plasma membrane (ΔΦ) can be obtained according to the law of total current (see Yao, C. G., D. B. Mo, C. X. Li, C. X. Sun, and Y. Mi, *Study of transmembrane potentials of inner and outer membranes induced by pulsed-electric-field model and simulation*. IEEE Trans Plasma Sci, 2007. 35(5): p. 1541-1549, "Yao 2007"):

$$\nabla \cdot \left(\varepsilon_0 \varepsilon_r \frac{\partial E}{\partial t} + \sigma E\right) = \Lambda_k \nabla \cdot E = 0 \qquad (1)$$

$$\Lambda_k = \sigma + \varepsilon_0 \varepsilon_r \frac{\partial}{\partial t} \qquad (2)$$

where Λ is the admittivity operator and the subscript k denotes cellular regions including the nucleoplasm (n), nuclear envelop (ne), cytoplasm (c), plasma membrane (pm), and extracellular space (e). Transforming (2), (5), and (6) into the frequency domain (see Yao 2007):

$$E = -\nabla \Phi(s) \qquad (3)$$

$$\Lambda_k \nabla \cdot E(s) = 0 \qquad (4)$$

$$\Lambda_k(s) = \sigma + \varepsilon_0 \varepsilon_r \varepsilon \qquad (5)$$

where $s = j\omega = j2\pi f$, and applying the appropriate boundary conditions of potential continuity and normal vector continuity of current density at the interface between the different regions yields the solution for TMP (see Yao 2007):

$$\Delta\Phi(s) = F(\Lambda_n, \Lambda_{ne}, \Lambda_c, \Lambda_{pm}, \Lambda_e) E(s) \cos\theta \qquad (6)$$

where θ represents the polar angle at the cell center between the electric field and the point of interest along the membrane. TMP is defined as the potential directly outside the membrane minus the inside. The natural, resting component of the plasma membrane TMP was ignored in all simulations, because it is typically an order of magnitude less than the induced TMP. See Gowrishankar 2006. Further, the TMP across the nuclear envelope never reached a permeabilizing threshold with the chosen pulsing protocols, and reference to TMP from this point forward refers only to the plasma membrane. As shown in Table 3, the term $F(\Lambda_k)$ represents a transfer function of the TMP that reflects the geometric and dielectric properties of the cellular regions as a function of the admittivity. See Hu, Q., S. Viswanadham, R. P. Joshi, K. H. Schoenbach, S. J. Beebe, and P. F. Blackmore, *Simulations of transient membrane behavior in cells subjected to a high-intensity ultrashort electric pulse*. Physical Review E, 2005. 71(3). Dielectric properties at the cellular level are assumed to be frequency independent, which is valid for predicting TMP up to around 100 MHz. Kotnik, T. and D. Miklavcic, *Theoretical evaluation of the distributed power dissipation in biological cells exposed to electric fields*. Bioelectromagnetics, 2000. 21(5): p. 385-394.

TABLE 3

Dielectric properties of various cellular regions.

| Geometry | σ [S/m] | $\varepsilon_r$ | Dimensions [m] |
|---|---|---|---|
| Extracellular Space | 0.6 | 80.0 | — |
| Plasma Membrane | $5.3 \times 10^{-6}$ | 7.0 | $7.0 \times 10^{-9}$ (thickness) |
| Cytoplasm | 0.13 | 60.0 | $5.0 \times 10^{-6}$ (radius) |

TABLE 3-continued

Dielectric properties of various cellular regions.

| Geometry | σ [S/m] | $\varepsilon_r$ | Dimensions [m] |
|---|---|---|---|
| Nuclear Envelope | 4.3 × 10$^{-3}$ | 22.8 | 40.0 × 10$^{-9}$ (thickness) |
| Nucleoplasm | 0.18 | 120.0 | 2.5 × 10$^{-6}$ (radius) |

The exact formulation for $F(\Lambda_k)$ is lengthy and can be found in (see Kotnik, T. and D. Miklavcic, *Theoretical evaluation of voltage inducement on internal membranes of biological cells exposed to electric fields*. Biophysical Journal, 2006. 90(2): p. 480-491), but is not included here for brevity. The term E(s) represents the Laplace transform of the pulsed electric field as a function of time.

Figure 5:
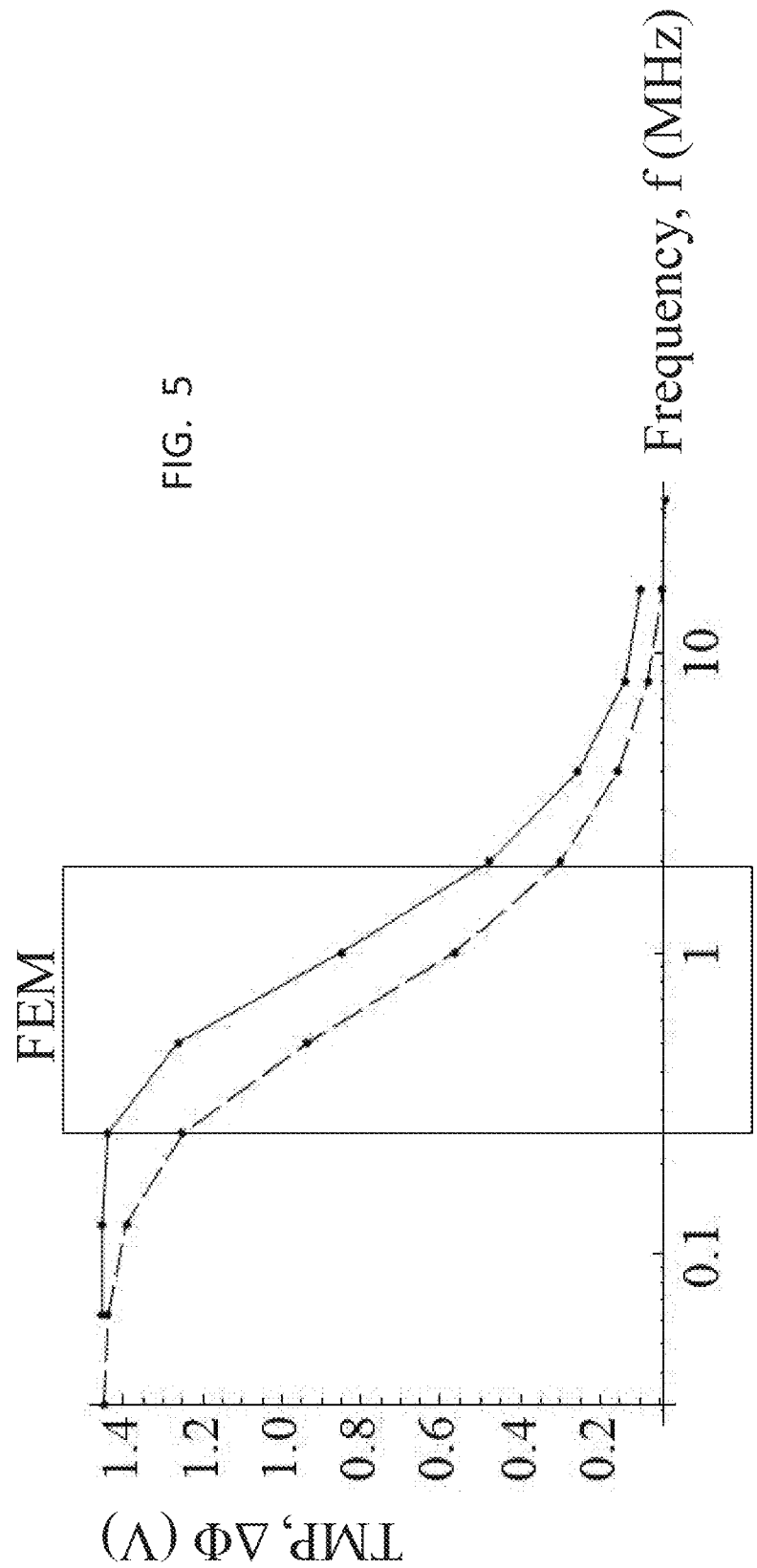
FIG. 5 is a graph showing frequency (f) response of the TMP at the cell pole (θ=0) for rectangular bipolar pulses (-) and sinusoidal waveforms (- -). The box illustrates the frequency window implemented in the FEM.

Using the analytical model, the frequency dependence of the induced TMP can be investigated for both rectangular and sinusoidal electric fields with identical maximum amplitude. By substituting the transient electric fields into (6) the results of a parametric study on TMP for frequencies spanning from 62.5 kHz to 16 MHz are shown in FIG. 5. The maximum amplitude of the sinusoidal and bipolar rectangular electric fields was 2000 V/cm (peak). For this applied field and the given geometric and dielectric properties of the modeled cell, the TMP never exceeds 1.46 V. Additionally, the time constant of the plasma membrane is 345 ns. All measurement were taken at the cell pole (θ=0) to depict the maximum achieved TMP after the system reached a steady oscillatory state. From the curve, as the frequency increases, the magnitude of the TMP is reduced. For the sinusoidal waveform, the reduction is evident at lower frequencies compared to the rectangular waveform. This has to do with the fact that the rectangular waveform maintains its maximum amplitude for a longer period of time than the sinusoidal waveform. It is not until the frequency of the rectangular waveform surpasses 250 kHz that a dramatic decrease in TMP occurs. For this reason, only rectangular pulses in a frequency window of 250 kHz to 2 MHz are best suited for electroporation with high-frequency, bipolar pulses.

Based on the analytical model for TMP presented above, the time constant of the plasma membrane for a constant field (2000 V/cm) is 345 ns. The time constant of 345 ns falls between the 2 MHz (250 ns pulse duration) and 1 MHz (500 ns pulse duration) bursts. Further, the 500 kHz burst (1 μs pulse duration) is close to the time it takes the TMP to reach steady state. As frequency is increased, the dielectric properties different tissues become more macroscopically homogeneous, but above 2 MHz, the pulse duration is not adequate for the cell to charge and induce electroporation. According to in vitro experiments that utilize bipolar rectangular pulses, the typical burst width required to induce either reversible electroporation or IRE increases with the frequency of the applied field. For EGT, a 60 kHz bipolar square with a burst width of 400 μs and an amplitude of 1600 V/cm has a six times greater transfection efficiency than a 1 MHz bipolar square wave with equal amplitude and width. Tekle, E., R. D. Astumian, and P. B. Chock, *Electroporation by Using Bipolar Oscillating Electric-Field—an Improved Method for DNA Transfection of Nih 3t3 Cells*. Proceedings of the National Academy of Sciences of the United States of America, 1991. 88(10): p. 4230-4234 (Telke 1991). In terms of IRE, a 60 kHz bipolar square with a burst width of 400 μs and an amplitude of 4000 V/cm results in 19% cell viability. Telke 1991. These results were obtained when a single burst was delivered to the sample. The inventors, however, appear to be the first in providing data on high-frequency electroporation with rectangular pulses that implemented multiple bursts. Similar to how multiple unipolar pulses are typically delivered in ECT, EGT, or IRE protocols to enhance the desired outcome (see Belehradek, J., S. Orlowski, L. H. Ramirez, G. Pron, B. Poddevin, and L. M. Mir, *Electropermeabilization of Cells in Tissues Assessed by the Qualitative and Quantitative Electroloading of Bleomycin*. Biochimica Et Biophysica Acta-Biomembranes, 1994. 1190(1): p. 155-163; and Garcia, P. A., J. H. Rossmeisl, R. E. Neal, T. L. Ellis, J. D. Olson, N. Henao-Guerrero, J. Robertson, and R. V. Davalos, *Intracranial Nonthermal Irreversible Electroporation: In Vivo Analysis*. Journal of Membrane Biology, 2010. 236(1): p. 127-136) multiple bipolar bursts would likely produce similar trends. Data is also available for burst sinusoidal waveforms in the frequency range of 2 kHz to 50 MHz (see Jordan, D. W., R. M. Gilgenbach, M. D. Uhler, L. H. Gates, and Y. Y. Lau, *Effect of pulsed, high-power radiofrequency radiation on electroporation of mammalian cells*. Ieee Transactions on Plasma Science, 2004. 32(4): p. 1573-1578; and Katsuki, S., N. Nomura, H. Koga, H. Akiyama, I. Uchida, and S. I. Abe, *Biological effects of narrow band pulsed electric fields*. Ieee Transactions on Dielectrics and Electrical Insulation, 2007. 14(3): p. 663-668), but the results are inconclusive, and sinusoidal waveforms are less efficient than rectangular bipolar pulses for inducing electroporation. Kotnik, T., G. Pucihar, M. Rebersek, D. Miklavcic, and L. M. Mir, *Role of pulse shape in cell membrane electropermeabilization*. Biochimica Et Biophysica Acta-Biomembranes, 2003. 1614 (2): p. 193-200.

There is a narrow window of pulse parameters where ECT and EGT have proven to be effective without reducing cell viability by IRE. For ECT, the field for inducing optimal reversible electroporation conditions is between 300 and 500 V/cm in tumors, when eight square-wave pulses 100 μs in duration are delivered at a frequency of 1 Hz. Mir, L. M., *Therapeutic perspectives of in vivo cell electropermeabilization*. Bioelectrochemistry, 2001. 53: p. 1-10 (Mir 2001). For EGT, permeabilization conditions are optimal when eight square-wave pulses 20 ms in duration are delivered at a frequency of 1 Hz, which constitutes a field of around 90 V/cm. Mir 2001. To maintain its non-thermal benefits, the pulse parameters for IRE procedures are restricted to those that minimize any associated Joule heating. Davalos, R. V. and B. Rubinsky, *Temperature considerations during irreversible electroporation*. International Journal of Heat and Mass Transfer, 2008. 51(23-24): p. 5617-5622. However, a similar field strength and duration to those required for ECT can induce IRE when the number of pulses is raised above the traditional 8 pulses to 90 pulses, and the temperature of the tissue remains below 50° C. Rubinsky, J., G. Onik, P. Mikus, and B. Rubinsky, *Optimal Parameters for the Destruction of Prostate Cancer Using Irreversible Electroporation*. Journal of Urology, 2008. 180(6): p. 2668-2674.

In addition to being bipolar, the pulses used according to methods of the invention can have a duration of single polarity (~1 μs) that is two orders of magnitude less than the duration of a conventional electroporation pulse (~100 μs) and an amplitude that is one order of magnitude less than supraporation protocols with nanosecond pulsed electric field (nsPEF). Supraporation involves pulses with a duration ranging from 1-100 ns and an amplitude ranging from 10-100 kV/cm. These electric fields are capable of causing electroporation within the membranes of intracellular organelles. Vernier, P. T., Y. H. Sun, and M. A. Gundersen, *Nanoelectropulse-driven membrane perturbation and small*

*molecule permeabilization*. Bmc Cell Biology, 2006. 7. When the pulse length is shorter than the charging time of the plasma membrane, the field can penetrate the plasma membrane to reach the cell interior. Beebe, S. J., P. M. Fox, L. J. Rec, L. K. Willis, and K. H. Schoenbach, *Nanosecond, high-intensity pulsed electric fields induce apoptosis in human cells*. FASEB J, 2003. 17(9): p. 1493-5. Because organelles are smaller in diameter than cells, the amplitude required to raise the TMP on organelles up to ~1 V is greater than that in ECT and IRE procedures. However, due to the ultra-short nature of the pulses, the accompanying Joule heating is still negligible. Schoenbach, K. H., S. J. Beebe, and E. S. Buescher, *Intracellular effect of ultrashort electrical pulses*. Bioelectromagnetics, 2001. 22(6): p. 440-8. While immediate necrosis is suspected as the primary mechanism of cell death following IRE, apoptosis triggered by DNA fragmentation and the release of calcium from intracellular stores occurs in cells exposed to sufficiently high nsPEFs. Beebe, S. J., J. White, P. F. Blackmore, Y. P. Deng, K. Somers, and K. H. Schoenbach, *Diverse effects of nanosecond pulsed electric fields on cells and tissues*. DNA and Cell Biology, 2003. 22(12): p. 785-796.

According to the methods of the invention, the electric pulses for electroporation and supra-poration are ultra-short, such as in the order of nanoseconds. Surprisingly, it has been found that durations shorter than the charging time of the cell plasma membrane, which is typically taken to be around one microsecond, can be employed in the present invention to successfully cause controlled cell killing. Therefore, durations of the electric pulses include less than 1 microsecond, such as less than 900 nanoseconds, less than 500 nanoseconds, less 100 nanoseconds, and less than 50 nanoseconds. While no particular lower limit is envisioned, from a practical standpoint, pulse durations of greater than 1 picosecond is the current lower limit, due to device dimensions. Individual picosecond or nanosecond pulses can be combined spatially and temporally to produce a single supra-poration pulse or even an individual IRE pulse. As pulse duration is lowered, a larger number of pulses or a higher voltage per pulse is required to induce IRE or supra-poration. By reducing the pulse length, larger electric fields can be applied to the treatment area while avoiding thermal damage to non-target tissue (as well as to target tissue). As a result of the decreased pulse length and concomitant reduction in heat production, the methods of the invention allow for treatment of tissues having higher volumes (e.g., larger tumors) than possible if prior art methods were to be employed for in situ treatment of aberrant cell growth. Furthermore, the use of multiple ultra-short pulses allows not only for direct cell killing by way of supra-poration, but also allows for stacking of pulses at a single or multiple electrodes, and delivery of cell killing electrical charges by IRE.

Figure 6:
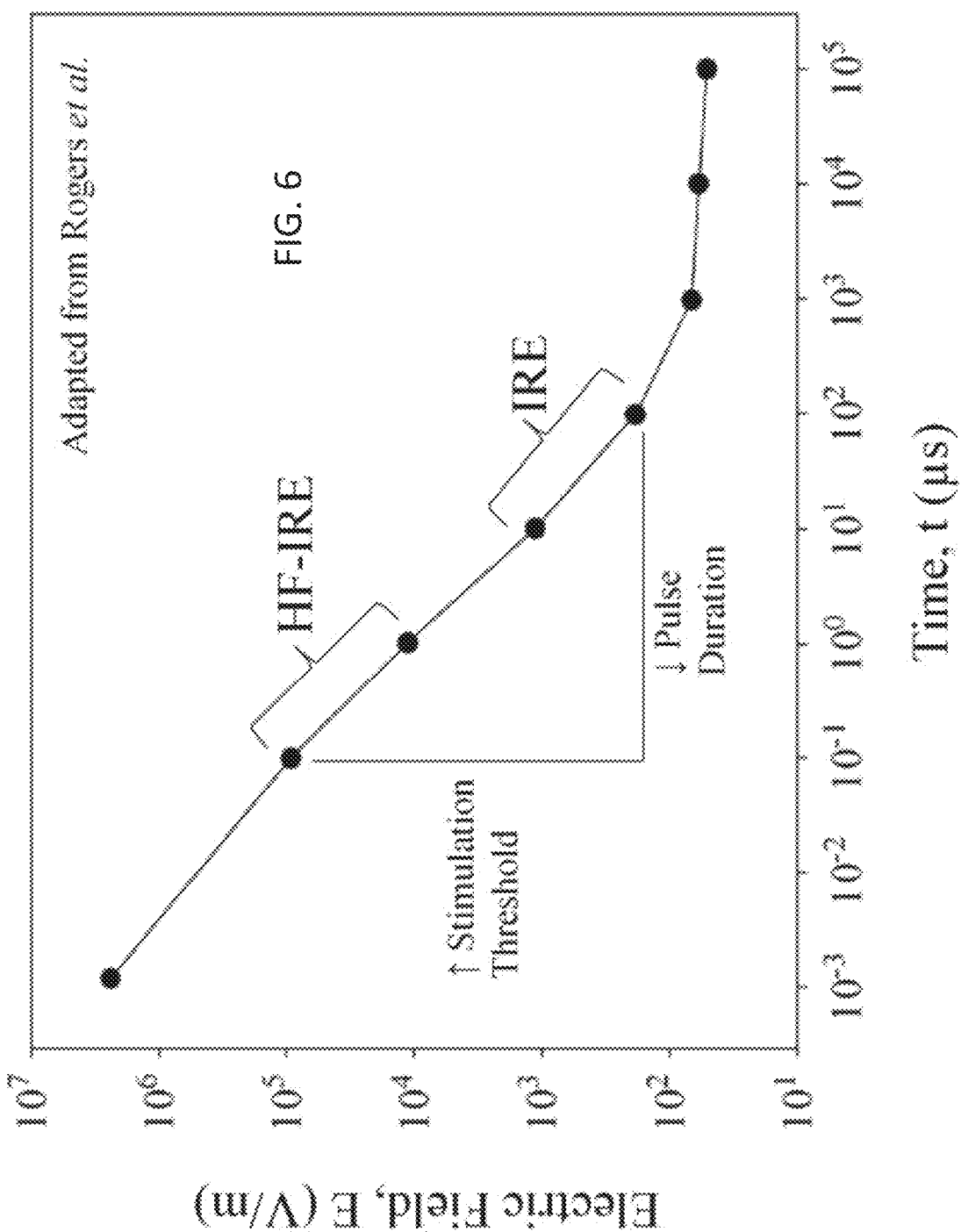
FIG. 6 is a graph of the strength-duration curve for unipolar electric pulses expressed as electric field strength in tissue. Adapted from Rogers, W. R., J. H. Merritt, J. A. Comeaux, C. T. Kuhnel, D. F. Moreland, D. G. Teltschik, J. H. Lucas, and M. R. Murphy, *Strength-duration curve for an electrically excitable tissue extended down to near 1 nanosecond.* Ieee Transactions on Plasma Science, 2004. 32(4): p. 1587-1599 ("Reilly 2004").

In vivo experiments on supraporation have shown that the ultra-short, unipolar pulses do not cause stimulation of excitable tissue, such as muscle and nerves. Long, G., P. K. Shires, D. Plescia, S. J. Beebe, J. F. Kolb, and K. H. Schoenbach, *Targeted Tissue Ablation With Nanosecond Pulses*. Ieee Transactions on Biomedical Engineering, 2011. 58(8). This is a consequence of the pulses being below the strength-duration threshold determined by Rogers et al. Rogers, W. R., J. H. Merritt, J. A. Comeaux, C. T. Kuhnel, D. F. Moreland, D. G. Teltschik, J. H. Lucas, and M. R. Murphy, *Strength-duration curve for an electrically excitable tissue extended down to near 1 nanosecond*. Ieee Transactions on Plasma Science, 2004. 32(4): p. 1587-1599. As seen in FIG. 6, for IRE pulses, the electric field threshold for stimulation is between 1-10 V/cm. The present invention describes pulses where the duration of single polarity is as low as 100 ns. At this duration, the electric field threshold for stimulation increases to 1000 V/cm, which is above the amplitude required for reversible electroporation and on the order of the amplitude for IRE.

Figure 7:
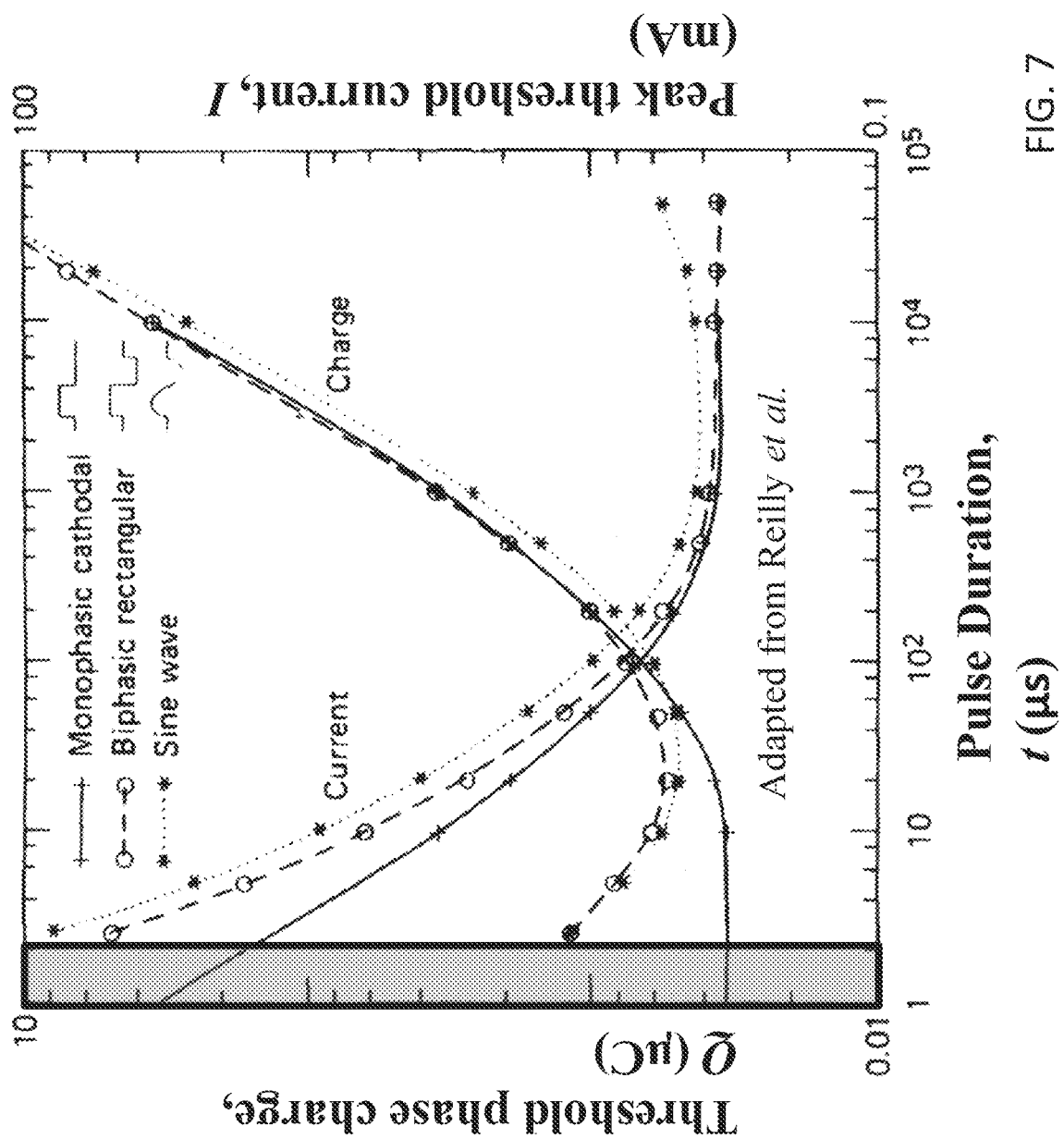
FIG. 7 is a strength-duration graph comparing unipolar to bipolar rectangular and sine waveforms expressed as phase charge and current. Adapted from Reilly 2004.

In addition to the duration of single polarity being reduced, the fact that the inventive waveforms are inherently bipolar offers an additional benefit in terms of the stimulation of excitable tissue. As shown in FIG. 7, biphasic waveforms have a higher threshold current for inducing nerve stimulation. Reilly, J. P., V. T. Freeman, and W. D. Larkin, *Sensory Effects of Transient Electrical-Stimulation—Evaluation with a Neuroelectric Model*. IEEE Trans Biomed Eng, 1985. 32(12): p. 1001-1011. Further, the threshold increases exponentially as the duration of single polarity is decreased. While the mechanism of this phenomenon is unknown, it is thought that the reversal in polarity prevents an action potential from being generated by limiting the flow of sodium ions down their concentration gradient. This has been shown to translate to a reduced muscle twitch force during bipolar functional electrical stimulation as opposed to monopolar. Vandenhonert, C. and J. T. Mortimer, *Response of the Myelinated Nerve Fiber to Short Duration Biphasic Stimulating Currents*. Annals of Biomedical Engineering, 1979. 7(2): p. 117-125.

The inventors have shown that bipolar waveforms can induce IRE at center frequencies high enough to eliminate muscle contraction completely. This procedure is termed high-frequency IRE (H-FIRE). Overall, the results indicate that H-FIRE can produce more predictable treatment outcomes, reduce the potential for thermal damage, and obviate the need for (or reduce the necessity of) neuroparalytic agents delivered prior to or during treatment.

The methods of the invention comprise, in embodiments, treatment of tissue surrounding a site of aberrant cell growth. In embodiments, this treatment causes cell killing of some healthy cells surrounding the aberrant cell growth. For example, in treating an invasive or aggressive tumor, it is often advisable to eliminate a zone of apparently healthy cells surrounding a tumor site to improve treatment outcome by destroying tumor cells that have invaded the healthy tissue outside of the defined tumor. The following examples show that bursts of bipolar, nanosecond pulses can maintain a critical TMP beneath epithelial layers, while minimizing Joule heating. This has to do with the ability of high-frequency waveforms to achieve a macroscopically homogeneous field distribution in a heterogeneous system. At high-frequencies, tissues with a low passive DC conductivity become more conductive. Additionally, it is proven that high-frequency IRE (H-FIRE) can be applied to non-thermally ablate tissue while eliminating muscle contractions seen in conventional IRE protocols with longer duration unipolar pulses. These results have implications not only for skin, brain, and liver as presented here, but for other tissues, such as bone, breast, pancreas, kidney, and lung. These examples should not be considered as limiting the invention in any way.

As a general background to the examples, it is noted that the inventors and their colleagues have successfully demonstrated that finite element models (FEMs) can accurately predict treatment outcomes of pulsed electric field therapies for cancer treatment. See Edd, J. F. and R. V. Davalos, *Mathematical modeling of irreversible electroporation for treatment planning*. Technol Cancer Res Treat, 2007. 6: p. 275-286; and Edd, J. F., L. Horowitz, R. V. Davalos, L. M. Mir, and B. Rubinsky, *In vivo results of a new focal tissue*

*ablation technique: irreversible electroporation.* IEEE Trans Biomed Eng, 2006. 53(7): p. 1409-15.

Example 1: High-Frequency Electroporation Results in More Uniform and Predictable Treatment Outcomes in Heterogeneous Tissues A 2D axisymmetric FEM representative of a cylindrical section of non-infiltrated fat encapsulated by dry skin was simulated using COMSOL 3.5a (Burlington, Mass.). The electric potential distribution within the tissue was obtained by transiently solving:

$$-\nabla \cdot (\sigma \nabla \Phi) - \varepsilon_0 \varepsilon_r \nabla \cdot \left(\frac{\partial \nabla \Phi}{\partial t}\right) = 0 \qquad (7)$$

where $\Phi$ is the electric potential and $\sigma$ and $\varepsilon_r$ are the conductivity and relative permittivity of each tissue layer, respectively, which depends on frequency (Table 2). Equation (7) is obtained from Maxwell's equations assuming no external current density ($J=\sigma E$), no remnant displacement ($D=\varepsilon_0\varepsilon_r E$), and the quasi-static approximation. This approximation implies a negligible coupling between the electric and magnetic fields ($\Delta \times E=0$), which allows for the expression of electric field only in terms of electric potential:

$$E = -\nabla \Phi \qquad (8)$$

Figure 8A:
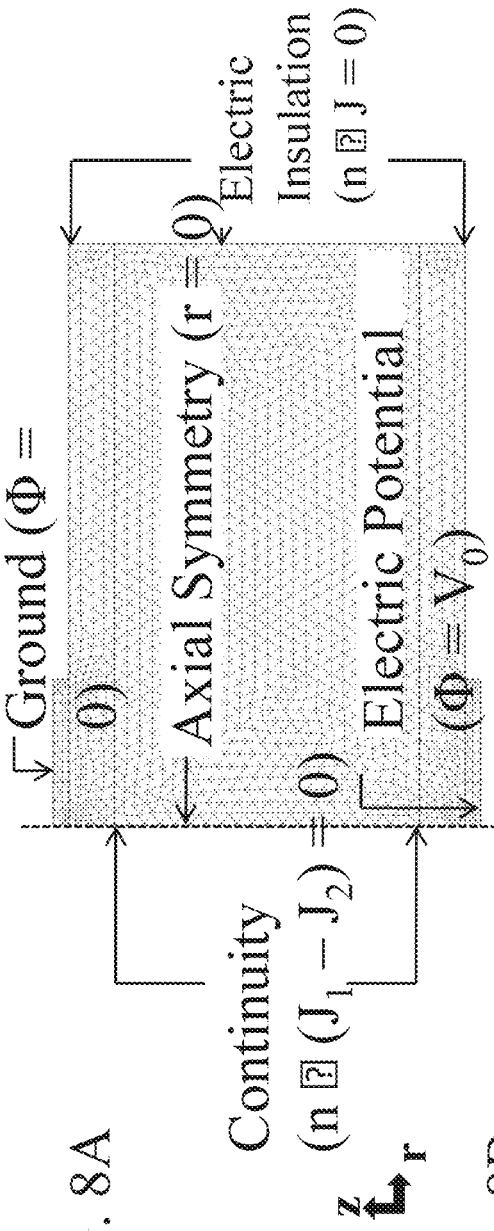
FIGS. 8A-B are schematic diagrams showing meshed geometry of the FEM with boundary settings (FIG. 8A) and the geometry with dimensions (FIG. 8B).
Figure 8B:
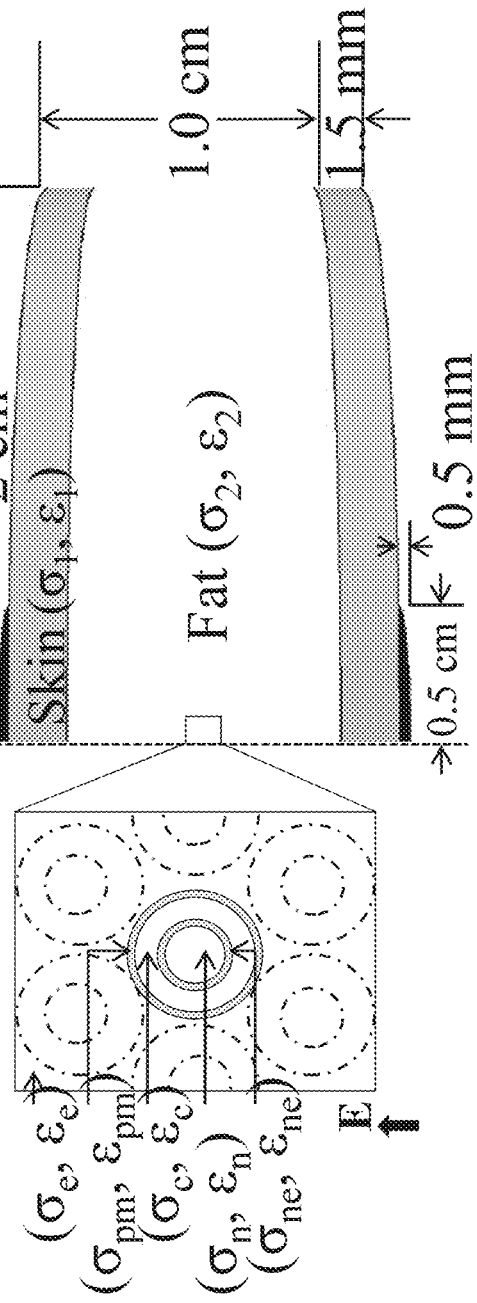

Dielectric properties of the bulk tissue were chosen from data generated by Gabriel et al. (see Gabriel, S., R. W. Lau, and C. Gabriel, *The dielectric properties of biological tissues .2. Measurements in the frequency range 10 Hz to 20 GHz.* Physics in Medicine and Biology, 1996. 41(11): p. 2251-2269) available at (http://niremf.ifac.cnr.it/docs/dielectric/home.html). The data was interpolated in Mathematica 7 (Wolfram Research, Inc.) in order to estimate the dielectric properties at the desired frequencies. Dielectric properties of the electrode were chosen to be stainless steel, as incorporated in the Comsol material library. All electrical boundary conditions are shown in FIGS. 8A-B, which provides in FIG. 8A, a meshed geometry of the FEM with boundary settings. The mesh consists of 3028 elements and was refined until there was <0.1% change in the magnitude of the electric field at the center of the tissue. FIG. 8B provides a schematic diagram of the geometry with dimensions. The box represents an expanded view of the tissue that describes the link between the macroscopic electric field (E) and the microscopic analysis of TMP. Adjacent cells are drawn with dashed lines, indicating their role was ignored in calculating TMP.

Because rectangular waveforms are comprised of components with various frequencies and amplitudes, tissue properties at frequencies associated with the center frequency, defined as the inverse of twice the duration of single polarity, are chosen. Intuitively, the duration of single polarity defines the frequency at which the current changes direction in the tissue. The pulses were constructed by multiplying the applied voltage by a function consisting of two smoothed Heaviside functions with a continuous second derivative and a tolerance of 5 ns (rise and fall times). The quasi-static assumption is confirmed based on the fact that the primary frequency of the pulses is lower than 200 MHz (rise and fall times), which corresponds to a wavelength that is greater than the longest dimension in the geometry. Chen, M. T., C. Jiang, P. T. Vernier, Y. H. Wu, and M. A. Gundersen, *Two-dimensional nanosecond electric field mapping based on cell electropermeabilization.* PMC Biophys, 2009. 2(1): p. 9. The inclusion of a permittivity term in (1) differs from previous, simplified models (see Edd, J. F. and R. V. Davalos, *Mathematical Modeling of irreversible electroporation for treatment planning.* Technology in Cancer Research & Treatment, 2007. 6(4): p. 275-286; and Neal, R. E. and R. V. Davalos, *The Feasibility of Irreversible Electroporation for the Treatment of Breast Cancer and Other Heterogeneous Systems.* Annals of Biomedical Engineering, 2009. 37(12): p. 2615-2625), and accounts for reactive component of tissue to time dependent pulsing, which is required for obtaining accurate potential distributions in heterogeneous models. Yousif, N., R. Bayford, and X. Liu, *The Influence of Reactivity of the Electrode-Brain Interface on the Crossing Electric Current in Therapeutic Deep Brain Stimulation.* Neuroscience, 2008. 156(3): p. 597-606.

FIGS. 9A-D show the electric field distribution at the end of a 2 µs burst with various frequencies given in Table 2. In each case, the maximum applied voltage was set to 2600 V (peak) in order to set up a voltage to distance ratio of 2000 V/cm between the electrodes (1.3 cm spacing). From the surface contour map, as frequency is increased, the electric field in the fat rises while the field in the skin drops. This trend extends to the point that at 2 MHz the field in the skin is lower than the fat, which is a direct result of the tissue dielectric properties at that frequency (greater conductivity and permittivity of skin as compared to fat). Therefore, high-frequency fields, or pulses with shorter duration, are better suited to penetrate epithelial layers, such as the skin, and reach underlying tissue.

Example 2: High-Frequency Electroporation Results in Homogeneous Energy Deposition and Reduces the Potential for Thermal Damage in Low Passive Conductivity Tissue The temperature distribution in the model described in EXAMPLE 1 was obtained by transiently solving a modified version of the Pennes bioheat equation (see Pennes, H. H., *Analysis of tissue and arterial blood temperatures in the resting human forearm.* J Appl Physiol, 1948. 1(2): p. 93-122) with the inclusion of a Joule heating term:

$$\rho C \frac{\partial T}{\partial t} = \nabla \cdot (k \nabla T) + \rho_b \omega_b C_b (T_b - T) + Q_m + |J \cdot E| \qquad (9)$$

where T is the tissue temperature, $T_b$ is the blood temperature, k is the thermal conductivity of the tissue, C and $C_b$ are the tissue and blood specific heat, respectively, $\rho$ and $\rho_b$ are the tissue and blood density, respectively, $Q_m$ is the metabolic heat source term, $\omega_b$ is the blood perfusion coefficient, and $|J \cdot E|$ is the Joule heating term. All thermal tissue properties are given in Table 4. Fiala, D., K. J. Lomas, and M. Stohrer, *A computer model of human thermoregulation for a wide range of environmental conditions: the passive system.* Journal of Applied Physiology, 1999. 87(5): p. 1957-1972.

TABLE 4

Thermal tissue properties of various tissues.

| | Tissue | | |
|---|---|---|---|
| Property | Blood | Skin | Fat |
| $\rho$ [kg/m$^3$] | 1069 | 1085 | 850 |
| C [J/Kg·K)] | 3650 | 3680 | 2300 |

TABLE 4-continued

Thermal tissue properties of various tissues.

| Property | Tissue | | |
|---|---|---|---|
| | Blood | Skin | Fat |
| k [W/(m·K)] | — | 0.47 | 0.16 |
| ω [1/s] | — | 1.1 | 0.0036 |
| $Q_m$ [kg/m³] | — | 368 | 58 |

Due to the presence of different tissue layers and the high frequencies under consideration (250 kHz-2 MHz), displacement currents are considered along with conduction currents in the formulation of Joule heating:

$$J = J_D + J_C = \varepsilon_0 \varepsilon_r \frac{\partial E}{\partial t} + \sigma E \tag{10}$$

where J is the total current density, $J_D$ is the displacement current density, and $J_C$ is the conduction current density. In order to ensure that negative current components due to polarity changes add to the total current in the tissue, the absolute value of the resistive heating term was taken prior to temperature calculations. It was assumed that all subdomains were initially at physiologic temperature ($T_0$=310.15 K). The boundaries between the electrode-skin interface and the skin-fat interface were treated as continuous (n·($k_1 \nabla T_1$ − $k_2 \nabla T_2$)=0), the centerline was defined as axial symmetry (r=0), and the remaining boundaries were thermally insulated (n·(k∇T)=0) for conservative temperature estimates. Temperature profiles were investigated along the centerline (r=0 mm) in the middle of the fat (z=0 mm) and skin (z=5.75 mm) layers. Data was imported into Mathematica, and a moving average with a period of 100 ns was taken to smooth the plots. Additionally, the data was fit with a linear trendline in order to extrapolate to longer burst widths and predict the onset of thermal damage.

Temperature changes predicted by the FEM at the center of the skin and fat are shown in FIGS. 10A-B, which provides temperature changes predicted by the FEM at the center of the skin (FIG. 10A) and fat (FIG. 10B) for frequencies of 250 kHz (- -), 500 kHz (- - -), 1 MHz (• • •), and 2 MHz (-). Equations represent a linear fit to the data. In this case, a burst width of 4 μs was simulated in order to capture the trends in temperature development. Polarity of the 2 μs pulse (250 kHz) was switched between pulses to maintain consistency with the other waveforms that are inherently bipolar. With respect to the skin, as the frequency of the applied field increases, the temperature rises at a slower rate. This is a consequence of the fact that the electric field within the skin also decreases with increasing frequency. In the case of the fat, the temperature rises at a faster rate when the frequency of the applied field is increased. At first glance, this seems to be detrimental, however, it is merely an indication that energy is preferentially being deposited more uniformly into the fat at higher frequencies. Again, this can be correlated to the electric field profile. In both tissues, the sharp rises in temperature are due to the spikes in displacement current that occur at the onset and offset of each pulse (data not shown). The total temperature increase in all cases is less than 0.003 K for a burst width of 4 μs. As explained in the discussion, even for bursts of longer widths, the temperature increase is not enough to promote thermal damage.

The onset of protein denaturation and loss of cell structure occurs above 318.15 K (see Bilchik, A. J., T. F. Wood, and D. P. Allegra, *Radiofrequency ablation of unresectable hepatic malignancies: Lessons learned*. Oncologist, 2001. 6(1): p. 24-33), which correlates to an increase in temperature of 8 K above physiological temperature. Using this information, the maximum energy delivery period (number of pulses multiplied by pulse duration) can be calculated for an amplitude of 2000 V/cm at each of the frequencies investigated using the trendlines generated by the FEM data (FIGS. 9A-D). In the skin layer, heating is reduced by increasing the frequency of the applied field. This shows that the potential for thermal damage in the skin is reduced when the frequency of the applied field is increased. At higher frequencies, the energy is preferentially deposited in the fat layer. For 2 MHz, the total energy delivery period required to cause an 8 K increase in temperature is 12 ms. An example treatment plan can include 12, 1 ms pulses separated by a delay of 1 s. If the frequency is reduced to 500 kHz, which shows the greatest electroporation efficiency (Table 5, see EXAMPLE 3), the allowable energy delivery period increases to 16 ms, which would permit the delivery of an additional 4, 1 ms pulses before the onset of thermal damage.

TABLE 5

Various exemplary treatment protocols.

| Frequency (pulse duration) | Time (μs), \|TMP\| > 0.5 V | % of Pulse, \|TMP\| > 0.5 V |
|---|---|---|
| 250 kHz (2 μs) | 1.2 | 60 |
| 500 kHz (1 μs (×2)) | 1.9 | 95 |
| 1 MHz (500 ns (×4)) | 1.3 | 65 |
| 2 MHz (250 ns (×8)) | 0.1 | 5 |

The restrictions could be increased if less conservative estimates are obtained that account for heat dissipation between pulses and heat convection at the tissue surface. Lackovic, I., R. Magjarevic, and D. Miklavcic, *Three-dimensional Finite-element Analysis of Joule Heating in Electrochemotherapy and in vivo Gene Electrotransfer*. Ieee Transactions on Dielectrics and Electrical Insulation, 2009. 16(5): p. 1338-1347. These projected protocols represent a maximum, and it is likely that the desired effects will be induced at a significantly lower energy. See Belehradek, J., S. Orlowski, L. H. Ramirez, G. Pron, B. Poddevin, and L. M. Mir, *Electropermeabilization of Cells in Tissues Assessed by the Qualitative and Quantitative Electroloading of Bleomycin*. Biochimica Et Biophysica Acta-Biomembranes, 1994. 1190(1): p. 155-163; and Garcia, P. A., J. H. Rossmeisl, R. E. Neal, T. L. Ellis, J. D. Olson, N. Henao-Guerrero, J. Robertson, and R. V. Davalos, *Intracranial Nonthermal Irreversible Electroporation: In Vivo Analysis*. Journal of Membrane Biology, 2010. 236(1): p. 127-136.

Example 3: High-Frequency Electroporation can Overcome Shielding Effects of Low Passive Conductivity Tissues and Induce Electroporation in Underlying Layers The analytical model for TMP described in this specification was utilized to investigate electroporation in a hypothetical cell located along the centerline (r=0 mm) in the middle of the fat (z=0) and skin (z=5.75 mm) layers of the FEM described in EXAMPLE 1. The equations for TMP are derived under the assumption that there is no influence on the microscopic electric field from neighboring cells. Therefore, the macroscopic electric field in the bulk tissue predicted by the FEM dictates the microscopic electric field experienced by the cell. The vertical z-component of the electric field was imported from the specific locations within FEM into Mathematica to account for polarity changes. The radial r-component was neglected due to the fact that it never surpassed 3 V/cm as current traveled primarily in the z-direction. Non-uniform electric field data was fit with a series of step functions (50 ns duration), such that the Laplace transform of the field could be performed and the solution for TMP could be obtained in the frequency domain as the summation of individual steps. The inverse Laplace transform of the data was taken to obtain the complete time courses. Measurements were taken at the pole ($\theta=0$) to depict the maximum induced TMP around the cell.

With respect to the skin, as the frequency of the applied field increases, the maximum oscillation amplitude of the TMP decreases, as shown in FIGS. 11A-B. This occurs for two reasons. First, as seen in FIGS. 8A-B, the electric field in the skin decreases with increasing frequency. Second, as seen in FIG. 5, even with constant field amplitude, the TMP decreases with increasing frequency, because the time during which the membrane has to charge before the polarity switches is less at higher frequencies. In the case of the fat, the behavior is slightly more complex. At lower frequencies, a majority of the voltage drop occurs across the skin as demonstrated in FIGS. 9A-D, resulting in a reduced electric field in the fat. This shielding effect is best shown in FIGS. 10A-B along the 250 kHz trace. According to FIG. 5, at 250 kHz, the maximum TMP should be reached. However, due to the shielding effect from the skin, a reduction in the TMP prior to the polarity change is seen. This reduction in TMP can be alleviated by increasing the frequency of the applied field. However, the tradeoff between increased frequency and reduced TMP is still evident at a frequency of 2 MHz (FIGS. 11A-B).

As mentioned, there is a balance between employing pulses that are delivered on a short enough timescale to flow through epithelial cells but are long enough to induce electroporation in underlying cells. The time constant of 345 ns, predicted by the analytical model for TMP, falls between the 2 MHz (250 ns pulse duration) and 1 MHz (500 ns pulse duration) bursts. Further, the 500 kHz burst (1 µs pulse duration) is close to the time it takes the TMP to reach steady state. Table 5 summarizes the results based on the time that the TMP on a hypothetical cell at the center of the fat layer is above 0.5 V. This amplitude was chosen such that even the highest frequency burst was above the set voltage level for a certain amount of time. The results would hold if the applied field was doubled and the voltage level was set to the 1 V threshold for pore formation, due to the linear dependence of TMP on the electric field. Based on this criterion, a frequency of 500 kHz is best suited to treat cells in the fat layer, followed by 1 MHz and 250 kHz. As frequency is increased, the dielectric properties and electric field distribution in the skin and fat become more macroscopically homogeneous, but above 1 MHz, the pulse duration is not adequate for the cell to charge.

Figure 12:
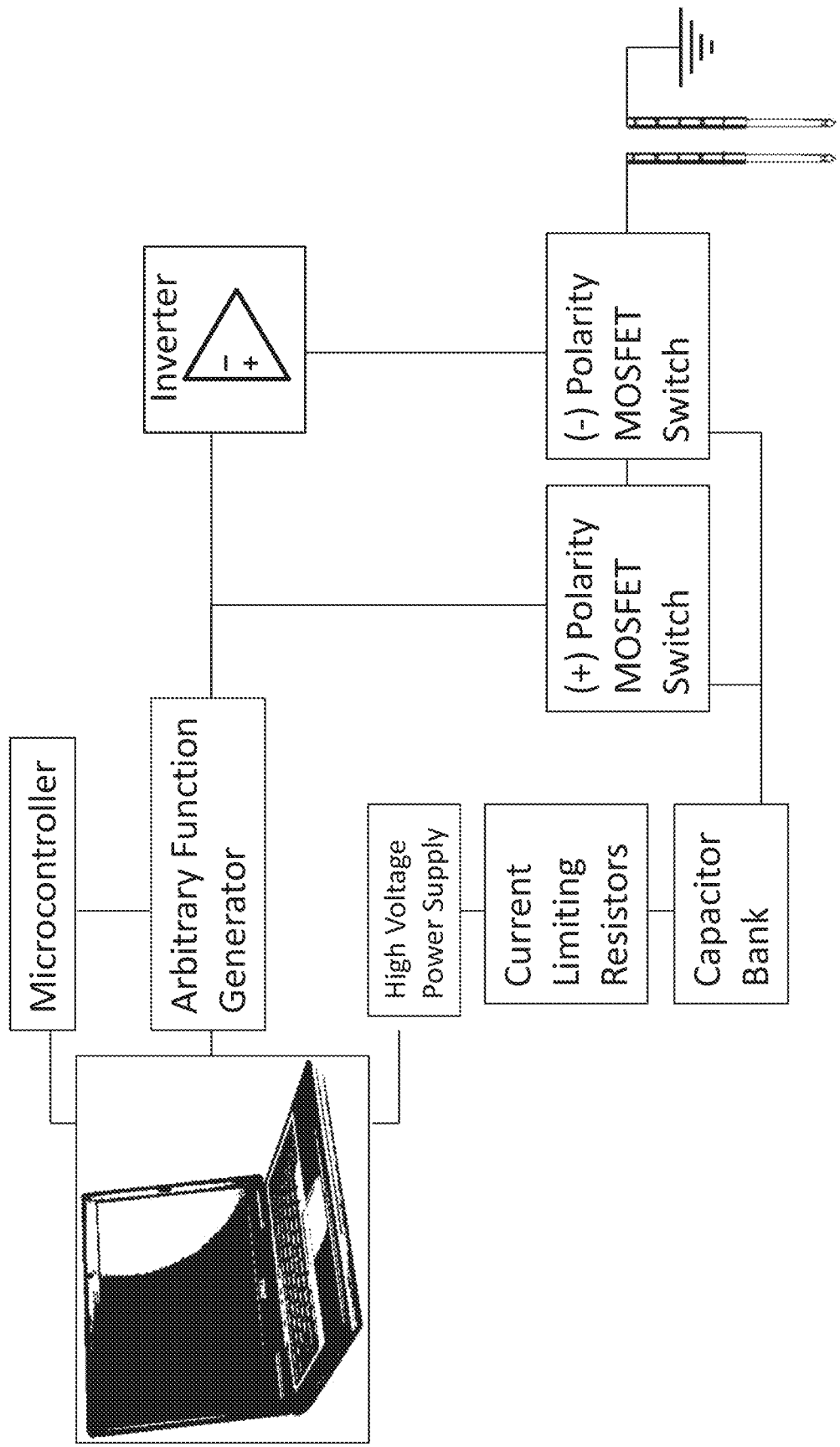
FIG. 12 is a diagram of a system for implementing high-frequency, bipolar pulses for tissue electroporation.

Example 4: System for Implementing High-Frequency, Bipolar Pulses for Tissue Electroporation The electronic drive system for delivering bipolar electroporation signals is schematically depicted in FIG. 12. The system relies upon both commercially available components and circuits built by the inventors. An arbitrary function generator (Tektronix AFG 3011) is programmed to output a tri-state square waveform. The AFG 3011 is capable of generating 20 V peak-to-peak into a 50 ohm load and has an effective analog bandwidth of 8 MHz. The burst width, interval between bursts, and total number of bursts is externally controlled by a microcontroller (Arduino Duemilanove) through the general purpose input/output (GPIO) pins. The output signal for a 1 MHz waveform with a burst width of 10 µs and amplitude of 6 V peak is given in FIG. 12. This signal is simultaneously fed through both positive polarity and negative polarity high voltage MOSFET switches (IXYS Colorado HV 1000). The signal into the negative polarity HV 1000 is inverted using an LM 7171 op amp with a slew rate of 4100 V/µs in order to properly sequence the amplification of the positive and negative polarity pulses without delay. The maximum output of each HV 1000 is 17 A and +/−850 V into a 50 ohm load. Additionally the pulse rise time is 10 ns or less. This results in an amplification of the AFG 3011 trigger signal up to 1700 V peak-to-peak, which is capable of inducing electroporation when the electrodes are spaced approximately 3 cm apart or less. The input power to each HV 1000 is maintained by a high voltage sequencer (Lab Smith HVS 448), which can regulate voltage up to +/−3000 V and current up to 100 mA. In order to increase current storage up to 17 A, an external capacitor bank was included between the HVS 448 and HV 1000. The total capacitance of the bank can be adjusted depending on the desired voltage and current output or electrode spacing. This system allows for a flexible treatment program that may be tailored to meet a patient's individual needs.

Other systems are available in the literature for generating bipolar pulses, and the invention should not be limited to the system described above. For example, De Vuyst et al. built a generator around an NE555 timer configured as an astable multivibrator capable of producing up to 50 kHz bipolar pulses. De Vuyst, E., M. De Bock, E. Decrock, M. Van Moorhem, C. Naus, C. Mabilde, and L. Leybaert, *In situ bipolar Electroporation for localized cell loading with reporter dyes and investigating gap junctional coupling.* Biophysical Journal, 2008. 94(2): p. 469-479. However, the frequency of the pulses administered according to embodiments of the invention are an order of magnitude greater, which is easily met by the bandwidth of the AFG 3011. Additionally, the MOSFET switches provide an excellent means to produce high-frequency pulses for high voltage switching. However, MOSFETs are not the only semiconductor devices that can be utilized to produce a pulse. Bipolar Junction Transistors (BJTs), Insulated Gate Bipolar Transistors (IGBTs), and Junction Field Effect Transistors (JFETs) are examples of some of the semiconductor devices that may be used to produce an output pulse.

Example 5: Experimental Results of High-Frequency, Bipolar Pulses for Electroporation of Cells A chemical reaction technique was performed to fabricate parallel silver electrodes on glass microscope slides with 100 µm spacing. Briefly, a commercially available mirroring kit was used to deposit pure silver onto the microscope slides (Angel Gilding Stained Glass Ltd, Oak Park, Ill.). A negative thin film photoresist (#146DFR-4, MG Chemicals, Surrey, British Colombia, Canada) was laid on top of the slide and passed through an office laminator (#4, HeatSeal H212, General Binding Corporation, Lincolnshire, Ill.). A photo-mask printed at 20k DPI on a transparent film (Output City, Cad/Art Services Inc, Bandon, Oreg.) was placed ink side down onto the photoresist, and slides were exposed to UV light for 45 seconds. After exposure, the slides were placed in a 200 mL bath containing a 10:1 DI water to negative photo developer (#4170-500ML, MG Chemicals, Surrey, British Colombia, Canada). The slides were placed in a beaker containing DI water to stop the development process and gently dried using pressurized air. Electrode structures on the microscope slides were fabricated by removing all silver not covered by the patterned photoresist. A two part silver remover was included in the mirroring kit used to deposit the silver. The photoresist was then removed by placing the slide in a bath of acetone.

Microfluidic channels were fabricated using the patterned photoresist on a microscope slide that had not undergone the silvering process. Liquid phase polydimethylsiloxane (PDMS) in a 10:1 ratio of monomers to curing agent (Sylgrad 184, Dow Corning, USA) was degassed under vacuum prior to being poured onto the photoresist master and cured for 1 hour at 100° C. After removing the cured PDMS from the mold, fluidic connections to the channels were punched in the devices using 1.5 mm core borers (Harris Uni-Core, Ted Pella Inc., Redding, Calif.). The PDMS mold was then bonded over the glass slides containing the patterned electrodes by treating with air plasma for 2 minutes in a PDC-001 plasma cleaner (Harrick Plasma, Ithaca, N.Y.).

Figure 13B:
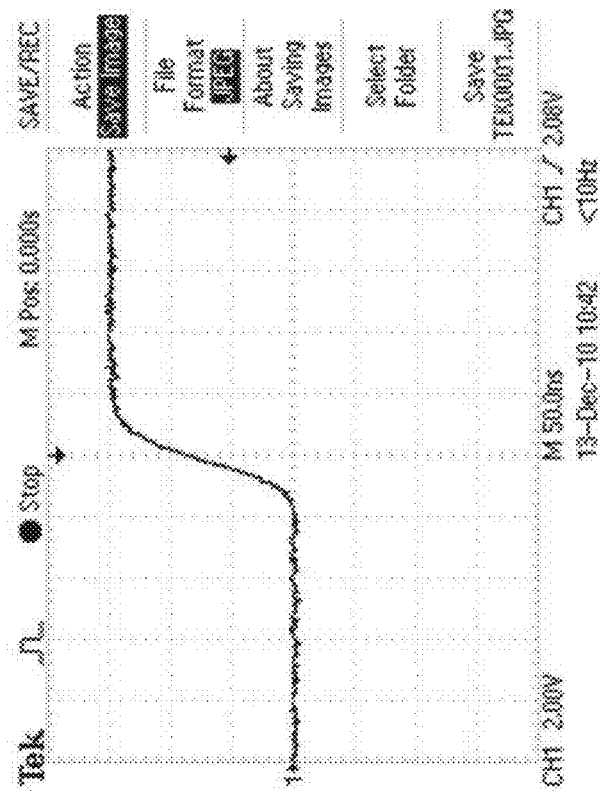
FIGS. 13A-B are graphs showing output of the arbitrary function generator prior to signal amplification by the high voltage MOSFET positive and negative polarity switches.
Figure 13A:
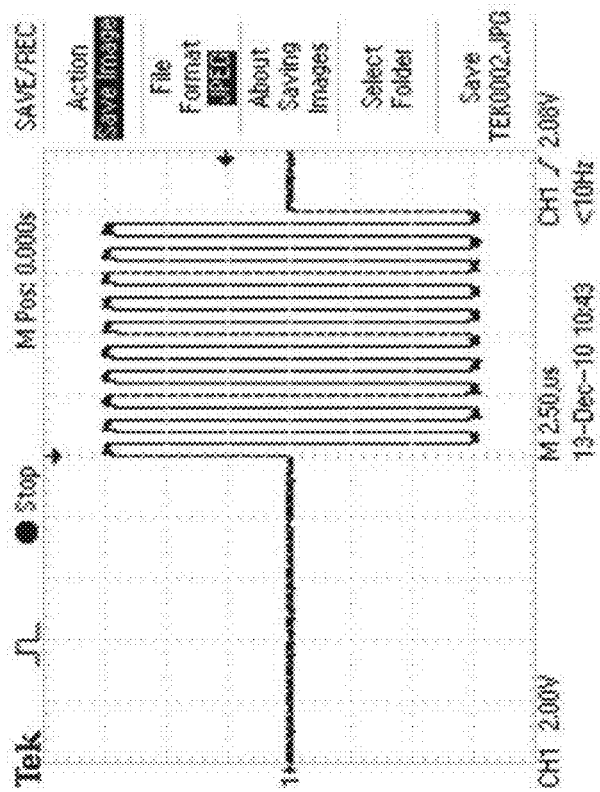

High voltage electrical wires were taped to the glass slide with exposed wire placed in direct contact with the electrical pads. A drop of high purity silver paint (Structure Probe Inc., West Chester, Pa.) was placed on the pad and allowed to dry for one hour creating a solid electrical connection. A drop of 5 minute epoxy (Devcon, Danvers, Mass.), used to secure the electrical connections, was placed on top of each electrode pad and allowed to cure for 24 hours. Pulses were delivered across the electrodes as described in EXAMPLE 4 prior to the amplification stage. No amplification was needed as the gap between the electrodes was only 100 µm. Therefore, the output signal of a function generator (GFG-3015, GW Instek, Taipei, Taiwan)+/−10 V can be used to generate an electric field capable of inducing electroporation, as shown in FIGS. 13A-B.

Figure 14B:
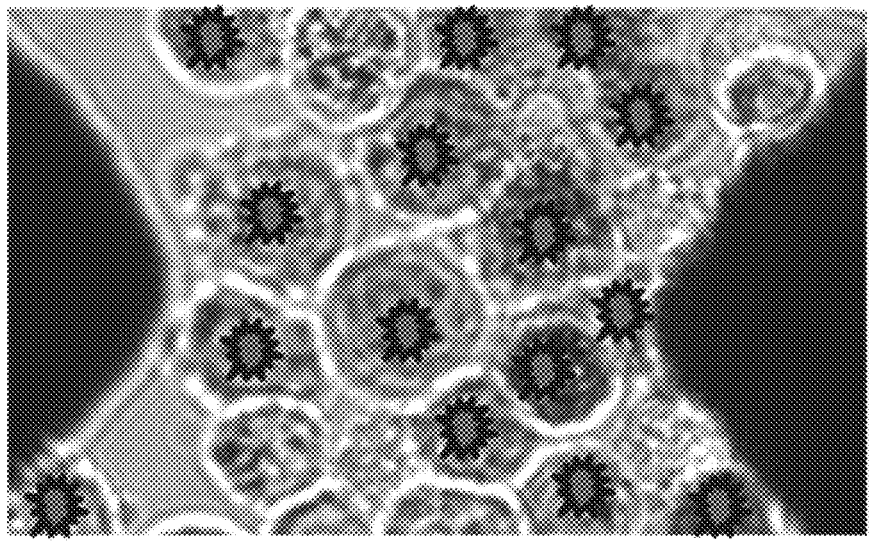
FIGS. 14A-B are micrographs showing in vitro experimental results on electroporation with high-frequency bipolar, pulses using a trypan blue dye exclusion assay.
Figure 14A:
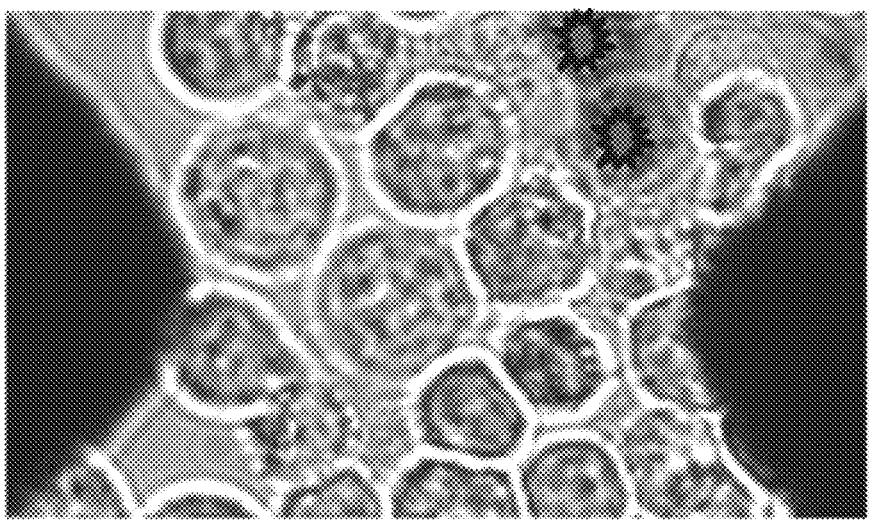

Following culture in DMEM-F12 (supplemented with 10% FBS and 1% penicillin streptomycin) MDA-MB-231 cells were resuspended in a PBS solution 1:1 with Trypan Blue (0.4%). Trypan Blue is a determinant of cell membrane integrity, and stains electroporated cells blue, whereas non-electroporated cells remain transparent. Cells at a concentration of $10^6$/ml were injected into the microfluidic channel using a syringe. The function generator was triggered by the microcontroller to deliver 80, 50 kHz bursts with a width of 1 ms and an amplitude of 500 V/cm. Results shown in FIGS. 14A-B, which shows that 60% transfection efficiency was obtained when starting with cells that are 92% viable. This efficiency of reversible electroporation could be improved by either increasing the number of pulses or the burst width. Additionally, IRE could be performed by increasing the applied voltage.

Example 6: Alternate Waveforms for Performing High-Frequency Electroporation

Figure 16:
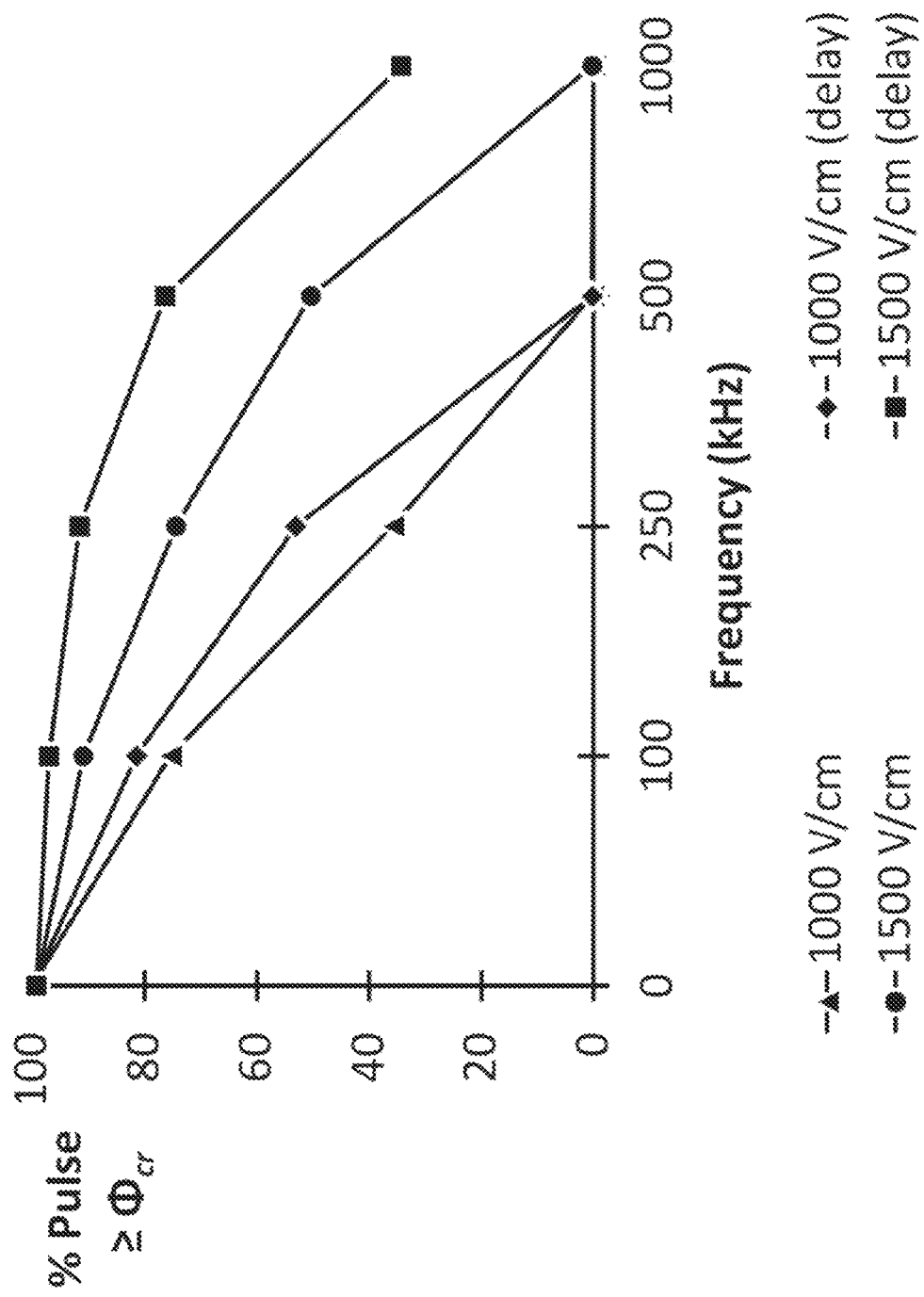
FIG. 16 is a graph comparing time above the critical threshold ($\Phi_{cr}$) for IRE at various center frequencies.

The analytical model for TMP described in the detailed description of the invention was utilized to investigate electroporation of a spherical cell subject to alternative waveforms. As mentioned, the critical TMP ($\Phi_{cr}$) across the plasma membrane required to induce IRE is approximately 1 V. Belehradek, J., S. Orlowski, L. H. Ramirez, G. Pron, B. Poddevin, and L. M. Mir, *Electropermeabilization of Cells in Tissues Assessed by the Qualitative and Quantitative Electroloading of Bleomycin*. Biochimica Et Biophysica Acta-Biomembranes, 1994. 1190(1): p. 155-163. This threshold is illustrated in FIGS. 15A-C by the dashed, horizontal line on the TMP profiles. Characteristic waveforms of IRE with unipolar pulses and high-frequency IRE with the corresponding TMP development across the plasma membrane ($\Phi_{pm}$). All results are presented at the cell pole (θ=0) to show the maximum TMP around the cell. Further, results are only shown for TMP across the plasma membrane, as the TMP across the nuclear envelope never approached the permeabilizing threshold. For an electric field of 1500 V/cm, results indicate that a unipolar pulse (FIG. 15A), a 250 kHz bipolar burst (FIG. 15B), and 250 kHz bipolar burst that includes delays between the pulses (FIG. 15C) are all capable of inducing IRE. However, the time above the threshold TMP varies between the different cases. The 1500 V/cm unipolar pulse causes the TMP to rise above the critical threshold for IRE (1 V, dashed line). The 1500 V/cm bipolar burst without a delay and with a delay causes the TMP to oscillate around the same critical threshold. This is investigated further in FIG. 16 for center frequencies of 0, 100, 250, 500, and 1000 kHz, with the 0 kHz case representing the unipolar pulse, and electric fields of 1000 V/cm and 1500 V/cm. FIG. 16 provides a comparison of time above the critical threshold ($\Phi_{cr}$) for IRE at various center frequencies. The burst width of the bipolar waveform that included delays was twice as long (40 µs) as the corresponding burst with no delays in order to generate an equivalent pulse on-time (20 µs). The amount of time that the TMP was above the critical value was normalized by the on-time and converted to a percentage. FIG. 16 illustrates that, for a given frequency, as the electric field is increased from 1000 V/cm to 1500 V/cm, the percentage of the burst above the critical TMP also increases. At 250 kHz, IRE is possible during all waveforms, but at 500 kHz, only the waveforms with amplitudes of 1500 V/cm are capable of inducing IRE. As the center frequency of the burst increases, the percentage of the burst above the critical TMP decreases. However, with the inclusion of delays between the pulses, this characteristic dispersion is shifted towards higher frequencies. At 1 MHz, only the 1500 V/cm waveform with delays can theoretically cause IRE.

The theoretical model of TMP suggests that IRE should be possible up to 1 MHz for an electric field of 1500 V/cm. Including a delay between the positive and negative pulses comprising the bipolar burst offers a therapeutic advantage in addition to protecting the MOSFETs in the pulse generation system (see EXAMPLE 4) from ringing. By not forcing a discharge of the TMP with an immediate reversal of polarity, the cell is allowed to return to the resting TMP according to its characteristic time constant. As a result, the TMP is maintained above the critical voltage required for IRE for a longer amount of time. This metric has been recognized as a potential indicator of treatment outcomes in electroporation based therapies with bipolar waveforms. Garcia, P. A., J. H. Rossmeisl, R. E. Neal, T. L. Ellis, J. D. Olson, N. Henao-Guerrero, J. Robertson, and R. V. Davalos, *Intracranial Nonthermal Irreversible Electroporation: In Vivo Analysis*. Journal of Membrane Biology, 2010. 236(1): p. 127-136.

Figures 17A, 17B, 17C:
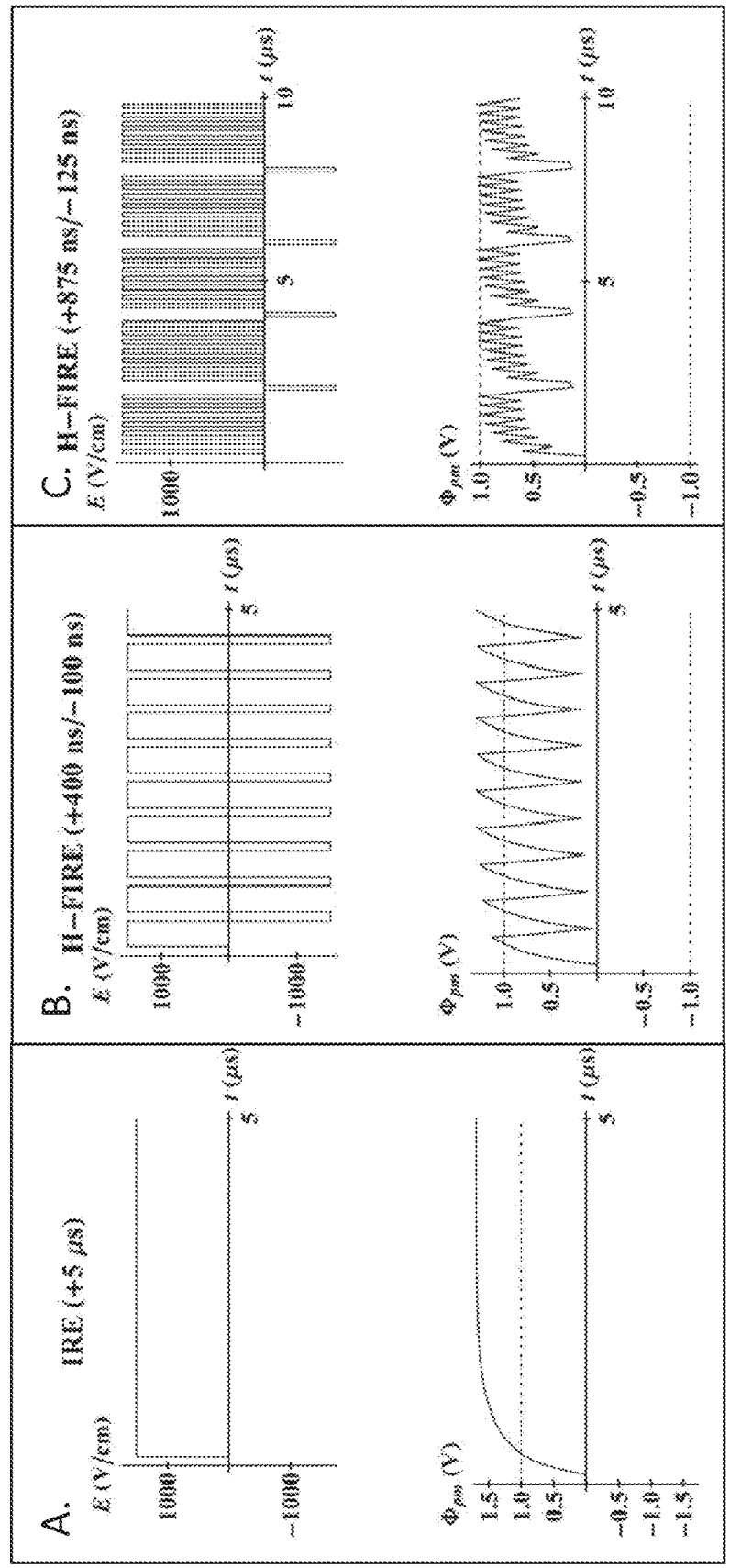
FIGS. 17A-C are waveforms of IRE with unipolar pulses and high-frequency IRE with the corresponding TMP development across the plasma membrane ($\Phi_{pm}$) for a 1500 V/cm unipolar pulse (FIG. 17A), a 1500 V/cm bipolar burst without a delay and with a shortened negative phase (FIG. 17B), and a 1500 V/cm bipolar burst with a delay and with a shortened, lower amplitude negative phase (FIG. 17C).
Figure 18:
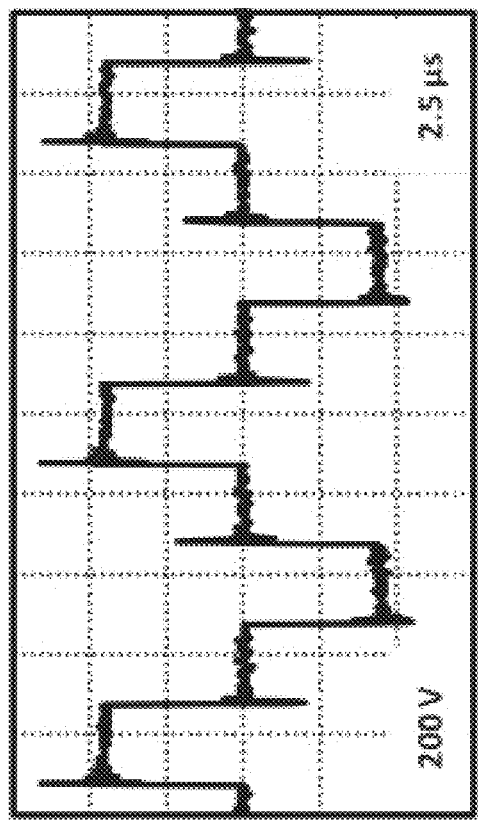
FIG. 18 is a chart showing an exemplary output from an in vivo treatment of the brain with high-frequency, bipolar pulses, where the snapshot is taken within a single burst.

Other potential waveforms for performing high-frequency electroporation are shown in FIGS. 17A-C, which provide characteristic waveforms of IRE with unipolar pulses and high-frequency IRE with the corresponding TMP development across the plasma membrane ($\Phi_{pm}$). A unipolar pulse with an amplitude of 1500 V/cm is shown for comparison (FIG. 17A). A waveform without delays between polarity reversals (FIG. 17B) can maintain a positive TMP throughout the entire treatment if the duration of positive polarity is tuned to be slightly longer than the duration of negative polarity. Similarly, for a waveform that includes delays (FIG. 17C), a train of positive ultra-short pulses could be used to gradually increase the TMP up to the critical permeabilizing threshold, and a single ultra-short pulse of negative polarity could follow the train without causing the TMP to go negative. In both examples, the ultra-short negative going pulse is designed to maintain the predicted benefits of high-frequency electroporation. Namely, it is predicted that the negative going pulse will prevent action potential generation and still permit a degree of capacitive coupling across epithelial layers. FIG. 18 is a chart showing an exemplary output from an in vivo treatment of the brain with high-frequency, bipolar pulses, where the snapshot is taken within a single burst.

Example 7: Experimental Results of High-Frequency IRE (H-FIRE) of Brain Tissue

H-FIRE was performed using a custom pulse generator as described in EXAMPLE 4 with minor modifications. An unregulated DC power supply was constructed to replace the both the high voltage sequencer and external capacitor in order to maintain a sufficient level of charge to deliver 20 A over a 100 µs burst. A center tapped 400 VA transformer (AS-4T320, Antek, Inc., North Arlington, N.J., USA) was rectified and smoothed by a capacitor bank to provide positive and negative power rails to the HV1000P and HV1000N, respectively. The voltage rails were controlled by adjusting the input voltage using a variable transformer, and the maximum output rating of the system was +/−450 V. A delay equal to the duration of single polarity was included between the pulses in order to protect the MOSFETs from ringing. A unity gain inverting amplifier (AD844, Analog Devices, Norwood, Mass., USA) was used to invert this signal and appropriately trigger the negative pulse generator. The outputs of the two monopolar pulse generators were terminated into a 50Ω load in parallel with the electrodes. This load was used to maintain appropriate pulse characteristics and as a safety to ensure the system was never triggered without an attached load. For comparison, the IRE treatments were performed using the BTX ECM 830 electroporation system (Harvard Apparatus, Holliston, Mass., USA).

All study procedures were conducted following Institutional Animal Care and Use Committee approval and performed in a GLP compliant facility. Four, Fischer 344 male rats weighing 200-240 g were anesthetized by intraperitoneal injection of 10 mg/kg xylazine and 60 mg/kg ketamine hydrochloride, and a surgical plane of anesthesia was assessed by loss of the tail pinch reflex. To monitor muscle contractions, a 3-axis accelerometer breakout board (ADXL335, Adafruit Industries, New York, N.Y., USA) with a sensing range of ±3 g's was sutured to the dorsum of each rat in the interscapular region at the cervicothoracic junction using 5-0 monocryl suture. Low-pass filter capacitors (0.1 µF) were included at the x, y, and z outputs of the accelerometer for noise reduction. The hair of the skull was clipped and aseptically prepared using povidone-iodine and alcohol solutions. Anesthetized rats were placed in a small animal stereotactic head frame (Model 1350M, David Kopf Instruments, Tungisten, Calif., USA). A routine lateral rostrotentorial surgical approach to the skull was made, and 6 mm by 3 mm rectangular parieto-occipital craniectomy defects were created in the right and left aspects of the skull of each rat using a high-speed electric drill. Custom electrodes were inserted into the center of the forelimb area of the sensorimotor cortex of each rat (coordinates relative to Bregma: 1 mm anterior, 2.5 mm lateral, 2 mm dorsoventral) and advanced to a depth of 2 mm beneath the surface of the exposed dura. The electrodes were fashioned by blunting stainless steel acupuncture needles (0.45 mm diameter, Kingli Medical Appliance Co., Wuxi, China) with high grade sandpaper. Exposure length was set to 1 mm by insulating the electrodes with miniature polyimide tubing (25 AWG, Small Parts, Seattle, Wash., USA), and the edge-to-edge electrode spacing was set to 1 mm by molding the electrodes in liquid phase polydimethylsiloxane (PDMS) cured in a 10:1 ratio with Sylgard 184 (Dow Corning Corp., Midland, Mich., USA) at 150° C. for 30 min.

Pulse parameters were chosen based on the results from the analytical and numerical models to ensure the greatest potential for non-thermal tissue ablation. Following electrode insertion, pulses were applied to the right and left cerebral hemispheres, resulting in two treatments per rat (Table 6).

TABLE 6

Pulse parameters of various treatment protocols.

| Rat Number | Treatment | Hemisphere | Frequency (kHz) | Voltage (V) |
|---|---|---|---|---|
| 1 | IRE | Left | — | 100 |
|  | H-FIRE | Right | 250 | 100 |
| 2 | IRE | Left | — | 200 |
|  | H-FIRE | Right | 250 | 200 |
| 3 | H-FIRE | Left | 250 | 300 |
|  | H-FIRE | Right | 250 | 400 |
| 4 | IRE | Left | — | 50 |
|  | H-FIRE | Right | 500 | 400 |

H-FIRE experiments were performed using 180 bursts with a pulse on-time of 200 µs within each burst, and bursts were delivered at a rate of one per second. In Rat #1 and Rat #2, H-FIRE was applied at voltages of 100 V and 200 V, respectively, to the right hemisphere with a center frequency of 250 kHz (duration of single polarity equal to two microseconds). The left hemisphere of Rat #1 and Rat #2 were treated with 180 IRE pulses (200 µs duration) of equivalent energy. In Rat #3, H-FIRE was applied to the left and right hemispheres at voltages of 300 V and 400 V, respectively, with a frequency of 250 kHz. In Rat #4, H-FIRE was applied at a voltage of 400 V to the right hemisphere with a frequency of 500 kHz (duration of single polarity equal to one microsecond). The left hemisphere of Rat #4 was treated with 90 IRE pulses (200 µs) and an applied voltage of 50V. This lower energy scenario was designed to compare H-FIRE treatment outcomes to traditional IRE protocols in the brain. Kotnik, T. and D. Miklavcic, *Theoretical evaluation of voltage inducement on internal membranes of biological cells exposed to electric fields.* Biophysical Journal, 2006. 90(2): p. 480-491.

Immediately following treatment, Rats #3 and #4 were subjected to MRI examinations of the brain while under general anesthesia. The MRI was performed with a 0.2 T MRI scanner using a dual phased array hand/wrist coil for RF signal transmission and reception. Sequence acquisition parameters were as follows: T1-weighted images were acquired using spin echo pulse sequence (TR=200 ms, TE=16 ms, FOV=6 cm, matrix=256×196, slice thickness=2 mm), and T2-weighted images were acquired using a gradient echo pulse sequence (TR=3000 ms, TE=90 ms, FOV=6 cm, matrix=256×196, slice thickness=3 mm). T1-weigthed images were obtained following intraperitoneal injection of 0.1 mmol/kg of gadopentetate dimeglumine (Magnevist, Berlex Laboratories, NJ, USA). In all rats, humane euthanasia was performed by cervical dislocation approximately 1 hr post-treatment, and the brain was removed and fixed intact in 10% neutral buffered formalin. Following fixation for 48 hours, an adult rat brain matrix slicer (Zivic Instruments, Pittsburgh, Pa.) was used to obtain contiguous 2 mm coronal brain sections from each animal. Brain and sections were embedded routinely in paraffin, sectioned at 5 µm, and stained with hematoxylin and eosin (H&E).

Treatments evaluated in this study produced ablative lesions in brain tissue, as evaluated with MRI examinations (FIGS. 21A-F) and pathologic preparations (FIGS. 20A-D). In Rats #3 and #4, the MM characteristics of both H-FIRE and IRE lesions were similar. The MRI appearance of lesions in rat brain appeared as focal, ovoid to elliptical, T1 iso- to hypo-intense, uniformly and markedly contrast enhanced (FIGS. 21A, B, C, D, F) and T2 hyper-intense (FIG. 21E). In all panels, lesions appear as focal hyperintense regions (white) compared to adjacent untreated cerebrocortical tissue (gray). Top Panels (A-C) obtained from Rat #3, in which both the left and right cerebral hemispheres were treated with high-frequency waveforms at 300 V/250 kHz and 400 V/250 kHz, respectively. Bottom Panels (D-F), Rat #4, which underwent high-frequency, bipolar pulses in the right cerebrum at 400 V/500 kHz, and conventional IRE with unipolar pulses at 50 V in the left cerebrum. Panels A and D, post-gadolinium T1-weighted MRI sequences in the axial plane. Panel B, post-gadolinium T1-weighted MRI sequences in the right parasagittal plane. Panels C and F, post-gadolinium T1-weighted MRI sequences in the dorsal plane. Panel D, T2-weighted MM sequence in the transverse plane. In all panels, the right side of the brain is on the left side of the panel.

Figure 20B:
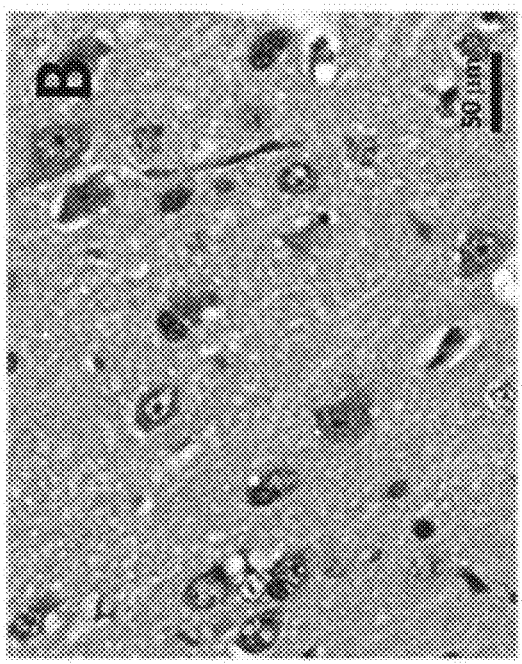
FIGS. 20A-D are micrographs showing the histopathology of rat brain tissue for untreated rats (FIGS. 20A-B) and treated with high-frequency, bipolar pulses at 200 V/250 kHz (FIG. 20C-D, Rat #2, right hemisphere), with the delineation between treated and untreated tissue shown in FIG. 20C (black, dotted line).
Figure 20D:
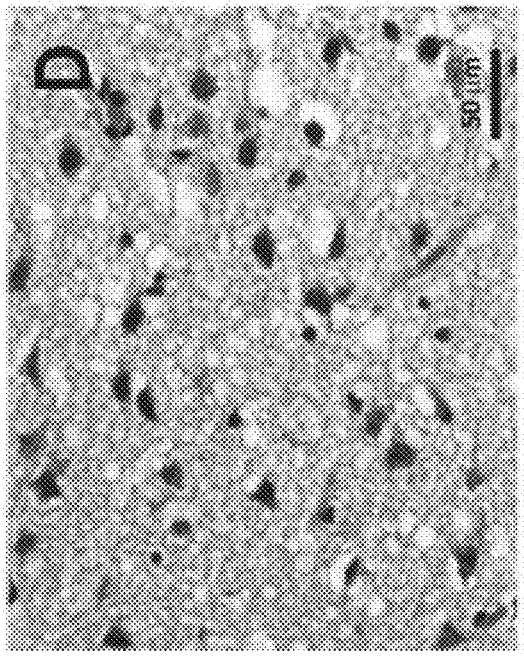
Figure 20A:
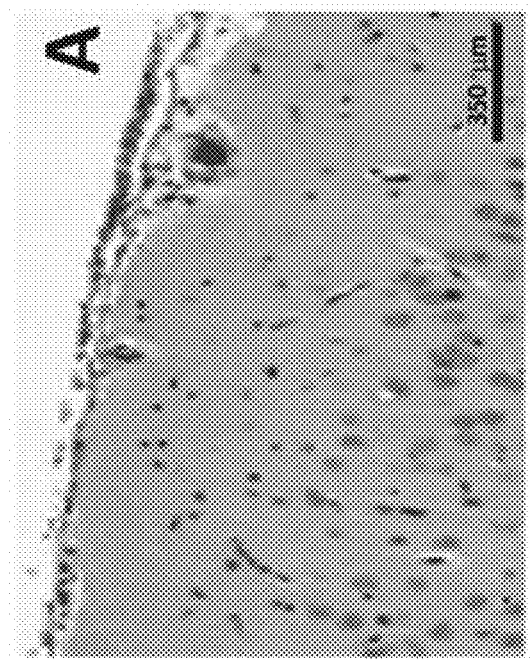
Figure 20C:
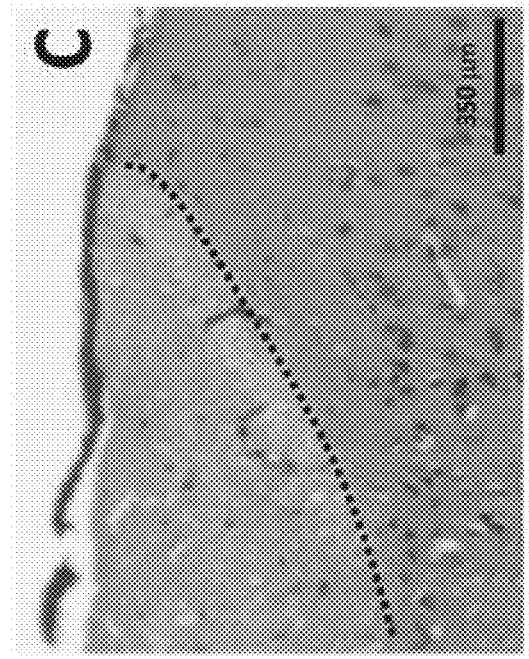

All lesions were well demarcated from adjacent, normal brain tissue and appeared similar in size. Compared to untreated brain (FIGS. 20A and B), histopathologic examination of brain sections from all treatments demonstrated clear areas of ablation indicated by pallor of the treated tissue that was sharply delineated from adjacent normal brain (FIG. 20C). H-FIRE and IRE lesions were predominantly characterized by areas of complete obliteration of cerebrocortical architecture by an eosinophilic, vacuolated amorphous debris (FIGS. 20C and D). In Rat #1, the H-FIRE ablation zone was confined to regions of elevated electric field surrounding the electrodes, whereas all other pulsing protocols resulted in ablation zones spanning the entire region between the electrodes. Cavitary cerebrocortical defects were induced with H-FIRE in Rat #1 and IRE in Rat #4. Variably sized regions of intraparenchymal hemorrhage were most pronounced immediately adjacent to and within electrode insertion tracks. The morphology of remnant neuronal and glial elements within H-FIRE ablated regions demonstrated features of both apoptosis and necrosis, including shrunken and hypereosinophilic cytoplasm, nuclear chromatin condensation, and nuclear pyknosis and karyolysis (FIG. 20D). Free glial and neuronal nuclei in various states of degeneration were scattered throughout ablation zones. Inflammation was not a significant feature of IRE or H-FIRE lesions at the time point brains were examined.

Figure 23:
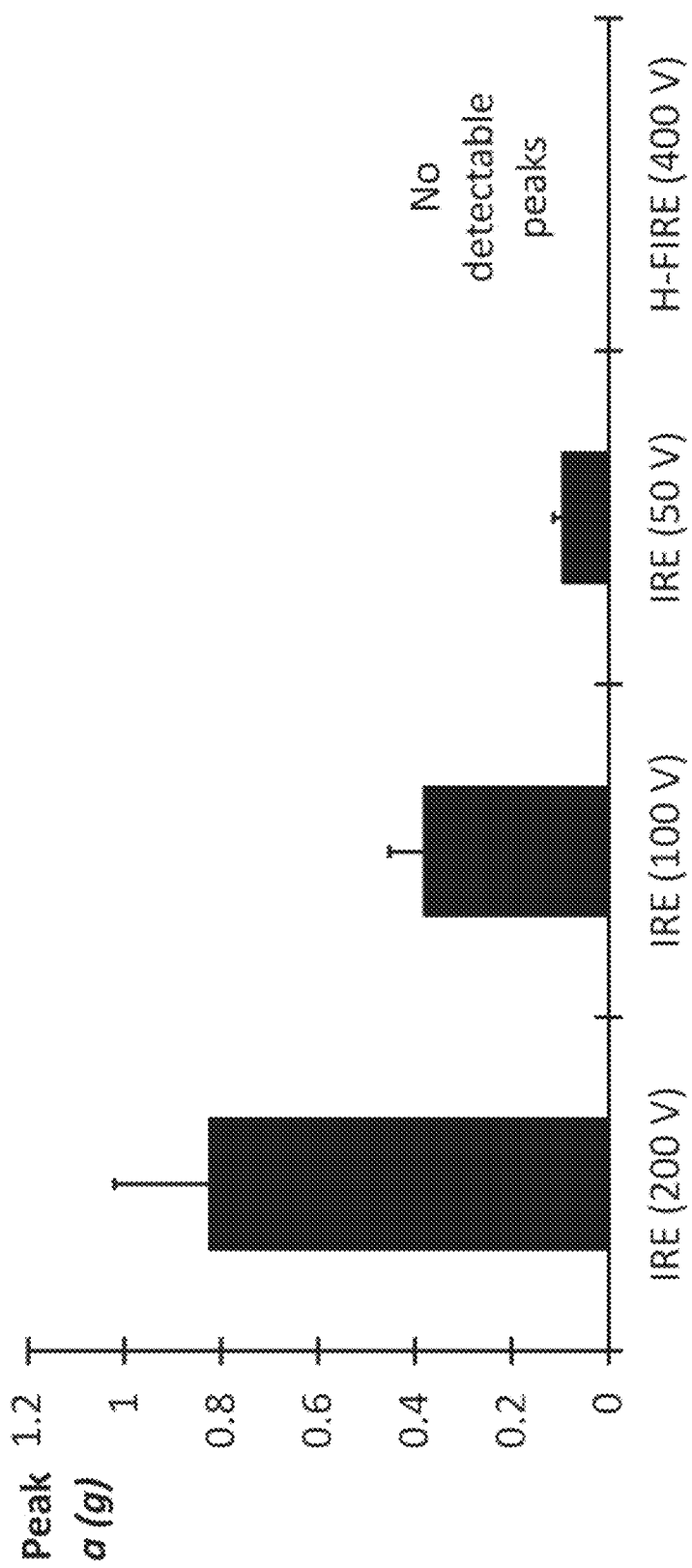
FIG. 23 is a chart showing peak acceleration (a) during pulsing protocols averaged over the first 90 pulses.

Example 8: Elimination of Muscle Contractions During High-Frequency IRE (H-FIRE) of Brain Tissue Muscle contractions were monitored throughout the procedure described in EXAMPLE 7 with the accelerometer located in the interscapular region at the cervicothoracic junction. All IRE pulsing protocols were associated with macroscopic muscular contractions of the cervicothoracic junction, which were also palpable to the neurosurgeon, while no visual or tactile evidence of muscular contraction was seen during any of the H-FIRE bursts. These results were quantitatively confirmed by the data recordings from the accelerometer (FIGS. 22A-D). Peak acceleration was determined during the first 90 bursts of the highest energy H-FIRE protocol (400 V/250 kHz) and the first 90 pulses of each IRE protocol (50 V, 100 V, 200 V). A one-way ANOVA was used to investigate the effects of each protocol on the ranks of peak acceleration at the cervicothoracic junction. In the event of a significant main effect, pairwise comparisons were completed using Tukey's Honestly Significant Difference (HSD). All statistical analyses were conducted using JMP 7 (Cary, N.C., USA) with a significance level of $p \leq 0.05$. Results indicate that, even in the highest energy H-FIRE protocol, there are no detectable peaks in acceleration above the inherent noise of the system. However, in all IRE protocols, peaks in acceleration associated with each pulse are detectable above the baseline noise. Further, pairwise comparisons between the various IRE protocols indicated that the mean peak acceleration during each treatment was energy dependent. Specifically, the mean peak acceleration decreased as the applied voltage decreased (FIG. 23).

Example 9: Experimental Results of High-Frequency IRE (H-FIRE) of Liver Tissue

All study procedures were conducted following Institutional Animal Care and Use Committee approval and performed in a GLP compliant facility. Two, Fischer 344 male rats weighing 200-240 g were anesthetized by intraperitoneal injection of 10 mg/kg xylazine and 60 mg/kg ketamine hydrochloride, and a surgical plane of anesthesia was assessed by loss of the tail pinch reflex. A routine laparotomy surgical approach to the abdomen was made in order to expose the liver. Custom electrodes were inserted into the liver parenchyma and advanced to a depth of 2 mm beneath the surface. The electrodes were fashioned from steel pins (Dritz, 0.5 mm diameter), and the edge-to-edge electrode spacing was set to 1 mm by inserting the electrodes in a custom polycarbonate spacer.

In Rat #1, H-FIRE was applied at 1000 V/cm with 80 unipolar bursts at a center frequency of 2 MHz and, 50% duty cycle, and 50 µs burst width. In Rat #2 IRE was applied at an equivalent energy using 80 unipolar pulses with a duration of 50 µs and amplitude of 1000 V/cm. In all rats, humane euthanasia was performed by cervical dislocation approximately 1 hr post-treatment, and the liver was removed and fixed intact in 10% neutral buffered formalin. Following fixation for 48 hours, 5 mm sections from each animal were obtained and embedded routinely in paraffin, sectioned at 5 µm, and stained with hematoxylin and eosin (H&E).

Figure 19B:
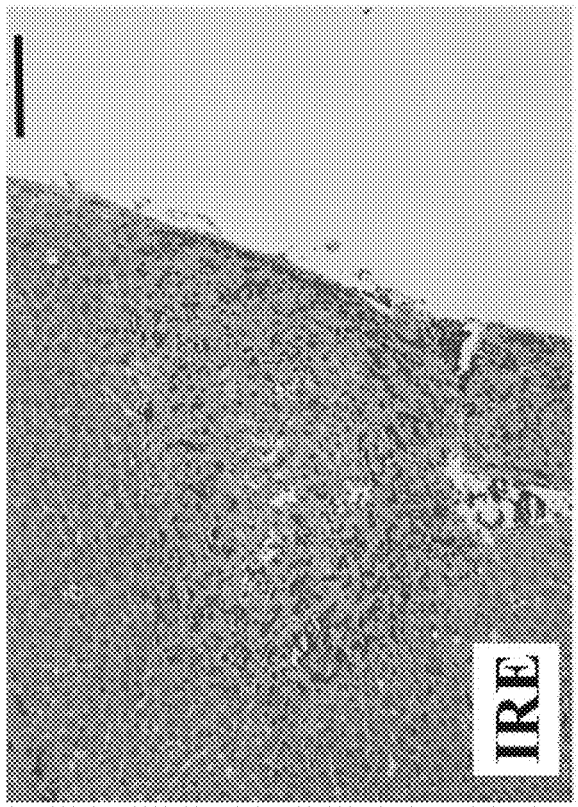
FIGS. 19A-B are photographs showing histological sections of liver tissue treated with high-frequency IRE (FIG. 19A) and conventional IRE with unipolar (FIG. 19B), with cross sections of tissue taken between the electrodes (scale bar=250 µm).
Figure 19A:

Histologically, in both treatments, there is evidence of necrosis and sinusoidal congestion (FIGS. 19A-B). Additionally, the lesions are well demarcated with cell scale resolution between treated and untreated tissue. Both of these features are common to IRE ablation of liver. No evidence of muscle contraction was observed visually. These results supplement those presented in EXAMPLE 7 and confirm that H-FIRE ablation can be achieved in multiple tissue types.

Example 10: The Electric Field Distribution During High-Frequency Electroporation can be Approximated by the Laplace Equation A 2D axisymmetric FEM representative of a slab of non-infiltrated fat adjacent to dry skin was simulated using COMSOL 4.2a (Burlington, Mass.). An energized and grounded electrode were modeled as infinite fins (0.5 mm diameter) separated 0.5 cm from the skin-fat interface, for a total spacing of 1 cm. The electric potential distribution within the tissue was obtained by transiently solving Equation 7 (see Example 1). Additionally, the homogeneous solution was solved according to the Laplace equation:

$$-\nabla \cdot (\nabla \Phi) = 0 \quad (11)$$

For the heterogeneous case, the dielectric properties of various tissues were chosen from data generated by Gabriel et al. available at (http://niremf.ifac.cnr.it/docs/dielectric/home.html). Gabriel, S., R. W. Lau, and C. Gabriel, *The dielectric properties of biological tissues .2. Measurements in the frequency range 10 Hz to 20 GHz*. Physics in Medicine and Biology, 1996. 41(11): p. 2251-2269. The data was interpolated in Mathematica 7 (Wolfram Research, Inc.) in order to estimate the dielectric properties at 1 kHz and 1 MHz. For the homogeneous case, the electric field distribution is independent of the dielectric properties. The energized and grounded electrodes were subtracted from the skin and fat subdomains, and treated purely as boundary conditions at 1000 V and 0V, respectively.

Figures 24A, 24B, 24C:
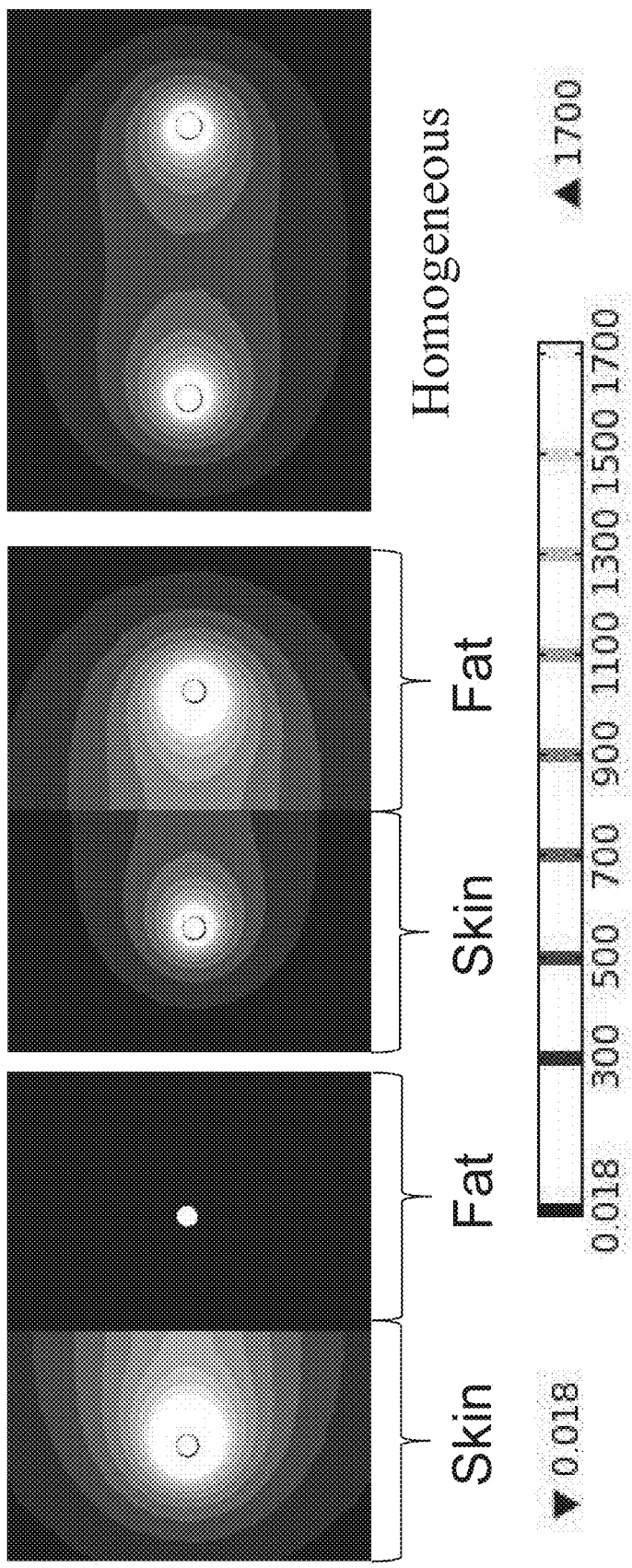
FIGS. 24A-C are schematic diagrams showing electric field, norm (V/cm) contours predicted by the FEM during a 1000 V amplitude burst with a center frequency of 1 kHz (FIG. 24A) and 1 MHz (FIG. 24B).

FIGS. 24A and B show the electric field distribution during a bipolar burst with the frequencies given in Table 7.

TABLE 7

Dielectric properties of skin and fat tissue at various frequencies.

| Frequency | Property | Tissue | |
|---|---|---|---|
| | | Skin | Fat |
| 1 kHz | $\sigma$ [S/m] | 0.000180 | 0.0246 |
| | $\varepsilon_r$ | 1170 | 20800 |
| 1 MHz | $\sigma$ [S/m] | 0.0119 | 0.0267 |
| | $\varepsilon_r$ | 792 | 25 |

From the surface contour map, at 1 kHz, which is representative of a 500 μs traditional electroporation pulse, the electric field is highly non-uniform. A majority of the voltage drop occurs within the skin layer, and the fat layer remains untreated. However, at 1 MHz, which is representative of a 500 ns high-frequency electroporation pulse, the voltage drop is distributed more uniformly throughout the entire domain. As a result, both the skin and fat layers can be treated. Additionally, the electric field distribution at 1 MHz closely resembles that of the homogenous solution. Therefore, knowledge of dielectric properties and intricate geometrical arrangements of heterogeneous tissues can be neglected during treatment planning for high-frequency electroporation. This greatly reduces treatment planning protocols and produces more predictable outcomes.

Example 11

Figure 28:
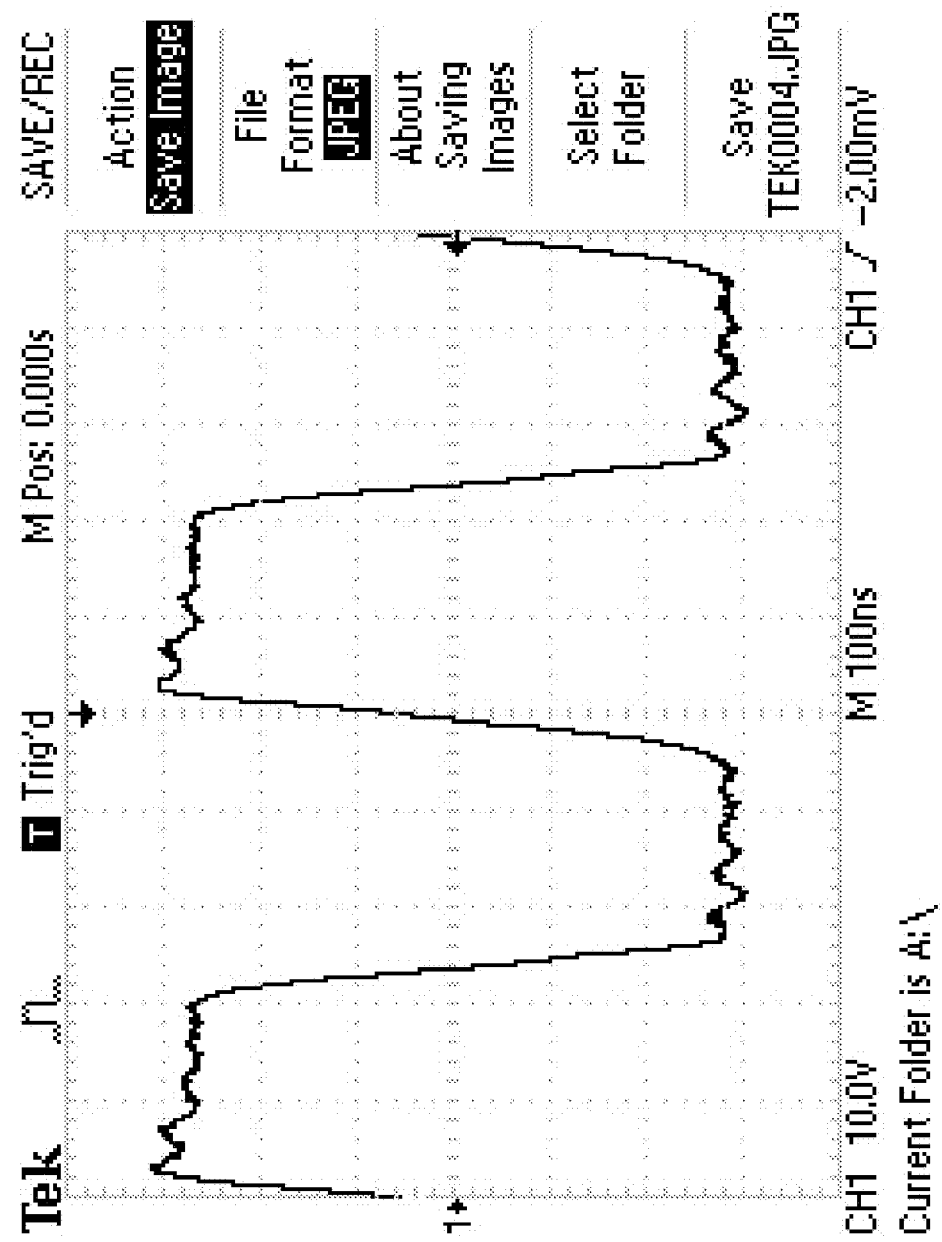
FIG. 28 shows an output waveform by a simple circuit using a wideband amplified to create ultra-short high frequency pulses.

Demonstration of Varying the Region of Treatment Through the Adjustment of Pulse Parameters The mechanism of the present invention may be demonstrated in vitro by culturing cells on a micro-fabricated electrode array. These cultured cells would then be treated with dyes in order to indicate the state of the cell's viability. By applying pulses to the micro-electrode array the cells grown on the array will undergo electroporation or supraporation depending on the pulse parameters used in the experiment. The present invention suggests that the location of the treated cells in relation to the electrode array may be changed by adjustment of pulse parameters. The combination of a wideband amplifier with dedicated pulse generation equipment or computer-based pulse generation equipment would allow for the investigation of the effect of various pulse parameters on the region of effected cells. The use of a wideband amplifier to create ultra-short high frequency pulses has been demonstrated as a viable method and the output waveform produced by a simple circuit is shown in FIG. 28. By performing this experiment at the microscope scale, much lower voltages may be used and the use of a wideband amplifier would also allow for much higher pulse repetition frequencies than dedicated switched-semiconductor devices. It will be apparent to those skilled in the art that various modifications and variations can be made in the practice of the present invention without departing from the scope or spirit of the invention. Other embodiments of the invention will be apparent to those skilled in the art from consideration of the specification and practice of the invention. It is intended that the specification and examples be considered as exemplary only, with a true scope and spirit of the invention being indicated by the following claims.

Example 12

Optimization of Voltage Parameters and Nanorod Concentrations for Selectively Killing Leukemia Cells In Vitro Gold nanorods can be used to enhance the selectivity of pulsed electric field therapies to treat leukemia, a cancer that starts in the bone marrow and causes a large number of blood cells to be produced. Treatment of leukemia depends on the type and extent of the disease but often involves chemotherapy or radiation therapy. In autologous stem cell transplantation, stem cells from the patient's own marrow or blood are obtained and engrafted after the patient receives an intense dose of chemotherapy or radiation in an attempt to restore hematologic and immunologic function following treatment. There is the potential for disease recurrence if the engrafted stem cells contain even a single leukemic cell. Gold nanorods combined with antibody targeting techniques provide a means to selectively kill leukemic cells through the localized amplification of an applied external electric field. This treatment can be used as either an alternative to stem cell transplantation or as a means to purge stem cells of leukemia prior to engraftment.

In this Example, sample preparation is performed using previously established protocols developed by Lapotko et al.

(Lasers SurgMed, 2006). Specifically, cryopreserved samples of primary human cells derived from the bone marrow of leukemia patients (acute B-lymphoblast leukemia) and healthy donors are used. Normal bone marrow samples have no tumor cells and leukemic samples are comprised mainly of tumor cells (up to 98%) in samples from different patients. Normal and tumor samples are prepared and analyzed as separate samples in 6 well-plates, but they are treated with the same protocols. The trial groups (Table 1) include a control group without nanorods and antibodies (−NR, −Y), an enhancement group (+NR, −Y), and a targeting group (+NR, +Y). Gold nanorods are purchased (Nanopartz) with a dense coating of hydrophilic polymers for conjugation to secondary antibody and uniform suspension. Leukemia cells express diagnosis specific genes that are determined individually for each patient using standard clinical protocols developed by Jennings and Foon (Blood, 1997). Flow cytometry is used for phenotyping and specific monoclonal antibodies raised against cell membrane receptors corresponding to specific genes are used for each sample of tumor cells. For different patients, different monoclonal antibodies yield different expression levels and an optimal monoclonal antibody is used for each patient-specific sample in all experiments. In the targeting trial group, samples are incubated for 30 minutes with their corresponding primary antibody that selectively attaches to blast cells. In the enhancement and targeting trial group, samples are incubated for an additional 30 minutes with gold nanorods that are conjugated with a secondary antibody that has a high coupling efficiency for primary antibody. Additionally, R-phycoerythrin (PE), a fluorescent dye (#P9787, Ted Pella Inc.) factory conjugated with a tertiary antibody that has a high coupling efficiency for secondary antibody, is used as a marker for nanorods in quantifying distribution. PE is incubated with samples for 30 minutes. All incubation is performed at 4° C. to minimize physiological processes and allow for the efficient antibody-receptor or antibody-antibody interactions.

The sample size for each pulsing protocol with varying nanorods concentrations is 4 (Table 1). Sample size was calculated based on a one-sided t-test with an alpha value of 0.05, a power of 0.80, and an anticipated Cohen's d of 2.00 (considered to be a large effect size). This effect size is consistent with published data on cell survival following IRE as compared to untreated controls. A conservative estimate calculates the value of Cohen's d with a mean percent survival of 90% (0.3 standard deviation) for untreated controls and 30% (0.3 standard deviation) for cells treated with IRE for inducing cell death.

For the electric pulse protocol, the ECM 830 Square Wave Electroporation System (BTX Harvard Apparatus) is used to induce IRE in cell suspensions. The device is capable of generating a wide range of voltages (5 to 3000 V) and pulse durations (10 µs to 10 s). Additionally, the device can be used in combination with a variety of specialty electrodes (BTX Harvard Apparatus). Specifically, cells are electroporated using the BTX Petri Pulser. This device is designed to electroporate cells grown in a 6-well plate and is comprised of 13 gold plated electrodes spaced 2 mm apart. Because there is no commercially available nanosecond pulsed generator for bioelectric studies, one is constructed according to a previously established protocol developed by Sun et al. (Dielectrics and Electrical Insulation, IEEE Transactions on, 2007). The supra-poration generator can be used with the BTX Petri Pulser and provides a 10 ns pulse duration with a rise time of approximately 2 ns and an amplitude up to 35 kV. The experiments are designed around these device restrictions (Table 1). Immediately prior to exposure to electric pulses, samples are imaged to perform a nanorod distribution analysis. After exposure to electric pulses, the samples are incubated for 12 hrs prior to performing a subsequent nanorod distribution analysis and cell viability analysis to allow adequate time for the induction of cell death following supra-poration.

A CCD camera (U2C-145415, Ormins Ltd.) is used with a fluorescent light microscope (Leica DMI6000B, Leica Microsystems) in order to image and quantify the distribution of nanorods around individual cells and the cell viability following supra-poration. Bright field images of cells are taken of all samples and overlaid with fluorescent images in all trial groups. Leica image processing software is used to reconstruct a representative image of each entire well by automatically tiling individual field of view images. The bright field images are used to distinguish cell type and dimension, and the fluorescent images are used to quantify nanorod association with the cell membrane and cell death. To quantify nanorod association with the cell membrane, a standard "green" fluorescent excitation mode is applied, and intensity measurements are recorded both at the cell membrane and throughout the rest of the sample using the Leica image processing software. The peak image amplitude is treated as an estimation of the total number of nanorods. The CCD camera is calibrated using several different known concentrations of homogeneous dispersions of nanorods in water. Previous studies have shown that the mean pixel amplitude of a fluorescent signal is almost linearly proportional to the concentration of nanorods. To analyze cell viability, all samples are stained with propidium iodide (PI), and a standard "red" fluorescent excitation mode is applied. PI gets taken up in cells with compromised plasma membranes, such that cells that are counted as PI-positive are considered dead, and cells that are counted as PI-negative are considered live. A software program in LabVIEW can be used to analyze the reconstructed well images and distinguish dead from live cells to output a viability percentage. Additionally, the software can determine the concentration of nanoparticles around each cell.

A Multi-way ANOVA with SPSS software is used to determine statistical significance among endpoint measurements for all pulsing protocols, and a TukeyKramer test identifies significant differences between cell response to supra-poration alone or in combination with gold nanorods. Data is presented as mean±standard deviation of 4 independent determinations, and a statistical probability of $P<0.05$ is considered significant. In the tested pulsing protocols (Table 8), electric fields resulting in greater than 90% cell death are considered the threshold for inducing supra-poration with and without the inclusion of gold nanorods.

TABLE 8

Trial groups, pulsing parameters, and nanorod characteristics for in vitro experiments.

| Trial Group | Applied Voltage (N = 4) | Pulse Duration | Cell Line | Conc. | Number of Pulses | Frequency |
|---|---|---|---|---|---|---|
| Control (−NR, −Y) | 0, 50, 100, 150, 200, 250, and 300 Volts | 10 μs | Normal Cancer | — | 100 | 1 Hz |
| Enhancement (+NR, −Y) | 0, 50, 100, 150, 200, 250, and 300 V | 10 μs | Normal Cancer | 0.1, 0.5, and 1 mg/ml | 100 | 1 Hz |
|  | 0, 5, 10, 15, 20, 25, and 30 kV | 10 ηs | Normal Cancer |  |  |  |
| Targeting (+NR, +Y) | 0, 50, 100, 150, 200, 250, and 300 Volts | 10 μs | Normal Cancer | 0.1, 0.5, and 1 mg/ml | 100 | 1 Hz |
|  |  | 10 ηs | Normal Cancer |  |  |  |

Example 13: Cell Death in Bony Tissue Using Pulsed Electric Fields

To demonstrate that pulsed electric fields can safely and predictably induce cell death in bony tissue, a rabbit model is used as the animal of study because techniques have been established for performing imaging and histological analysis on bony substructures in rabbits. Like humans, rabbits have a well-developed haversian system, making them ideal candidates for obtaining translatable results from experiments on bone substructures. Six-month old rabbits are used because it is known that they achieve skeletal maturity at nineteen to twenty-four weeks. The IRE and supra-poration pulse generators are used in conjunction with a custom made bipolar electrode (4 mm in diameter) to deliver the electric pulses. Two IRE pulsing protocols and two supra-poration pulsing protocols are implemented for a comparison of treatment areas (Table 8). For each of the trial groups, including an untreated control group, four rabbits are utilized, thereby requiring a total of 20 rabbits. Rabbit numbers were calculated based on a one-sided t-test with an alpha value of 0.05, a power of 0.80, and an anticipated Cohen's d of 2.00 (considered to be a large effect size). Using four rabbits for treatment area calculations account for variations in bone structure and tissue response.

Prior to surgery, rabbit femurs are imaged using micro-CT scanning. Rabbits are sedated under isoflurane anesthesia using a mask. The left hind-leg is extended and held in place with a strap. The distal femoral is chosen as the region of interest, because it has a sufficient, continuous spongy bone structure. A commercially available low dose in vivo x-ray micro-CT scanner is utilized (Skyscan 1076, Micro Photonics Inc.). The device is capable of performing non-invasive slice imaging and 3D image reconstruction from small animals, such as rabbits. The technique can capture a cross-section up to 17 mm in length along any region of the specimen, and the images have pixel sizes as fine as 9 pm. The data is used to create realistic 3D images and to calculate internal morphological parameters. The 3D images are imported into COMSOL to create a customized FEM geometry for each rabbit. In vivo micro-CT scanning of rabbit distal femurs is repeatable and reproducible and can be used with confidence to measure differences in trabecular bone architecture. Five in vivo scans of the left hind-leg of each rabbit are performed within approximately 30 minutes, with x-ray exposure lasting under 10 minutes.

TABLE 9

Trial groups and pulsing parameters for in vivo experiments

| Trial Group (N = 4) | Voltage | Pulse Duration | Number of Pulses | Frequency |
|---|---|---|---|---|
| Control | — | — | — | — |
| IRE 1 | 250 V | 10 μs | 100 | 1 Hz |
| IRE2 | 500 V | 10 μs | 100 | 1 Hz |
| Supra-poration 1 | 10 kV | 10 ns | 100 | 1 Hz |
| Supra-poration 2 | 30 kV | 10 s | 100 | 1 Hz |

Following imaging, rabbits are maintained under anesthesia, and the bipolar electrode is advanced centrally into the distal femur of the restricted left hind-leg until the energized and grounded surfaces are within the tissue. The x-ray micro-CT scanner is used to ensure proper placement of the electrode. Following delivery of the pulsing protocols, the electrode is removed, and the wound is closed in a routine fashion. Gold nanorods act as dense x-ray absorbing agents, further justifying the use of x-ray micro-CT in this experiment. Rabbits are humanely euthanized 12 hrs post-treatment, to allow adequate time for the induction of cell death following IRE and supra-poration.

After sacrifice, all left femurs are harvested and reserved for histological analysis. Histology specimens are stripped of surrounding soft tissues, fixed in 10% neutral formalin, and embedded in paraffin. Square fragments of tissue are enumerated in a grid format to ensure the spatial location of each tissue fragment is known and can be correlated to regions of injury. Thick sections of 5 μm are taken longitudinally around the electrode implantation site using a microtome (Microm International). The sections are stained with hematoxylin and eosin and imaged on an inverted microscope (Leica DMI6000B, Leica Microsystems). Treatment area is determined through an examination of four sections from each specimen for regions of necrosis. There is a sharp delineation between normal and necrotic tissue following the in vivo application of pulsed electric fields. Images are imported into LabVIEW, and a software program can be used to trace the delineation lines and calculate the internal areas within regions of bone marrow. The measurements are imported into COMSOL to refine the properties of the computational model to better predict treatment outcomes.

A Multi-way ANOVA with SPSS software is used to determine statistical significance among endpoint measurements for all pulsing protocols and a Tukey-Kramer test identifies significant differences in treatment area measurements between IRE and supra-poration. Data is presented as mean±standard deviation of four independent determinations, and a statistical probability of P<0.05 is considered significant. This novel nanoparticle-mediated pulsed electric field therapy can be used to purge stem cells of leukumeic cells prior to engraftment in autologous stem cell transplantations, effectively eliminating disease recurrence.

This novel therapy can replace autologous stem cell transplantations completely, and patients will no longer be subject to a high risk of infection and toxicity following chemotherapy and radiation. Additionally, this is the first treatment planning model to incorporate nanorods with pulsed electric field therapies. Such a treatment planning model allows surgeons to optimize the electrode geometry, voltage parameters, and nanorod concentrations for varying types of tissue and heterogeneities to ensure that only leukemic cells with bound nanorods receive a lethal dose of IRE or supra-poration.

Example 14

Figure 29:
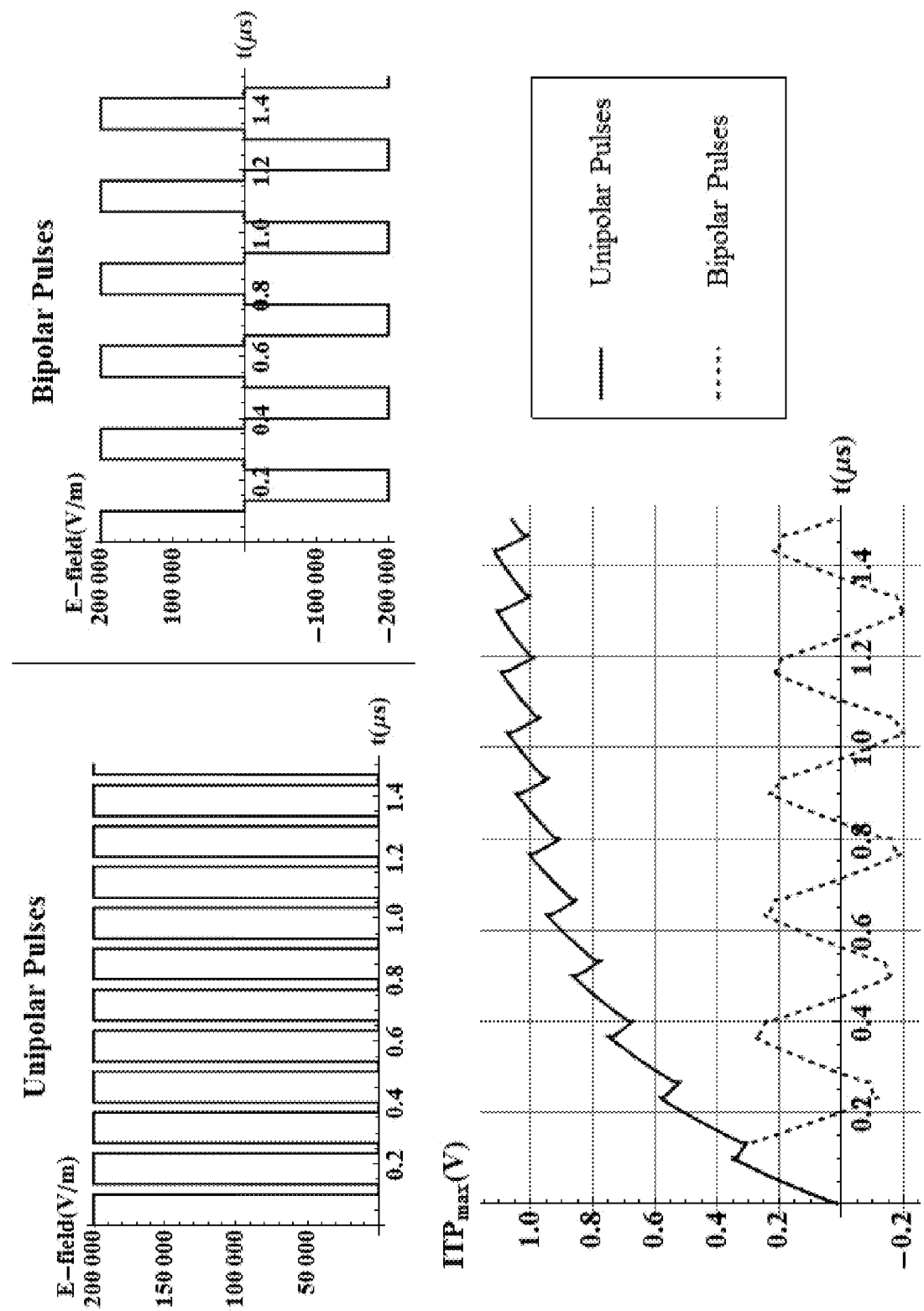
FIG. 29 depicts the results of analytical calculations on transmembrane potential (TMP) for leukemia cells exposed to monopolar and bipolar pulse trains comprised of ultra-short pulses. In each case, the pulse duration (100 ns) is less than the charging time of the plasma membrane.

Ultra-Short Pulses can be Integrated Temporally and Spatially to Induce Membrane Permeabilization FIG. 29 illustrates the ability for multiple ultra-short pulses to generate an electric field capable of inducing a transmembrane potential large enough to promote irreversible membrane breakdown. When cells are placed in a uniform electric field, and their membranes are treated as spherical, ideal dielectric shells containing and surrounded by a conductive medium, the analytical solution for induced. TMP across the plasma membrane and nuclear envelope can be described as a function of time by solving the Laplace equation. The exact formula has been described in the section on detailed description of various embodiments of the invention. The pulse duration was defined to be 100 ns using a Heaviside step function (ideal rise time) in order to investigate the timescale of complete plasma membrane and nuclear envelope charging and discharging, respectively. The duty cycle was defined as 75% (−33 ns delay between pulses), and the pulse amplitude was defined to be 2000 V/cm delivered either uni-directionally (monopolar pulses) or bi-directionally (bipolar pulses). The solution was obtained by frequency domain analysis in Mathematica 7 (Wolfram Research, Inc.) and converted back into the time domain by taking the inverse Laplace transform according to, TMP (t)=$L^{-1}$[(TMP(s)]. Results of the model confirm the hypothesis that if multiple, ultra-short pulses are delivered at a sufficient duty cycle, which temporally and spatially sum to the charging time of the plasma membrane, then cells can remain polarized long enough for the transmembrane potential to reach levels necessary for electroporation. However, when the pulses spatially offset, as is the cases when bipolar pulses are employed, then the IMP never reaches a permeabilizing threshold.

These results can be extended by using finite-element techniques to investigate the limits of pulse directionality. A three-dimensional geometry representative of a multiple-cells enclosed by an epithelial layer was simulated using CORTISOL. The "quasi-static, electric" module was selected for its ability to perform a transient analysis of conducting and dielectric materials with small currents in the (r,z)-plane and a negligible coupling between the electric and magnetic fields. The model essentially solves the complex Laplace equation in order to predict the electric field distribution in a non-uniform electric field. The equation accounts for the resistive and capacitive components of tissue, which must be included when modeling heterogeneous systems.

Four application modes were defined to represent the tissue exterior, extracellular space, cytoplasm, and nucleoplasm subdomains. The volume representing the tissue exterior (between the epithelial layer and the electrodes) was filled with a conductive gel ($\sigma$=48/m; $\epsilon_r$=80), which is commonly used in electroporation procedures to homogenize the electric field. The epithelial layer, plasma membrane, and nuclear envelope forming the interface between the different subdomains were treated as thin sheets of resistive material following the distributed impedance boundary condition:

$$\vec{n} \cdot \vec{J} = \frac{\sigma_m(V_i - V_o)}{d} + \frac{\varepsilon_o \varepsilon_m}{d} \frac{\partial(V_i - V_o)}{\partial t},$$

where J is the total current density (normal) in the membrane, $\sigma_e$, is the conductivity of the membrane, $\epsilon_o$ is the permittivity of a vacuum, $\epsilon_m$ is the relative permittivity of the membrane, d is the thickness of the membrane, and $V_i$ and $V_o$ are the electric potentials inside and outside the membrane, respectively. Lipid bilayers are three orders of magnitude thinner than the dimensions of a typical cell, and the reduction of epithelial cells to a single boundary avoids the creation of extremely fine mesh elements within tight junctions between cells. A perfectly tight epithelium is assumed, in which tight junctions have an infinite resistance.

The thickness of the epithelium (Table 9) was chosen to be four times as thick as the plasma membrane in order to depict a double layer of mesothelial cells encapsulating the tissue section. The surface of peritoneal tissue generally consists of mesothelial cells, but the number of cell layers varies depending on location. To compensate for the fact that the thickness of the epithelium was four times as thick as the plasma membrane, the conductivity of the boundary layer was scaled according to the relation a'=(d'/d)×$\sigma$. The remaining horizontal faces of the simulation domain were modeled as electrically insulating, and the vertical faces, representing non-puncturing plate electrodes, were modeled as either electrically insulating, constant potential, or grounded, depending on the electrode activation pattern. Individual, or trains of square-wave electric pulses (0.1 ns rise time) were delivered from the energized electrodes using the function flc2hs, which constructs a smoothed Heaviside step function with continuous second derivative between two different potentials.

The potential distribution within each subdomain was obtained by transiently solving the complex Laplace equation for 13001 degrees of freedom with no external current density in each application mode. The geometry and dielectric properties associated with the cellular subdomains and boundaries are given in Table 1. Calculations of the TMP across the plasma membrane and nuclear envelope were performed by taking the difference between potentials on both sides of the respective membranes. In the first set of experiments, the epithelial layer was treated as a continuous boundary instead of distributed impedance in order to compare our prediction of IMP with analytical techniques of a single cell placed in a uniform electric field. Results are in agreement with those of Pucihar et al. (Annals of Biomedical Engineering, 2006; IEEE Transactions on Biomedical Engineering, 2009), and validate the use of the FEM to investigate multi-cellular system enclosed by an epithelial layer.

Figure 30:
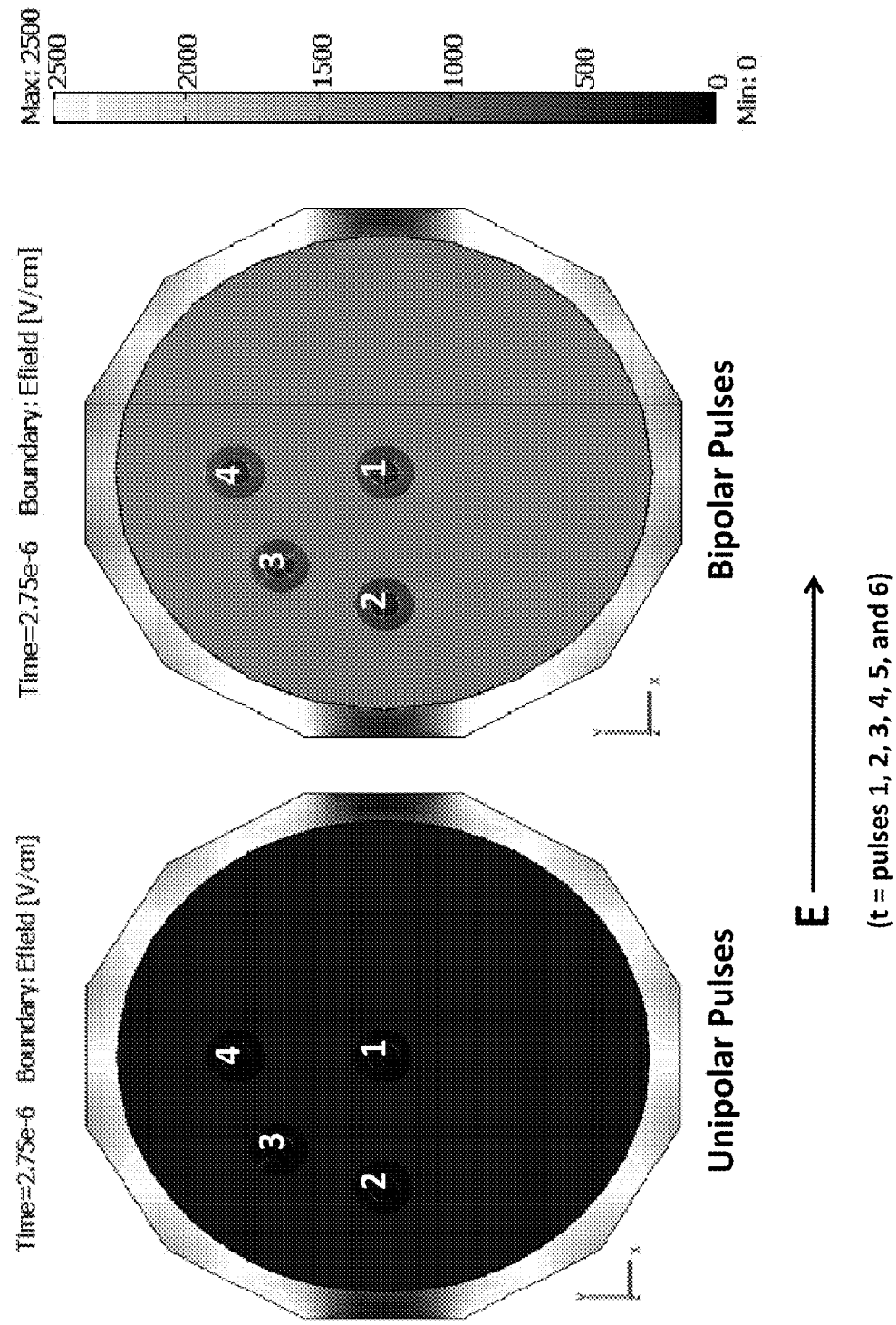
FIG. 30 shows the electric field distribution resulting from the FEM for predicting TMP on a group of cells encapsulated by an epithelial layer. A train of unipolar (left) and bipolar (right) pulses are delivered, and the electric field distribution is shown at the middle of the last pulse in the train. The numbers correspond to locations of cells where plasma membrane TMP was recorded.
Figure 31:
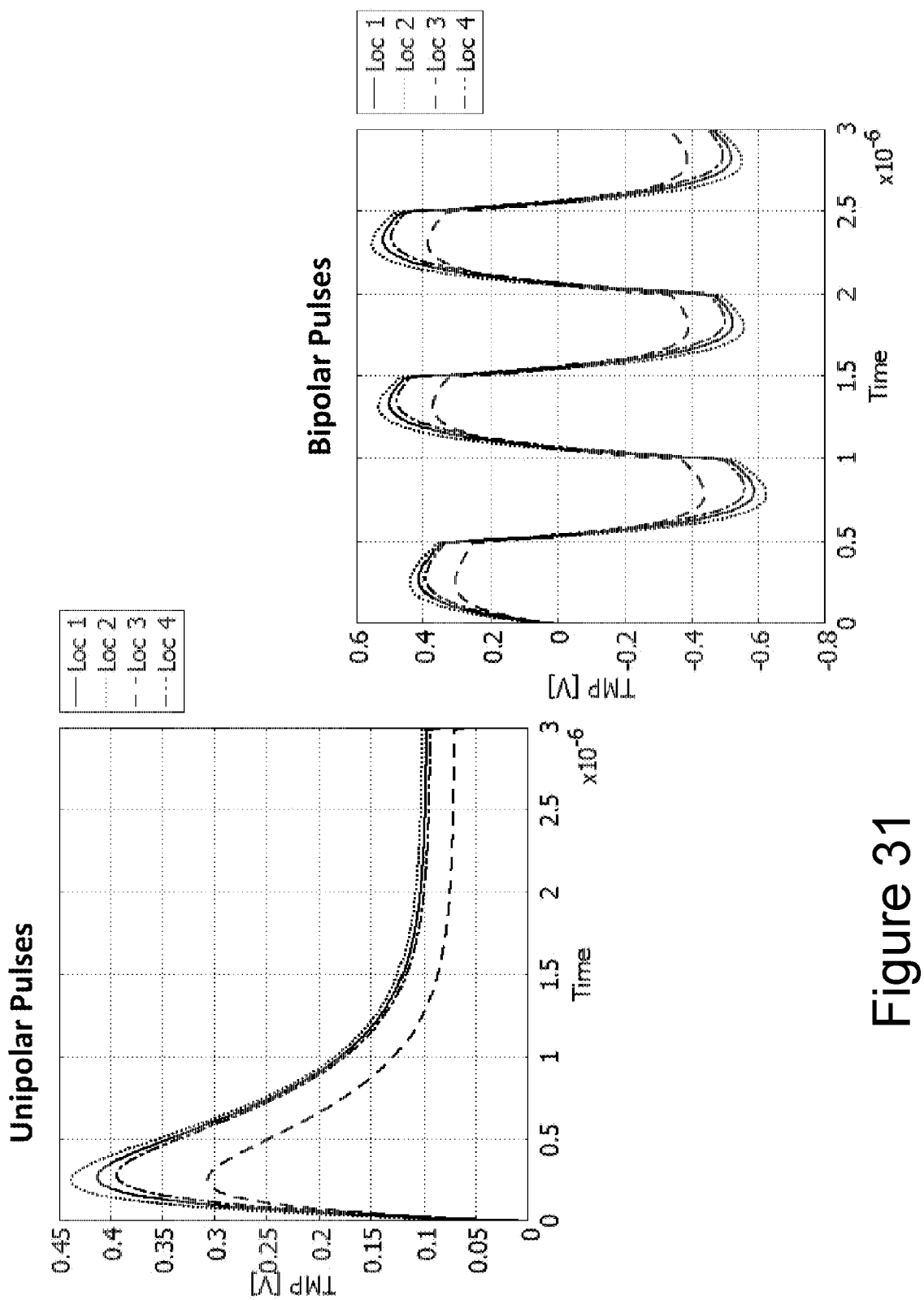
FIG. 31 shows the maximum induced plasma membrane TMP at four different cellular locations in the corresponding FEM model. A train of unipolar (left) and bipolar (right) pulses are delivered, and the maximum TMP is shown throughout the entire pulse in the train.
Figure 32:
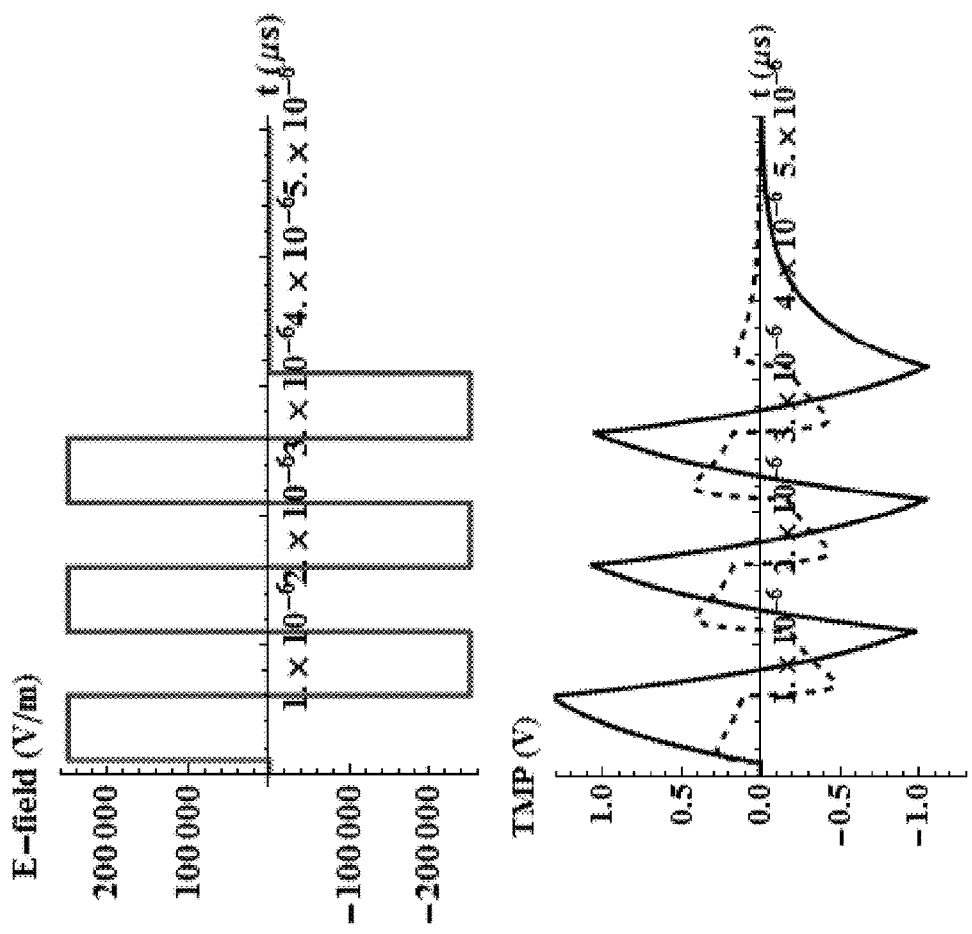
FIG. 32 depicts the results of analytical calculations on transmembrane potential (TMP) for leukemia cells exposed to a bipolar pulse train comprised of ultra-short pulses. The pulse duration has been tuned to equal the charging time of the plasma membrane (~500 ns).

The potential of the present invention to treat tissues enclosed by epithelial layers is emphasized by the results of the FEM shown in FIG. 30 and FIG. 31. A train of unipolar pulses is compared to a train of bipolar pulses, where both are delivered horizontally across the simulation domain. The pulse duration (500 ns), number (6), amplitude (2500 V/m), and duty cycle (100%) are held constant in each iteration, such that the polarity is the only parameter of interest. The effects of using unipolar pulses are similar to conventional IRE treatment, in that the integration of pulses results in a single puke on the order of microseconds. In this case, once the epithelial layer is fully charged, the remaining pulses in the train are not effective for treating the underlying cells. This is evident in FIG. 30, which shows that the epithelial layer shields the electric field from the underlying cells, and in FIG. 31, which shows that the induced IMP on the plasma membrane of the underlying cells drops off after the epithelial layer is fully charged. In the bipolar case, each pulse within the train is tuned to charge the epithelial layer to its critical permeabilizing threshold, and once the TMP approaches its asymptotic value at the fully charged state, the pulse polarity flips and the procedure is repeated. These results, extend those of the analytical model shown in FIG. 32, and indicate that the bipolar pulses are more effective at continually penetrating the epithelial layer and treating the entire tissue volume throughout the duration of the pulse train. In embodiments, each pulse parameter can be increased or decreased according to how long the plasma membrane of the cells comprising a given tissue must be held at a TMP 1 V to induce cell death.

Figure 33:
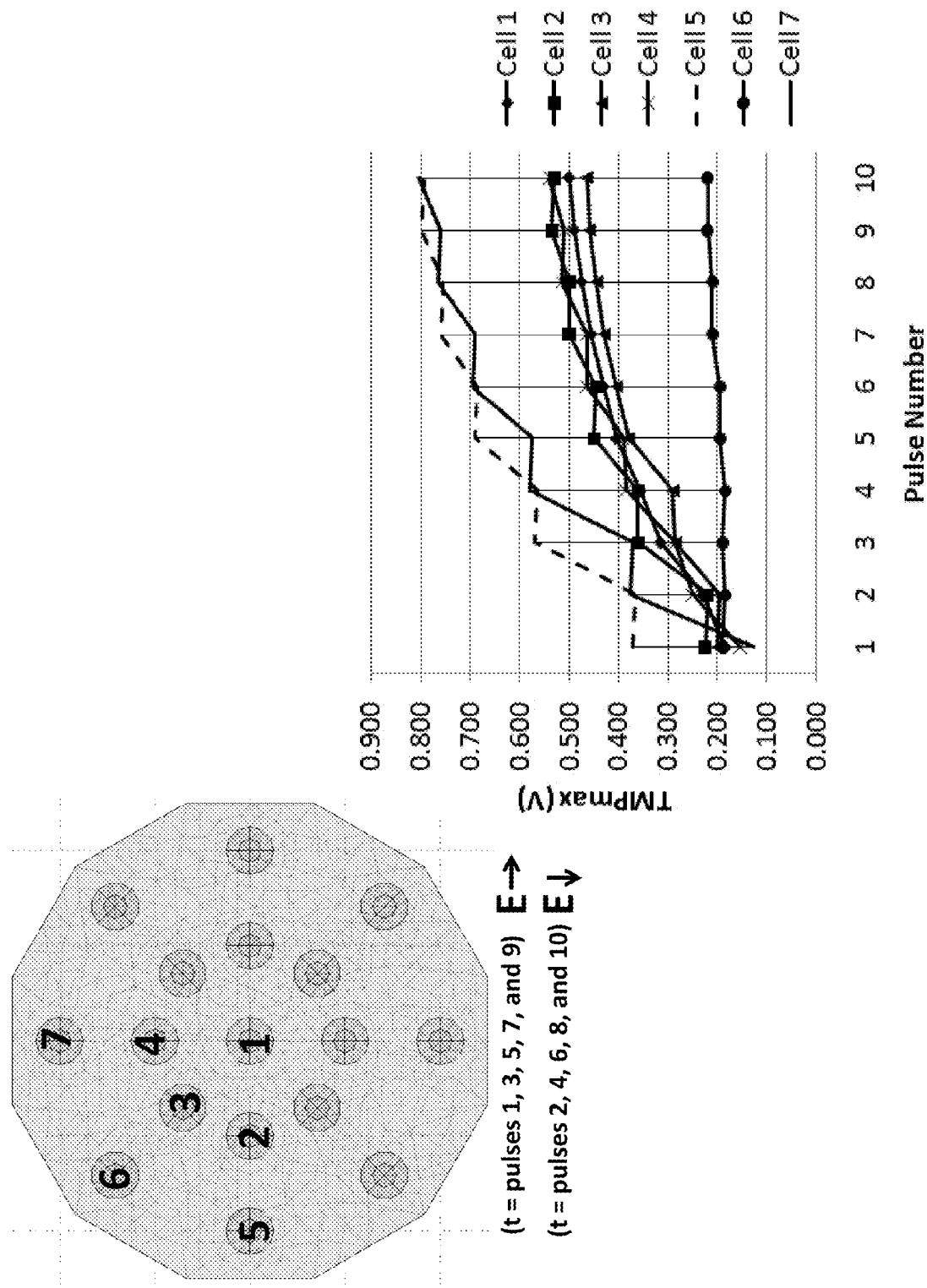
FIG. 33 shows the effect of pulse directionality on induced plasma membrane TMP (right) for a multi-cellular mesh (left). A train of unipolar pulses is implemented, where each sequential pulse within the train is either delivered horizontally (pulses 1, 3, 5, 7, and 9) or vertically (pulses 2, 4, 6, 8, and 10) across the simulation domain. TMP is recorded at seven different cell locations.
Figure 34:
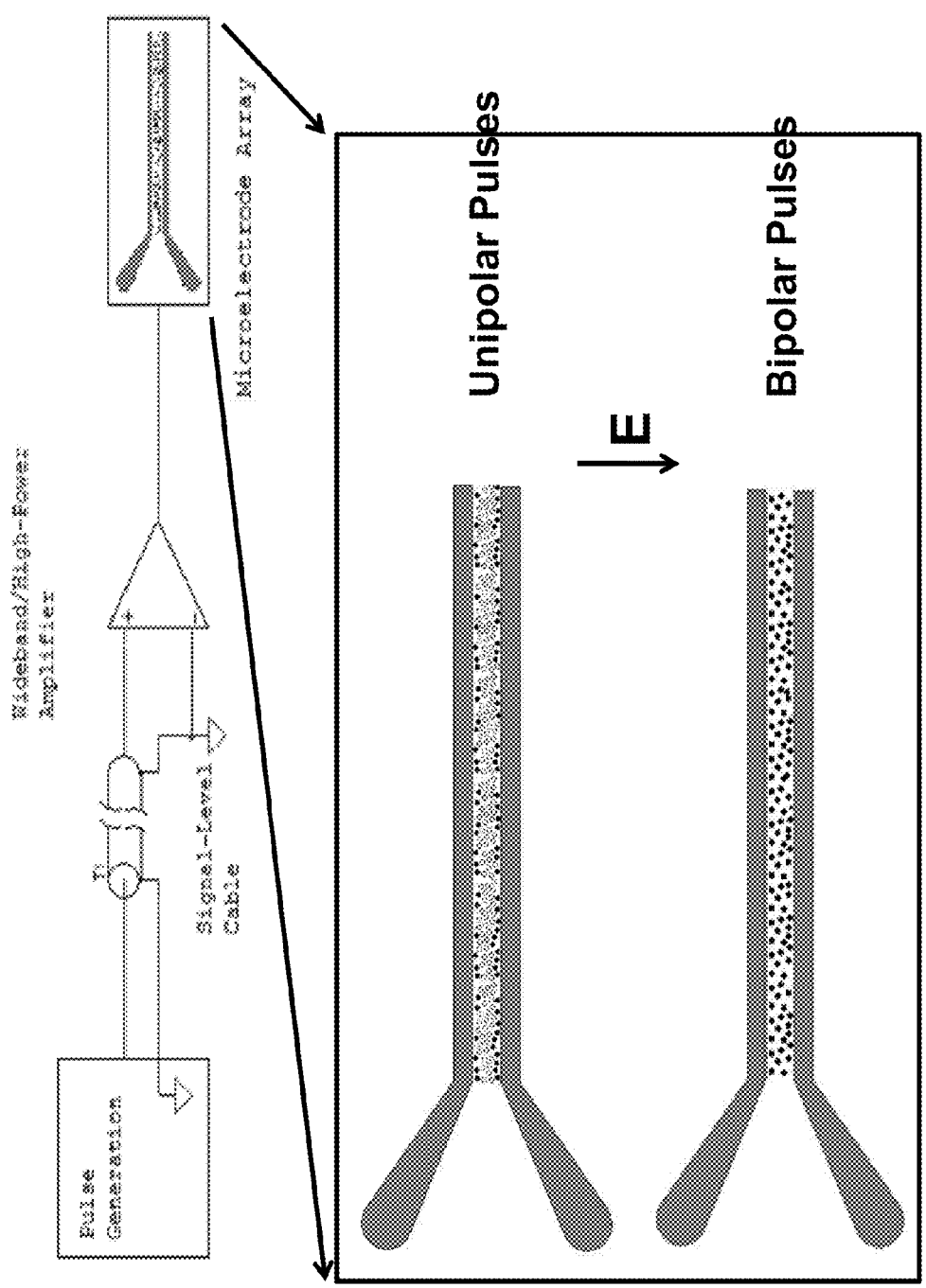
FIG. 34 illustrates a system for varying the region of treated cells in vitro, and two microelectrode arrays with cells cultured in between the electrodes (cut-out). By varying pulse parameters, the region of cell death (shown in black) will be changed.
Figure 35:
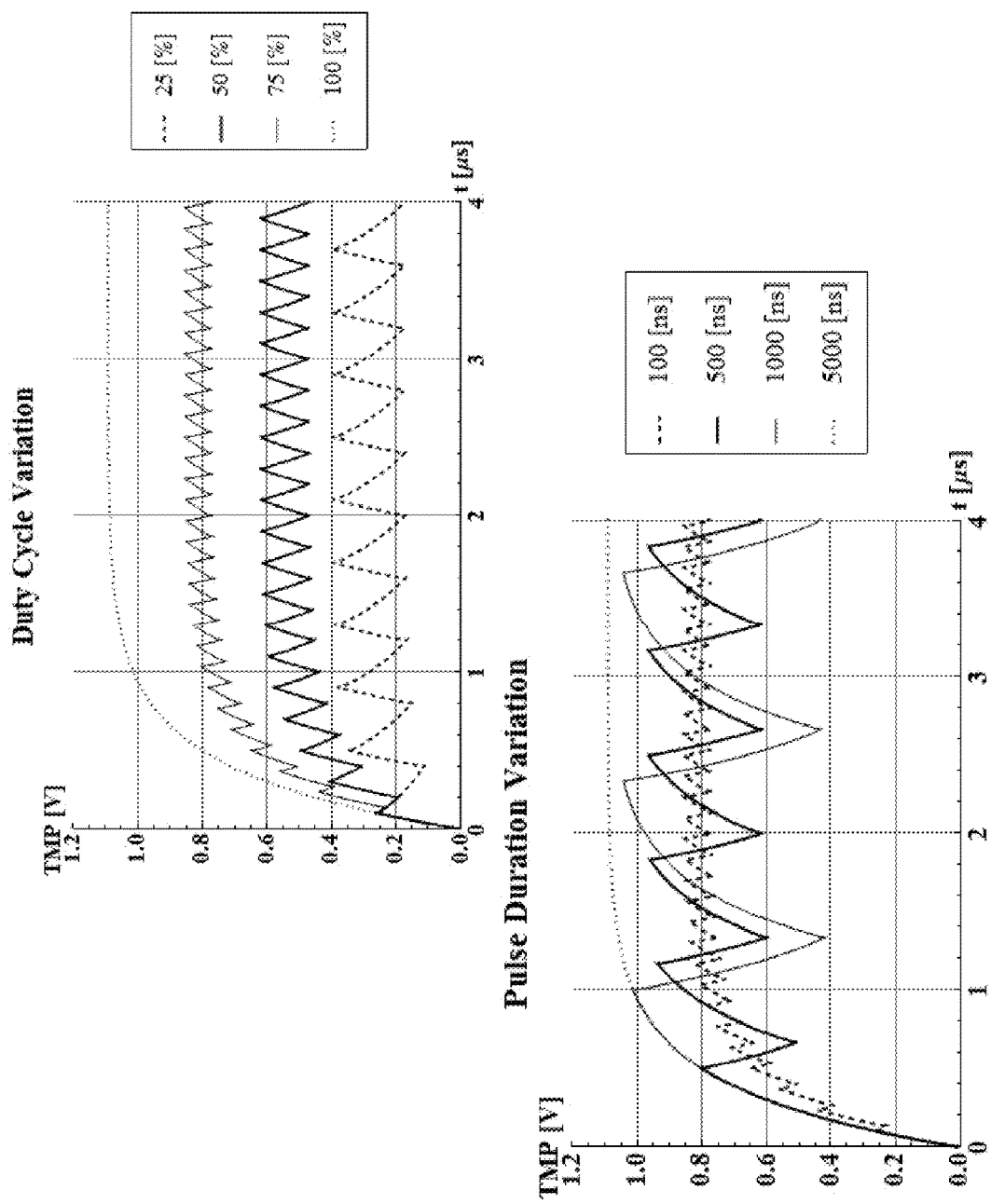
FIG. 35 depicts the results of analytical calculations on transmembrane potential (TMP) for leukemia cells exposed to ultra-short pulse trains of varying duration and duty cycle. In all cases, the applied electric field is 2000 V/cm, and the maximum value of TMP around the cell at the pole is shown. When duty cycle is varied, pulse duration is held constant at 100 ns, and when pulse duration is varied, duty cycle is held constant at 75%.

The potential of the present invention to perform non-invasive, targeted electroporation is emphasized by the results of the FEM shown in FIG. 33. In this simulation, the epithelial layer was removed and only three application modes were defined to represent the extracellular space, cytoplasm, and nucleoplasm subdomains. The potential distribution within each subdomain was obtained by transiently solving the complex Laplace equation for 33397 degrees of freedom with no external current density in each application mode. A train of unipolar pulses is delivered horizontally and vertically across the simulation domain in an alternating fashion. The pulse duration (100 ns), number (10), amplitude (1500 V/cm), and duty cycle (100%) are held constant in each iteration, such that the varying components of the electric field are the only parameters of interest. The maximum TMP is recorded at seven cell locations to investigate the effects of pulse directionality on inducing electroporation. The results shown in FIG. 33 indicate that cells 5 and 7 can undergo IRE while cells 1-4 experience reversible electroporation. Interestingly, cell 6 is spared from all pulsed electric field therapy. Further, if a second train of pulses is delivered at a 45 degree offset from the current train, cells 5 and 7 will be spared. The effect of this embodiment of the invention allows cells 1-4 to experience a permeabilizing field longer than cells 5-7, resulting in a targeted form of electroporation.

The present invention has been described with reference to particular embodiments having various features. It will be apparent to those skilled in the art that various modifications and variations can be made in the practice of the present invention without departing from the scope or spirit of the invention. One skilled in the art will recognize that these features may be used singularly or in any combination based on the requirements and specifications of a given application or design. Other embodiments of the invention will be apparent to those skilled in the art from consideration of the specification and practice of the invention. Where a range of values is provided in this specification, each value between the upper and lower limits of that range is also specifically disclosed. The upper and lower limits of these smaller ranges may independently be included or excluded in the range as well. As used in this specification, the singular forms "a," "an," and "the" include plural referents unless the context clearly dictates otherwise. It is intended that the specification and examples be considered as exemplary in nature and that variations that do not depart from the essence of the invention are intended to be within the scope of the invention. Further, the references cited in this disclosure are incorporated by reference herein in their entireties.

The invention claimed is:

1. A method of selectively treating cells, comprising:
applying to a tissue a plurality of electrical pulses with a delay between successive pulses, wherein the length of each pulse and the delay between successive pulses are optimized to produce a first treatment zone and a second treatment zone;
wherein only selected cells are affected in the second treatment zone.

2. The method of claim 1, wherein the applying is performed in vitro.

3. The method of claim 1, wherein the applying is performed in vivo.

4. The method of claim 1, wherein the applying is performed ex vivo.

5. The method of claim 1, wherein the first treatment zone comprises cancer cells and non-cancer cells which are killed by necrosis.

6. The method of claim 1, wherein the second treatment zone comprises cancer cells which are killed by apoptosis.

7. The method of claim 1, wherein the first treatment zone comprises some cancer cells and some non-cancer cells which are killed.

8. The method of claim 1, wherein the second treatment zone comprises cancer cells and non-cancer cells and some of the cancer cells are killed or inhibited and some of the non-cancer cells are spared.

9. The method of claim 5, wherein the first treatment zone comprises cancer cells and non-cancer cells which are killed as a result of an increase of their transmembrane potential to a lethal threshold.

10. The method of claim 1, wherein the second treatment zone comprises cancer cells which are killed as a result of an increase in their nuclear transmembrane potential to a lethal threshold.

11. The method of claim 1, wherein the delay between successive pulses is greater than the length of each pulse.

12. The method of claim 1, wherein the delay between successive pulses is a fraction of the length of each pulse.

13. The method of claim 1, wherein the selected cells are cancer cells and the length of each pulse is equivalent to the charging time of the cell membrane of the cancer cells plus the discharge time of the nuclear membrane of the cancer cells, while the delay between successive pulses is equivalent to the charging time of the cell membrane of the cancer cells.

14. The method of claim 13, wherein the charging time of the cell membrane of the cancer cells and the discharge time of the nuclear membrane of the cancer cells are determined through numerical modeling.

15. The method of claim 1, wherein the plurality of electrical pulses comprises an electric field waveform which is a rectangular pulse, ramp, decaying exponential, or sine wave.

16. The method of claim 15, wherein the electric field waveform is unipolar or bipolar.

17. The method of claim 15, wherein the electric field waveform is a superimposed, bimodal signal comprising a first frequency harmonic and a second frequency harmonic, wherein the second frequency harmonic has a frequency higher than that of the first frequency harmonic.

18. The method of claim 15, wherein the electric field waveform comprises alternating nanosecond-order pulses with microsecond order pulses in succession.

19. The method of claim 15, wherein the electric field waveform is asymmetric.

20. The method of claim 15, wherein the electric field waveform has a carrier frequency in the range of 100 kHz to 10 MHz.

21. The method of claim 15, wherein carrier frequency or pulse duration of the waveforms are based on the cross-over frequency of the cancer cells.

22. The method of claim 1, wherein the length of each pulse and the delay between successive pulses are optimized based on the physical nucleus to cytoplasm size ratio of the cancer cells.

23. The method of claim 1, wherein the pulses are bipolar square waves and the length of each pulse is between 250 nanoseconds and 50 microseconds.

24. A method of selectively treating cells, comprising:
applying a plurality of electrical pulses to a substance containing cells, wherein the plurality of electrical pulses has a frequency, amplitude, and pulse waveform selected to treat target cells of one type of cell and spare non-target cells of another type of cell;
determining a nucleus-to-cytoplasm ratio for the target cells; and
selecting the frequency, amplitude, and pulse waveform based on the nucleus-to-cytoplasm ratio for the target cells.

25. The method of claim 24, wherein the substance containing cells is a tissue.

26. The method of claim 24, wherein the applying is performed in vitro.

27. The method of claim 24, wherein the applying is performed in vivo.

28. The method of claim 24, wherein the applying is performed ex vivo.

29. A method of selectively treating cells, comprising:
applying to a tissue a plurality of electrical pulses with a delay between successive pulses, wherein the length of each pulse and the delay between successive pulses are optimized to produce a first treatment zone and a second treatment zone;
wherein only selected cells are killed by non-thermal ablation in the second treatment zone.

30. The method of claim 29, wherein the non-thermal ablation is irreversible electroporation.

* * * * *